US012592321B2

(12) United States Patent
Bratman et al.

(10) Patent No.: US 12,592,321 B2
(45) Date of Patent: Mar. 31, 2026

(54) CANCER DETECTION AND CLASSIFICATION USING METHYLOME ANALYSIS

(71) Applicant: University Health Network, Toronto (CA)

(72) Inventors: Scott Victor Bratman, Toronto (CA); Justin Matthew Burgener, Toronto (CA); Daniel Diniz De Carvalho, Toronto (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 18/820,166

(22) Filed: Aug. 29, 2024

(65) Prior Publication Data

US 2025/0006375 A1      Jan. 2, 2025

Related U.S. Application Data

(63) Continuation-in-part of application No. 18/067,661, filed on Dec. 16, 2022, now abandoned, which is a continuation of application No. PCT/CA2021/050842, filed on Jun. 18, 2021.

(60) Provisional application No. 63/041,151, filed on Jun. 19, 2020.

(51) Int. Cl.
| | |
|---|---|
| *G16H 50/20* | (2018.01) |
| *G01N 33/53* | (2006.01) |
| *G16H 50/30* | (2018.01) |
| *G16H 50/70* | (2018.01) |

(52) U.S. Cl.
CPC ......... *G16H 50/20* (2018.01); *G01N 33/5308* (2013.01); *G16H 50/30* (2018.01); *G16H 50/70* (2018.01)

(58) Field of Classification Search
CPC ........ C12Q 1/68; C12Q 1/6806; G16H 50/20; G16H 50/30
See application file for complete search history.

(56) References Cited

U.S. PATENT DOCUMENTS

| | | | |
|---|---|---|---|
| 6,730,478 | B1 | 5/2004 | Lee et al. |
| 9,249,462 | B2 | 2/2016 | Patsalis et al. |
| 10,706,957 | B2 | 7/2020 | Lo et al. |
| 11,078,475 | B2 | 8/2021 | Diniz De Carvalho et al. |
| 11,560,558 | B2 | 1/2023 | Diniz De Carvalho et al. |
| 12,031,184 | B2 * | 7/2024 | Diniz De Carvalho .................... G16B 40/00 |
| 12,227,737 | B2 * | 2/2025 | Diniz De Carvalho .................... C12Q 1/6804 |

| | | | |
|---|---|---|---|
| 2003/0003455 | A1 | 1/2003 | Rundell et al. |
| 2003/0092019 | A1 | 5/2003 | Meyer et al. |
| 2003/0190616 | A1 | 10/2003 | Goggins et al. |
| 2011/0236903 | A1 | 9/2011 | McClelland et al. |
| 2012/0208711 | A1 * | 8/2012 | Cortese ................ C12Q 1/6837 506/2 |
| 2012/0282613 | A1 | 11/2012 | Patsalis et al. |
| 2014/0080715 | A1 | 3/2014 | Lo et al. |
| 2015/0132754 | A1 | 5/2015 | Wang et al. |
| 2015/0299812 | A1 * | 10/2015 | Talasaz ................ C12Q 1/6869 |
| 2016/0017419 | A1 | 1/2016 | Chiu et al. |
| 2016/0032396 | A1 * | 2/2016 | Diehn .................. C12Q 1/6886 506/26 |
| 2019/0005395 | A1 | 1/2019 | Dutkowski |
| 2019/0024127 | A1 | 1/2019 | Yeh |
| 2019/0071727 | A1 | 3/2019 | Lo et al. |
| 2019/0144848 | A1 * | 5/2019 | De Carvalho ....... C12Q 1/6806 506/17 |
| 2020/0131582 | A1 | 4/2020 | Zhou et al. |
| 2020/0160936 | A1 * | 5/2020 | Fang ...................... G16B 30/10 |
| 2020/0165675 | A1 * | 5/2020 | Marsh ...................... C12Q 1/68 |
| 2021/0156863 | A1 | 5/2021 | Dinz De Carvalho et al. |
| 2022/0119796 | A1 | 4/2022 | Diniz De Carvalho et al. |
| 2022/0177956 | A1 | 6/2022 | Frumkin et al. |
| 2022/0251665 | A1 | 8/2022 | Diniz De Carvalho et al. |
| 2023/0024827 | A1 | 1/2023 | Wilson et al. |
| 2023/0203473 | A1 | 6/2023 | Diniz De Carvalho et al. |
| 2023/0212690 | A1 * | 7/2023 | Bratman ................ G16H 50/20 435/6.11 |
| 2023/0287384 | A1 | 9/2023 | Diniz et al. |
| 2023/0374601 | A1 | 11/2023 | Lo et al. |

(Continued)

FOREIGN PATENT DOCUMENTS

| | | |
|---|---|---|
| CA | 3080215 A1 | 5/2019 |
| CN | 104781422 A | 7/2015 |
| CN | 109415763 A | 3/2019 |

(Continued)

OTHER PUBLICATIONS

Liu et al., Cloud-based bioinformatics workflow platform for large-scale next-generation sequencing analyses. J. of Biomedical Informatics 49:119-133 (Year: 2014).*

(Continued)

*Primary Examiner* — Ethan C Whisenant

(74) *Attorney, Agent, or Firm* — WILSON SONSINI GOODRICH & ROSATI

(57)      ABSTRACT

This is described herein, a method of capturing cell-free methylated DNA from a sample having less than 100 mg of cell-free DNA, comprising the steps of: subjecting the sample to library preparation to permit subsequent sequencing of the cell-free methylated DNA; adding a first amount of filler DNA to the sample, wherein at least a portion of the filler DNA is methylated; denaturing the sample; and capturing cell-free methylated DNA using a binder selective for methylated polynucleotides.

23 Claims, 63 Drawing Sheets
(61 of 63 Drawing Sheet(s) Filed in Color)

(56) References Cited

U.S. PATENT DOCUMENTS

2025/0002904 A1      1/2025  Bratman et al.

FOREIGN PATENT DOCUMENTS

| | | |
|---|---|---|
| CN | 109642227 A | 4/2019 |
| CN | 111094590 A | 5/2020 |
| CN | 111154846 A | 5/2020 |
| JP | 2005525084 A | 8/2005 |
| JP | 2010535513 A | 11/2010 |
| JP | 2014506788 A | 3/2014 |
| JP | 2015519084 A | 7/2015 |
| JP | 2015536639 A | 12/2015 |
| JP | 2017514499 A | 6/2017 |
| JP | 2019521315 A | 7/2019 |
| WO | WO-2012143481 A2 | 10/2012 |
| WO | WO-2014043763 A1 | 3/2014 |
| WO | WO-2015009844 A2 | 1/2015 |
| WO | WO-2016094330 A2 | 6/2016 |
| WO | WO-2016115530 A1 | 7/2016 |
| WO | WO-2017008912 A1 | 1/2017 |
| WO | WO-2017070497 A1 | 4/2017 |
| WO | WO-2017190215 A1 | 11/2017 |
| WO | WO-2018017710 A1 | 1/2018 |
| WO | WO-2019010564 A1 | 1/2019 |
| WO | WO-2019028470 A2 | 2/2019 |
| WO | WO-2019084659 A1 | 5/2019 |
| WO | WO-2020232109 A1 | 11/2020 |
| WO | WO-2021041726 A1 | 3/2021 |
| WO | WO-2021087615 A1 | 5/2021 |
| WO | WO-2021133993 A2 | 7/2021 |
| WO | WO-2021253138 A1 | 12/2021 |
| WO | WO-2023107709 A1 | 6/2023 |
| WO | WO-2023135600 A1 | 7/2023 |
| WO | WO-2023230289 A1 | 11/2023 |
| WO | WO-2024192294 A1 | 9/2024 |
| WO | WO-2024216205 A1 | 10/2024 |

OTHER PUBLICATIONS

Kalinich et al., An RNA-based signature enables high specificity detection of circulating tumor cells in hepatocellular carcinoma. PNAS 114(5) :1123-1128 Jan. 2017.*

Pantel et al. Clinical Applications of Circulating Tumor Cells and Circulating Tumor DNA as Liquid Biopsy . . . Cancer Discovery 6(5) :479-491 (Year: 2015).*

Saxonov et al., A genome-wide analysis of CpG dinucleotides in the human genome distinguishes two distinct classes of promoters. PNAS 103(5) :1412-1417 (Year: 2006).*

Stansky et al., The Mutational Landscape of Head and Neck Squamous Cell Carcinoma. Science 333:1157 (Year: 2011).*

Underhill et al., Fragment Length of Circulating Tumor DNA. PLOS: Genetics : 1006162 :24pgs (Year: 2016).*

Vandeweyer et al., VariantDB: a flexible annotation and filtering portal for next generation sequencing data. Genome Medicine 6:74 (Year: 2014).*

Wang et al., An evaluation of new criteria for CpG islands in the human genome as gene markers. Bioinformatics 20(7) : 1170-1179 (Year: 2004).*

Bettegowda et al., Detection of Circulating tumor DNA in Early- and Late-Stage Human Malignancies. Science Translational Medicine 6(224) : 224ra 24 (Year: 2014).*

Mazurek et al., Assessment of the total cfDNA and HPV16/18 detection in plasma samples of head and neck squamous cell carcinoma patients. Oral Oncology 54:36-41 (Year: 2016).*

Taiwo et al . . . Methylome analysis using MeDIP-seq with low DNA concentrations. Nature Protocols 7() :617 (Year: 2012).*

Abbosh et al., "Phylogenetic ctDNA analysis depicts early-stage lung cancer evolution", Nature, vol. 545, Apr. 26, 2017, pp. 446-451.

Basu, et al. Genome-wide DNA methylation profile identified a unique set of differentially methylated immune genes in oral squamous cell carcinoma patients in India. Clin Epigenetics. Feb. 3, 2017:9:13. doi: 10.1186/s13148-017-0314-x. eCollection 2017.

Bratman et al. Potential clinical utility of ultrasensitive circulating tumor DNA detection with CAPP-Seq. Expert Review of Molecular Diagnostics. 15(6), 715-719 (2015).

Burgener et al. Abstract PR13: Comprehensive detection of ctDNA in localized head and neck cancer by genome- and methylome-based analysis. Clin. Cancer Res. Jun. 1, 2020. 26(11 Supple.) PR13.

Dai, et al. Identification of hub methylated-CpG sites and associated genes in oral squamous cell carcinoma. Cancer Med. May 2020; 9(9): 3174-3187. Published online Mar. 10, 2020. doi: 10.1002/cam4.2969.

EP21825516.4 European Search Report and Opinion dated Jan. 25, 2024.

International search report with written opinion dated Oct. 5, 2021 for PCT/CA2021/050842.

Juppner, H. Functional Properties of the PTH/PTHrP Receptor. Bone vol. 17,2: pp. 39S-42S (1995).

Liu, Jianfang et al. An Integrated TCGA Pan-Cancer Clinical Data Resource to Drive High-Quality Survival Outcome Analytics. Cell. Apr. 5, 2018;173(2):400-416.e11. doi: 10.1016/j.cell.2018.02.052.

Muhanna et al. Cell-Free DNA Kinetics in a Pre-Clinical Model of Head and Neck Cancer. Scientific Reports 2017 7: 16723. p. 1-11.

Newman, Aaron M. et al. Integrated Digital Error Suppression for Improved Detection of Circulating Tumor DNA. Nature Biotechnology 34(5):547-555 (2016).

Shen, Shu Yi. et al. Preparation of cfMeDIP-seq libraries for methylome profiling of plasma cell-free DNA. Nature Protocols 14(10):2749-2780 (2019).

Steinmann, et al. Frequent promoter hypermethylation of tumor-related genes in head and neck squamous cell carcinoma. Oncol Rep. Dec. 2009;22(6):1519-26. doi: 10.3892/or_00000596.

The Cancer Genome Atlas Network. Comprehensive genomic characterization of head and neck squamous cell carcinomas. Nature 517:576-582 (2015a).

U.S. Appl. No. 18/067,661 Office Action dated May 8, 2024.

Wong, Karen et al. Point-of-care outcome assessment in the cancer clinic: Audit of data quality. Radiotherapy and Oncology. vol. 95, Issue 3, Jun. 2010, pp. 339-343.

Akalin et al. MethylKit: A Comprehensive R Package for the Analysis of Genome-Wide DNA Methylation Profiles. Genome Biology 13(10):R87 (2012).

Altschul, Stephen F. et al. Basic Local Alignment Search Tool. Journal of Molecular Biology 215(3):403-410 (1990).

Amemiya, Haley M. et al. The ENCODE blacklist: Identification of problematic regions of the genome. Scientific Reports 9(1):9354, 1-5 (2019).

Amplicons 1CpG, 5CpG, and 10CpG, GC Calculator evidence :1-3 (2025).

Aravanis, Alexander M. et al. Next-Generation Sequencing of Circulating Tumor DNA for Early Cancer Detection. Cell 168(4):571-574 (2017).

Bagley, et al. Pretreatment neutrophil-to-lymphocyte ratio as a marker of outcomes in nivolumab-treated patients with advanced non-small-cell lung cancer. Lung Cancer. Apr. 2017;106:1-7. doi: 10.1016/j.lungcan.2017.01.013. Epub Jan. 25, 2017.

Bailey, Peter. et al. Genomic Analyses Identify Molecular Subtypes of Pancreatic Cancer. Nature 531(7592):47-52 (2016).

Beltran, et al. Divergent clonal evolution of castration resistant neuroendocrine prostate cancer. Nat Med. Mar. 2016; 22(3): 298-305. Published online Feb. 8, 2016. doi: 10.1038/nm.4045.

Bettegowda, Chetan. et al. Detection of Circulating Tumor DNA in Early- and Late-Stage Human Malignancies. Science translational medicine 6(224):1-25 (2014).

Bewick, et al. Statistics review 13: receiver operating characteristic curves. Crit Care. Dec. 2004;8(6):508-12. Epub Nov. 4, 2004.

Blackburn et al. Use of synthetic DNA spike-in controls (sequins) for human genome sequencing. Nature Protocols 14, 2119-2151 (2019).

Borgel, et al. Targets and Dynamics of Promoter DNA Methylation During Early Mouse Development, Nature Genetics 42 (2010): 1093-1101.

(56)         References Cited

OTHER PUBLICATIONS

Brena, et al. Toward a human epigenome. Nat Genet. Dec. 2006;38(12):1359-1360. doi: 10.1038/ng1206-1359.

Broad Institute. Adult Genotype-Tissue Expression (GTEx) Data and Resources. GTEx Portal. Retrieved from Internet on May 31, 2024. pp. 1-2. URL: https://www.gtexportal.org/home/datasets.

Bupathi et al. Biomarkers for immune therapy in colorectal cancer: mismatch-repair deficiency and others. Journal of Gastrointestinal Oncology 2016;7(5):713-720.

Burgener. et al. (2016) Utilization of methylated circulating tumour DNA in oral squamous cell carcinoma for risk stratification and detection of recurrence. TFRI-Ontario Node Research Symposium Program & Abstracts. p. 79. Accessed online: https://www.tfri.ca/docs/default-source/nodes/ontario/2016-symposiumbook.pdf.

Butcher, Lee M, and Stephan Beck. Nano-MeDIP-seq Methylome Analysis Using Low DNA Concentrations. Methods in molecular biology 1589:115-138 (2015).

Cao et al. Integrated epigenetic biomarkers in circulating cell-free DNA as a robust classifier for pancreatic cancer. Clinical Epigenetics (2020) 12:112; 1-14.

Cassidy, et al. Neutrophil to Lymphocyte Ratio is Associated With Outcome During Ipilimumab Treatment. EBioMedicine. Apr. 2017;18:56-61. doi: 10.1016/j.ebiom.2017.03.029. Epub Mar. 24, 2017.

Chabon, Jacob J., et al. Integrating genomic features for non-invasive early lung cancer detection. Nature 580.7802: 245-251. (2020).

Chakravarthy, et al. Human Papillomavirus Drives Tumor Development Throughout the Head and Neck: Improved Prognosis Is Associated With an Immune Response Largely Restricted to the Oropharynx. J Clin Oncol. Dec. 2016;34(34):4132-4141. doi: 10.1200/JCO.2016.68.2955. Epub Oct. 31, 2016.

Chan, K C Allen et al. Noninvasive Detection of Cancer-associated Genome-wide Hypomethylation and Copy Number Aberrations by Plasma DNA Bisulfite Sequencing. Proceedings of the National Academy of Sciences of the United States of America vol. 110,47: pp. 18761-18768 (2013).

Chen, et al. A Study of Cell-free DNA Fragmentation Pattern and Its Application in DNA Sample Type Classification. IEEE/ACM Trans Comput Biol Bioinform. Jul. 4, 2017. doi: 10.1109/TCBB.2017.2723388. Online ahead of print.

Chen, Kaifu. et al. The Overlooked Fact: Fundamental Need for Spike-In Control for Virtually All Genome-Wide Analyses. Molecular and cellular biology 36(5):662-667 (2015).

Chen, Shifu et al. Fastp: an Ultra-Fast All-in-One FASTQ Preprocessor. Bioinformatics vol. 34,17: pp. i884-i890 (2018).

Chiu, et al. Noninvasive prenatal diagnosis of fetal chromosomal aneuploidy by massively parallel genomic sequencing of DNA in maternal plasma. Proc Natl Acad Sci USA. Dec. 23, 2008;105(51):20458-20463. doi: 10.1073/pnas.0810641105. Epub Dec. 10, 2008.

Christensen, et al. DNA methylation, isocitrate dehydrogenase mutation, and survival in glioma. J Natl Cancer Inst. Jan. 19, 2011;103(2):143-153. doi: 10.1093/jnci/djq497. Epub Dec. 16, 2010.

Co-pending U.S. Appl. No. 18/954,991, inventors Diniz; De Carvalho Daniel et al., filed Nov. 21, 2024.

Co-pending U.S. Appl. No. 18/959,302, inventors Diniz; De Carvalho Daniel et al., filed Nov. 25, 2024.

Co-pending U.S. Appl. No. 19/028,028, inventors Diniz De Carvalho; Daniel et al., filed Jan. 17, 2025.

Daniels et al. New Map of Bacteriophase Lambda DNA. Journal of Virology, Jan. 1980, p. 390-400.

De Carvalho D. Real-time liquid biopsy cancer diagnosis and monitoring. Flintbox. May 16, 2017; Available at URL: https://www.flintbox.com/public/project/31470 pp. 1.

Deininger, Prescott. Alu Elements: Know the SINEs. Genome Biology 12(12):236, 1-21 (2011).

Deveson et al., Representing genetic variation with synthetic DNA standards. Nature Methods 13: 784-791 (2016).

Di Giacomo, et al. Long-term survival and immunological parameters in metastatic melanoma patients who responded to ipilimumab 10 mg/kg within an expanded access programme. Cancer Immunol Immunother. Jun. 2013;62(6):1021-1028. doi: 10.1007/s00262-013-1418-6. Epub Apr. 17, 2013.

Diaz Jr, Luis A, and Alberto Bardelli. Liquid biopsies: genotyping circulating tumor DNA. Journal of clinical oncology 32(6):579-586 (2014).

Eckhardt, Florian, et al., DNA Methylation Profiling of Human Chromosomes 6, 20 and 22. Nature Genetics 38(12): 1378-1385 (2006).

Encode. Experiment summary for ENCSR000DFS. Stanford University. Date released: Sep. 30, 2011. 2 pages. doi:10.17989/ENCSR000DFS.

Esteller, et al. Inactivation of the DNA-repair gene MGMT and the clinical response of gliomas to alkylating agents. N Engl J Med. Nov. 9, 2000;343(19):1350-1354. doi: 10.1056/NEJM200011093431901.

Ewing, et al. Base-Calling of Automated Sequencer Traces Using Phred. II. Error probabilities. Genome Research. 1998;8:186-194.

Fan et al., Noninvasive diagnosis of fetal aneuploidy by shotgun sequencing DNA from maternal blood. Proc Natl Acad Sci U S A :105(42):16266-71 (2008).

Fang, et al. Breast cancer methylomes establish an epigenomic foundation for metastasis. Sci Transl Med. Mar. 23, 2011;3(75):75ra25. doi: 10.1126/scitranslmed.3001875.

Feber, et al. Comparative methylome analysis of benign and malignant peripheral nerve sheath tumors. Genome Res. Apr. 2011; 21(4): 515-524. doi: 10.1101/gr.109678.110.

Ferrucci, et al. Baseline neutrophils and derived neutrophil-to-lymphocyte ratio: prognostic relevance in metastatic melanoma patients receiving ipilimumab. Ann Oncol. Apr. 2016;27(4):732-738. doi: 10.1093/annonc/mdw016. Epub Jan. 22, 2016.

Flach, Peter. et al. A Coherent Interpretation of AUC as a Measure of Aggregated Classification Performance. Proceedings of the 28th International Conference on Machine Learning:1-8 (2011).

Fleischhacker, M et al. Circulating Nucleic Acids (CNAs) and Cancer—a Survey. Biochimica et Biophysica Acta vol. 1775,1: pp. 181-232 (2007).

Flusberg, Benjamin A, et al., Direct Detection of DNA Methylation During Single-molecule, Real-time Sequencing. Nature Methods vol. 7,6: pp. 461-465 (2010).

Fraga, et al. The affinity of different MBD proteins for a specific methylated locus depends on their intrinsic binding properties. Nucleic Acids Res. Mar. 15, 2003;31(6):1765-1774. doi: 10.1093/nar/gkg249.

Galardi et al., Cell-free DNA-methylation-based methods and applications in oncology. Biomolecules. 10(12):1677 (2020).

Gao, et al. miR-615-5p is epigenetically inactivated and functions as a tumor suppressor in pancreatic ductal adenocarcinoma. Oncogene. Mar. 26, 2015;34(13):1629-1640. doi: 10.1038/onc.2014.101. Epub Apr. 28, 2014.

Gevaert, et al. Pancancer analysis of DNA methylation-driven genes using MethylMix. Genome Biol. Jan. 29, 2015;16(1):17. doi: 10.1186/s13059-014-0579-8.

Gonzalgo, et al. Identification and characterization of differentially methylated regions of genomic DNA by methylation-sensitive arbitrarily primed PCR. Cancer Res. Feb. 15, 1997;57(4):594-599.

Gosho, et al. Study Designs and Statistical Analyses for Biomarker Research. Sensors (Basel). 2012; 12(7): 8966-8986. Published online Jun. 29, 2012. doi: 10.3390/s120708966.

Graves, et al. Quantitative and qualitative analysis of [(18)F]FDG and [(18)F]FAZA positron emission tomography of head and neck cancers and associations with HPV status and treatment outcome. Eur J Nucl Med Mol Imaging. Apr. 2016;43(4):617-625. doi: 10.1007/s00259-015-3247-7. Epub Nov. 18, 2015.

GTEx Consortium. Human genomics. The Genotype-Tissue Expression (GTEx) pilot analysis: multitissue gene regulation in humans. Science. May 8, 2015;348(6235):648-660. doi: 10.1126/science.1262110. Epub May 7, 2015.

(56) References Cited

OTHER PUBLICATIONS

Gu, et al. Preparation of reduced representation bisulfite sequencing libraries for genome-scale DNA methylation profiling. Nat Protoc. Apr. 2011;6(4):468-81. doi: 10.1038/nprot.2010.190. Epub Mar. 18, 2011.

Hegi et al., MGMT Gene Silencing and Benefit from Temozolomide in Glioblastoma. The New England Journal of Medicine 352(10): 997-1003 (2005).

Heinz, et al. Simple combinations of lineage-determining transcription factors prime cis-regulatory elements required for macrophage and B cell identities. Mol Cell. May 28, 2010;38(4):576-589. doi: 10.1016/j.molcel.2010.05.004.

Heyn, et al. DNA methylation profiling in the clinic: applications and challenges. Nature Reviews Genetics 13(10):679-692 (2012).

Hinoue, et al. Genome-scale analysis of aberrant DNA methylation in colorectal cancer. Genome Res. Feb. 2012;22(2):271-282. doi: 10.1101/gr.117523.110. Epub Jun. 9, 2011.

Hoadley, et al. Multiplatform analysis of 12 cancer types reveals molecular classification within and across tissues of origin. Cell. Aug. 14, 2014;158(4):929-944. doi: 10.1016/j.cell.2014.06.049. Epub Aug. 7, 2014.

Holm, S. A Simple Sequentially Rejective Multiple Test Procedure. Scand J. Statist 6: 65-70, 1979.

Houseman, et al. Reference-free deconvolution of DNA methylation data and mediation by cell composition effects. BMC Bioinformatics. Jun. 29, 2016;17:259. doi: 10.1186/s12859-016-1140-4.

Hu, et al. DNA methylation presents distinct binding sites for human transcription factors. Elife. Sep. 3, 2013;2:e00726. doi: 10.7554/eLife.00726.

Huang, et al. Cell-Free DNA Methylation Profiling Analysis-Technologies and Bioinformatics. Cancers (Basel). Nov. 6, 2019;11(11):1741. doi: 10.3390/cancers11111741.

Hughey et al. Robust meta-analysis of gene expression using the elastic net. Nucleic Acids Research 2015, vol. 43, No. 12, e79, 11 pages.

Hung, et al. Detection of circulating fetal nucleic acids: a review of methods and applications. J Clin Pathol. Apr. 2009;62(4):308-313. doi: 10.1136/jcp.2007.048470.

International search report with written opinion dated Feb. 14, 2019 for PCT/CA2018/000203.

International search report with written opinion dated Jun. 28, 2017 for PCT/CA2017/000108.

International search report with written opinion dated Oct. 3, 2018 for PCT/CA2018/000141.

Ji, Yinqiu. et al. Spikepipe: A metagenomic pipeline for the accurate quantification of eukaryotic species occurrences and intraspecific abundance change using DNA barcodes or mitogenomes. BioRxiv :1-59 (2019).

Jiang et al., Synthetic spike-in standards for RNA-seq experiments. Genome Res. 21(9):1543-1551 (2011).

Jiang, Lichun. et al. Synthetic spike-in standards for RNA-seq experiments. Genome research 21(9):1543-1551 (2011).

Kandoth et al. Mutational landscape and significance across 12 major cancer types. Nature 502(7471):333-339 (2013).

Karimzadeh et al. Umap and Bismap: quantifying genome and methylome mapability. Nucleic Acids Research, 2018, vol. 46, No. 20, e120. 13 pages.

Karolchik, Donna, et al., The UCSC Table Browser Data Retrieval Tool. Nucleic Acids Research 32:D493-D496 (2004).

Keravnou, Anna. et al. MeDIP combined with in-solution targeted enrichment followed by NGS: Inter-individual methylation variability of fetal-specific biomarkers and their implementation in a proof of concept study for NIPT. Plos one 13(6):e0199010, 1-13 (2018).

Keravnou, Anna. et al. Whole-genome fetal and maternal DNA methylation analysis using MeDIP-NGS for the identification of differentially methylated regions. Genetics research 98:e15, 1-9 (2016).

Kirkwood, et al. Immunotherapy of cancer in 2012. CA Cancer J Clin. Sep.-Oct. 2012;62(5):309-35. doi: 10.3322/caac.20132. Epub May 10, 2012.

Koestler, et al. DNA Methylation-Derived Neutrophil-to-Lymphocyte Ratio: An Epigenetic Tool to Explore Cancer Inflammation and Outcomes. Cancer Epidemiol Biomarkers Prev. Mar. 2017;26(3):328-338. doi: 10.1158/1055-9965.EPI-16-0461. Epub Dec. 13, 2016.

Krueger, et al. Bismark: a flexible aligner and methylation caller for Bisulfite-Seq applications. Bioinformatics. Jun. 1, 2011;27(11):1571-2. doi: 10.1093/bioinformatics/btr167. Epub Apr. 14, 2011.

Kuzman, et al. Neutrophil-lymphocyte ratio as a predictive biomarker for response to high dose interleukin-2 in patients with renal cell carcinoma. BMC Urol. Jan. 5, 2017;17(1):1. doi: 10.1186/s12894-016-0192-0.

Langmead, Ben et al. Fast gapped-read alignment with Bowtie 2. Nature methods 9(4):357-359 (2012).

Lasseter et al. Plasma cell-free DNA variant analysis compared with methylated DNA analysis in renal cell carcinoma. Genetics in Medicine, vol. 22, No. 8, Aug. 2020, p. 1366-1373.

Law, et al. voom: precision weights unlock linear model analysis tools for RNA-seq read counts. Genome Biol (2014) 15, R29. https://doi.org/10.1186/GB-2014-15-2-r29 (17 pages).

Lee, et al. Strategy of Using Intratreatment Hypoxia Imaging to Selectively and Safely Guide Radiation Dose De-escalation Concurrent With Chemotherapy for Locoregionally Advanced Human Papillomavirus-Related Oropharyngeal Carcinoma. Int J Radiat Oncol Biol Phys. Sep. 1, 2016;96(1):9-17. doi: 10.1016/j.ijrobp.2016.04.027. Epub May 7, 2016.

Legendre, et al. Whole-genome bisulfite sequencing of cell-free DNA identifies signature associated with metastatic breast cancer. Clin Epigenet (2015). 7:100. https://doi.org/10.1186/s13148-015-0135-8 (10 pages).

Lehmann-Werman, et al. Identification of tissue-specific cell death using methylation patterns of circulating DNA. Proc Natl Acad Sci USA 2016;113:E1826-34.

Leontiou, et al. Bisulfite Conversion of DNA: Performance Comparison of Different Kits and Methylation Quantitation of Epigenetic Biomarkers that Have the Potential to Be Used in Non-Invasive Prenatal Testing. PLoS One. Aug. 6, 2015;10(8):e0135058. doi: 10.1371/journal.pone.0135058. eCollection 2015.

Liang, Wenhua. et al. Non-invasive diagnosis of early-stage lung cancer using high-throughput targeted DNA methylation sequencing of circulating tumor DNA (ctDNA). Theranostics 9(7):2056-2070 (2019).

Lienhard, et al. MEDIPS: genome-wide differential coverage analysis of sequencing data derived from DNA enrichment experiments. Bioinformatics. Jan. 15, 2014;30(2):284-286. doi: 10.1093/bioinformatics/btt650. Epub Nov. 13, 2013.

Lienhard et al. QSEA—modelling of genome-wide DNA methylation from sequencing enrichment experiments. Nucleic Acids Research, 2017, vol. 45, No. 6, e44. 13 pages.

Liggett, Thomas. et al. Differential methylation of cell-free circulating DNA among patients with pancreatic cancer versus chronic pancreatitis. Cancer 116(7):1674-1680 (2010).

Lisanti, et al. Standardization and quality controls for the methylated DNA immunoprecipitation technique. Epigenetics. Jun. 1, 2012;7(6):615-625. doi: 10.4161/epi.20028. Epub Jun. 1, 2012.

Ito, et al. Role of Tet Proteins in 5mC to 5hmC Conversion, ES Cell Self-Renewal, and ICM Specification. Nature 466 (2010): 1129-1133.

Lui, Yanni Y N et al. Predominant Hematopoietic Origin of Cell-free DNA in Plasma and Serum After Sex-mismatched Bone Marrow Transplantation. Clinical Chemistry vol. 48,3: pp. 421-427 (2002).

Mack, et al. Epigenomic alterations define lethal CIMP-positive ependymomas of infancy. Nature. Feb. 27, 2014;506(7489):445-450. doi: 10.1038/nature13108. Epub Feb. 19, 2014.

Martincorena et al. Tumor evolution. High burden and pervasive positive selection of somatic mutations in normal human skin. Science 348(6237):880-6 (May 22, 2015).

(56)          References Cited

OTHER PUBLICATIONS

Mcgranahan, et al. Clonal status of actionable driver events and the timing of mutational processes in cancer evolution. Sci Transl Med. Apr. 15, 2015;7(283):283ra54. doi: 10.1126/scitranslmed.aaa1408. (22 pages).

Menden, et al. Machine learning prediction of cancer cell sensitivity to drugs based on genomic and chemical properties. PLoS One. Apr. 30, 2013;8(4):e61318. doi: 10.1371/journal.pone.0061318. Print 2013.

Michot et al., "Immune-Related Adverse Events With Immune Checkpoint Blockade: A Comprehensive Review," European Journal of Cancer 54:139-148 (Feb. 2016) (Epublished on Jan. 5, 2016) DOI: 10.1016/j.ejca.2015.11.016.

Mikeska, et al. DNA methylation biomarkers: cancer and beyond. Genes (Basel). Sep. 16, 2014;5(3):821-864. doi: 10.3390/genes5030821.

Moore, Lisa D. et al. DNA methylation and its basic function. Neuropsychopharmacology 38(1):23-38 (2013).

Mouliere et al. Enhanced Detection of Circulating Tumor DNA by Fragment Size Analysis. Science Translational Medicine 10(466):eaat4921 (2018).

Narkhede, Sarang. Understang AUC-ROC Curve. Towards Data Science, Jun. 26, 2018; [retrieved on Aug. 10, 2019]. Available at URL:https://towardsdatascience.com/understanding-auc-roc-curve-68b2303cc9c5. pp. 1-6.

Nassiri et al. Detection and discrimination of intracranial tumors using plasma cell-free DNA methylomes. Nat. Med. 2020; 26(7):1044-1047.

NCBI. GEO accession GSM1465024. HCT116 whole genome bisulfite sequence. Public on Sep. 10, 2014. Last update May 15, 2019. 2 pages. URL: https://www.ncbi.nlm.nih.gov/geo/query/acc.cgi?acc=GSM1465024.

Neary, et al. Comparative analysis of MBD-seq and MeDIP-seq and estimation of gene expression changes in a rodent model of schizophrenia. Genomics. Jul. 2017;109(3-4):204-213. doi: 10.1016/j.ygeno.2017.03.004. Epub Mar. 29, 2017.

Newman, Aaron M. et al. An Ultrasensitive Method for Quantitating Circulating Tumor DNA With Broad Patient Coverage. Nature Medicine 20(5):548-554 (2014).

NIH Guidelines for Research Involving Recombinant or Synthetic Nucleic Acid Molecules :1-149 (2019).

Northwestern University. Oligo Calc: Oligonucleotide Properties Calculator. Retrieved from the internet: http://biotools.nubic.northwestern.edu/OligoCalc.html (Year: 2022).

Notice of Allowance dated Mar. 19, 2021 for U.S. Appl. No. 16/098,620.

Notice of Allowance dated Aug. 31, 2022 for U.S. Appl. No. 17/519,350.

Notice of Allowance dated Sep. 15, 2022 for U.S. Appl. No. 17/519,350.

Nuzzo et al., Detection of renal cell carcinoma using plasma and urine cell-free DNA methylomes. Nat Med. 26(7):1041-1043 (2020).

Office action dated Jan. 28, 2022 for U.S. Appl. No. 17/519,350.

Office action dated Mar. 23, 2023 for U.S. Appl. No. 16/760,522.

Office action dated Apr. 26, 2023 for U.S. Appl. No. 16/630,299.

Office action dated May 11, 2022 for U.S. Appl. No. 16/630,299.

Office action dated Jun. 1, 2022 for U.S. Appl. No. 17/519,350.

Office action dated Jun. 25, 2020 for U.S. Appl. No. 16/098,620.

Office action dated Jun. 29, 2022 for U.S. Appl. No. 17/668,314.

Office action dated Jul. 19, 2023 for U.S. Appl. No. 18/061,273.

Office action dated Aug. 31, 2021 for U.S. Appl. No. 16/630,299.

Office action dated Oct. 6, 2023 for U.S. Appl. No. 16/760,522.

Office action dated Nov. 30, 2023 for U.S. Appl. No. 18/061,273.

Office action dated Dec. 6, 2023 for U.S. Appl. No. 16/630,299.

Office action dated Dec. 21, 2020 for U.S. Appl. No. 16/098,620.

Orlando et al. Quantitative ChIP-Seq Normalization Reveals Global Modulation of the Epigenome. Cell Reports 9, 2014, 1163-1170.

Owczarzy et al. IDT SciTools: a suite for analysis and design of nucleic acid oligomers. Nucleic Acids Research, 2008, vol. 36, W163-W169.

PCT/CA2017/000108 International Preliminary Report on Patentability dated Nov. 6, 2018.

PCT/CA2018/000141 International Preliminary Report on Patentability dated Jan. 14, 2020.

PCT/CA2018/000203 International Preliminary Report on Patentability dated May 5, 2020.

PCT/CA2020/051507 International Preliminary Report on Patentability dated May 10, 2022.

PCT/CA2020/051507 International Search Report and Written Opinion dated Jan. 11, 2021.

PCT/CA2021/050842 International Preliminary Report on Patentability dated Dec. 13, 2022.

PCT/US2022/052432 International Search Report and Written Opinion dated Mar. 21, 2023.

PCT/US2023/023625 International Preliminary Report on Patentability dated Dec. 5, 2024.

PCT/US2023/023625 International Search Report and Written Opinion dated Aug. 9, 2023.

PCT/US2024/020012 International Search Report and Written Opinion dated May 22, 2024.

PCT/US2024/024491 International Search Report and Written Opinion dated Jul. 5, 2024.

PCT/US2025/016672 International Search Report and Written Opinion dated Jun. 6, 2025.

Ponty et al. GenRGenS: software for generating random genomic sequences and structures. Bioinformatics, vol. 22, No. 12, 2006, pp. 1534-1535.

Potter et al., Validation of a real-time PCR-based qualitative assay for the detection of methylated SEPT9 Dna in human plasma. Clin Chem. 60(9):1183-1191 (2014).

QIAGEN®: QIAamp® Circulating Nucleic Acid Handbook. 64 pages, (2019).

Quinlan, Aaron R, and Ira M. Hall. BEDTools: a flexible suite of utilities for comparing genomic features. Bioinformatics 26(6):841-842 (2010).

R Core Team (2021). R: A language and environment for statistical computing. R Foundation for Statistical Computing, Vienna, Austria. URL: https://www.R-project.org/. homepage provided (3 pages); obtained online on Sep. 11, 2023.

Rahmani, et al. BayesCCE: a Bayesian framework for estimating cell-type composition from DNA methylation without the need for methylation reference. Genome Biol 19, 141 (2018). https://doi.org/10.1186/s13059-018-1513-2 (18 pages).

Rauch, et al. MIRA-assisted microarray analysis, a new technology for the determination of DNA methylation patterns, identifies frequent methylation of homeodomain-containing genes in lung cancer cells. Cancer Res. Aug. 15, 2006;66(16):7939-7947. doi: 10.1158/0008-5472.CAN-06-1888.

Razavi, Pedram. et al. High-intensity sequencing reveals the sources of plasma circulating cell-free DNA variants. Nature Medicine 25(12):1928-1937 (2019).

Re, A.C.D. compute.es: Compute Effect Sizes (2022).

ReGEO. GSE Accession GSE89473. DNA methylation patterns in twins discordant for ALS reveal concordant signatures of disease [RRBS]. Submission Date Nov. 2, 2016. Last Update Mar. 14, 2017. 1 page. URL: https://regeo.org:8443/details.jsp?gseld=GSE89473.

Rodríguez-Paredes, et al. Cancer epigenetics reaches mainstream oncology. Nat Med. Mar. 2011;17(3):330-339. doi: 10.1038/nm.2305.

Ruan, et al. Role of hypoxia in the hallmarks of human cancer. J Cell Biochem. Aug. 15, 2009;107(6):1053-1062. doi: 10.1002/jcb.22214.

Sanders, Alison et al. Cadmium exposure and the epigenome: Exposure-associated patterns of DNA methylation in leukocytes from mother-baby pairs. Epigenetics, 9(2), 212-221. Published online: Oct. 28, 2013. https://doi.org/10.4161/epi.26798.

Santos et al. Prognostic value of FLT3 mutations among different cytogenetic subgroups in acute myeloid leukemia. JNCI 117(10): 2145-2155. Year: 2011.

Schatz et al. Cloud computing and the DNA data race. Nature Biotechnology, vol. 28, No. 7, Jul. 2010. p. 691-693.

(56)                    References Cited

OTHER PUBLICATIONS

Schneider, Valerie A. et al. Evaluation of GRCh38 and De Novo Haploid Genome Assemblies Demonstrates the Enduring Quality of the Reference Assembly. Genome Research 27(5):849-864 (2017).

Schwarzenbach, Heidi. et al. Cell-free nucleic acids as biomarkers in cancer patients. Nature Reviews Cancer 11(6):426-437 (2011).

Shamay, et al. CpG methylation as a tool to characterize cell-free Kaposi sarcoma herpesvirus DNA. J Infect Dis. Apr. 1, 2012;205(7):1095-1099. doi: 10.1093/infdis/jis032. Epub Feb. 22, 2012.

Sharma, et al. Epigenetics in cancer. Carcinogenesis. Jan. 2010; 31(1): 27-36. Published online Sep. 13, 2009. doi: 10.1093/carcin/bgp220.

Shen, Shu Yi. et al. Sensitive Tumour Detection and Classification Using Plasma cell-free DNA Methylomes. Nature 563(7732):579-583(2018).

Simpson, Jared T. et al. Detecting DNA Cytosine Methylation Using Nanopore Sequencing. Nature methods 14(4):407-410 (2017).

Snyder, et al. Cell-free DNA comprises an in vivo nucleosome footprint that informs its tissues-of-origin. Cell 164(1-2):57-68 (2016).

Snyder, Thomas M et al. Universal Noninvasive Detection of Solid Organ Transplant Rejection. Proceedings of the National Academy of Sciences of the United States of America vol. 108,15: pp. 6229-6234 (2011).

Song et al. Potential functional roles of DNA demethylation intermediates. Trends Biochem Sci Oct. 2013; 38(10): 480-484.

Staunstrup, et al. Genome-wide DNA methylation profiling with MeDIP-seq using archived dried blood spots. Clin Epigenetics. Jul. 26, 2016;8:81. doi: 10.1186/s13148-016-0242-1. eCollection 2016.

Stevens, Michael. et al. Estimating Absolute Methylation Levels at Single-CpG Resolution From Methylation Enrichment and Restriction Enzyme Sequencing Methods. Genome Research 23(9):1541-1553 (2013).

Stirzaker et al: "Methylome sequencing in triple-negative breast cancer reveals distinct methylation clusters with prognostic value", Nature Communications, vol. 6, No. 5899, Jan. 1, 2015 (Jan. 1, 2015), XP055418632, GB ISSN: 2041-1723, DOI: 10.1038/ncomms6899.

Strichman-Almashanu et al. A Genome-Wide Screen for Normally Methylated Human CpG Islands That Can Identify Novel Imprinted Genes. Genome Research 12:543-554. 2002.

Sturm, et al. Hotspot mutations in H3F3A and IDH1 define distinct epigenetic and biological subgroups of glioblastoma. Cancer Cell. Oct. 16, 2012;22(4):425-437. doi: 10.1016/j.ccr.2012.08.024.

Stutheit-Zhao, Eric Y. et al. Early Changes in Tumor-Naive Cell-Free Methylomes and Fragmentomes Predict Outcomes in Pembrolizumab-Treated Solid Tumors. Cancer Discov. Feb. 22, 2024;14(6):1048-1063. doi: 10.1158/2159-8290.CD-23-1060.

Su, Andrew I. et al. A gene atlas of the mouse and human protein-encoding transcriptomes. Proceedings of the National Academy of Sciences 101(16):6062-6067 (2004).

Sun et al., Plasma DNA tissue mapping by genome-wide methylation sequencing for noninvasive prenatal, cancer, and transplantation assessments. Proc Natl Acad Sci USA. 112(40): E5503-E5512 (2015).

Tarailo-Graovac, et al. Using RepeatMasker to identify repetitive elements in genomic sequences. Curr Protoc Bioinformatics. Mar. 2009; Chapter 4:Unit 4.10. doi: 10.1002/0471250953.bi0410s25.

Templeton, et al. Prognostic role of neutrophil-to-lymphocyte ratio in solid tumors: a systematic review and meta-analysis. J Natl Cancer Inst. May 29, 2014;106(6):dju124. doi: 10.1093/jnci/dju124. Print Jun. 2014.

Teschendorff, et al. A comparison of reference-based algorithms for correcting cell-type heterogeneity in Epigenome-Wide Association Studies. BMC Bioinformatics. Feb. 13, 2017;18(1):105. doi: 10.1186/s12859-017-1511-5.

TFCheckpoint. Transcription Factor checkpoint 2.0. Website. Retrieved online Feb. 21, 2025. 6 pages. URL: https://www.tfcheckpoint.org/.

The Cancer Genome Atlas Program (TCGA). National Cancer Institute. Available at URL: https://www.cancer.gov/ccg/research/genome-sequencing/tcga pp. 1-4 (2022).

Thienpont, et al. Tumor hypoxia causes DNA hypermethylation by reducing TET activity. Nature. Sep. 1, 2016; 537(7618): 63-68. Published online Aug. 17, 2016. doi: 10.1038/nature19081.

Thierry, Alain R. et al. Origins, structures, and functions of circulating DNA in oncology. Cancer and metastasis reviews 35:347-376 (2016).

Titus, et al. Cell-type deconvolution from DNA methylation: a review of recent applications. Hum Mol Genet. Oct. 1, 2017;26(R2):R216-R224. doi: 10.1093/hmg/ddx275.

Toustrup, et al. Gene expression classifier predicts for hypoxic modification of radiotherapy with nimorazole in squamous cell carcinomas of the head and neck. Radiother Oncol. Jan. 2012;102(1):122-129. doi: 10.1016/j.radonc.2011.09.010. Epub Oct. 11, 2011.

Travis, W.D. Pathology of lung cancer, Clin Chest Med., Dec. 2011;32(4):669-92. doi:10.1016/j.ccm.2011.08.005. PMID: 22054879.

U.S. Appl. No. 16/630,299 Notice of Allowance dated Feb. 26, 2024.

U.S. Appl. No. 16/760,522 Corrected Notice of Allowability dated Jun. 10, 2025.

U.S. Appl. No. 16/760,522 Notice of Allowance dated Jun. 2, 2025.

U.S. Appl. No. 16/760,522 Office Action dated Sep. 20, 2024.

U.S. Appl. No. 17/353,756 Office Action dated Aug. 22, 2024.

U.S. Appl. No. 17/353,756 Office Action dated May 28, 2025.

U.S. Appl. No. 17/736,570 Office Action dated Feb. 19, 2025.

U.S. Appl. No. 18/061,273 Corrected Notice of Allowability dated Jan. 16, 2025.

U.S. Appl. No. 18/061,273 Notice of Allowance dated Aug. 27, 2024.

U.S. Appl. No. 18/067,661 Office Action dated Nov. 22, 2024.

Van De Voorde, et al. DNA methylation-based biomarkers in serum of patients with breast cancer. Mutat Res. Oct.-Dec. 2012;751(2):304-325. doi: 10.1016/j.mrrev.2012.06.001. Epub Jun. 12, 2012.

Van Der Maaten, et al. Visualizing Data using t-SNE. Journal of Machine Learning Research 9 (2008) pp. 2579-2605.

Varley, et al. Dynamic DNA methylation across diverse human cell lines and tissues. Genome Res. Mar. 2013;23(3):555-567. doi: 10.1101/gr.147942.112. Epub Jan. 16, 2013.

Visvanathan, et al. Monitoring of Serum DNA Methylation as an Early Independent Marker of Response and Survival in Metastatic Breast Cancer: TBCRC 005 Prospective Biomarker Study. J Clin Oncol. Mar. 2017;35(7):751-758. doi: 10.1200/JCO.2015.66.2080. Epub Nov. 21, 2016.

Wang et al. DNA methylation signatures in circulating cell-free DNA as biomarkers for the early detection of cancer. Science China. 2017, vol. 60, No. 4: 356-362.

Wang et al. High efficiency error suppression for accurate detection of low-frequency variants. Nucleic Acids Research 2019, vol. 47, No. 15, e87. 11 pages.

Wang, Zheng. et al. MGMT promoter methylation in serum and cerebrospinal fluid as a tumor-specific biomarker of glioma. Biomedical reports 3(4):543-548 (2015).

Warton, et al. Methylated circulating tumor DNA in blood: power in cancer prognosis and response. Endocr Relat Cancer. Mar. 2016;23(3):R157-R171. doi: 10.1530/ERC-15-0369. Epub Jan. 13, 2016.

Warton, et al. Methylation of cell-free circulating DNA in the diagnosis of cancer. Front Mol Biosci. Apr. 22, 2015;2:13. doi: 10.3389/fmolb.2015.00013. eCollection 2015.

Weisenberger, D. Characterizing DNA methylation alterations from The Cancer Genome Atlas. J Clin Invest. Jan. 2014;124(1):17-23. doi: 10.1172/JCI69740. Epub Jan. 2, 2014.

Wen, Lu. et al. Genome-scale detection of hypermethylated CpG islands in circulating cell-free DNA of hepatocellular carcinoma patients. Cell research 25(11):1250-1264 (2015).

Wiencke, et al. Immunomethylomic approach to explore the blood neutrophil lymphocyte ratio (NLR) in glioma survival. Clin Epigenetics. Feb. 2, 2017;9:10. doi: 10.1186/s13148-017-0316-8. eCollection 2017.

(56)     References Cited

OTHER PUBLICATIONS

Wu et al. A novel cell-free DNA methylation-based model improves the early detection of colorectal cancer. Molecular Oncology 15 (2021) 2702-2714.

Wu, et al. BioGPS: building your own mash-up of gene annotations and expression profiles. Nucleic Acids Res. Jan. 4, 2016;44(D1):D313-316. doi: 10.1093/nar/gkv1104. Epub Nov. 17, 2015.

Wu, et al. Genome-wide Analysis of 5-Hydroxymethylcytosine Distribution Reveals its Dual Function in Transcriptional Regulation in Mouse Embryonic Stem Cells. Genes & Development 25 (2011): 679-684.

Wu, Xiwei. et al. CpG island hypermethylation in human astrocytomas. Cancer research 70(7):2718-2727 (2010). With supplementary Information.

Xia, et al. Recent advances in hypoxia-inducible factor (HIF)-1 inhibitors. Eur J Med Chem. Mar. 2012;49:24-40. doi: 10.1016/j.ejmech.2012.01.033. Epub Jan. 24, 2012.

Xiang, Yuqian. et al. DNA methylome profiling of maternal peripheral blood and placentas reveal potential fetal DNA markers for non-invasive prenatal testing. Molecular human reproduction 20(9):875-884 (2014).

Xu et al. Secondary structure prediction of single sequences using RNA structure. RNA Structure Determination. Springer, 2016, pp. 15-34.

Yagi, et al. DNA methylation profile of tissue-dependent and differentially methylated regions (T-DMRs) in mouse promoter regions demonstrating tissue-specific gene expression. Genome Res. Dec. 2008;18(12):1969-1978. doi: 10.1101/gr.074070.107. Epub Oct. 29, 2008.

Zauber, et al. KRAS gene mutations are more common in colorectal villous adenomas and in situ carcinomas than in carcinomas. Int J Mol Epidemiol Genet. 2013;4(1):1-10. Epub Mar. 18, 2013.

Zhang, Lin. et al. Cancer progression prediction using gene interaction regularized elastic net. IEEE/ACM transactions on computational biology and bioinformatics 14(1):145-154 (2015).

Zhao, Ming-Tao. et al. Methylated DNA immunoprecipitation and high-throughput sequencing (MeDIP-seq) using low amounts of genomic DNA. Cellular reprogramming 16(3):175-184 (2014).

Zhou et al. Alterations of biomarker profiles after neoadjuvant chemotherapy in breast cancer: tumor heterogeneity should be taken into consideration. Oncotarget 6(34): 36894-36902. 2015.

Zhou et al. SeSAMe: reducing artifactual detection of DNA methylation by Infinium BeadChips in genomic deletions. Nucleic Acids Research, 2018, vol. 46, No. 20. e123. 15 pages.

Zou, et al. Epigenome-wide association studies without the need for cell-type composition. Nat Methods. Mar. 2014;11(3):309-11. doi: 10.1038/nmeth.2815. Epub Jan. 26, 2014.

Zymo Research. 5-Methylcytosine & 5-Hydroxymethylcytosine DNA Standard Set. 2010. 2 pages.

Butcher, Lee M, and Stephan Beck. AutoMeDIP-seq: a high-throughput, whole genome, DNA methylation assay. Methods 52(3):223-231 (2010).

Chen, Rui et al. Whole-Exome Enrichment with the Agilent SureSelect Human All Exon Platform. Cold Spring Harbor protocols 2015(7):626-633 (2015).

DNA Methylation Control Package Manual. Technical Data Sheet. Diagenode, Mar. 28, 2019. Available at URL: https://www.diagenode.com/files/products/kits/Datasheet_DNA_methylation_control_package.pdf pp. 1-2.

MagMeDIP qPCR Kit Manual: Magnetic Methylated DNA Immunoprecipitation Kit. Version 2. Diagenode, Mar. 2019. Available at URL: https://www.diagenode.com/files/products/kits/MagMeDIP-kit-complete-manual.pdf pp. 1-52.

Choy, L.Y.; et al. Single-Molecule Sequencing Enables Long Cell-Free DNA Detection and Direct Methylation Analysis for Cancer Patients, Clinical Chemistry, vol. 68, Issue 9, pp. 11511163. (2022).

Pappalardo, Xena Giada; et al. Losing DNA methylation at repetitive elements and breaking bad. Epigenetics & chromatin 14.1: 25. (2021).

* cited by examiner

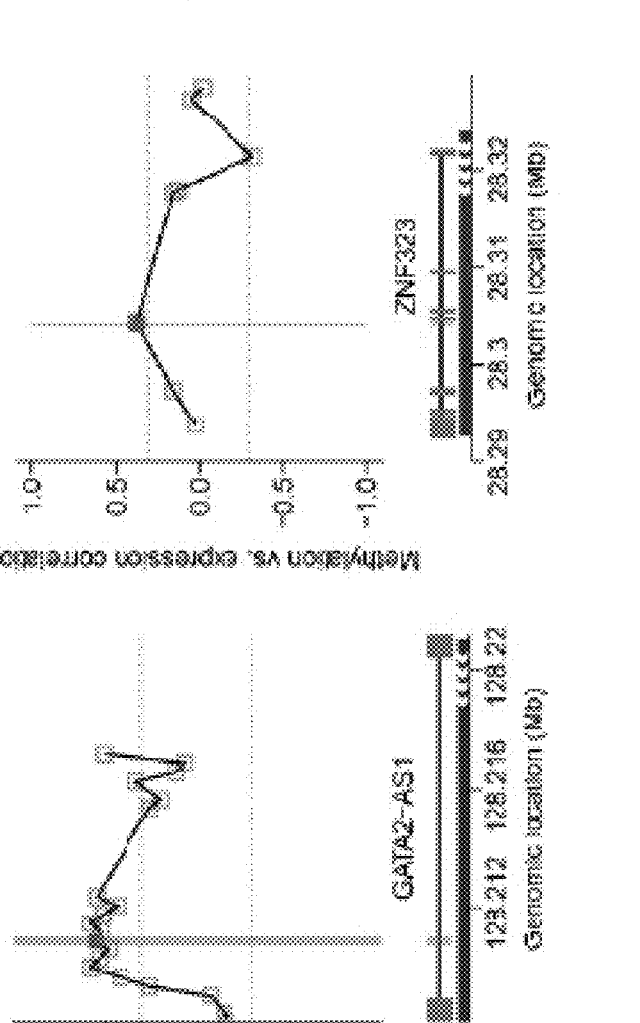
FIG. 17C
FIG. 17B
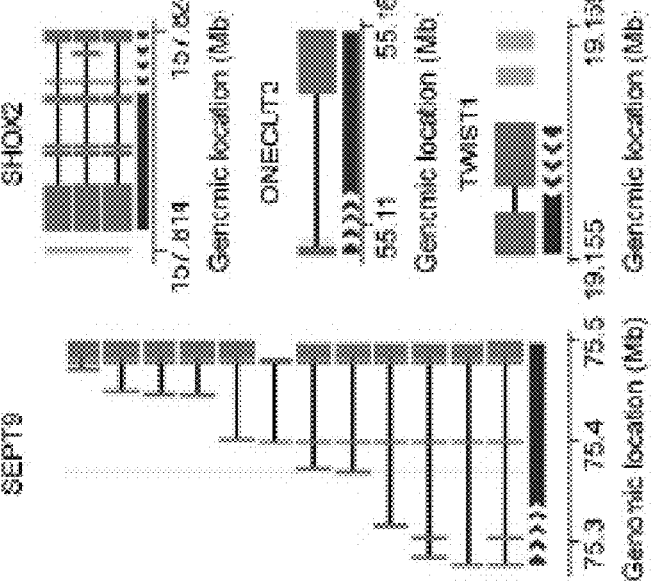
FIG. 17A

Repeat process 50 times with different class-balanced splits of the discovery cohort into training & test sets.

CANCER DETECTION AND CLASSIFICATION USING METHYLOME ANALYSIS

CROSS REFERENCES

This application is a continuation-in-part of U.S. application Ser. No. 18/067,661, filed Dec. 16, 2022, which is a continuation of PCT/CA2021/050842, filed Jun. 18, 2021, which claims priority to U.S. Provisional Application No. 63/041,151, filed Jun. 19, 2020, each of which is incorporated by referenced in its entirety.

BACKGROUND

Circulating tumor DNA (ctDNA) has increasingly demonstrated potential as a non-invasive, tumor-specific biomarker for routine clinical use. ctDNA is derived from tumor cells predominately undergoing cell-death and released into circulation of various bodily fluids including blood. In most cancer patients, the majority of blood-derived cell-free DNA originates from peripheral blood leukocytes (PBLs); therefore, identification of tumor-derived genetic and epigenetic alterations are required for ctDNA detection and quantification. In addition, the fraction of ctDNA observed may range from <0.1% to 90% of total cell-free DNA at diagnosis depending on several factors including primary site of the tumor and disease burden. ctDNAs has been providing non-invasive access to the tumor's molecular landscape and disease burden. Methods for detecting ctDNA with increased sensitivity especially in subjects with lower abundance of ctDNA are needed.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

In an aspect, there is provided a method of detecting the presence of ctDNA from cancer cells in a subject comprising:
  (a) providing a sample of cell-free DNA from a subject;
  (b) subjecting the sample to library preparation to permit subsequent sequencing of the cell-free methylated DNA;
  (c) optionally adding a first amount of filler DNA to the sample, wherein at least a portion of the filler DNA is methylated, then further optionally denaturing the sample;
  (d) capturing cell-free methylated DNA using a binder selective for methylated polynucleotides;
  (e) sequencing the captured cell-free methylated DNA;
  (f) comparing the sequences of the captured cell-free methylated DNA to control cell-free methylated DNAs sequences from healthy and cancerous individuals;
  (g) identifying the presence of DNA from cancer cells if there is a statistically significant similarity between one or more sequences of the captured cell-free methylated DNA and cell-free methylated DNAs sequences from cancerous individuals;
  wherein in at least one of the capturing step, the comparing step or the identifying step, the subject cell-free methylated DNA is limited to a sub-population according to a fragment length metric.

In as aspect, the present disclosure provides methods for determining whether a subject has or is at risk of having a disease. The methods comprise: subjecting a plurality of nucleic acid molecules derived from a cell-free nucleic acid sample obtained from said subject to sequencing to generate at least one profile selected from the group consisting of (i) a methylation profile, (ii) a mutation profile, and (iii) a fragment length profile; and processing said at least one profile to determine whether said subject has or is at risk of said disease at a sensitivity of at least 80% or at a specificity of at least about 90%, wherein said cell-free nucleic acid sample comprises less than 30 nanograms (ng)/milliliter (ml) of said plurality of nucleic acid molecules.

In some embodiments, the cell-free nucleic acid sample comprises less than 10 ng/ml of said plurality of nucleic acid molecules. In some embodiments, the cell-free nucleic acid sample comprises less than 5 ng/ml of said plurality of nucleic acid molecules. In some embodiments, the cell-free nucleic acid sample comprises less than 1 ng/ml of said plurality of nucleic acid molecules. In some embodiments, the subjecting of (a) generates at least two profiles selected from the group consisting of (i), (ii) and (iii). In some embodiments, the at least two profiles comprise said methylation profile and said fragment length profile.

In some embodiments, the at least two profiles comprise said mutation profile and said fragment length profile. In some embodiments, the at least two profiles comprise said methylation profile and said mutation profile. In some embodiments, the subjecting of (a) generates said methylation profile, said mutation profile, and said fragment length profile.

In another aspect, the present disclosure provides methods for processing a cell-free nucleic acid sample of a subject to determine whether said subject has or is at risk of having a disease. The methods comprise providing said cell-free nucleic acid sample comprising a plurality of nucleic acid molecules; subjecting said plurality of nucleic acid molecules or derivatives thereof to sequencing to generate a plurality of sequencing reads; computer processing said plurality of sequencing reads to identify, for said plurality of nucleic acid molecules, (i) a methylation profile, (ii) a mutation profile, and (iii) a fragment length profile; and using at least said methylation profile, said mutation profile and said fragment length profile to determine whether said subject has or is at risk of having said disease.

In some embodiments, the disease comprises a cancer. In some embodiments, the cancer is selected from the group consisting of the cancer is selected from the group consisting of adrenal cancer, anal cancer, bile duct cancer, bladder cancer, bone cancer, brain/cns tumors, breast cancer, castleman disease, cervical cancer, colon/rectum cancer, endometrial cancer, esophagus cancer, ewing family of tumors, eye cancer, gallbladder cancer, gastrointestinal carcinoid tumors, gastrointestinal stromal tumor (gist), gestational trophoblastic disease, hodgkin disease, kaposi sarcoma, kidney cancer, laryngeal and hypopharyngeal cancer, leukemia (acute lymphocytic, acute myeloid, chronic lymphocytic, chronic myeloid, chronic myelomonocytic), liver cancer, lung cancer (non-small cell, small cell, lung carcinoid tumor), lymphoma, lymphoma of the skin, malignant mesothelioma, multiple myeloma, myelodysplastic syndrome, nasal cavity and paranasal sinus cancer, nasopharyngeal cancer, neuroblastoma, non-hodgkin lymphoma, oral cavity and oropharyngeal cancer, osteosarcoma, ovarian cancer, penile cancer, pituitary tumors, prostate cancer, retinoblastoma, rhabdomyosarcoma, salivary gland cancer, sarcoma-adult soft tissue cancer, skin cancer (basal and squamous cell, melanoma, merkel cell), small intestine cancer, stomach cancer, testicular cancer, thymus cancer, thyroid cancer, uterine sarcoma, vaginal cancer, vulvar cancer, waldenstrom macroglobulinemia, wilms tumor, squamous cell carcinoma, and head and neck squamous cell carcinoma. In some embodiments, the cancer is squamous cell carcinoma. In some embodiments, the cancer is head and neck squamous cell carcinoma.

In some embodiments, the plurality of cell-free nucleic acid molecules comprises circulating tumor nucleic acid molecules. In some embodiments, the circulating tumor nucleic acid comprises circulating tumor DNA. In some embodiments, the circulating tumor nucleic acid comprises circulating tumor RNA. In some embodiments, the methylation profile comprises a plurality of Differentially Methylated Regions (DMRs). In some embodiments, the plurality of DMRs is ctDNA derived. In some embodiments, a plurality of DMRs derived from peripheral blood leukocytes is removed from said methylation profile. In some embodiments, the plurality of DMRs comprises at least about 56 genomic regions with hypo-methylation levels compared to corresponding genomic regions from a normal healthy subject. In some embodiments, the plurality of DMRs comprises at least about 941 genomic regions with hyper-methylation levels compared to corresponding genomic regions from a normal healthy subject. In some embodiments, a DMR comprises a size of at least about 300 bp. In some embodiments, a DMR comprises a size of at least about 100 bp to at least about 200 bp. In some embodiments, a DMR comprises a size of at least about 100 bp to at least about 150 bp. In some embodiments, a DMR comprises at least 8 CpG genomic islands. In some embodiments, the normal healthy subject comprises a same set of risk factors as said subject.

In some embodiments, the mutation profile comprises a missense variant, a nonsense variant, a deletion variant, an insertion variant, a duplication variant, an inversion variant, a frameshift variant, or a repeat expansion variant. In some embodiments, any variant that is present in a genomic DNA sample obtained from a plurality of peripheral blood leukocytes, wherein said plurality of peripheral blood leukocytes is obtained from said subject, is removed from the mutation profile. In some embodiments, any variant that is derived from clonal hematopoiesis is removed from said mutation profile. In some embodiments, the mutation profile does not comprise a variant of gene DNMT3A, TET2, or ASXL1. In some embodiments, the mutation profile does not comprise a canonical cancer driver gene. In some embodiments, the mutation profile comprises non-canonical cancer driver gene, where said non-canonical gene is GRIN3A or MYC.

In some embodiments, the fragment length profile comprises selecting cell free nucleic acid molecules based on a range of fragment length of about at least 80 bp to 170 bp. In some embodiments, the fragment length profile comprises selecting cell free nucleic acid molecules based on a range of fragment length of about at least 100 bp to 150 bp. In some embodiments, the circulating tumor nucleic acid molecules are enriched.

In some embodiments, the methods further comprise mixing said cell free nucleic acid sample with a filler DNA molecules to yield a DNA mixture. In some embodiments, the filler DNA molecules comprise a length of about 50 bp to 800 bp. In some embodiments, the filler DNA molecules comprise a length of about 100 bp to 600 bp. In some embodiments, the filler DNA molecules comprises at least about 5% methylated filler DNA molecules. In some embodiments, the filler DNA molecules comprises at least about 20% methylated filler DNA. In some embodiments, the filler DNA molecules comprises at least about 30% methylated filler DNA. In some embodiments, the filler DNA molecules comprises at least about 50% methylated filler DNA.

In some embodiments, the methods further comprise incubating said DNA mixture with a binder that is configured to bind methylated nucleotides to generate an enriched sample. In some embodiments, the binder comprises a protein comprising a methyl-CpG-binding domain. In some embodiments, the protein is a MBD2 protein. In some embodiments, the binder comprises an antibody. In some embodiments, the antibody is a 5-MeC antibody. In some embodiments, the antibody is a 5-hydroxymethyl cytosine antibody. In some embodiments, the sequencing does not comprise bisulfite sequencing. In some embodiments, the cell-free nucleic acid sample comprises a blood sample. In some embodiments, the blood sample comprises a plasma sample. In some embodiments, the methods further comprise detecting an origin of cancer tissue.

In some embodiments, the methods further comprise generating a report comprising a prognosis of said subject's survival rate. In some embodiments, the methods further comprise providing a treatment to said subject. In some embodiments, subsequent to treatment of said disease, the methods further comprise providing a second report indicating whether said treatment is effective.

In another aspect, the present disclosure provides methods for determining whether a subject has or is at risk of having a condition, comprising: assaying a cell-free nucleic acid molecule from at least a portion of a sample from said subject; detecting a methylation level of at least a portion of said cell-free nucleic acid molecule comprised in a differentially methylated region (DMR) listed in Table 5; and comparing, using at least one computer processor, said methylation level detected in (b) to a methylation level of corresponding portion(s) of said cell-free nucleic acid molecules comprised in said DMR listed in Table 5.

In some embodiments, the cell-free nucleic acid molecule comprises ctDNA. In some embodiments, the methods comprise performing the sequence analysis, and wherein said sequencing analysis comprises a cell-free methylated DNA immunoprecipitation (cfMeDIP) sequencing. In some embodiments, the detecting comprises measuring a methylation level of at least a portion of said nucleic acid molecule comprised in: six or more, ten or more, fifteen or more, twenty or more, thirty or more, forty or more, fifty or more, sixty or more, seventy or more, eighty or more, ninety or more, or one hundred or more DMRs listed in Table 5.

In another aspect, the present disclosure provides methods method for determining whether a subject has a higher survival rate after receiving a treatment for a disease, comprising: assaying a cell-free nucleic acid molecule from at least a portion of a sample from said subject; detecting a methylation level of at least a portion of said cell-free nucleic acid molecule comprised in a differentially methylated region (DMR) listed in Table 6; and processing, using at least one computer processor, said methylation level detected in (b) to a methylation level of corresponding portion(s) of said cell-free nucleic acid molecules comprised in said DMR listed in Table 6.

In some embodiments, the cell-free nucleic acid molecule comprises ctDNA. In some embodiments, the detecting comprises providing a composite methylation score (CMS). In some embodiments, the CMS comprises a sum of beta-values of DMRs listed in Table 6. In some embodiments, a higher CMS indicates an inferior survival for said subject. In some embodiments, the CMS is not dependent on an abundance of ctDNA. In some embodiments, the disease is squamous cell carcinoma. In some embodiments, the cancer is head and neck squamous cell carcinoma.

In another aspect, the present disclosure provides systems for determining whether a subject has or is at risk of having a disease, comprising one or more computer processors that are individually or collectively programmed to implement a process comprising: subjecting a plurality of nucleic acid molecules derived from a cell-free nucleic acid sample obtained from said subject to sequencing to generate at least one profile of (i) a methylation profile, (ii) a mutation profile, and (iii) a fragment length profile; and processing said at least one profile to determine whether said subject has or is at risk of said disease at a sensitivity of at least 80% or at a specificity of at least about 90%, wherein said cell-free nucleic acid sample comprises less than 30 ng/ml of said plurality of nucleic acid molecules.

In another aspect, the present disclosure provides systems for processing a cell-free nucleic acid sample of a subject to determine whether said subject has or is at risk of having a disease, comprising one or more computer processors that are individually or collectively programmed to implement a process comprising: providing said cell-free nucleic acid sample comprising a plurality of nucleic acid molecules; subjecting said plurality of nucleic acid molecules or derivatives thereof to sequencing to generate a plurality of sequencing reads; computer processing said plurality of sequencing reads to identify, for said plurality of nucleic acid molecules, (i) a methylation profile, (ii) a mutation profile, and (iii) a fragment length profile; and using at least said methylation profile, said mutation profile and said fragment length profile to determine whether said subject has or is at risk of having said disease.

BRIEF DESCRIPTION OF FIGURES

The patent or application file contains at least one drawing executed in color. Copies of this patent or patent application publication with color drawing(s) will be provided by the Office upon request and payment of the necessary fee. These and other features of the preferred embodiments of the invention will become more apparent in the following detailed description in which reference is made to the appended drawings wherein:

FIG. 4A shows median fragment length of detected SNVs across HNSCC patients by CAPP-seq. For each patient, the median fragment length of each SNV and matched reference allele was measured. The distribution of median fragment length for each mutation or matched reference allele is shown per patient. Extremes of boxes and centerlines define upper and lower quartiles and medians, respectively. In cases with a single SNV, the coloured line denotes the median length of fragments containing the SNV or matched reference allele, respectively. FIG. 4B shows fragment length distributions within HNSCC hyper-methylated regions by cfMeDIP-seq. Fragment lengths from healthy donors were pooled prior to analysis, where each subsequent box denotes an individual HNSCC cfMeDIP-seq profile. Extremes of boxes and centerlines define upper and lower quartiles and medians, respectively. Individual HNSCC samples are ordered based on increasing mean methylation (RPKM) within the hyper-methylated regions. Dashed blue line defines the median fragment length across all healthy donors. FIG. 4C shows ratio of enrichment for hyper-DMR regions by fragments between 100-150 bp compared to enrichment for hyper-DMR regions by fragments between 100-220 bp. Ratios were converted to percent increase/decrease for ease of interpretation. FIG. 4D shows ratio of enrichment for hyper-DMR regions by fragments between 100-150 bp compared to enrichment for hyper-DMR regions by fragments between 100-220 bp.+ symbols denote HNSCC patients with detectable ctDNA by CAPP-Seq (CAPP-Seq positive). FIG. 4E shows supervised hierarchal classification of cfMeDIP-seq profiles limited to 100-150 bp, by log-transformed RPKM values across HNSCC hyper-methylated regions. RPKM values for each cfMeDIP-seq profile was log 2-transformed prior to Euclidean transformation and clustered using Ward's method. Methylation clusters were defined at a threshold of k=4. FIG. 4F shows relationship of mean mutant allele frequency and mean RPKM from identified SNVs and hyper-methylated regions by CAPP-seq and cfMeDIP-seq (limited to 100-150 bp), respectively. Points denote individual samples from HNSCC or healthy donor plasma. Solid red line and shaded grey area denotes the fitted linear regression model and associated 95% confidence interval, respectively. FIG. 4G shows AUROC analysis based on methylation values (limited to 100-150 bp) within HNSCC hyper-methylated regions, comparing HNSCC to healthy donor cfMeDIP-seq profiles. Detection of ctDNA was defined as instances where mean methylation was above the max value across healthy donors. FIG. 4H shows Kaplan-Meier curve analysis for overall survival of patients within methylation cluster 1+2+ 3, compared to methylation cluster 4. FIGS. 4I-4J shows comparison of median fragment lengths from CAPP-Seq and cfMeDIP-seq profiles (FIG. 4I) and median fragment length from CAPP-Seq and 100-150:151-220 bp ratio from cfMeDIP-seq profiles (FIG. J). Points defined individual HNSCC samples within methylation cluster 1 and 2. Solid red line and shaded grey area denotes the fitted linear regression model and 95% confidence interval, respectively.

FIG. 5A shows relationship of mean mutant allele fraction and mean RPKM from identified mutations and hyper-methylated regions by CAPP-seq and cfMeDIP-seq (limited to 100-150 bp), respectively. Points denote individual samples from HNSCC or healthy control plasma. Solid red line: fitted linear regression model. Grey boundaries: 95% confidence interval. FIG. 5B shows Kaplan-Meier analysis depicting overall survival of patients with detectable ctDNA both by CAPP-Seq and cfMeDIP-seq (mean methylation above healthy controls within hyper-DMRs). FIG. 5C shows identification of prognostic regions based on disease-specific survival by multivariate Cox Proportional Hazard regression analysis across HNSCC primary tumors provided by the TCGA (n=520). Regions were defined as 300-bp windows as previously described. HumanMethylation450K data was obtained from the TCGA and beta-values from probe IDs overlapping with each region were averaged. Candidate regions for prognostic analysis was selected based on elevated methylation across primary tumors (n=520) compared to solid adjacent normal tissue (n=50) (Wilcoxon's test, adjusted p value <0.05, log 2FC >1). FIG. 5D shows identification of regions across all primary tumors. FIG. 5E shows Kaplan-Meier curve of overall survival for HNSCC-TCGA patients based on total methylation across five regions affecting expression of ZNF323/ ZSCAN1, LINC01391, GATA-AS1, OSR1, and STK3/ MST2 respectively. Patients were stratified based on either being below (Blw med. blue) or above (Abv med. red) the median total methylation of the five regions previously identified in (FIG. 5D) across all primary tumors. FIG. 5F shows Kaplan-Meier curve of overall survival as described in (E) for HNSCC plasma cohort with detectable ctDNA by CAPP-Seq. To calculate total methylation across the five genes with prognostic association, RPKM values were scaled accordingly across all hyper-DMR regions previously identified prior to survival analysis. FIGS. 5G-5H show Spearman's correlation from methylation of a particular 300-bp region (boxes) to the RNA expression of a particular transcript. Regions with an absolute R value >=0.3 (denoted by dashed grey lines) were labeled as significant associations. Methylated regions which were prognostic for disease-specific survival of HNSCC patients provided by the TCGA (n=520) are denoted with a red outline. Prognostic regions which were further associated with RNA expression are denoted as solid red. Example prognostic methylated regions associated with RNA expression, (FIG. 5G) OSR1, (FIG. 5H) LINC01391 are provided.

FIG. 6A shows ctDNA kinetics typically observed across patients throughout treatment. Complete clearance was defined as a change from detected ctDNA at diagnosis to a decrease in ctDNA abundance below the threshold of detection (i.e., 0.2%) at first available mid-/post-treatment timepoint. Partial clearance was defined as a change from detected ctDNA at diagnosis to a decrease (>=90%) in ctDNA abundance above the threshold of detection at first available mid-/post-treatment timepoint. No clearance was defined as an increase in ctDNA abundance in mid-/post-treatment samples compared to at diagnosis. lastFU=sample collection at last follow-up, RT=radiotherapy. FIG. 6B shows changes in ctDNA abundance at diagnosis to first available mid-/post-treatment timepoint across HNSCC patients (n=30). Red lines denote patients that demonstrated kinetics of no-clearance, whereas grey lines denote patients with kinetics of clearance/partial-clearance. FIG. 6C shows Kaplan-Meier curve of recurrence-free survival. Patients were stratified based on kinetics of clearance (i.e., no clearance vs. clearance/partial clearance).

FIG. 7A shows mutant allele frequency of mutations identified by CAPP-Seq vs. mean RPKM values of previously identified HNSCC hyperDMRs in cfMeDIP-seq profiles containing all fragments (left) or ctDNA-enriched fragments (right). FIG. 7B shows area under the curve analysis (AUROC) for ctDNA detection in HNSCC cfMeDIP-seq profiles (CAPP-Seq positive only: red, CAPP-Seq positive and negative: blue) versus healthy donors. Results of cross-validation analysis using CAPP-Seq positive patients is also shown (replicates=50). Analysis is shown for cfMeDIP-seq profiles with all fragments (left) or ctDNA-enriched fragments (right). FIG. 7C shows Kaplan-Meier analysis for recurrence-free survival based on longitudinal cfMeDIP-seq profiling with all fragments (left) or ctDNA-enriched fragments. Patients were classified as being positive for post-treatment ctDNA if they demonstrated methylation abundance within the previously identified hyperDMRs greater than 0.2% ctDNA.

FIG. 9A shows schematic defining timepoints of blood isolation. FIG. 9B shows cfDNA yields (normalized to per mL of plasma) across timepoints for HNSCC patients as well as healthy donors (i.e., "Normal").

FIG. 12A shows median RPKM values of genome-wide (chromosomes 1-22) 300-bp non-overlapping bins based on >=n CpGs. FIG. 12B shows differential methylation analysis between HNSCC and healthy donor PBLs within PBL-depleted windows as described in FIG. 2B and Methods. Hypomethylated regions (i.e., regions with elevated methylation in healthy donor PBLs) are denoted in blue.

FIG. 13A shows that DMRs were defined based on the original 300-bp non-overlapping windows used for the initial analysis. DMRs immediately adjacent to each other were binned into their respective widths (i.e., two 300-bp windows are each independently defined as having a length of 600-bp). FIG. 13B shows permutation analysis of CpG features as defined in FIG. 2E, based on hypo-methylated regions.

FIG. 15A shows median fragment length of identified SNVS by CAPP-Seq per patient compared to mean mutant allele fraction. FIG. 15B shows median fragment length within hyper-DMRS by cfMeDIP-seq per patient compared to mean RPKM of hyper-DMRs.

FIG. 16A shows area under the curve values obtained from cross-validation analysis (n=50) of differentially methylated region calling between CAPP-Seq positive HNSCC cfDNA samples and healthy donors. FIG. 16B shows Kaplan-Meir analysis for overall survival of HNSCC patients based on the detection of ctDNA by CAPP-Seq. FIG. 16C and FIG. 16D shows mean RPKM and mean mutant allele fraction of HNSCC patient samples stratified based on methylation cluster (shown in FIG. 4D).

FIG. 17A shows genome-track of genes currently used in commercially available liquid biopsy tests with overlap to HNSCC primary tumors within the TCGA as well as plasma-derived hyper-DMRs from our HNSCC cohort. Bottom dark blue bar with arrows denotes the direction of transcription for the specified gene. Red bars indicate location of 300-bp windows overlapping with hyper-DMRs from plasma of our HNSCC cohort as well as primary tumors from the TCGA. FIGS. 17B-17D shows Spearman's correlation from methylation of a particular 300-bp region (boxes) to the RNA expression of a particular transcript. Regions with an absolute R value >=0.3 (denoted by dashed grey lines) were labeled as significant associations. Methylated regions which were prognostic for disease-specific survival of HNSCC patients provided by the TCGA (n=520) are denoted with a red outline. Prognostic regions which were further associated with RNA expression are denoted as solid red. Figures were generated for all five genes contained prognostic methylated regions associated with RNA expression: (FIG. 17B) GATA2-AS1, (FIG. 17C) ZNF323, (FIG. 17D) STK3, (FIG. 17E) OSR1, (FIG. 17F) LINC01391. Boxes denote 300-bp regions overlapping with hm450k probes. Y-axis: Correlation (Spearman's R) between methylation within a particular 300-bp region and RNA expression among HNSCC primary tumors from TCGA (n=520). A meaningful association was defined as an absolute R value ≥0.3 (denoted by horizontal dashed grey lines). 300-bp regions that were prognostic for disease-specific survival in TCGA are denoted with a red outline. Prognostic regions which were further associated with RNA expression are denoted as solid red and with a red vertical bar.

FIG. 19A shows a computer simulation of the probability to detect at least one epimutation as a function of the concentration of ctDNA (columns), number of DMRs being investigated (rows), and the sequencing depth (x-axis). FIG. 19B shows genome-wide Pearson correlation between DNA methylation signal for 1 to 100 ng of input DNA from HCT116 cell line fragmented to mimic plasma cfDNA. Each concentration has two biological replicates. FIG. 19C shows a DNA methylation profile obtained from cfMeDIP-seq from different concentrations of input DNA from HCT116 (Green Tracks) plus RRBS (Reduced Representation Bisulfite Sequencing) HCT116 data obtained from ENCODE (ENCSR000DFS) and WGBS (Whole-Genome Bisulfite Sequencing) HCT116 data obtained from GEO (GSM1465024). For the heatmap (RRBS track), yellow means methylated, blue means unmethylated and gray means no coverage. FIG. 19D and FIG. 19E show results of serial dilution of the CRC cell line HCT116 into the Multiple Myeloma (MM) cell line MM1.S. cfMeDIP-seq was performed in pure HCT116 DNA (100% CRC), pure MM1.S DNA (100% MM) and 10%, 1%, 0.1%, 0.01%, and 0.001% CRC DNA diluted into MM DNA. All DNA was fragmented to mimic plasma cfDNA. We observed an almost perfect linear correlation ($r^2$=0.99, p<0.0001) between the observed versus expected (FIG. 19D) numbers of DMRs and (FIG. 19E) the DNA methylation signal (in RPKM) within those DMRs. FIG. 19F illustrates that in the same dilution series, known somatic mutations are only detectable at 1/100 allele fraction by ultra-deep (>10,000×) targeted sequencing, above the background sequencer and polymerase error rate. Shown are the fractions of reads containing each base or an insertion/deletion at the site of each mutation in the CRC cell line. FIG. 19G depicts a bar graph showing frequency of ctDNA (human) as a percentage of total cfDNA (human+ mice) in the plasma of mice harboring patient-derived xenograft (PDX) from two colorectal cancer patients.

Figure 20A:
Figure 20A:
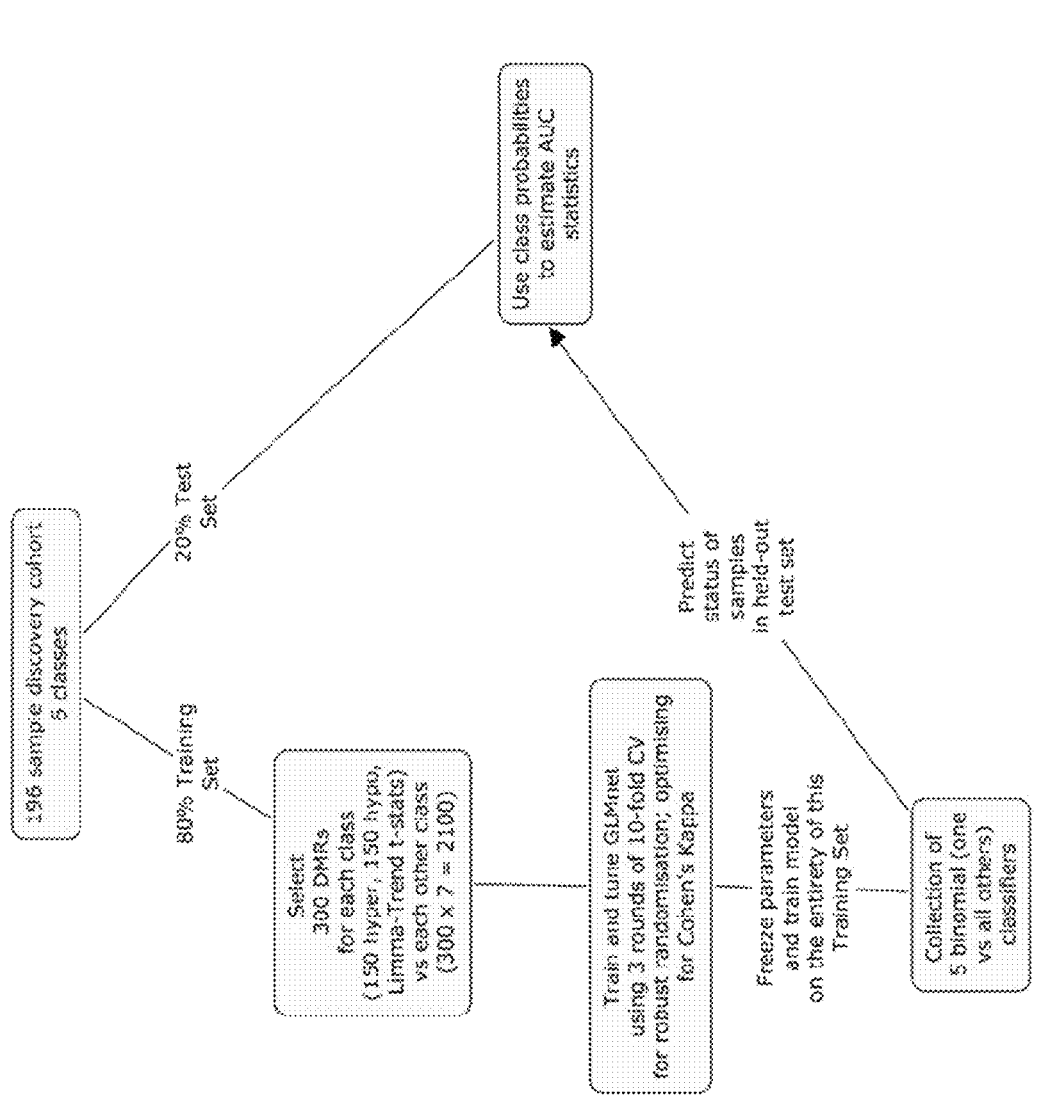
Figure 20B:
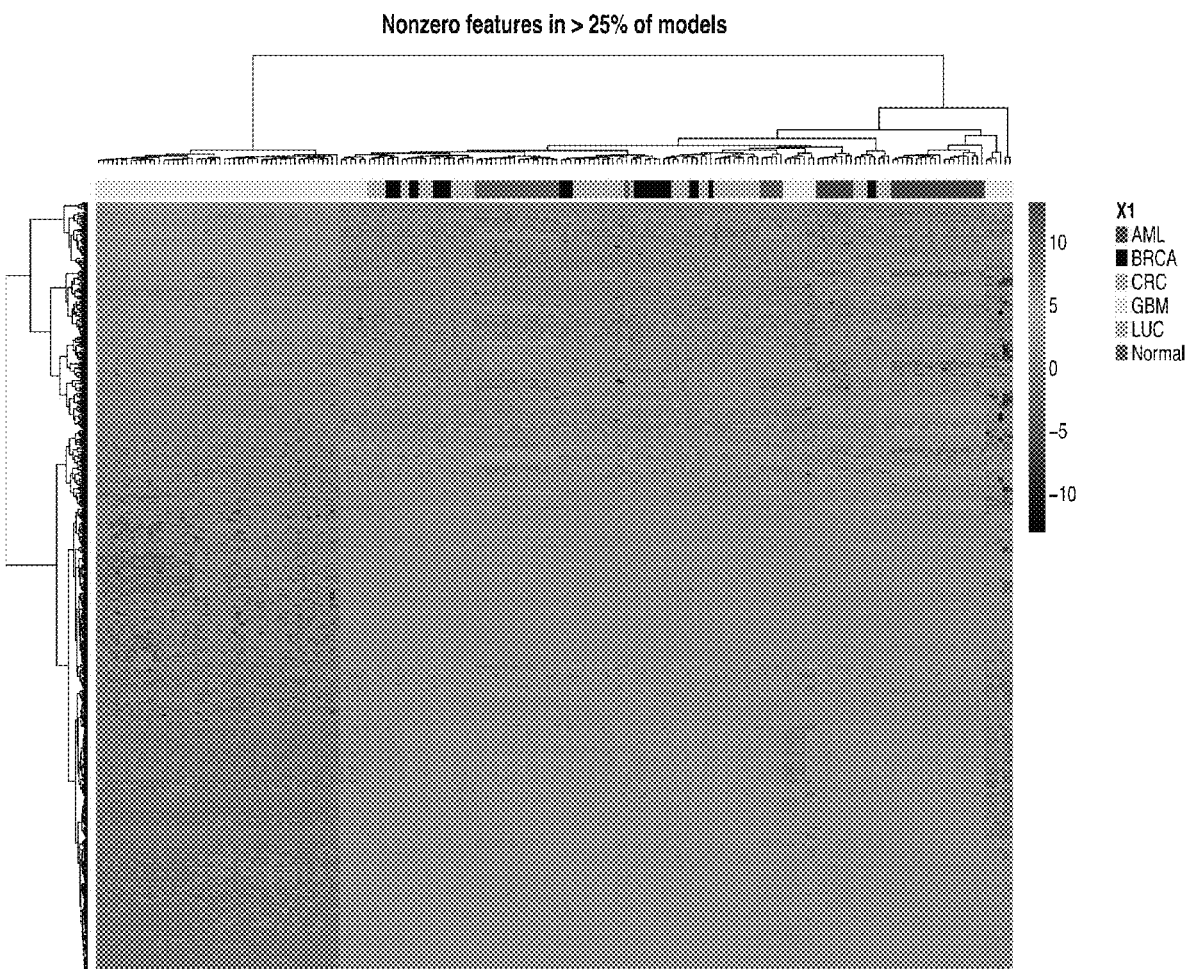
Figure 20C:
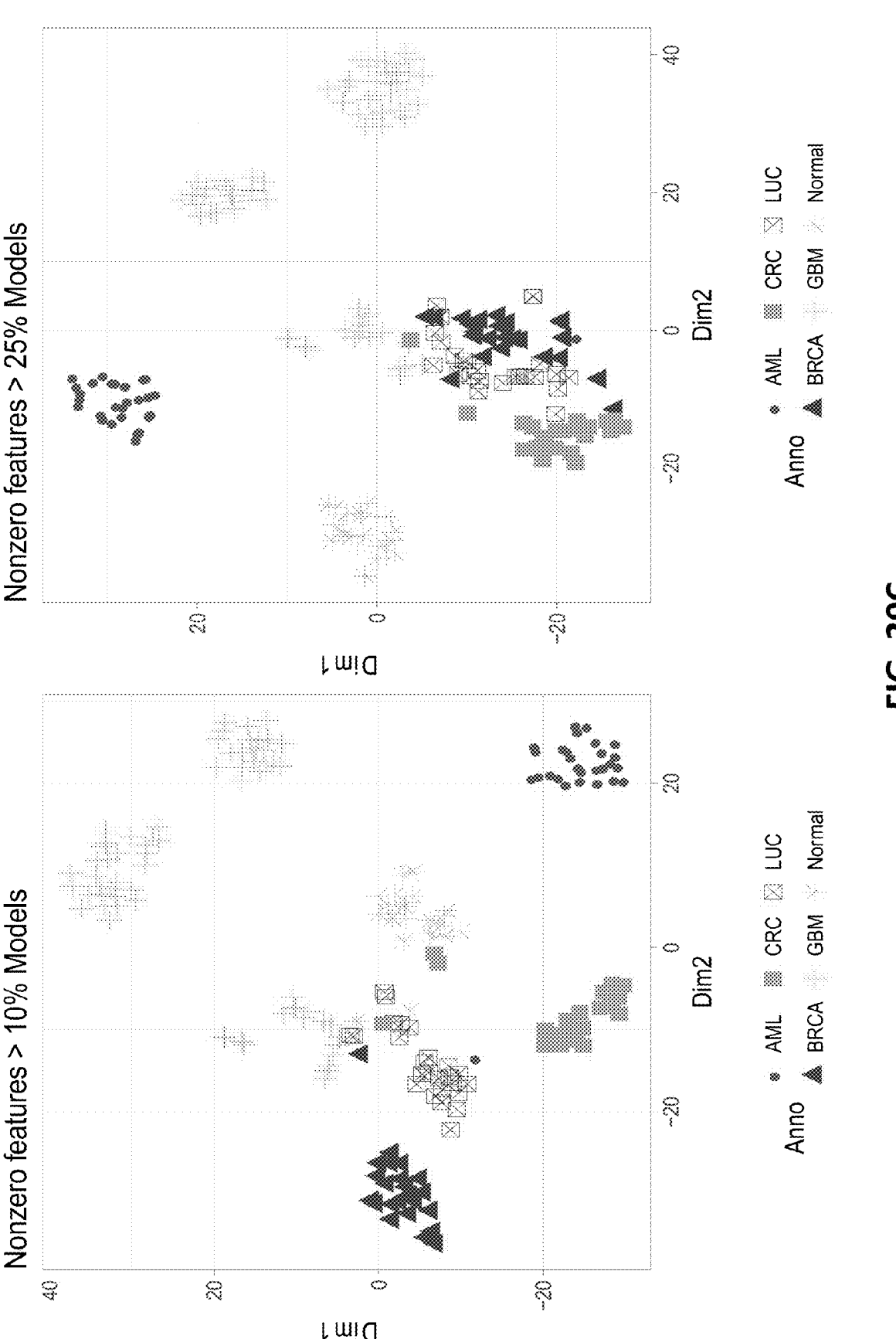
Figure 20D:
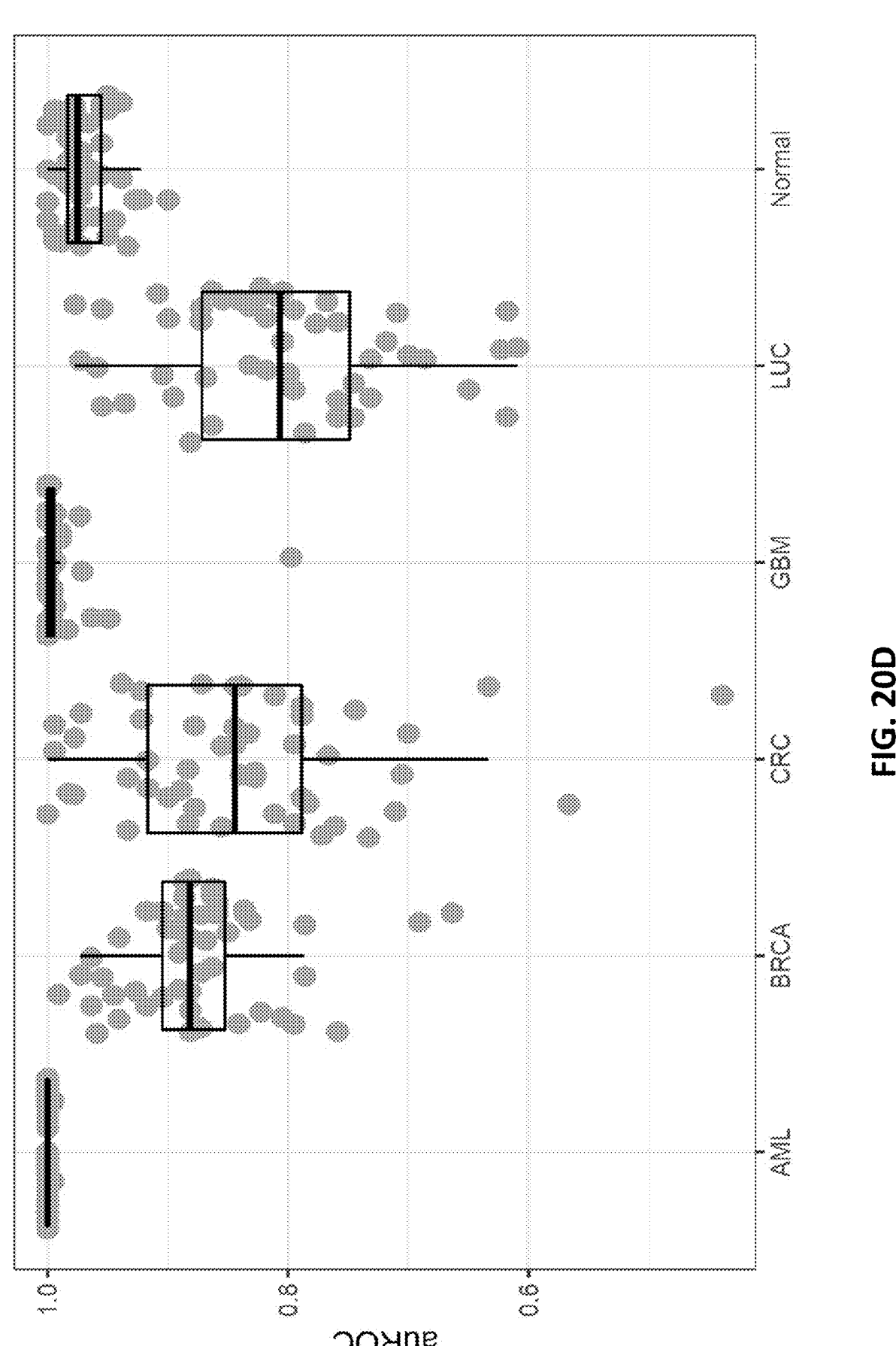

FIGS. 20A-20D show the methylome analysis of plasma cfDNA allows tumor classification. FIG. 20A illustrates a schematic demonstrating the approach of machine learning classifier construction for cancer classification. FIG. 20B depicts a heatmap of DMRs contained within the multi-class elastic net machine learning classifiers. The classifiers were trained on plasma DNA samples from healthy donors (n=24), lung cancer (n=25), breast cancer (n=25), colorectal cancer (n=23), acute myelogenous leukemia (AML) (n=28), and glioblastoma multiforme (GBM) (n=71). Hierarchical clustering method: Ward. FIG. 20C shows 2D visualizations by tSNE (t-Distributed Stochastic Neighbor Embedding) of the cancer-type associated DMRs identified in 10% or 25% of models. FIG. 20D depicts a plot showing metrics for the plasma cfDNA methylation-based multi-cancer classifier. Area under the receiver operator curve (auROC) shown on the y-axis for each cancer type and healthy donors following 50-fold generation of elastic net machine learning classifiers.

Figure 21A:
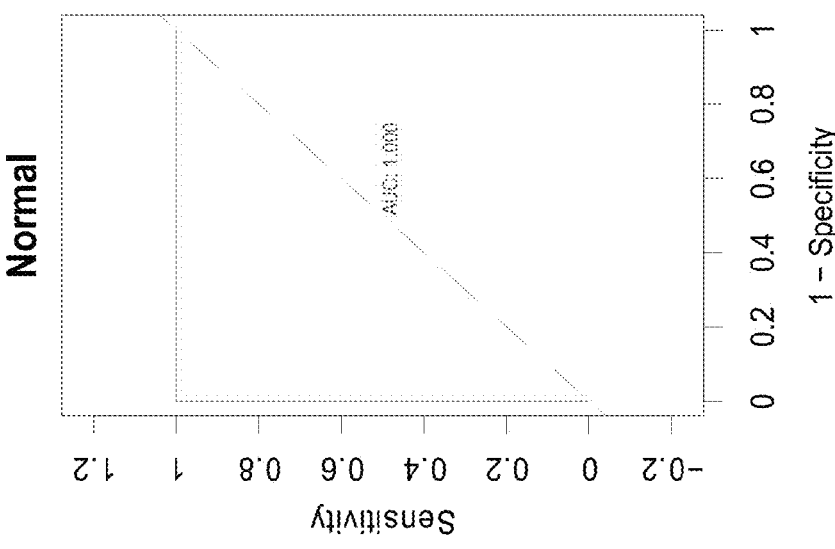
Figure 21A:
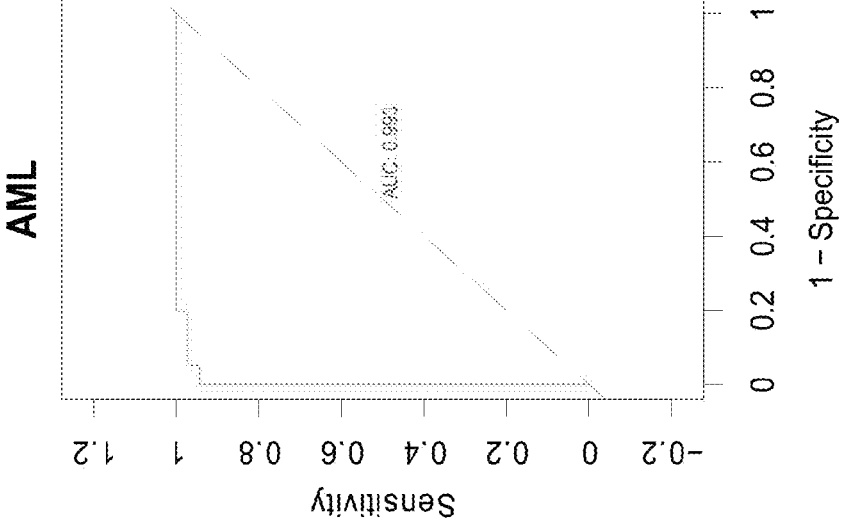
Figure 21A:
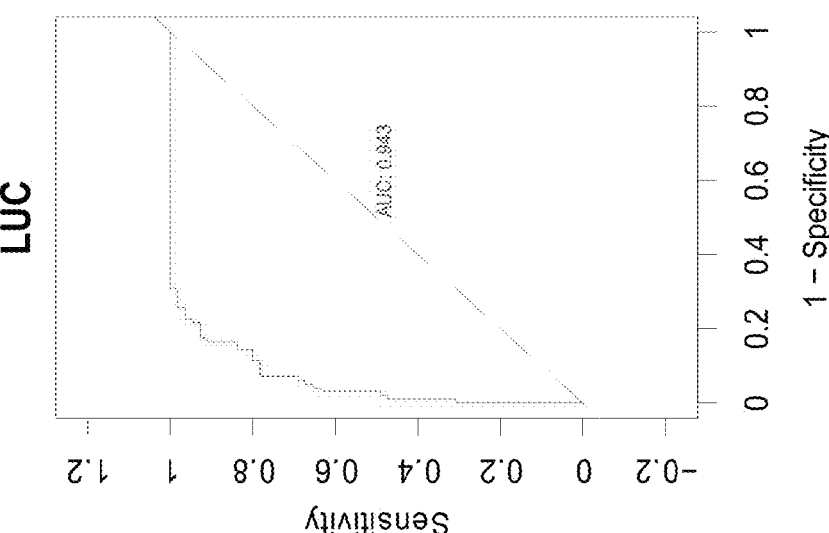
Figure 21B:
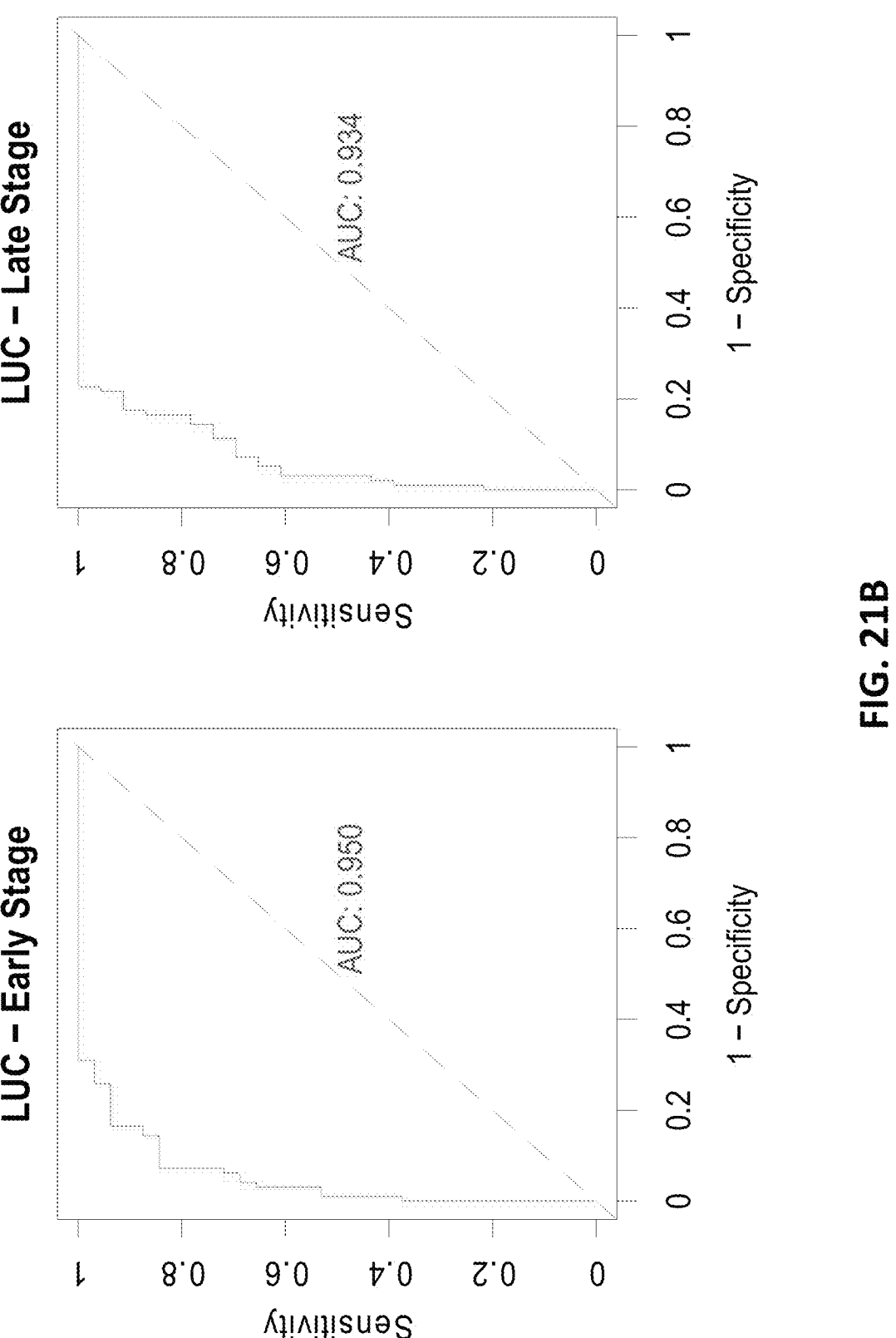

FIGS. 21A-21B show validation of the multi-cancer classifier on independent cohorts. FIG. 21A shows ROC curves for independent validation of the multi-cancer classifier on cohorts of lung cancer (LUC) (n=55 LUC vs n=97 other), AML (n=35 AML vs n=117 other), and healthy donors (n=62 healthy donors vs n=90 other). FIG. 21B shows ROC curves for independent validation of the multi-cancer classifier on early stage LUC (n=32 stage I-II LUC vs n=97 other) and late stage LUC (n=23 stage III-IV LUC vs n=97 other).

Figure 22A:
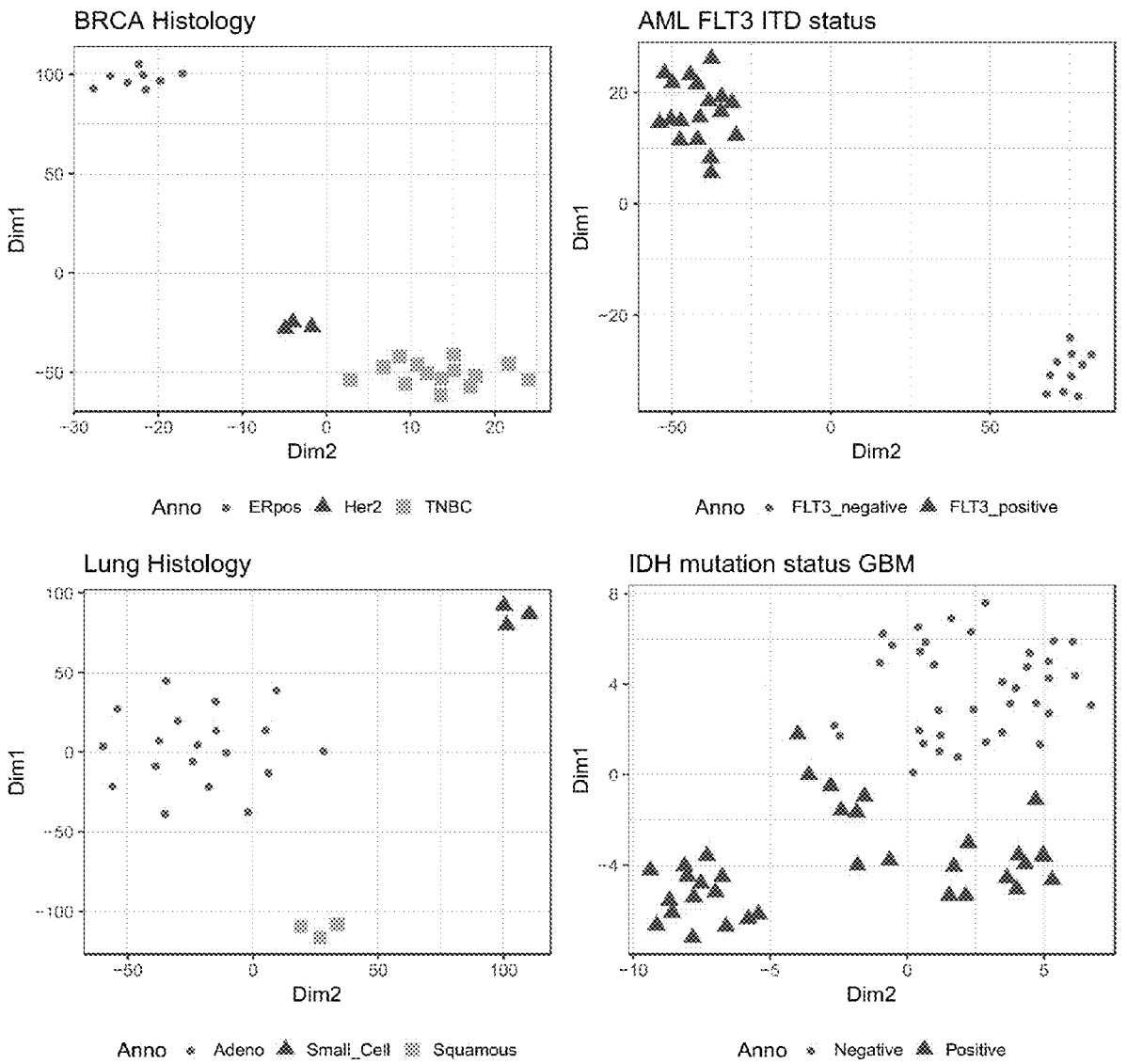
Figure 22B:
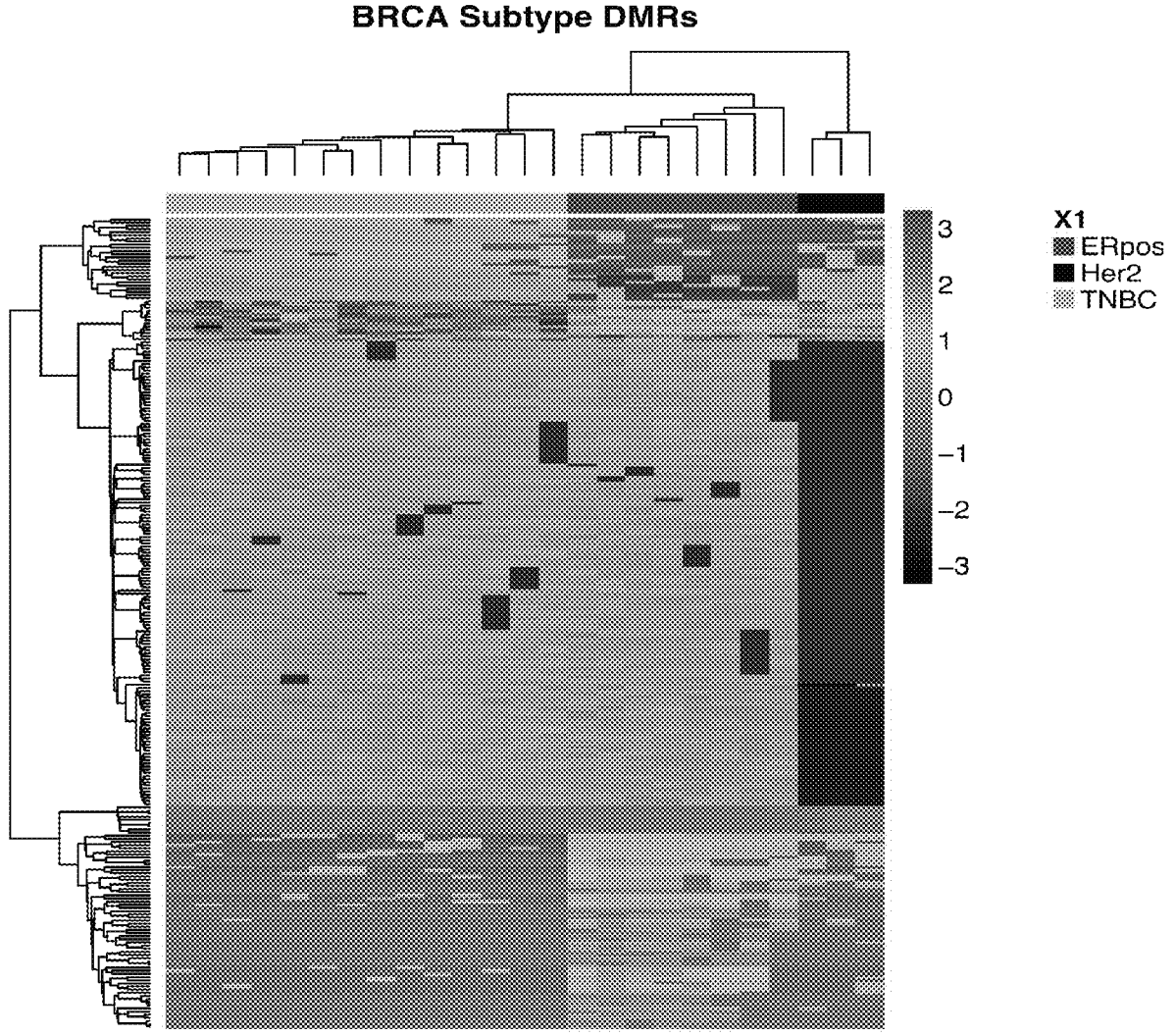
Figure 22C:
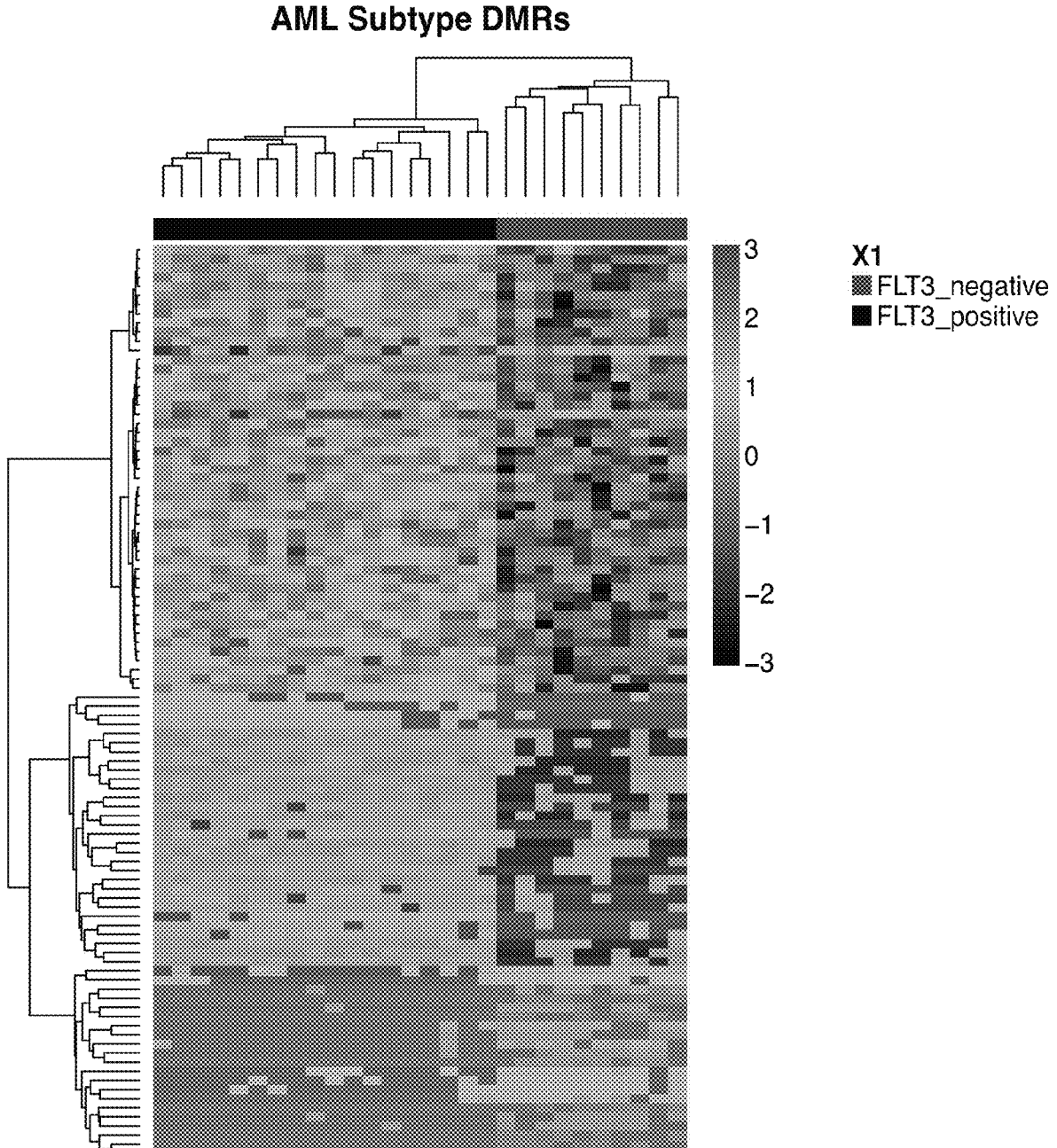
Figure 22D:
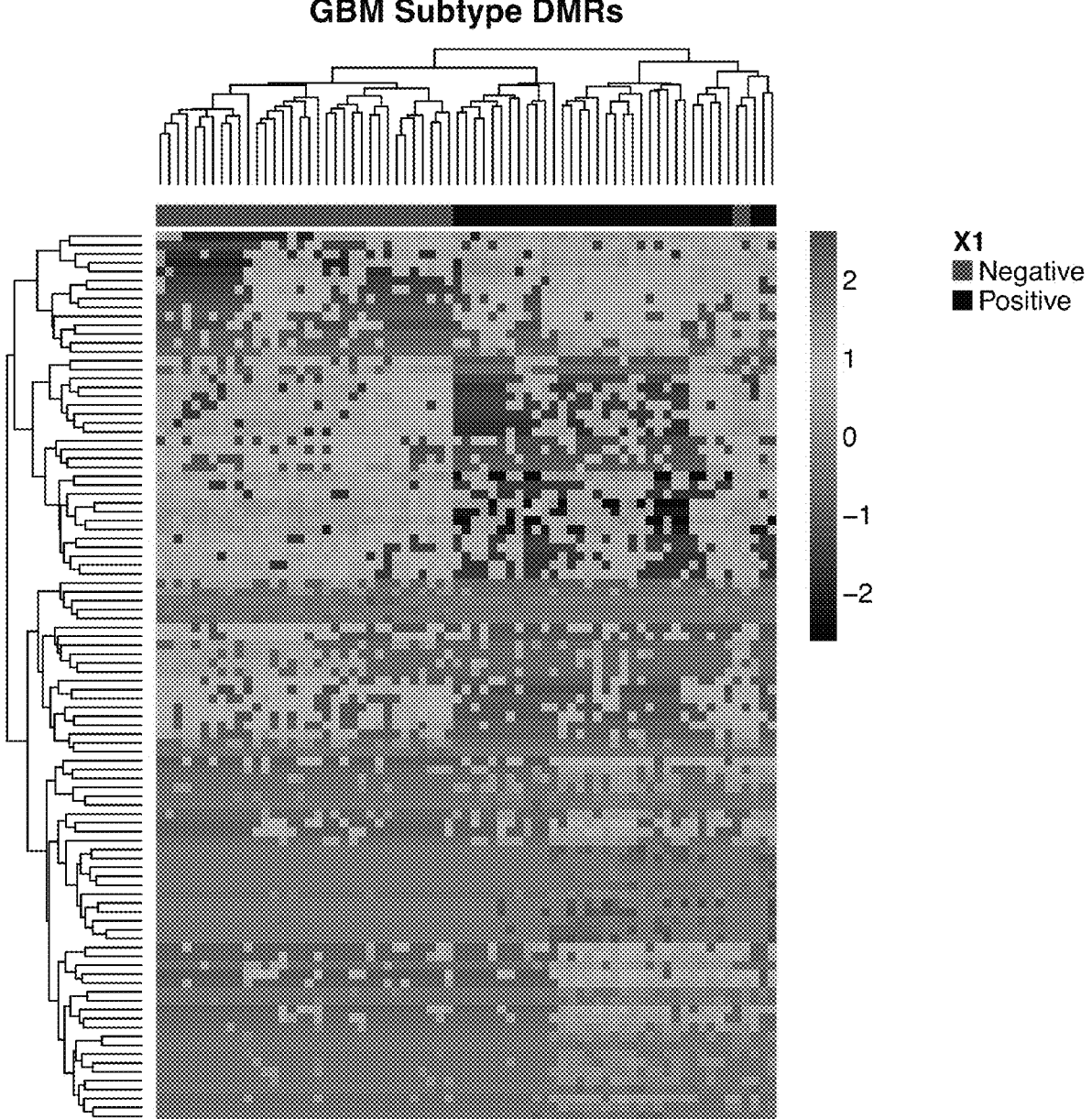
Figure 22E:
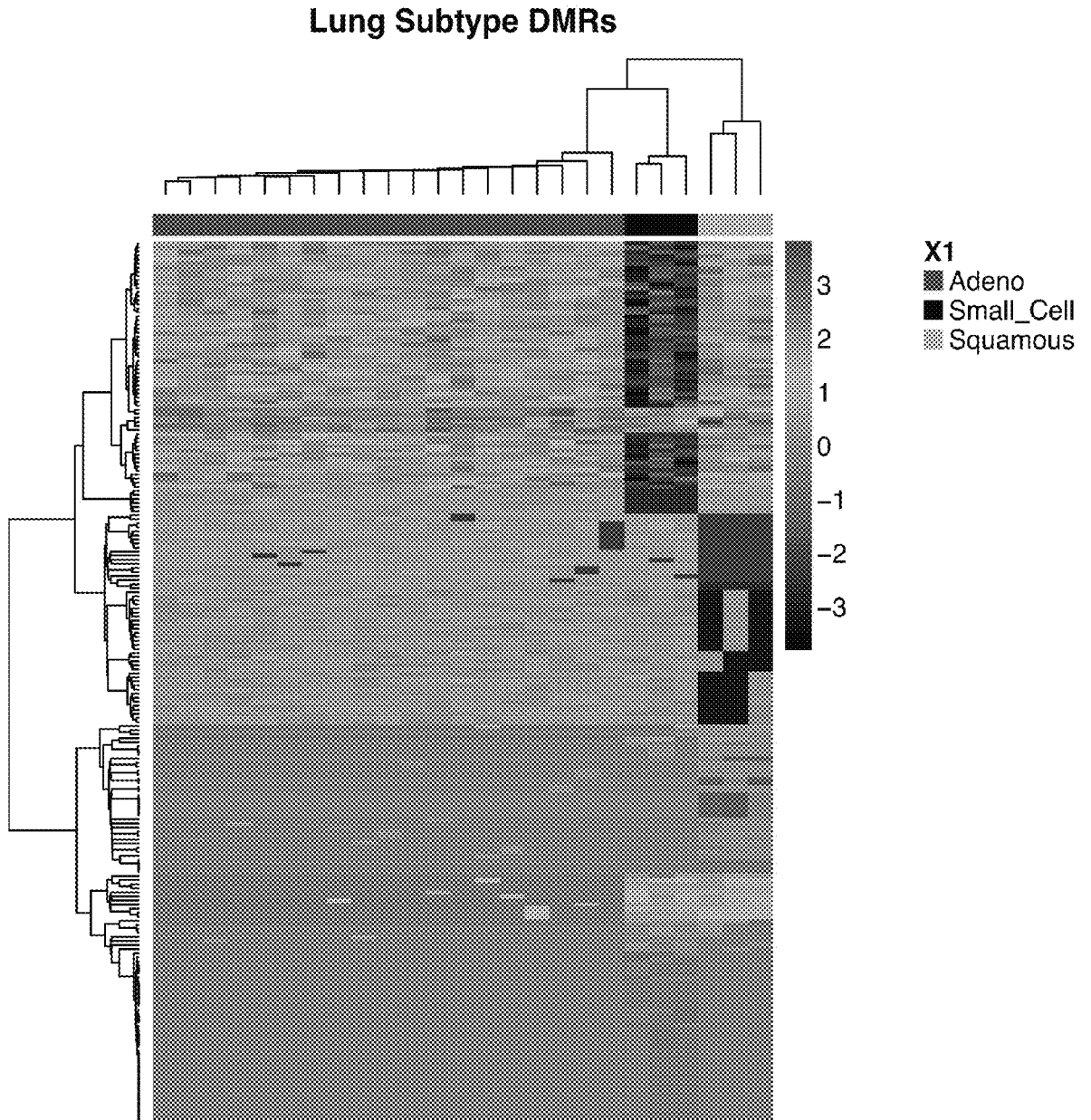

FIGS. 22A-22E show the methylome analysis of plasma cfDNA allows tumor subtype classification. FIG. 22A shows 2D visualizations by tSNE (t-Distributed Stochastic Neighbor Embedding) of cancer subtype associated DMRs. Breast cancer subtypes show ability to distinguish between patients harboring tumors with distinct gene expression pattern and transcription factor activity (ER status) as well as distinct tumor copy number aberrations (HER2 status). AML subtypes show ability to distinguish between patients harboring tumors with distinct rearrangements (FLT3 status). Glioblastoma multiforme (GBM) subtypes show ability to distinguish between patients harboring tumors with distinct point mutations (IDH gene mutational status). Lung cancer subtypes show ability to distinguish between patients harboring tumors with distinct histologies that have prognostic and therapeutic implications (adenocarcinoma vs. squamous carcinoma vs. small cell carcinoma). FIG. 22B depicts a heatmap showing the top DMRs that allow accurate discrimination of the three breast cancer subtypes in breast cancer plasma samples. FIG. 22C depicts a heatmap showing the top DMRs that allow accurate discrimination of the FLT3-ITD status in AML patient plasma samples. FIG. 22D depicts a heatmap showing the top DMRs that allow accurate discrimination of the IDH gene mutational status in glioblastoma multiforme (GBM) patient plasma samples. FIG. 22E depicts a heatmap showing the top DMRs that allow accurate discrimination of the three lung cancer histologies in lung cancer plasma samples.

Figure 23A:
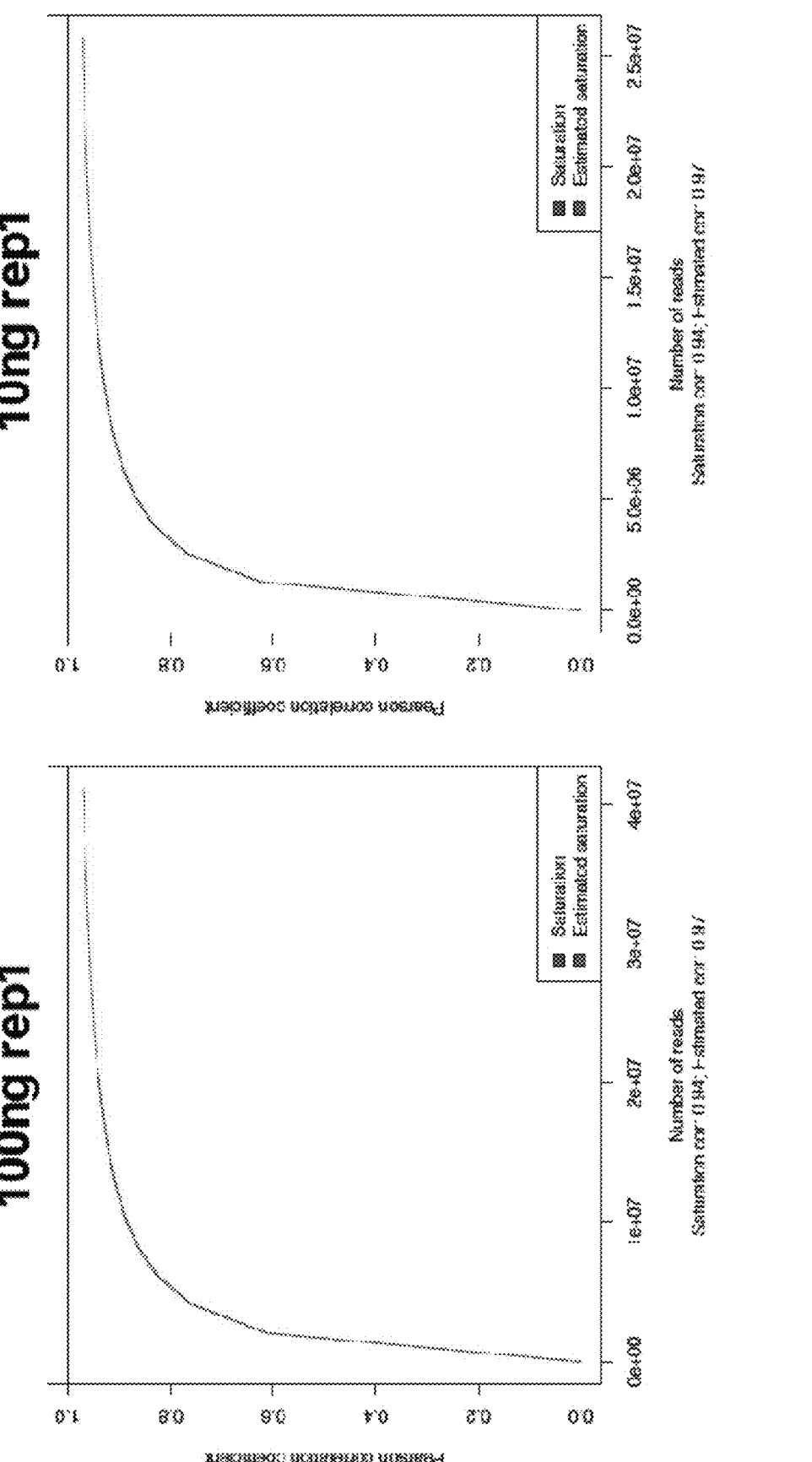
Figure 23B:
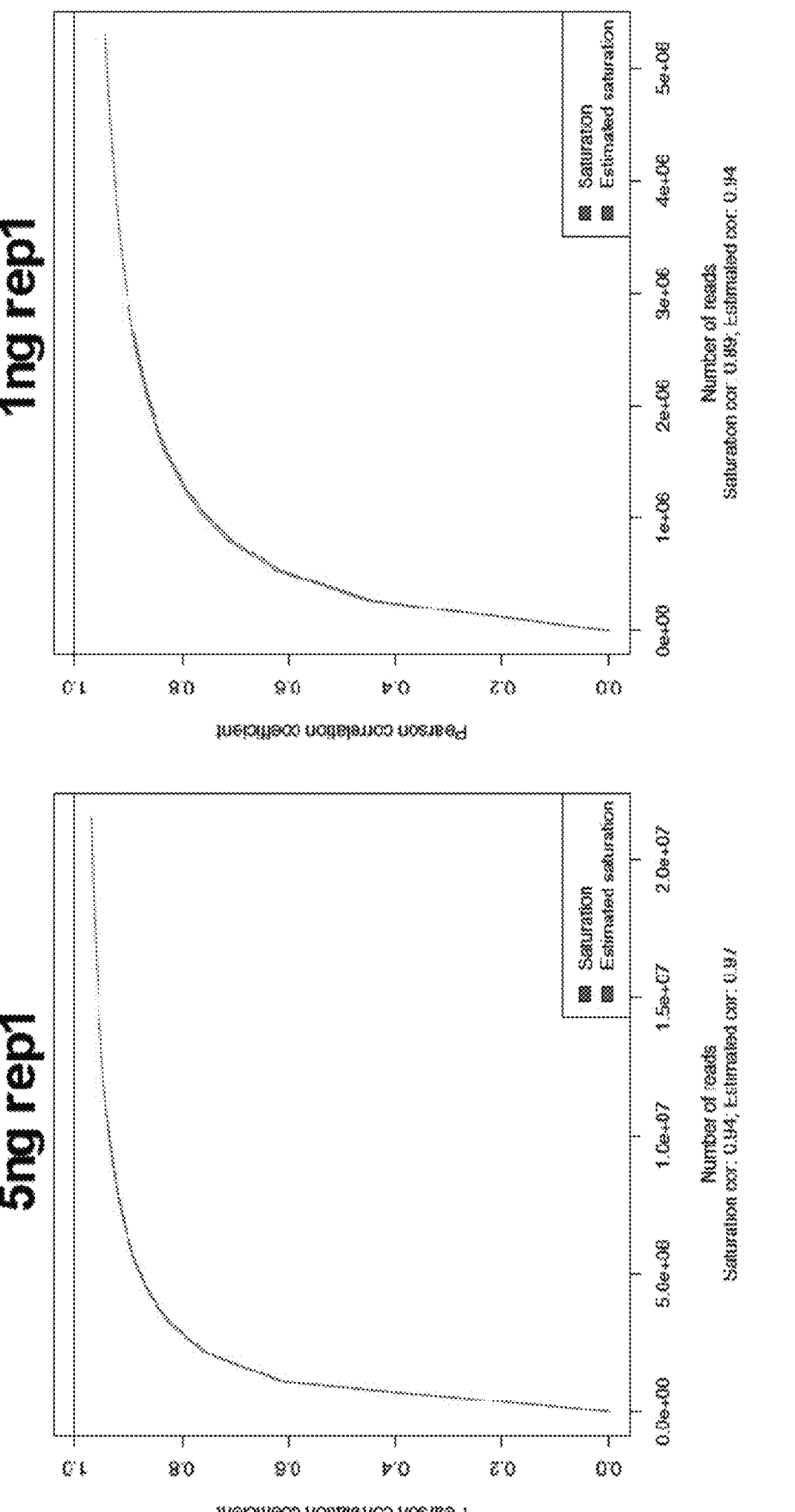
Figure 23C:
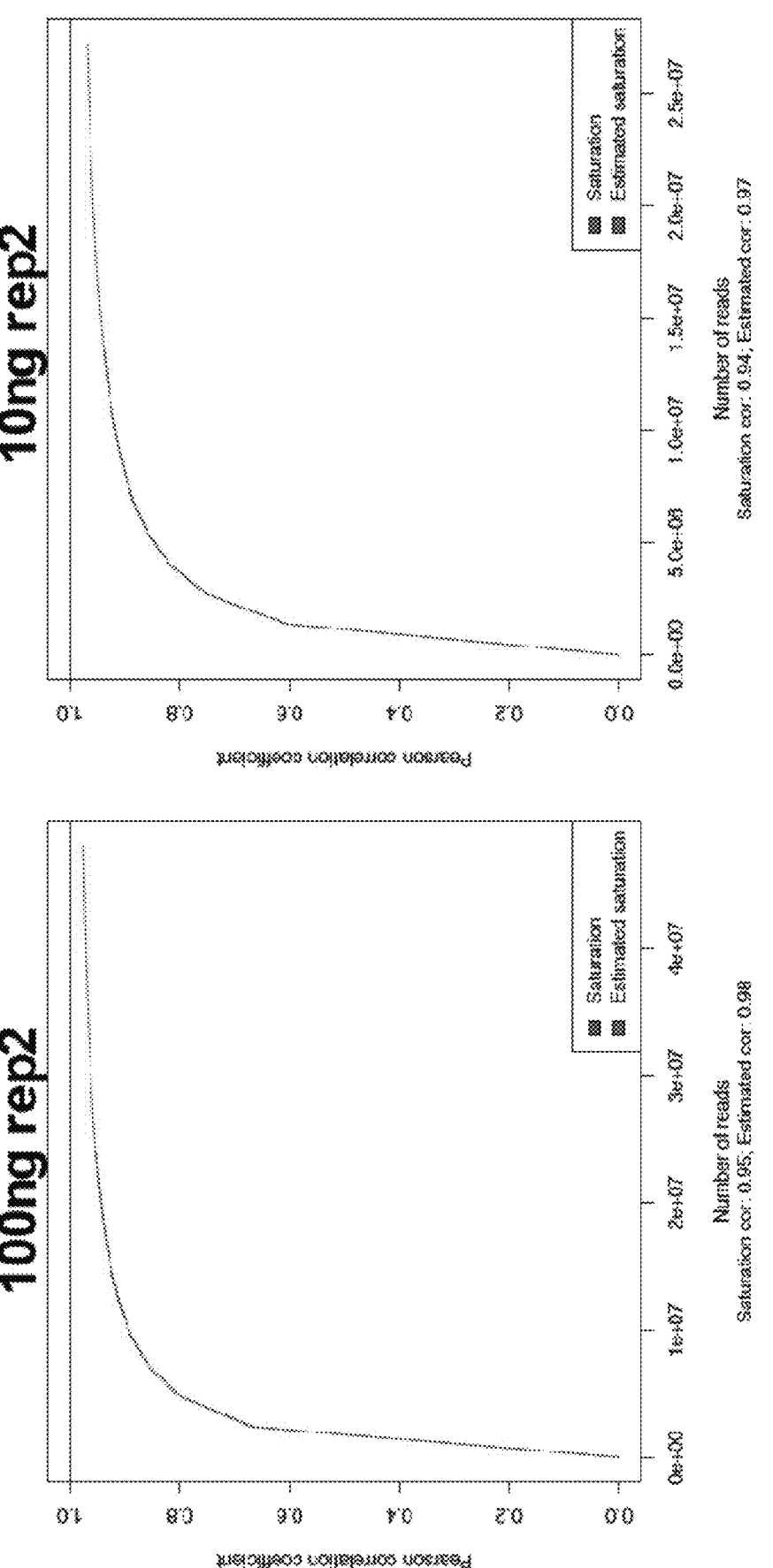
Figure 23D:
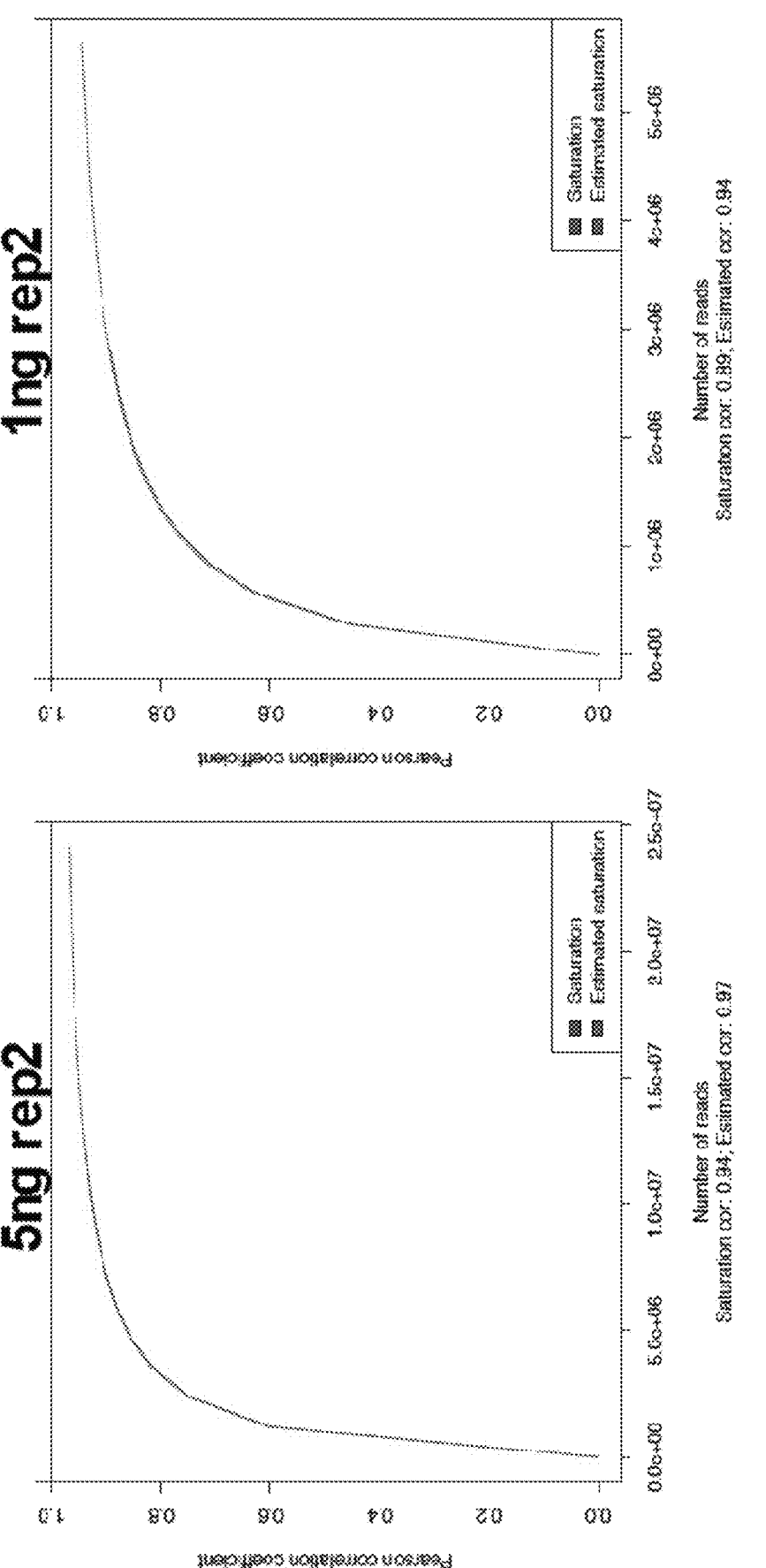
Figure 23E:
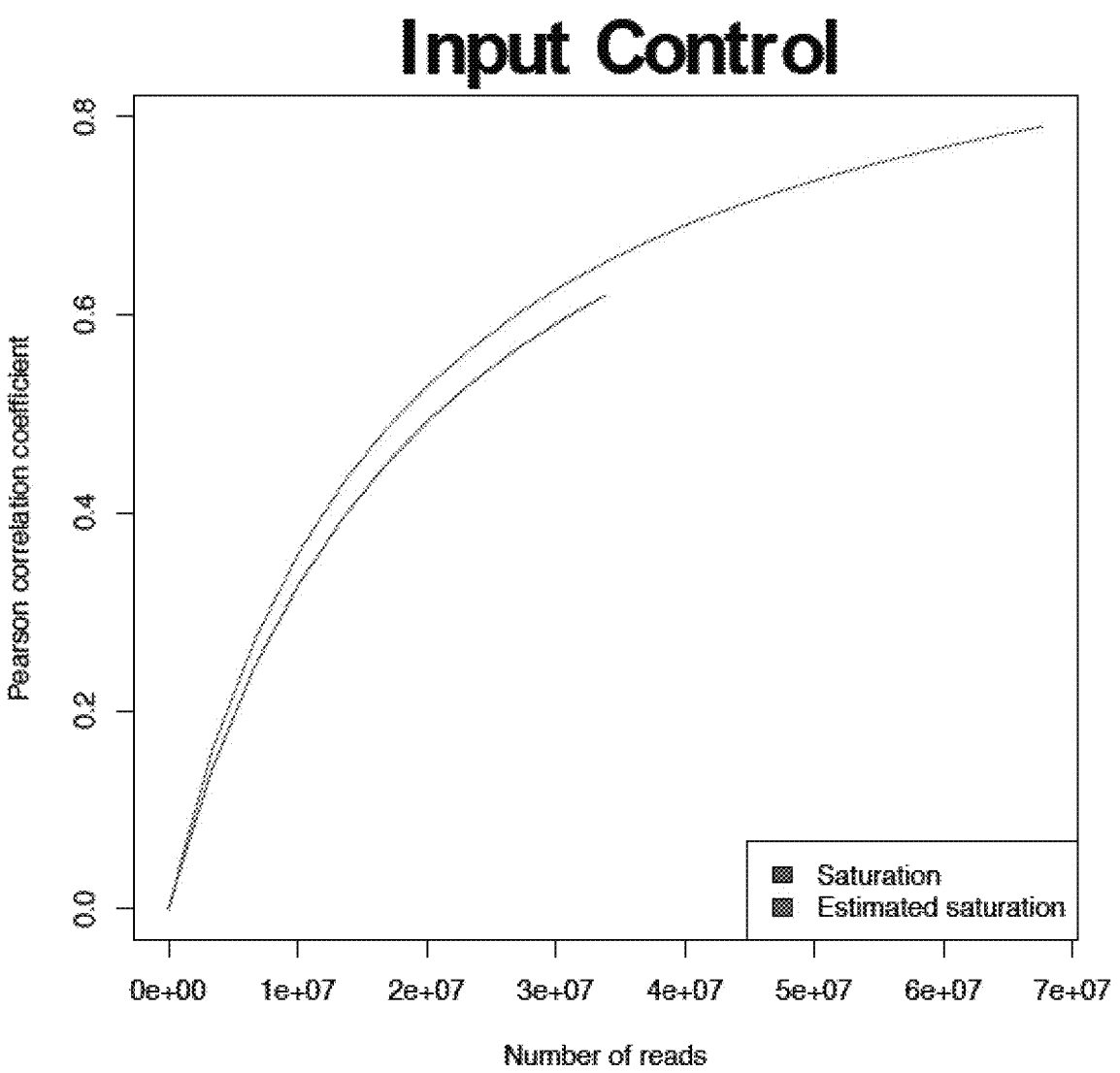
Figure 23F:
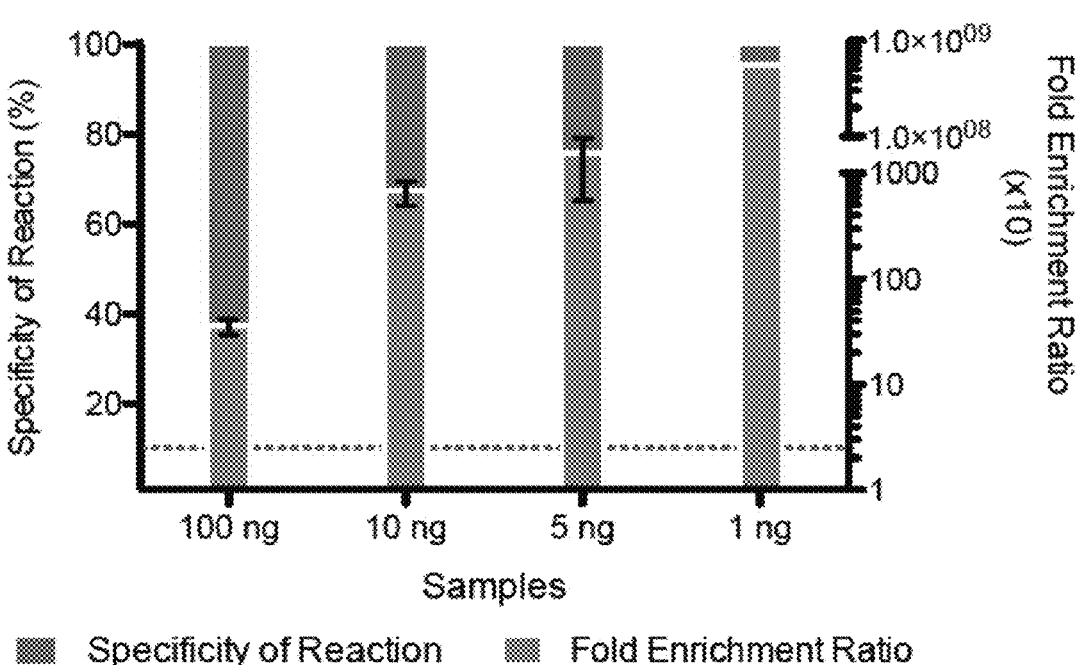
Figure 23G:
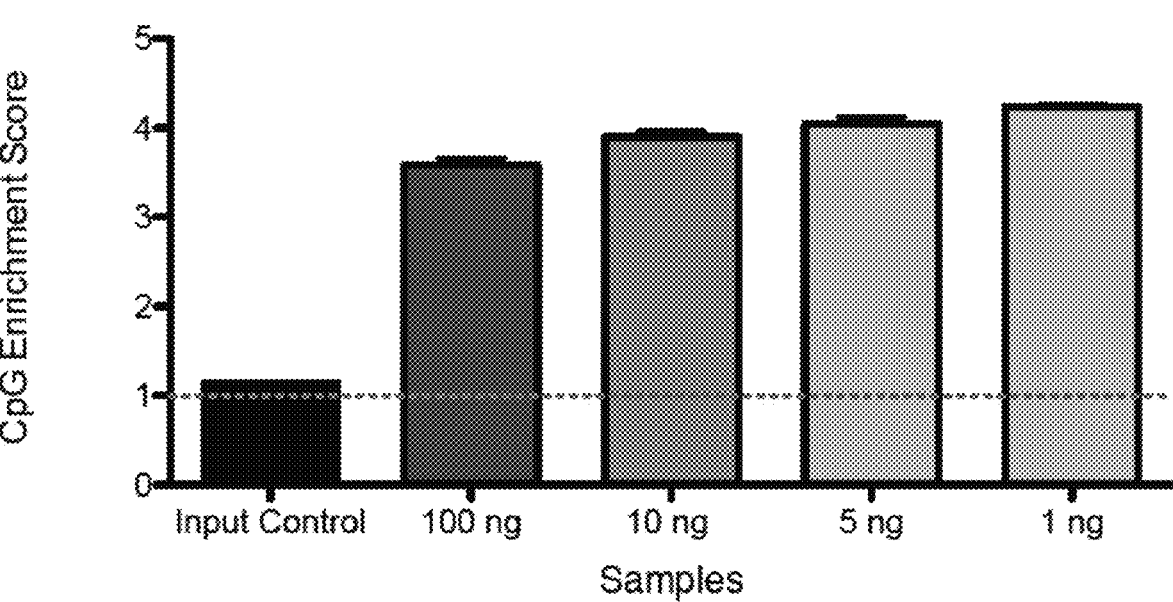

FIGS. 23A-23G show sequencing saturation analysis and quality controls. FIG. 23A, FIG. 23B, FIG. 23C, FIG. 23D, and FIG. 23E show the results of the saturation analysis from the Bioconductor package MEDIPS analyzing cfMe-DIP-seq data from each replicate for each input concentration from the HCT116 DNA fragmented to mimic plasma cfDNA. FIG. 23F is a graph showing the results of the protocol tested in two replicates of four starting DNA concentrations (100, 10, 5, and 1 ng) of HCT116 cell line. Specificity of the reaction was calculated using methylated and unmethylated spiked-in *A. thaliana* DNA. Fold enrichment ratio was calculated using genomic regions of the fragmented HCT116 DNA (Primers for methylated testis-specific H2B, TSH2B0 and unmethylated human DNA region (GAPDH promoter)). The horizontal dotted line indicates a fold-enrichment ratio threshold of 25. Error bars represent±1 s.e.m. FIG. 23G depicts a bar graph showing CpG Enrichment Scores of the sequenced samples show a robust enrichment of CpGs within the genomic regions from the immunoprecipitated samples compared to the input control. The CpG Enrichment Score was obtained by dividing the relative frequency of CpGs of the regions by the relative frequency of CpGs of the human genome. Error bars represent±1 s.e.m.

DETAILED DESCRIPTION

In the following description, numerous specific details are set forth to provide a thorough understanding of the invention. However, it is understood that the invention may be practiced without these specific details.

The present disclosure provides methods, systems, and kits for multimodal analysis of ctDNA in determining a likelihood of a subject having cancer with high sensitivity and/or high specificity. Further, the present disclosure provides methods, systems, and kits for detecting minimal residual disease (MRD) after a cancer treatment, and for evaluating whether such cancer treatment is therapeutically effective.

Identification of specific molecular features from ctDNA prior to treatment may inform prognosis and/or be predictive response to therapy, whereas detection of ctDNA after treatment may aid in identification of MRD and aid in identifying patients at high risk of recurrence and/or death. To achieve robust sensitivity, most clinical studies utilize ctDNA detection methods interrogating few regions, matched tumor profiling, and/or cases of high ctDNA abundance. However, for cancers that harbor low levels of ctDNA or lack common/known aberrations across patients, additional strategies may be utilized to achieve similar degrees of sensitivity. Genome-wide profiling techniques may help improve sensitivity by covering considerably more regions; however, the amount of cell-free DNA and sequencing depth required to achieve detection below a fraction of 1% has been cost-prohibitive.

Two tailored genome-wide profiling techniques capable of highly sensitive ctDNA detection have been described. The first, CAncer Personalized Profiling by deep Sequencing (CAPP-Seq), utilizes a broad panel of hybrid-capture probes targeting over 100 genes to identify low allele frequency mutations. The second, cell-free Methylated DNA ImmunoPrecipitation sequencing (cfMeDIP-seq), enriches for methylated cfDNA fragments through use of an anti-5-methylcytosine (anti-5mC) antibody. The identification of mutations or hypermethylation events by these respective methods have their respective advantages. Mutations may distinguish ctDNA from healthy sources of cell-free DNA due to their irreversible disposition, provided that appropriate error suppression tools are employed and any contribution of mutations from clonal hematopoiesis is taken into account. DNA hypermethylation events potentially affect a larger number of recurrent genomic regions in cancer, contributing to their ability to inform the tumor-of-origin through cell-free DNA analysis. Moreover, hypermethylation events in the vicinity of cancer driver genes may influence their expression, thereby potentially reflecting cancer behavior and providing prognostic value. To date no study has utilized the combination of both mutation- and methylation-based methods for improved tumor-naïve detection and characterization of ctDNA in localized cancers.

Utilization of fluid-based biomarkers for prognostication, risk stratification, and disease surveillance may improve patient outcomes by guiding treatment decisions without the need for invasive tumor sampling. Although circulating tumor (ct)DNA in particular has shown promise as a liquid biopsy tool, in patients with low disease burden such as those with localized non-metastatic cancer, paired tumor profiling is often required. We hypothesized that multimodal analysis of genetic and epigenetic features from plasma cell-free DNA may enable broad applications of tumor-naïve ctDNA profiling. Mutation- and methylation-based profiling identified ctDNA in 65% of localized head and neck cancer patients. Results from both approaches were quantitative and strongly correlated, and their combined analysis revealed common features of tumor-derived DNA fragments. Moreover, ctDNA methylomes revealed tumor histology, putative prognostic biomarkers, and dynamic patterns of treatment response. These findings will aid future non-invasive biomarker discovery efforts and will inform clinical implementation of ctDNA for localized cancers.

Certain methods of capturing cell-free methylated DNA are described in Applicant's WO 2017/190215 and WO 2019/010564, both of which are incorporated by reference.

Specifically, we utilize both CAPP-Seq and cfMeDIP-seq to perform tumor-naïve ctDNA detection within a cohort of localized head and neck squamous cell carcinoma (HNSCC) patients. HNSCC is a clinically heterogenous disease that frequently recurs after definitive treatment and may benefit greatly from ctDNA detection to better inform treatment decisions and disease management[33]. We demonstrate that utilization of both methods in parallel, as well as matched PBL-profiling, may achieve high-confidence tumor-naïve ctDNA detection. Furthermore, we show that the combined analysis reveals common molecular features of tumor-derived DNA fragments. Finally, we show that ctDNA methylomes revealed tumor histology, putative prognostic biomarkers, and dynamic patterns of treatment response, providing a blueprint for future biomarker studies in other disease settings.

In an aspect, there is provided a method of detecting the presence of ctDNA from cancer cells in a subject comprising:

(a) providing a sample of cell-free DNA from a subject;

(b) subjecting the sample to library preparation to permit subsequent sequencing of the cell-free methylated DNA;

(c) optionally adding a first amount of filler DNA to the sample, wherein at least a portion of the filler DNA is methylated, then further optionally denaturing the sample;

(d) capturing cell-free methylated DNA using a binder selective for methylated polynucleotides;

(e) sequencing the captured cell-free methylated DNA;

(f) comparing the sequences of the captured cell-free methylated DNA to control cell-free methylated DNAs sequences from healthy and cancerous individuals;

(g) identifying the presence of DNA from cancer cells if there is a statistically significant similarity between one or more sequences of the captured cell-free methylated DNA and cell-free methylated DNAs sequences from cancerous individuals;

wherein in at least one of the capturing step, the comparing step or the identifying step, the subject cell-free methylated DNA is limited to a sub-population according to a fragment length metric.

Various sequencing techniques are known to the person skilled in the art, such as polymerase chain reaction (PCR) followed by Sanger sequencing. Also available are next-generation sequencing (NGS) techniques, also known as high-throughput sequencing, which includes various sequencing technologies including: Illumina (Solexa) sequencing, Roche 454 sequencing, Ion torrent: Proton/PGM sequencing, SOLID sequencing, long reads sequencing (Oxford Nanopore and Pactbio). NGS allow for the sequencing of DNA and RNA much more quickly and cheaply than the previously used Sanger sequencing. In some embodiments, said sequencing is optimized for short read sequencing.

The term "subject" as used herein refers to any member of the animal kingdom. Thus, the methods and described herein are applicable to both human and veterinary disease and animal models. Preferred subjects are "patients," i.e., living humans that are being investigated to determine whether treatment or medical care is needed for a disease or condition; or that are receiving medical care for a disease or condition (e.g., cancer).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The term "nucleic acid" used herein refers to a polynucleotide comprising two or more nucleotides, i.e., a polymeric form of nucleotides of any length, either deoxyribonucleotides (dNTPs) or ribonucleotides (rNTPs), or analogs thereof. Non-limiting examples of nucleic acids include deoxyribonucleic (DNA), ribonucleic acid (RNA), coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), microRNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation or binding with a reporter agent. A "variant" nucleic acid is a polynucleotide having a nucleotide sequence identical to that of its original nucleic acid except having at least one nucleotide modified, for example, deleted, inserted, or replaced, respectively. The variant may have a nucleotide sequence at least about 80%, 90%, 95%, or 99%, identity to the nucleotide sequence of the original nucleic acid.

Cell-free methylated DNA is DNA that is circulating freely in the blood stream, and are methylated at various regions of the DNA. Samples, for example, plasma samples may be taken to analyze cell-free methylated DNA. Studies reveal that much of the circulating nucleic acids in blood arise from necrotic or apoptotic cells and greatly elevated levels of nucleic acids from apoptosis is observed in diseases such as cancer. Particularly for cancer, where the circulating DNA bears hallmark signs of the disease including mutations in oncogenes, microsatellite alterations, and, for certain cancers, viral genomic sequences, DNA or RNA in plasma has become increasingly studied as a potential biomarker for disease. For example, a quantitative assay for low levels of circulating tumor DNA in total circulating DNA may serve as a better marker for detecting the relapse of colorectal cancer compared with carcinoembryonic antigen, the standard biomarker used clinically. The circulating cfDNA may comprise circulating tumor DNA (ctDNA).

As used herein, "library preparation" includes list end-repair, A-tailing, adapter ligation, or any other preparation performed on the cell free DNA to permit subsequent sequencing of DNA.

As used herein, "filler DNA" may be noncoding DNA or it may consist of amplicons.

In some embodiments, the fragment length metric is fragment length. In some preferable embodiments, the subject cell-free methylated DNA is limited to fragments having a length of <170 bp, <165 bp, <160 bp, <155 bp, <150 bp, <145 bp, <140 bp, <135 bp, <130 bp, <125 bp, <120 bp, <115 bp, <110 bp, <105 bp, or <100 bp. In other preferable embodiments, the subject cell-free methylated DNA is limited to fragments having a length of between about 100-about 150 bp, 110-140 bp, or 120-130 bp.

In some embodiments, the fragment length metric is the fragment length distribution of the subject cell-free methylated DNA. In some preferable embodiments, the subject cell-free methylated DNA is limited to fragments within the bottom 50th, 45th, 40th, 35th, 30th, 25th, 20th, 15th, or 10th percentile based on length.

In some embodiments, the subject cell-free methylated DNA is further limited to fragments within Differentially Methylated Regions (DMRs).

In some embodiments, the limiting of the subject cell-free methylated DNA is during the capturing step.

In some embodiments, the limiting of the subject cell-free methylated DNA is during the comparing step.

In some embodiments, the limiting of the subject cell-free methylated DNA is during the identifying step.

In some embodiments, the comparison step is based on fit using a statistical classifier. Statistical classifiers using DNA methylation data may be used for assigning a sample to a particular disease state, such as cancer type or subtype. For the purpose of cancer type or subtype classification, a classifier would consist of one or more DNA methylation variables (i.e., features) within a statistical model, and the output of the statistical model would have one or more threshold values to distinguish between distinct disease states. The particular feature(s) and threshold value(s) that are used in the statistical classifier may be derived from prior knowledge of the cancer types or subtypes, from prior knowledge of the features that are likely to be most informative, from machine learning, or from a combination of two or more of these approaches.

In some embodiments, the classifier is machine learning-derived. Preferably, the classifier is an elastic net classifier, lasso, support vector machine, random forest, or neural network.

The genomic space that is analyzed may be genome-wide, or preferably restricted to regulatory regions (i.e., FANTOM5 enhancers, CpG Islands, CpG shores and CpG Shelves).

Preferably, the percentage of spike-in methylated DNA recovered is included as a covariate to control for pulldown efficiency variation.

For a classifier capable of distinguishing multiple cancer types (or subtypes) from one another, the classifier would preferably consist of differentially methylated regions from pairwise comparisons of each type (or subtype) of interest.

In some embodiments, the control cell-free methylated DNAs sequences from healthy and cancerous individuals are comprised in a database of Differentially Methylated Regions (DMRs) between healthy and cancerous individuals.

In some embodiments, the control cell-free methylated DNA sequences from healthy and cancerous individuals are limited to those control cell-free methylated DNA sequences which are differentially methylated as between healthy and cancerous individuals in DNA derived from cell-free DNA from bodily fluids, such as from blood serum, cerebral spinal fluid, urine stool, sputum, pleural fluid, ascites, tears, sweat, pap smear fluid, endoscopy brushings fluid, etc., preferably from blood plasma.

Samples

A sample can be any biological sample isolated from a subject. For example, a sample may comprise, without limitation, bodily fluid, whole blood, platelets, serum, plasma, stool, red blood cells, white blood cells or leukocytes, endothelial cells, tissue biopsies, synovial fluid, lymphatic fluid, ascites fluid, interstitial or extracellular fluid, the fluid in spaces between cells, including gingival crevicular fluid, bone marrow, cerebrospinal fluid, saliva, mucous, sputum, semen, sweat, urine, fluid from nasal brushings, fluid from a pap smear, or any other bodily fluids. A bodily fluid may include saliva, blood, or serum. A sample may also be a tumor sample, which may be obtained from a subject by various approaches, including, but not limited to, venipuncture, excretion, ejaculation, massage, biopsy, needle aspirate, lavage, scraping, surgical incision, or intervention or other approaches. A sample may be a cell-free sample (e.g., substantially free of cells).

DNA samples may be denatured, for example, using sufficient heat.

In some embodiments, the present disclosure provides a system, method, or kit that includes or uses one or more biological samples. The one or more samples used herein may comprise any substance containing or presumed to contain nucleic acids. A sample may include a biological sample obtained from a subject. In some embodiments, a biological sample is a liquid sample.

In some embodiments, the sample comprises less than about 100 ng, 90 ng, 80 ng, 75 ng, 70 ng, 60 ng, 50 ng, 40 ng, 30 ng, 20 ng, 10 ng, 5 ng, 1 ng or any amount in between the numbers of cell-free nucleic acid molecules. Further, in some embodiments, the sample comprises less than about 1 pg, less than about 5 pg, less than about 10 pg, less than about 20 pg, less than about 30 pg, less than about 40 pg, less than about 50 pg, less than about 100 pg, less than about 200 pg, less than about 500 pg, less than about 1 ng, less than about 5 ng, less than about 10 ng, less than about 20 ng, less than about 30 ng, less than about 40 ng, less than about 50 ng, less than about 100 ng, less than about 200 ng, less than about 500 ng, less than about 1000 ng, or any amount in between the numbers of cell-free nucleic acid molecules.

In some embodiments, the present disclosure comprises methods and systems for filling in the sample with an amount of filler DNA to generate a mixture sample, wherein the mixture sample comprises at least about 50 ng, 55 ng, 60 ng, 65 ng, 70 ng, 75 ng, 80 ng, 85 ng, 90 ng, 95 ng, 100 ng, 120 ng, 140 ng, 160 ng, 180 ng, 200 ng, or any amount in between the numbers of the total amount of the nucleic acid mixture. In some embodiments, the filler DNA comprises at least about 5%, 10%, 15%, 20%, 30%, 40%, 50%, 60%, 70%, 80%, 90%, or 100% methylated filler DNA with remainder being unmethylated filler DNA, and preferably between 5% and 50%, between 10%-40%, or between 15%-30% methylated filler DNA. In some embodiments, the first amount of filler DNA comprises at least about 5%, 10%, 15%, 20%, 30%, 40%, 50%, 60%, 70%, 80%, 90%, or 100% methylated filler DNA with remainder being unmethylated filler DNA, and preferably between 5% and 50%, between 10%-40%, or between 15%-30% methylated filler DNA. In some embodiments, the mixture sample comprise an amount of filler DNA from 20 ng to 100 ng, preferably 30 ng to 100 ng, more preferably 50 ng to 100 ng. In some embodiments, the first amount of filler DNA from 20 ng to 100 ng, preferably 30 ng to 100 ng, more preferably 50 ng to 100 ng. In some embodiments, the cell-free DNA from the sample and the first amount of filler DNA together comprises at least 50 ng of total DNA, preferably at least 100 ng of total DNA.

In some embodiments, the filler DNA is 50 bp to 800 bp long, preferably 100 bp to 600 bp long, and more preferably 200 bp to 600 bp long. The filler DNA is double stranded. The filler DNA is double stranded. For example, the filler DNA can be junk DNA. The filler DNA may also be endogenous or exogenous DNA. For example, the filler DNA is non-human DNA, and in preferred embodiments, A DNA. As used herein, "A DNA" refers to Enterobacteria phage A DNA. In some embodiments, the filler DNA has no alignment to human DNA.

In some embodiments, the sample may be taken before and/or after treatment of a subject with a disease or disorder. Samples may be obtained from a subject during a treatment or a treatment regime. Multiple samples may be obtained from a subject to monitor the effects of the treatment over time. The sample may be taken from a subject known or suspected of having a disease or disorder for which a definitive positive or negative diagnosis is not available via clinical tests. The sample may be taken from a subject suspected of having a disease or disorder. The sample may be taken from a subject experiencing unexplained symptoms, such as fatigue, nausea, weight loss, aches and pains, weakness, or bleeding. The sample may be taken from a subject having explained symptoms. The sample may be taken from a subject at risk of developing a disease or disorder due to factors such as familial history, age, hypertension or pre-hypertension, diabetes or pre-diabetes, overweight or obesity, environmental exposure, lifestyle risk factors (e.g., smoking, alcohol consumption, or drug use), or presence of other risk factors.

In some embodiments, a sample may be taken at a first time point and sequenced, and then another sample may be taken at a subsequent time point and sequenced. Such methods may be used, for example, for longitudinal monitoring purposes to track the development or progression of a disease. In some embodiments, the progression of a disease may be tracked before treatment, after treatment, or during the course of treatment, to determine the treatment's effectiveness. For example, a method as described herein may be performed on a subject prior to, and after, a medical treatment to measure the disease's progression or regression in response to the medical treatment.

After obtaining a sample from the subject, the sample may be processed to generate datasets indicative of a disease or disorder of the subject. For example, a presence, absence, or quantitative assessment of cell-free nucleic acid molecules (e.g., ctDNA molecules) of the sample at a panel of cancer-associated genomic loci or microbiome-associated loci may be indicative of a cancer of the subject. Processing the sample obtained from the subject may comprise (i) subjecting the sample to conditions that are sufficient to isolate, enrich, or extract a plurality of cell-free nucleic acid molecules, and (ii) assaying the plurality of cell-free nucleic acid molecules to generate the dataset (e.g., nucleic acid sequences). In some embodiments, a plurality of cell-free nucleic acid molecules is extracted from the sample and subjected to sequencing to generate a plurality of sequencing reads.

In some embodiments, the cell-free nucleic acid molecules may comprise cell-free ribonucleic acid (cfRNA) or cell-free deoxyribonucleic acid (cfDNA). The cell-free nucleic acid molecules (e.g., cfRNA or cfDNA) may be extracted from the sample by a variety of methods. The cell-free nucleic acid molecule may be enriched by a plurality of probes configured to enrich nucleic acid (e.g., RNA or DNA) molecules corresponding to a panel of cancer-associated genomic loci. The probes may have sequence complementarity with nucleic acid sequences from one or more of the panel of cancer-associated genomic loci. The panel of cancer-associated genomic loci may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, or more distinct cancer-associated genomic loci. The probes may be nucleic acid molecules (e.g., RNA or DNA) having sequence complementarity with nucleic acid sequences (e.g., RNA or DNA) of the one or more genomic loci (e.g., cancer-associated genomic loci). These nucleic acid molecules may be primers or enrichment sequences. The assaying of the sample using probes that are selective for the one or more genomic loci (e.g., cancer-associated genomic loci or microbiome-associated loci) may comprise use of array hybridization, polymerase chain reaction (PCR), or nucleic acid sequencing (e.g., RNA sequencing or DNA sequencing).

Nucleic Acid Molecules Sequencing

The present disclosure provides methods and technologies for determining the sequence of nucleotide bases in one or more polynucleotides. The polynucleotides may be, for example, nucleic acid molecules such as deoxyribonucleic acid (DNA) or ribonucleic acid (RNA), including variants or derivatives thereof (e.g., single stranded DNA). Sequencing may be performed by various systems currently available, such as, without limitation, a sequencing system by Illumina®, Pacific Biosciences (PacBio®), Oxford Nanopore®, or Life Technologies (Ion Torrent®). Further, any sequencing methods that provides fragment length such as pair-end sequencing may be utilized. Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

In some embodiments, the sequencing reads are obtained via a next-generation sequencing method or a next-next-generation sequencing method. In some embodiments, the sequencing methods comprises CAncer Personalized Profiling by deep Sequencing (CAPP-Seq), which is a next-generation sequencing based method used to quantify circulating DNA in cancer (ctDNA). This method may be generalized for any cancer type that is known to have recurrent mutations and may detect one molecule of mutant DNA in 10,000 molecules of healthy DNA. In some embodiments, the sequencing methods comprise cfMeDIP sequencing as described by Shen et al., sensitive tumor detection and classification using plasma cell-free DNA methylomes, (2018) Nature, which is incorporated herein in its entirety. In some embodiments, the sequencing comprises bisulfite sequencing.

In some embodiments, sequencing comprises modification of a nucleic acid molecule or fragment thereof, for example, by ligating a barcode, a unique molecular identifier (UMI), or another tag to the nucleic acid molecule or fragment thereof. Ligating a barcode, UMI, or tag to one end of a nucleic acid molecule or fragment thereof may facilitate analysis of the nucleic acid molecule or fragment thereof following sequencing. In some embodiments, a barcode is a unique barcode (e.g., a UMI). In some embodiments, a barcode is non-unique, and barcode sequences may be used in connection with endogenous sequence information such as the start and stop sequences of a target nucleic acid (e.g., the target nucleic acid is flanked by the barcode and the barcode sequences, in connection with the sequences at the beginning and end of the target nucleic acid, creates a uniquely tagged molecule). A barcode, UMI, or tag may be a known sequence used to associate a polynucleotide or fragment thereof with an input or target nucleic acid molecule or fragment thereof. A barcode, UMI, or tag may comprise natural nucleotides or non-natural (e.g., modified) nucleotides (e.g., as described herein). A barcode sequence may be contained within an adapter sequence such that the barcode sequence may be contained within a sequencing read. A barcode sequence may comprise at least 4, 5, 6, 7, 8, 9, 10, 11, 12, 13, 14, 15, 16, or more nucleotides in length. In some cases, a barcode sequence may be of sufficient length and may be sufficiently different from another barcode sequence to allow the identification of a sample based on a barcode sequence with which it is associated. A barcode sequence, or a combination of barcode sequences, may be used to tag and subsequently identify an "original" nucleic acid molecule or fragment thereof (e.g., a nucleic acid molecule or fragment thereof present in a sample from a subject). In some cases, a barcode sequence, or a combination of barcode sequences, is used in conjunction with endogenous sequence information to identify an original nucleic acid molecule or fragment thereof. For example, a barcode sequence, or a combination of barcode sequences, may be used with endogenous sequences adjacent to a barcode, UMI, or tag (e.g., the beginning and end of the endogenous sequences).

Processing a nucleic acid molecule or fragment thereof may comprise performing nucleic acid amplification. For example, any type of nucleic acid amplification reaction may be used to amplify a target nucleic acid molecule or fragment thereof and generate an amplified product. Non-limiting examples of nucleic acid amplification methods include reverse transcription, primer extension, polymerase chain reaction (PCR), ligase chain reaction, asymmetric amplification, rolling circle amplification, and multiple displacement amplification (MDA). Examples of PCR include, but are not limited to, quantitative PCR, real-time PCR, digital PCR, emulsion PCR, hot start PCR, multiplex PCR, asymmetric PCR, nested PCR, and assembly PCR. Nucleic acid amplification may involve one or more reagents such as one or more primers, probes, polymerases, buffers, enzymes, and deoxyribonucleotides. Nucleic acid amplification may be isothermal or may comprise thermal cycling. and/or with the length of the endogenous sequence.

Methylation Profile

The present disclosure provides methods, systems, and kits for producing a methylation profile of a subject that has a disease/condition or is suspected of having such disease/condition, wherein the methylation profile may be used to determine whether the subject has the disease/condition or is at risk of having the disease/condition. Before using cfMeDIP-seq, the samples disclosed herein are subjected to library preparation. In short, after end-repair and A-tailing, the samples are ligated to nucleic acid adapters and digested using enzymes. As described above under the sample section, the prepared libraries may be combined with filler nucleic acids (e.g., filler A DNAs) to minimize the effect of low abundance ctDNA in the prepared libraries and generate mixed samples. In some embodiments, when the disease/condition is a locoregionally (non-metastatic) cancer, the amount of ctDNA is low and may not be easily and accurately measured and quantified. The mixed samples are brought to at least about 50 ng, 80 ng, 100 ng, 120 ng, 150 ng, or 200 ng and are subjected to further enrichment.

The methods, system, and kits described herein are applicable to a wide variety of cancers, including but not limited to adrenal cancer, anal cancer, bile duct cancer, bladder cancer, bone cancer, brain/cns tumors, breast cancer, castleman disease, cervical cancer, colon/rectum cancer, endometrial cancer, esophagus cancer, ewing family of tumors, eye cancer, gallbladder cancer, gastrointestinal carcinoid tumors, gastrointestinal stromal tumor (gist), gestational trophoblastic disease, hodgkin disease, kaposi sarcoma, kidney cancer, laryngeal and hypopharyngeal cancer, leukemia (acute lymphocytic, acute myeloid, chronic lymphocytic, chronic myeloid, chronic myelomonocytic), liver cancer, lung cancer (non-small cell, small cell, lung carcinoid tumor), lymphoma, lymphoma of the skin, malignant mesothelioma, multiple myeloma, myelodysplastic syndrome, nasal cavity and paranasal sinus cancer, nasopharyngeal cancer, neuroblastoma, non-hodgkin lymphoma, oral cavity and oropharyngeal cancer, osteosarcoma, ovarian cancer, penile cancer, pituitary tumors, prostate cancer, retinoblastoma, rhabdomyosarcoma, salivary gland cancer, sarcoma-adult soft tissue cancer, skin cancer (basal and squamous cell, melanoma, merkel cell), small intestine cancer, stomach cancer, testicular cancer, thymus cancer, thyroid cancer, uterine sarcoma, vaginal cancer, vulvar cancer, waldenstrom macroglobulinemia, wilms tumor. In an embodiment, the cancer is head and neck squamous cell carcinoma.

A binder may be used to enrich the mixed samples. In some embodiments, the binder is a protein comprising a Methyl-CpG-binding domain. One such exemplary protein is MBD2 protein. As used herein, "Methyl-CpG-binding domain (MBD)" refers to certain domains of proteins and enzymes that is approximately 70 residues long and binds to DNA that contains one or more symmetrically methylated CpGs. The MBD of MeCP2, MBD1, MBD2, MBD4 and BAZ2 mediates binding to DNA, and in cases of MeCP2, MBD1 and MBD2, preferentially to methylated CpG. Human proteins MECP2, MBD1, MBD2, MBD3, and MBD4 comprise a family of nuclear proteins related by the presence in each of a methyl-CpG-binding domain (MBD). Each of these proteins, with the exception of MBD3, is capable of binding specifically to methylated DNA.

In other embodiments, the binder is an antibody and capturing cell-free methylated DNA comprises immunoprecipitating the cell-free methylated DNA using the antibody. As used herein, "immunoprecipitation" refers a technique of precipitating an antigen (such as polypeptides and nucleotides) out of solution using an antibody that specifically binds to that particular antigen. This process may be used to isolate and concentrate a particular protein or DNA from a sample and requires that the antibody be coupled to a solid substrate at some point in the procedure. The solid substrate includes for examples beads, such as magnetic beads. Other types of beads and solid substrates may be used.

One exemplary antibody is 5-MeC antibody. For the immunoprecipitation procedure, in some embodiments at least 0.05 µg of the antibody is added to the sample; while in more preferred embodiments at least 0.16 µg of the antibody is added to the sample. To confirm the immunoprecipitation reaction, in some embodiments the method described herein further comprises the step of adding a second amount of control DNA to the sample.

The enriched samples are further amplified, purified, and sequenced to generate a plurality of sequence reads. The plurality of sequence reads is analyzed to identify a plurality of Differentially Methylated Regions (DMRs). In some embodiments, the plurality of DMRs comprises DMRs derived from cell free nucleic acid molecules that are derived from peripheral blood leukocytes (PBLs). In some embodiments, the plurality of DMRs comprises at least about 750,000 non-overlapping about 300-bp nucleic acid fragment window. These fragments comprise greater than or equal to 8 CpG islands. In some embodiments, DMRs are identified from comparing sequence reads generated from samples obtained from patients with the disease/condition to sequence reads generated from samples obtained from healthy controls. In some embodiments, the healthy controls comprise a same set of risk factors for developing the disease/condition. In some embodiments, the plurality of DMRs comprises at least about 997 DMRs: about 941 hypermethylated in HNSCC and 56 hypomethylated in HNSCC (Table 5). Using the same disclosed approach here, hypermethylated DMRs may be detected for a different cancer (e.g., lung cancer, pancreatic cancer, colorectal cancer) and hypomethylated DMRs may be detected for the different cancer.

TABLE 5

A list of ctDNA derived DMRs

| windowPos (Genomic position of each DMR) | ensemblId Gene ID (a DMR related to a gene) | DMR methylation level |
|---|---|---|
| chr1.50881501.50881800 | ENSG00000142700 | hyper |
| chr1.50881801.50882100 | ENSG00000142700 | hyper |
| chr1.63786301.63786600 | ENSG00000230798 | hyper |
| chr1.119527501.119527800 | ENSG00000092607 | hyper |
| chr1.119550601.119550900 | ENSG00000239216 | hyper |
| chr1.148603801.148604100 | ENSG00000207205 | hyper |
| chr1.149155501.149155800 | ENSG00000202167 | hyper |
| chr1.149223301.149223600 | ENSG00000206737 | hyper |
| chr1.149223601.149223900 | ENSG00000206737 | hyper |
| chr1.17216101.17216400 | ENSG00000058453 | hyper |
| chr1.91182301.91182600 | ENSG00000143032 | hyper |
| chr1.98511601.98511900 | ENSG00000225206 | hyper |
| chr1.99470101.99470400 | ENSG00000117598 | hyper |

TABLE 5-continued

A list of ctDNA derived DMRs

| windowPos (Genomic position of each DMR) | ensemblId Gene ID (a DMR related to a gene) | DMR methylation level |
|---|---|---|
| chr1.145944901.145945200 | ENSG00000201105 | hyper |
| chr1.147486601.147486900 | ENSG00000206791 | hyper |
| chr1.148598101.148598400 | ENSG00000237253 | hyper |
| chr1.148760401.148760700 | ENSG00000237343 | hyper |
| chr1.149223901.149224200 | ENSG00000206737 | hyper |
| chr1.149224201.149224500 | ENSG00000206737 | hyper |
| chr1.17215801.17216100 | ENSG00000058453 | hyper |
| chr1.20810101.20810400 | ENSG00000162545 | hyper |
| chr1.26551801.26552100 | ENSG00000236155 | hyper |
| chr1.50893501.50893800 | ENSG00000142700 | hyper |
| chr1.57888301.57888600 | ENSG00000173406 | hyper |
| chr1.63785401.63785700 | ENSG00000230798 | hyper |
| chr1.63786001.63786300 | ENSG00000230798 | hyper |
| chr1.66258301.66258600 | ENSG00000184588 | hyper |
| chr1.75595801.75596100 | ENSG00000224127 | hyper |
| chr1.77334601.77334900 | ENSG00000117069 | hyper |
| chr1.91182601.91182900 | ENSG00000143032 | hyper |
| chr1.91183801.91184100 | ENSG00000143032 | hyper |
| chr1.92948101.92948400 | ENSG00000162676 | hyper |
| chr1.98511301.98511600 | ENSG00000225206 | hyper |
| chr1.99469801.99470100 | ENSG00000117598 | hyper |
| chr1.110612401.110612700 | ENSG00000143093 | hyper |
| chr1.111216901.111217200 | ENSG00000177272 | hyper |
| chr1.111506101.111506400 | ENSG00000121931 | hyper |
| chr1.119526601.119526900 | ENSG00000092607 | hyper |
| chr1.119526901.119527200 | ENSG00000092607 | hyper |
| chr1.119527201.119527500 | ENSG00000092607 | hyper |
| chr1.119532601.119532900 | ENSG00000092607 | hyper |
| chr1.119536201.119536500 | ENSG00000092607 | hyper |
| chr1.119543101.119543400 | ENSG00000226172 | hyper |
| chr1.119550901.119551200 | ENSG00000239216 | hyper |
| chr1.119551201.119551500 | ENSG00000239216 | hyper |
| chr1.145944601.145944900 | ENSG00000201105 | hyper |
| chr1.145963501.145963800 | ENSG00000207418 | hyper |
| chr1.145979401.145979700 | ENSG00000207418 | hyper |
| chr1.145990801.145991100 | ENSG00000229828 | hyper |
| chr1.147486301.147486600 | ENSG00000206791 | hyper |
| chr1.147505201.147505500 | ENSG00000206585 | hyper |
| chr1.147521101.147521400 | ENSG00000206585 | hyper |
| chr1.147752701.147753000 | ENSG00000234283 | hyper |
| chr1.147753001.147753300 | ENSG00000234283 | hyper |
| chr1.147775201.147775500 | ENSG00000238107 | hyper |
| chr1.147790501.147790800 | ENSG00000235988 | hyper |
| chr1.149156101.149156400 | ENSG00000202167 | hyper |
| chr1.149156401.149156700 | ENSG00000202167 | hyper |
| chr1.149224501.149224800 | ENSG00000206737 | hyper |
| chr1.149400001.149400300 | ENSG00000273213 | hyper |
| chr1.149719501.149719800 | ENSG00000234232 | hyper |
| chr1.242687101.242687400 | ENSG00000180287 | hyper |
| chr1.165323701.165324000 | ENSG00000162761 | hyper |
| chr1.177140401.177140700 | ENSG00000198797 | hyper |
| chr1.207999301.207999600 | ENSG00000203709 | hyper |
| chr1.217311301.217311600 | ENSG00000196482 | hyper |
| chr1.234041101.234041400 | ENSG00000183780 | hyper |
| chr1.237204901.237205200 | ENSG00000198626 | hyper |
| chr1.240255001.240255300 | ENSG00000155816 | hyper |
| chr2.19558501.19558800 | ENSG00000143867 | hyper |
| chr1.161039401.161039700 | ENSG00000186517 | hyper |
| chr1.165321601.165321900 | ENSG00000162761 | hyper |
| chr1.165323401.165323700 | ENSG00000162761 | hyper |
| chr1.165324301.165324600 | ENSG00000162761 | hyper |
| chr1.165324601.165324900 | ENSG00000162761 | hyper |
| chr1.167090701.167091000 | ENSG00000198842 | hyper |
| chr1.167682601.167682900 | ENSG00000198771 | hyper |
| chr1.169396501.169396800 | ENSG00000117477 | hyper |
| chr1.169396801.169397100 | ENSG00000117477 | hyper |
| chr1.170630101.170630400 | ENSG00000116132 | hyper |
| chr1.173638801.173639100 | ENSG00000183831 | hyper |
| chr1.180203701.180204000 | ENSG00000121454 | hyper |
| chr1.180204001.180204300 | ENSG00000121454 | hyper |
| chr1.180204301.180204600 | ENSG00000121454 | hyper |
| chr1.200010001.200010300 | ENSG00000116833 | hyper |
| chr1.200011201.200011500 | ENSG00000116833 | hyper |
| chr1.214159501.214159800 | ENSG00000230461 | hyper |

TABLE 5-continued

A list of ctDNA derived DMRs

| windowPos (Genomic position of each DMR) | ensemblId Gene ID (a DMR related to a gene) | DMR methylation level |
|---|---|---|
| chr1.217307401.217307700 | ENSG00000196482 | hyper |
| chr1.217307701.217308000 | ENSG00000196482 | hyper |
| chr1.217308001.217308300 | ENSG00000196482 | hyper |
| chr1.217309501.217309800 | ENSG00000196482 | hyper |
| chr1.217309801.217310100 | ENSG00000196482 | hyper |
| chr1.217310101.217310400 | ENSG00000196482 | hyper |
| chr1.217311601.217311900 | ENSG00000196482 | hyper |
| chr1.217313101.217313400 | ENSG00000196482 | hyper |
| chr1.217313401.217313700 | ENSG00000196482 | hyper |
| chr1.220959601.220959900 | ENSG00000186205 | hyper |
| chr1.224804401.224804700 | ENSG00000143786 | hyper |
| chr1.224804701.224805000 | ENSG00000143786 | hyper |
| chr1.228652201.228652500 | ENSG00000181201 | hyper |
| chr1.235814101.235814400 | ENSG00000168243 | hyper |
| chr1.239550601.239550900 | ENSG00000133019 | hyper |
| chr1.239550901.239551200 | ENSG00000133019 | hyper |
| chr1.239551201.239551500 | ENSG00000133019 | hyper |
| chr1.242686801.242687100 | ENSG00000180287 | hyper |
| chr2.1746901.1747200 | ENSG00000130508 | hyper |
| chr2.5830801.5831100 | ENSG00000224128 | hyper |
| chr2.5831101.5831400 | ENSG00000224128 | hyper |
| chr2.19555801.19556100 | ENSG00000143867 | hyper |
| chr2.45155101.45155400 | ENSG00000259439 | hyper |
| chr2.45159301.45159600 | ENSG00000259439 | hyper |
| chr2.45160201.45160500 | ENSG00000259439 | hyper |
| chr2.45170101.45170400 | ENSG00000138083 | hyper |
| chr2.45171301.45171600 | ENSG00000138083 | hyper |
| chr2.45228301.45228600 | ENSG00000170577 | hyper |
| chr2.45228601.45228900 | ENSG00000170577 | hyper |
| chr2.45231301.45231600 | ENSG00000170577 | hyper |
| chr2.45231901.45232200 | ENSG00000170577 | hyper |
| chr2.45233401.45233700 | ENSG00000170577 | hyper |
| chr2.50574301.50574600 | ENSG00000179915 | hyper |
| chr2.85107301.85107600 | ENSG00000186854 | hyper |
| chr2.119600401.119600700 | ENSG00000163064 | hyper |
| chr2.119607601.119607900 | ENSG00000163064 | hyper |
| chr2.176933401.176933700 | ENSG00000174279 | hyper |
| chr2.63280801.63281100 | ENSG00000115507 | hyper |
| chr2.80531701.80532000 | ENSG00000066032 | hyper |
| chr2.115920601.115920900 | ENSG00000175497 | hyper |
| chr2.131721901.131722200 | ENSG00000136002 | hyper |
| chr2.177030001.177030300 | ENSG00000128652 | hyper |
| chr2.63279001.63279300 | ENSG00000115507 | hyper |
| chr2.63279901.63280200 | ENSG00000115507 | hyper |
| chr2.63280201.63280500 | ENSG00000115507 | hyper |
| chr2.63280501.63280800 | ENSG00000115507 | hyper |
| chr2.63281101.63281400 | ENSG00000115507 | hyper |
| chr2.63281401.63281700 | ENSG00000115507 | hyper |
| chr2.63285301.63285600 | ENSG00000115507 | hyper |
| chr2.63285601.63285900 | ENSG00000115507 | hyper |
| chr2.71017201.71017500 | ENSG00000183733 | hyper |
| chr2.73147201.73147500 | ENSG00000135638 | hyper |
| chr2.73519501.73519800 | ENSG00000135625 | hyper |
| chr2.80529901.80530200 | ENSG00000066032 | hyper |
| chr2.80530201.80530500 | ENSG00000066032 | hyper |
| chr2.84743401.84743700 | ENSG00000115423 | hyper |
| chr2.85107001.85107300 | ENSG00000186854 | hyper |
| chr2.111876901.111877200 | ENSG00000153094 | hyper |
| chr2.119600701.119601000 | ENSG00000163064 | hyper |
| chr2.119614501.119614800 | ENSG00000163064 | hyper |
| chr2.119614801.119615100 | ENSG00000163064 | hyper |
| chr2.119616301.119616600 | ENSG00000163064 | hyper |
| chr2.119616601.119616900 | ENSG00000163064 | hyper |
| chr2.124782301.124782600 | ENSG00000228400 | hyper |
| chr2.139537201.139537500 | ENSG00000144227 | hyper |
| chr2.149645701.149646000 | ENSG00000231079 | hyper |
| chr2.157176601.157176900 | ENSG00000153234 | hyper |
| chr2.168150001.168150300 | ENSG00000228222 | hyper |
| chr2.172946101.172946400 | ENSG00000172878 | hyper |
| chr2.172952401.172952700 | ENSG00000144355 | hyper |
| chr2.173099701.173100000 | ENSG00000232555 | hyper |
| chr2.173100001.173100300 | ENSG00000232555 | hyper |
| chr2.175191901.175192200 | ENSG00000231453 | hyper |
| chr2.175193401.175193700 | ENSG00000231453 | hyper |

TABLE 5-continued

A list of ctDNA derived DMRs

| windowPos (Genomic position of each DMR) | ensemblId Gene ID (a DMR related to a gene) | DMR methylation level |
|---|---|---|
| chr2.175193701.175194000 | ENSG00000231453 | hyper |
| chr2.175205701.175206000 | ENSG00000217236 | hyper |
| chr2.176931601.176931900 | ENSG00000174279 | hyper |
| chr2.176931901.176932200 | ENSG00000174279 | hyper |
| chr2.176933101.176933400 | ENSG00000174279 | hyper |
| chr2.176936401.176936700 | ENSG00000174279 | hyper |
| chr2.176943301.176943600 | ENSG00000174279 | hyper |
| chr2.176946601.176946900 | ENSG00000174279 | hyper |
| chr2.176947201.176947500 | ENSG00000174279 | hyper |
| chr2.176948101.176948400 | ENSG00000174279 | hyper |
| chr2.176964901.176965200 | ENSG00000170178 | hyper |
| chr2.176965201.176965500 | ENSG00000170178 | hyper |
| chr2.176976901.176977200 | ENSG00000128710 | hyper |
| chr2.176981101.176981400 | ENSG00000128710 | hyper |
| chr2.177054301.177054600 | ENSG00000128645 | hyper |
| chr2.177054601.177054900 | ENSG00000128645 | hyper |
| chr2.182322601.182322900 | ENSG00000115232 | hyper |
| chr2.200333701.200334000 | ENSG00000119042 | hyper |
| chr2.200334001.200334300 | ENSG00000119042 | hyper |
| chr3.27770401.27770700 | ENSG00000163508 | hyper |
| chr3.62353801.62354100 | ENSG00000241472 | hyper |
| chr2.223161901.223162200 | ENSG00000135903 | hyper |
| chr2.223162801.223163100 | ENSG00000135903 | hyper |
| chr2.223166401.223166700 | ENSG00000163081 | hyper |
| chr2.223176301.223176600 | ENSG00000267034 | hyper |
| chr2.229046101.229046400 | ENSG00000153820 | hyper |
| chr2.237072601.237072900 | ENSG00000168505 | hyper |
| chr2.237082201.237082500 | ENSG00000233611 | hyper |
| chr3.27765001.27765300 | ENSG00000163508 | hyper |
| chr3.27765301.27765600 | ENSG00000163508 | hyper |
| chr3.62353501.62353800 | ENSG00000241472 | hyper |
| chr3.192126001.192126300 | ENSG00000114279 | hyper |
| chr4.4868101.4868400 | ENSG00000163132 | hyper |
| chr4.13532401.13532700 | ENSG00000109705 | hyper |
| chr4.13532701.13533000 | ENSG00000109705 | hyper |
| chr3.169377901.169378200 | ENSG00000085276 | hyper |
| chr3.170137201.170137500 | ENSG00000013297 | hyper |
| chr3.194409001.194409300 | ENSG00000185112 | hyper |
| chr3.128210701.128211000 | ENSG00000179348 | hyper |
| chr3.129693901.129694200 | ENSG00000170893 | hyper |
| chr3.129694201.129694500 | ENSG00000170893 | hyper |
| chr3.137480101.137480400 | ENSG00000168875 | hyper |
| chr3.138657301.138657600 | ENSG00000244578 | hyper |
| chr3.138657901.138658200 | ENSG00000244578 | hyper |
| chr3.147077401.147077700 | ENSG00000243620 | hyper |
| chr3.147105901.147106200 | ENSG00000174963 | hyper |
| chr3.147109501.147109800 | ENSG00000174963 | hyper |
| chr3.147109801.147110100 | ENSG00000174963 | hyper |
| chr3.147110101.147110400 | ENSG00000174963 | hyper |
| chr3.147114301.147114600 | ENSG00000174963 | hyper |
| chr3.147124201.147124500 | ENSG00000174963 | hyper |
| chr3.157812601.157812900 | ENSG00000168779 | hyper |
| chr3.157821301.157821600 | ENSG00000168779 | hyper |
| chr3.159944401.159944700 | ENSG00000180044 | hyper |
| chr3.170136901.170137200 | ENSG00000013297 | hyper |
| chr3.173302801.173303100 | ENSG00000169760 | hyper |
| chr3.181422001.181422300 | ENSG00000242808 | hyper |
| chr3.181441501.181441800 | ENSG00000242808 | hyper |
| chr3.192126301.192126600 | ENSG00000114279 | hyper |
| chr3.192231901.192232200 | ENSG00000114279 | hyper |
| chr4.4856401.4856700 | ENSG00000273396 | hyper |
| chr4.9178201.9178500 | ENSG00000229924 | hyper |
| chr4.13533001.13533300 | ENSG00000109705 | hyper |
| chr4.20255701.20256000 | ENSG00000145147 | hyper |
| chr4.20256001.20256300 | ENSG00000145147 | hyper |
| chr4.37245601.37245900 | ENSG00000174145 | hyper |
| chr4.37245901.37246200 | ENSG00000174145 | hyper |
| chr4.41749501.41749800 | ENSG00000109132 | hyper |
| chr4.41875501.41875800 | ENSG00000245870 | hyper |
| chr4.42398701.42399000 | ENSG00000178343 | hyper |
| chr4.44449501.44449800 | ENSG00000183783 | hyper |
| chr4.54969901.54970200 | ENSG00000145216 | hyper |
| chr4.85402801.85403100 | ENSG00000163623 | hyper |
| chr5.2743201.2743500 | ENSG00000170561 | hyper |

TABLE 5-continued

A list of ctDNA derived DMRs

| windowPos (Genomic position of each DMR) | ensemblId Gene ID (a DMR related to a gene) | DMR methylation level |
| --- | --- | --- |
| chr4.134071801.134072100 | ENSG00000138650 | hyper |
| chr4.174450001.174450300 | ENSG00000164107 | hyper |
| chr4.190938901.190939200 | ENSG00000201145 | hyper |
| chr4.81187501.81187800 | ENSG00000138675 | hyper |
| chr4.85414501.85414800 | ENSG00000163623 | hyper |
| chr4.85414801.85415100 | ENSG00000163623 | hyper |
| chr4.85417801.85418100 | ENSG00000163623 | hyper |
| chr4.85418101.85418400 | ENSG00000163623 | hyper |
| chr4.85418401.85418700 | ENSG00000163623 | hyper |
| chr4.104640901.104641200 | ENSG00000169836 | hyper |
| chr4.107956501.107956800 | ENSG00000155011 | hyper |
| chr4.110223601.110223900 | ENSG00000188517 | hyper |
| chr4.111533101.111533400 | ENSG00000250103 | hyper |
| chr4.111555301.111555600 | ENSG00000164093 | hyper |
| chr4.111562501.111562800 | ENSG00000164093 | hyper |
| chr4.121992301.121992600 | ENSG00000173376 | hyper |
| chr4.122686201.122686500 | ENSG00000164112 | hyper |
| chr4.134069401.134069700 | ENSG00000250241 | hyper |
| chr4.134071501.134071800 | ENSG00000138650 | hyper |
| chr4.134072101.134072400 | ENSG00000138650 | hyper |
| chr4.134072401.134072700 | ENSG00000138650 | hyper |
| chr4.134072701.134073000 | ENSG00000138650 | hyper |
| chr4.134073901.134074200 | ENSG00000138650 | hyper |
| chr4.144621301.144621600 | ENSG00000183090 | hyper |
| chr4.147561601.147561900 | ENSG00000151615 | hyper |
| chr4.158143201.158143500 | ENSG00000120251 | hyper |
| chr4.158143501.158143800 | ENSG00000120251 | hyper |
| chr4.172733701.172734000 | ENSG00000174473 | hyper |
| chr4.172734601.172734900 | ENSG00000174473 | hyper |
| chr4.174422101.174422400 | ENSG00000164107 | hyper |
| chr4.174427801.174428100 | ENSG00000164107 | hyper |
| chr4.174429601.174429900 | ENSG00000164107 | hyper |
| chr4.174430201.174430500 | ENSG00000164107 | hyper |
| chr4.174448501.174448800 | ENSG00000164107 | hyper |
| chr5.2754901.2755200 | ENSG00000186493 | hyper |
| chr5.3104701.3105000 | ENSG00000249808 | hyper |
| chr5.3116701.3117000 | ENSG00000249808 | hyper |
| chr5.3590701.3591000 | ENSG00000170549 | hyper |
| chr5.3599401.3599700 | ENSG00000170549 | hyper |
| chr5.3600601.3600900 | ENSG00000170549 | hyper |
| chr5.3602101.3602400 | ENSG00000170549 | hyper |
| chr5.54518701.54519000 | ENSG00000234602 | hyper |
| chr5.54519001.54519300 | ENSG00000234602 | hyper |
| chr5.122422501.122422800 | ENSG00000223652 | hyper |
| chr5.32712601.32712900 | ENSG00000113389 | hyper |
| chr5.40680901.40681200 | ENSG00000171522 | hyper |
| chr5.42994801.42995100 | ENSG00000271788 | hyper |
| chr5.42995101.42995400 | ENSG00000271788 | hyper |
| chr5.54519301.54519600 | ENSG00000234602 | hyper |
| chr5.57878101.57878400 | ENSG00000152932 | hyper |
| chr5.63257401.63257700 | ENSG00000248285 | hyper |
| chr5.72528901.72529200 | ENSG00000249743 | hyper |
| chr5.72529201.72529500 | ENSG00000249743 | hyper |
| chr5.72596701.72597000 | ENSG00000249743 | hyper |
| chr5.72740101.72740400 | ENSG00000251493 | hyper |
| chr5.72740401.72740700 | ENSG00000251493 | hyper |
| chr5.80256601.80256900 | ENSG00000251450 | hyper |
| chr5.94955701.94956000 | ENSG00000178015 | hyper |
| chr5.95768101.95768400 | ENSG00000251314 | hyper |
| chr5.95768701.95769000 | ENSG00000251314 | hyper |
| chr5.115152001.115152300 | ENSG00000129596 | hyper |
| chr5.115152301.115152600 | ENSG00000129596 | hyper |
| chr5.122423401.122423700 | ENSG00000223652 | hyper |
| chr5.134376301.134376600 | ENSG00000224186 | hyper |
| chr5.134825101.134825400 | ENSG00000249639 | hyper |
| chr5.134825401.134825700 | ENSG00000249639 | hyper |
| chr5.134826001.134826300 | ENSG00000249639 | hyper |
| chr5.140012101.140012400 | ENSG00000170458 | hyper |
| chr5.140012401.140012700 | ENSG00000170458 | hyper |
| chr5.140346601.140346900 | ENSG00000204970 | hyper |
| chr5.154026901.154027200 | ENSG00000221552 | hyper |
| chr5.172672201.172672500 | ENSG00000183072 | hyper |
| chr6.1378501.1378800 | ENSG00000261730 | hyper |
| chr6.10421701.10422000 | ENSG00000228478 | hyper |

TABLE 5-continued

A list of ctDNA derived DMRs

| windowPos (Genomic position of each DMR) | ensemblId Gene ID (a DMR related to a gene) | DMR methylation level |
| --- | --- | --- |
| chr6.26721001.26721300 | ENSG00000261584 | hyper |
| chr6.26722501.26722800 | ENSG00000261584 | hyper |
| chr6.26722801.26723100 | ENSG00000261584 | hyper |
| chr6.26745301.26745600 | ENSG00000261584 | hyper |
| chr6.26778601.26778900 | ENSG00000241549 | hyper |
| chr6.26778901.26779200 | ENSG00000241549 | hyper |
| chr6.26779201.26779500 | ENSG00000241549 | hyper |
| chr6.27258301.27258600 | ENSG00000158553 | hyper |
| chr6.27462901.27463200 | ENSG00000270666 | hyper |
| chr6.27533701.27534000 | ENSG00000219738 | hyper |
| chr6.27534001.27534300 | ENSG00000219738 | hyper |
| chr6.27648601.27648900 | ENSG00000216676 | hyper |
| chr6.27648901.27649200 | ENSG00000216676 | hyper |
| chr6.28740901.28741200 | ENSG00000221191 | hyper |
| chr6.39281101.39281400 | ENSG00000124780 | hyper |
| chr6.58147501.58147800 | ENSG00000272541 | hyper |
| chr5.178978501.178978800 | ENSG00000176783 | hyper |
| chr6.28411201.28411500 | ENSG00000187987 | hyper |
| chr5.170742001.170742300 | ENSG00000164438 | hyper |
| chr5.172665301.172665600 | ENSG00000183072 | hyper |
| chr5.174158701.174159000 | ENSG00000120149 | hyper |
| chr5.174159001.174159300 | ENSG00000120149 | hyper |
| chr5.174159301.174159600 | ENSG00000120149 | hyper |
| chr5.174486901.174487200 | ENSG00000204754 | hyper |
| chr5.177666601.177666900 | ENSG00000050767 | hyper |
| chr5.178368001.178368300 | ENSG00000178187 | hyper |
| chr6.5026501.5026800 | ENSG00000272142 | hyper |
| chr6.6004201.6004500 | ENSG00000124785 | hyper |
| chr6.10382101.10382400 | ENSG00000137203 | hyper |
| chr6.26614201.26614500 | ENSG00000271071 | hyper |
| chr6.26614501.26614800 | ENSG00000271071 | hyper |
| chr6.26614801.26615100 | ENSG00000271071 | hyper |
| chr6.26721301.26721600 | ENSG00000261584 | hyper |
| chr6.26723101.26723400 | ENSG00000261584 | hyper |
| chr6.27279901.27280200 | ENSG00000158553 | hyper |
| chr6.27280201.27280500 | ENSG00000158553 | hyper |
| chr6.27463201.27463500 | ENSG00000270666 | hyper |
| chr6.28303801.28304100 | ENSG00000235109 | hyper |
| chr6.28367101.28367400 | ENSG00000158691 | hyper |
| chr6.28367401.28367700 | ENSG00000158691 | hyper |
| chr6.28414801.28415100 | ENSG00000231162 | hyper |
| chr6.28554901.28555200 | ENSG00000232040 | hyper |
| chr6.28602601.28602900 | ENSG00000271440 | hyper |
| chr6.28753801.28754100 | ENSG00000265764 | hyper |
| chr6.28778101.28778400 | ENSG00000265764 | hyper |
| chr6.32977201.32977500 | ENSG00000263756 | hyper |
| chr6.41341501.41341800 | ENSG00000238867 | hyper |
| chr6.50818801.50819100 | ENSG00000008196 | hyper |
| chr6.56716201.56716500 | ENSG00000151914 | hyper |
| chr6.58147201.58147500 | ENSG00000272541 | hyper |
| chr6.58147801.58148100 | ENSG00000272541 | hyper |
| chr6.58148401.58148700 | ENSG00000272541 | hyper |
| chr6.58148701.58149000 | ENSG00000272541 | hyper |
| chr6.62995501.62995800 | ENSG00000112232 | hyper |
| chr6.74024401.74024700 | ENSG00000135314 | hyper |
| chr6.75794701.75795000 | ENSG00000111799 | hyper |
| chr6.78172201.78172500 | ENSG00000135312 | hyper |
| chr6.78172501.78172800 | ENSG00000135312 | hyper |
| chr6.78173101.78173400 | ENSG00000135312 | hyper |
| chr6.85473001.85473300 | ENSG00000112837 | hyper |
| chr6.99291301.99291600 | ENSG00000184486 | hyper |
| chr6.100056001.100056300 | ENSG00000112238 | hyper |
| chr6.100441801.100442100 | ENSG00000152034 | hyper |
| chr6.100912501.100912800 | ENSG00000112246 | hyper |
| chr6.101847001.101847300 | ENSG00000164418 | hyper |
| chr6.106433701.106434000 | ENSG00000200198 | hyper |
| chr6.108440101.108440400 | ENSG00000081087 | hyper |
| chr6.108488401.108488700 | ENSG00000112333 | hyper |
| chr6.108488701.108489000 | ENSG00000112333 | hyper |
| chr6.108489301.108489600 | ENSG00000112333 | hyper |
| chr6.117086401.117086700 | ENSG00000183807 | hyper |
| chr6.117591301.117591600 | ENSG00000170162 | hyper |
| chr6.133562401.133562700 | ENSG00000112319 | hyper |
| chr6.133562701.133563000 | ENSG00000112319 | hyper |

TABLE 5-continued

A list of ctDNA derived DMRs

| windowPos (Genomic position of each DMR) | ensemblId Gene ID (a DMR related to a gene) | DMR methylation level |
|---|---|---|
| chr6.134214001.134214300 | ENSG00000118526 | hyper |
| chr6.137810401.137810700 | ENSG00000177468 | hyper |
| chr7.27260101.27260400 | ENSG00000243766 | hyper |
| chr7.35301001.35301300 | ENSG00000226063 | hyper |
| chr7.1959601.1959900 | ENSG00000002822 | hyper |
| chr7.8474701.8475000 | ENSG00000122584 | hyper |
| chr7.19184701.19185000 | ENSG00000229533 | hyper |
| chr6.137808901.137809200 | ENSG00000177468 | hyper |
| chr6.137816701.137817000 | ENSG00000177468 | hyper |
| chr6.151562401.151562700 | ENSG00000131016 | hyper |
| chr6.159654901.159655200 | ENSG00000164694 | hyper |
| chr6.166074601.166074900 | ENSG00000112541 | hyper |
| chr6.166580401.166580700 | ENSG00000164458 | hyper |
| chr6.166582801.166583100 | ENSG00000164458 | hyper |
| chr6.166583101.166583400 | ENSG00000164458 | hyper |
| chr7.1270801.1271100 | ENSG00000164853 | hyper |
| chr7.8475001.8475300 | ENSG00000122584 | hyper |
| chr7.8475301.8475600 | ENSG00000122584 | hyper |
| chr7.8481301.8481600 | ENSG00000122584 | hyper |
| chr7.8482501.8482800 | ENSG00000122584 | hyper |
| chr7.8482801.8483100 | ENSG00000122584 | hyper |
| chr7.15726601.15726900 | ENSG00000106511 | hyper |
| chr7.19146001.19146300 | ENSG00000122691 | hyper |
| chr7.19146301.19146600 | ENSG00000122691 | hyper |
| chr7.19146901.19147200 | ENSG00000122691 | hyper |
| chr7.19147201.19147500 | ENSG00000122691 | hyper |
| chr7.19152001.19152300 | ENSG00000122691 | hyper |
| chr7.19158001.19158300 | ENSG00000122691 | hyper |
| chr7.19158601.19158900 | ENSG00000236536 | hyper |
| chr7.19184401.19184700 | ENSG00000229533 | hyper |
| chr7.19185001.19185300 | ENSG00000229533 | hyper |
| chr7.22589401.22589700 | ENSG00000105889 | hyper |
| chr7.23507401.23507700 | ENSG00000136231 | hyper |
| chr7.24324301.24324600 | ENSG00000122585 | hyper |
| chr7.24324601.24324900 | ENSG00000122585 | hyper |
| chr7.27192301.27192600 | ENSG00000254369 | hyper |
| chr7.27196501.27196800 | ENSG00000122592 | hyper |
| chr7.27204301.27204600 | ENSG00000078399 | hyper |
| chr7.27204601.27204900 | ENSG00000078399 | hyper |
| chr7.27205201.27205500 | ENSG00000078399 | hyper |
| chr7.27205501.27205800 | ENSG00000078399 | hyper |
| chr7.27205801.27206100 | ENSG00000078399 | hyper |
| chr7.27206101.27206400 | ENSG00000078399 | hyper |
| chr7.27225001.27225300 | ENSG00000240990 | hyper |
| chr7.27244501.27244800 | ENSG00000243766 | hyper |
| chr7.27244801.27245100 | ENSG00000243766 | hyper |
| chr7.27252601.27252900 | ENSG00000243766 | hyper |
| chr7.27284701.27285000 | ENSG00000253405 | hyper |
| chr7.27291301.27291600 | ENSG00000106038 | hyper |
| chr7.27291601.27291900 | ENSG00000106038 | hyper |
| chr7.27291901.27292200 | ENSG00000106038 | hyper |
| chr7.30721201.30721500 | ENSG00000106113 | hyper |
| chr7.31092601.31092900 | ENSG00000078549 | hyper |
| chr7.35293201.35293500 | ENSG00000164532 | hyper |
| chr7.35297401.35297700 | ENSG00000226063 | hyper |
| chr7.35301301.35301600 | ENSG00000226063 | hyper |
| chr7.37955701.37956000 | ENSG00000086289 | hyper |
| chr7.52156201.52156500 | ENSG00000233960 | hyper |
| chr7.54609601.54609900 | ENSG00000170419 | hyper |
| chr7.64349101.64349400 | ENSG00000198039 | hyper |
| chr7.64349401.64349700 | ENSG00000198039 | hyper |
| chr7.71800801.71801100 | ENSG00000183166 | hyper |
| chr7.79083601.79083900 | ENSG00000234456 | hyper |
| chr7.88388101.88388400 | ENSG00000182348 | hyper |
| chr7.93203701.93204000 | ENSG00000004948 | hyper |
| chr7.93519301.93519600 | ENSG00000127928 | hyper |
| chr7.93519601.93519900 | ENSG00000127928 | hyper |
| chr7.94284901.94285200 | ENSG00000127990 | hyper |
| chr7.96647401.96647700 | ENSG00000105880 | hyper |
| chr7.96650701.96651000 | ENSG00000105880 | hyper |
| chr7.96651001.96651300 | ENSG00000105880 | hyper |
| chr7.97362301.97362600 | ENSG00000006128 | hyper |
| chr7.97362601.97362900 | ENSG00000006128 | hyper |
| chr7.97362901.97363200 | ENSG00000006128 | hyper |

TABLE 5-continued

A list of ctDNA derived DMRs

| windowPos (Genomic position of each DMR) | ensemblId Gene ID (a DMR related to a gene) | DMR methylation level |
|---|---|---|
| chr7.97363201.97363500 | ENSG00000006128 | hyper |
| chr7.107641801.107642100 | ENSG00000091136 | hyper |
| chr7.107642101.107642400 | ENSG00000091136 | hyper |
| chr7.113722801.113723100 | ENSG00000128573 | hyper |
| chr7.113723101.113723400 | ENSG00000128573 | hyper |
| chr8.99951301.99951600 | ENSG00000104375 | hyper |
| chr8.99951601.99951900 | ENSG00000104375 | hyper |
| chr8.99951901.99952200 | ENSG00000104375 | hyper |
| chr7.123173101.123173400 | ENSG00000164675 | hyper |
| chr8.38008201.38008500 | ENSG00000147465 | hyper |
| chr8.55372201.55372500 | ENSG00000164736 | hyper |
| chr8.60032401.60032700 | ENSG00000167912 | hyper |
| chr8.99960601.99960900 | ENSG00000164920 | hyper |
| chr7.117119401.117119700 | ENSG00000001626 | hyper |
| chr7.121956901.121957200 | ENSG00000081803 | hyper |
| chr7.123172801.123173100 | ENSG00000164675 | hyper |
| chr7.136554001.136554300 | ENSG00000234352 | hyper |
| chr7.136554301.136554600 | ENSG00000234352 | hyper |
| chr7.136554601.136554900 | ENSG00000234352 | hyper |
| chr7.136554901.136555200 | ENSG00000234352 | hyper |
| chr7.137532001.137532300 | ENSG00000157680 | hyper |
| chr7.137532301.137532600 | ENSG00000157680 | hyper |
| chr7.155241901.155242200 | ENSG00000236544 | hyper |
| chr7.155242801.155243100 | ENSG00000236544 | hyper |
| chr7.155243701.155244000 | ENSG00000236544 | hyper |
| chr7.155259301.155259600 | ENSG00000164778 | hyper |
| chr7.155259601.155259900 | ENSG00000164778 | hyper |
| chr7.155301601.155301900 | ENSG00000146910 | hyper |
| chr7.156795601.156795900 | ENSG00000130675 | hyper |
| chr7.156797101.156797400 | ENSG00000130675 | hyper |
| chr7.156797401.156797700 | ENSG00000130675 | hyper |
| chr7.156810901.156811200 | ENSG00000243479 | hyper |
| chr7.156811201.156811500 | ENSG00000243479 | hyper |
| chr7.157482001.157482300 | ENSG00000155093 | hyper |
| chr7.157482301.157482600 | ENSG00000155093 | hyper |
| chr8.4849501.4849800 | ENSG00000183117 | hyper |
| chr8.4849801.4850100 | ENSG00000183117 | hyper |
| chr8.21996601.21996900 | ENSG00000168476 | hyper |
| chr8.23563801.23564100 | ENSG00000180053 | hyper |
| chr8.23564101.23564400 | ENSG00000180053 | hyper |
| chr8.23564401.23564700 | ENSG00000253471 | hyper |
| chr8.24858901.24859200 | ENSG00000253832 | hyper |
| chr8.25905001.25905300 | ENSG00000221818 | hyper |
| chr8.33372001.33372300 | ENSG00000129696 | hyper |
| chr8.33372301.33372600 | ENSG00000129696 | hyper |
| chr8.37655701.37656000 | ENSG00000020181 | hyper |
| chr8.55366201.55366500 | ENSG00000164736 | hyper |
| chr8.55367101.55367400 | ENSG00000164736 | hyper |
| chr8.55367401.55367700 | ENSG00000164736 | hyper |
| chr8.57026101.57026400 | ENSG00000172680 | hyper |
| chr8.65283301.65283600 | ENSG00000253554 | hyper |
| chr8.65290801.65291100 | ENSG00000254377 | hyper |
| chr8.65499601.65499900 | ENSG00000172817 | hyper |
| chr8.67873501.67873800 | ENSG00000261787 | hyper |
| chr8.70981801.70982100 | ENSG00000147596 | hyper |
| chr8.70983901.70984200 | ENSG00000147596 | hyper |
| chr8.70984201.70984500 | ENSG00000147596 | hyper |
| chr8.72470401.72470700 | ENSG00000253379 | hyper |
| chr8.72471001.72471300 | ENSG00000253379 | hyper |
| chr8.72754501.72754800 | ENSG00000235531 | hyper |
| chr8.72754801.72755100 | ENSG00000235531 | hyper |
| chr8.72917101.72917400 | ENSG00000235531 | hyper |
| chr8.72917401.72917700 | ENSG00000235531 | hyper |
| chr8.76316701.76317000 | ENSG00000164749 | hyper |
| chr8.76317001.76317300 | ENSG00000164749 | hyper |
| chr8.85094401.85094700 | ENSG00000184672 | hyper |
| chr8.85094701.85095000 | ENSG00000184672 | hyper |
| chr8.93114001.93114300 | ENSG00000079102 | hyper |
| chr8.97167001.97167300 | ENSG00000156466 | hyper |
| chr8.97170001.97170300 | ENSG00000156466 | hyper |
| chr8.97170301.97170600 | ENSG00000156466 | hyper |
| chr8.97170601.97170900 | ENSG00000156466 | hyper |
| chr8.99952201.99952500 | ENSG00000104375 | hyper |
| chr8.99960301.99960600 | ENSG00000164920 | hyper |

TABLE 5-continued

A list of ctDNA derived DMRs

| windowPos (Genomic position of each DMR) | ensemblId Gene ID (a DMR related to a gene) | DMR methylation level |
|---|---|---|
| chr8.99960901.99961200 | ENSG00000164920 | hyper |
| chr8.99961201.99961500 | ENSG00000164920 | hyper |
| chr8.99986101.99986400 | ENSG00000229625 | hyper |
| chr9.970801.971100 | ENSG00000137090 | hyper |
| chr9.1045201.1045500 | ENSG00000173253 | hyper |
| chr9.1045801.1046100 | ENSG00000173253 | hyper |
| chr9.41454901.41455200 | ENSG00000237625 | hyper |
| chr9.79629301.79629600 | ENSG00000204612 | hyper |
| chr8.132053701.132054000 | ENSG00000155897 | hyper |
| chr8.109094701.109095000 | ENSG00000147655 | hyper |
| chr8.114444601.114444900 | ENSG00000164796 | hyper |
| chr8.114444901.114445200 | ENSG00000164796 | hyper |
| chr8.114447001.114447300 | ENSG00000164796 | hyper |
| chr8.132053401.132053700 | ENSG00000155897 | hyper |
| chr8.132054001.132054300 | ENSG00000155897 | hyper |
| chr9.117001.117300 | ENSG00000170122 | hyper |
| chr9.117301.117600 | ENSG00000170122 | hyper |
| chr9.117601.117900 | ENSG00000170122 | hyper |
| chr9.117901.118200 | ENSG00000170122 | hyper |
| chr9.843001.843300 | ENSG00000137090 | hyper |
| chr9.843301.843600 | ENSG00000137090 | hyper |
| chr9.973501.973800 | ENSG00000064218 | hyper |
| chr9.1042501.1042800 | ENSG00000173253 | hyper |
| chr9.1045501.1045800 | ENSG00000173253 | hyper |
| chr9.17907001.17907300 | ENSG00000107295 | hyper |
| chr9.19788301.19788600 | ENSG00000155886 | hyper |
| chr9.19788601.19788900 | ENSG00000155886 | hyper |
| chr9.34809601.34809900 | ENSG00000257198 | hyper |
| chr9.36739501.36739800 | ENSG00000165304 | hyper |
| chr9.36739801.36740100 | ENSG00000165304 | hyper |
| chr9.69201001.69201300 | ENSG00000204793 | hyper |
| chr9.79628701.79629000 | ENSG00000204612 | hyper |
| chr9.79629001.79629300 | ENSG00000204612 | hyper |
| chr9.79630501.79630800 | ENSG00000204612 | hyper |
| chr9.79631401.79631700 | ENSG00000204612 | hyper |
| chr9.79636801.79637100 | ENSG00000204612 | hyper |
| chr9.90114001.90114300 | ENSG00000196730 | hyper |
| chr9.96713401.96713700 | ENSG00000131668 | hyper |
| chr9.96715201.96715500 | ENSG00000131668 | hyper |
| chr9.100610701.100611000 | ENSG00000178919 | hyper |
| chr9.100611301.100611600 | ENSG00000178919 | hyper |
| chr9.133537201.133537500 | ENSG00000130711 | hyper |
| chr10.102996001.102996300 | ENSG00000227128 | hyper |
| chr10.102997201.102997500 | ENSG00000227128 | hyper |
| chr9.124414501.124414800 | ENSG00000136848 | hyper |
| chr9.126775201.126775500 | ENSG00000106689 | hyper |
| chr9.126777301.126777600 | ENSG00000106689 | hyper |
| chr9.127212901.127213200 | ENSG00000180264 | hyper |
| chr9.129380401.129380700 | ENSG00000136944 | hyper |
| chr9.129386101.129386400 | ENSG00000136944 | hyper |
| chr10.8076901.8077200 | ENSG00000197308 | hyper |
| chr10.8077201.8077500 | ENSG00000197308 | hyper |
| chr10.21783301.21783600 | ENSG00000204682 | hyper |
| chr10.22765501.22765800 | ENSG00000077327 | hyper |
| chr10.23462101.23462400 | ENSG00000168267 | hyper |
| chr10.23480401.23480700 | ENSG00000168267 | hyper |
| chr10.28035001.28035300 | ENSG00000230500 | hyper |
| chr10.44879101.44879400 | ENSG00000107562 | hyper |
| chr10.50605501.50605800 | ENSG00000165606 | hyper |
| chr10.63212401.63212700 | ENSG00000196932 | hyper |
| chr10.71337601.71337900 | ENSG00000236154 | hyper |
| chr10.94828201.94828500 | ENSG00000187553 | hyper |
| chr10.94833901.94834200 | ENSG00000095596 | hyper |
| chr10.102894901.102895200 | ENSG00000107807 | hyper |
| chr10.102996301.102996600 | ENSG00000227128 | hyper |
| chr10.106400401.106400700 | ENSG00000156395 | hyper |
| chr10.110671801.110672100 | ENSG00000222436 | hyper |
| chr10.118031101.118031400 | ENSG00000151892 | hyper |
| chr10.118031401.118031700 | ENSG00000151892 | hyper |
| chr10.118033801.118034100 | ENSG00000151892 | hyper |
| chr10.118891501.118891800 | ENSG00000148704 | hyper |
| chr10.118892401.118892700 | ENSG00000148704 | hyper |
| chr10.119301301.119301600 | ENSG00000229847 | hyper |
| chr10.119304901.119305200 | ENSG00000170370 | hyper |

TABLE 5-continued

A list of ctDNA derived DMRs

| windowPos (Genomic position of each DMR) | ensemblId Gene ID (a DMR related to a gene) | DMR methylation level |
|---|---|---|
| chr10.119305201.119305500 | ENSG00000170370 | hyper |
| chr10.119494201.119494500 | ENSG00000234952 | hyper |
| chr10.119494501.119494800 | ENSG00000234952 | hyper |
| chr11.18813901.18814200 | ENSG00000110786 | hyper |
| chr11.31826401.31826700 | ENSG00000007372 | hyper |
| chr11.69832501.69832800 | ENSG00000202070 | hyper |
| chr10.122709601.122709900 | ENSG00000227307 | hyper |
| chr10.124896601.124896900 | ENSG00000188620 | hyper |
| chr10.124905601.124905900 | ENSG00000188816 | hyper |
| chr10.124908901.124909200 | ENSG00000188816 | hyper |
| chr10.131761201.131761500 | ENSG00000108001 | hyper |
| chr10.131767801.131768100 | ENSG00000108001 | hyper |
| chr11.7041601.7041900 | ENSG00000158077 | hyper |
| chr11.14995501.14995800 | ENSG00000175868 | hyper |
| chr11.22363201.22363500 | ENSG00000091664 | hyper |
| chr11.31825801.31826100 | ENSG00000007372 | hyper |
| chr11.31826101.31826400 | ENSG00000007372 | hyper |
| chr11.31827001.31827300 | ENSG00000007372 | hyper |
| chr11.32454601.32454900 | ENSG00000184937 | hyper |
| chr11.32455801.32456100 | ENSG00000184937 | hyper |
| chr11.32459401.32459700 | ENSG00000183242 | hyper |
| chr11.32459701.32460000 | ENSG00000183242 | hyper |
| chr11.35641801.35642100 | ENSG00000179431 | hyper |
| chr11.43602901.43603200 | ENSG00000149084 | hyper |
| chr11.62693701.62694000 | ENSG00000168539 | hyper |
| chr11.66188701.66189000 | ENSG00000174576 | hyper |
| chr11.69451501.69451800 | ENSG00000110092 | hyper |
| chr11.69451801.69452100 | ENSG00000110092 | hyper |
| chr11.69452101.69452400 | ENSG00000110092 | hyper |
| chr11.69452401.69452700 | ENSG00000110092 | hyper |
| chr11.69517501.69517800 | ENSG00000162344 | hyper |
| chr11.69517801.69518100 | ENSG00000162344 | hyper |
| chr11.69831901.69832200 | ENSG00000202070 | hyper |
| chr11.69832201.69832500 | ENSG00000202070 | hyper |
| chr11.70211401.70211700 | ENSG00000131626 | hyper |
| chr11.91958401.91958700 | ENSG00000242248 | hyper |
| chr11.100999201.100999500 | ENSG00000082175 | hyper |
| chr11.100999501.100999800 | ENSG00000082175 | hyper |
| chr11.101453101.101453400 | ENSG00000137672 | hyper |
| chr11.101453401.101453700 | ENSG00000137672 | hyper |
| chr11.122848201.122848500 | ENSG00000188909 | hyper |
| chr11.123066601.123066900 | ENSG00000254710 | hyper |
| chr12.54424501.54424800 | ENSG00000273049 | hyper |
| chr12.106974901.106975200 | ENSG00000257545 | hyper |
| chr12.115173301.115173600 | ENSG00000257817 | hyper |
| chr12.128752501.128752800 | ENSG00000181234 | hyper |
| chr12.6184501.6184800 | ENSG00000110799 | hyper |
| chr12.14134201.14134500 | ENSG00000273079 | hyper |
| chr12.16500601.16500900 | ENSG00000008394 | hyper |
| chr12.22093801.22094100 | ENSG00000069431 | hyper |
| chr12.22094701.22095000 | ENSG00000069431 | hyper |
| chr12.25056301.25056600 | ENSG00000060982 | hyper |
| chr12.30323101.30323400 | ENSG00000257262 | hyper |
| chr12.43944901.43945200 | ENSG00000173157 | hyper |
| chr12.48397201.48397500 | ENSG00000139219 | hyper |
| chr12.54321301.54321600 | ENSG00000249641 | hyper |
| chr12.54329701.54330000 | ENSG00000249641 | hyper |
| chr12.54338701.54339000 | ENSG00000123364 | hyper |
| chr12.54339001.54339300 | ENSG00000123364 | hyper |
| chr12.54339301.54339600 | ENSG00000123364 | hyper |
| chr12.54345901.54346200 | ENSG00000123407 | hyper |
| chr12.54354601.54354900 | ENSG00000228630 | hyper |
| chr12.54408301.54408600 | ENSG00000273049 | hyper |
| chr12.54408601.54408900 | ENSG00000273049 | hyper |
| chr12.54423301.54423600 | ENSG00000273049 | hyper |
| chr12.54424801.54425100 | ENSG00000273049 | hyper |
| chr12.54441001.54441300 | ENSG00000198353 | hyper |
| chr12.58021801.58022100 | ENSG00000135454 | hyper |
| chr12.81471601.81471900 | ENSG00000111058 | hyper |
| chr12.85673101.85673400 | ENSG00000180318 | hyper |
| chr12.85673401.85673700 | ENSG00000180318 | hyper |
| chr12.85674301.85674600 | ENSG00000180318 | hyper |
| chr12.95941801.95942100 | ENSG00000136014 | hyper |
| chr12.103344301.103344600 | ENSG00000171759 | hyper |

TABLE 5-continued

A list of ctDNA derived DMRs

| windowPos (Genomic position of each DMR) | ensemblId Gene ID (a DMR related to a gene) | DMR methylation level |
|---|---|---|
| chr12.106979401.106979700 | ENSG00000257545 | hyper |
| chr12.114838201.114838500 | ENSG00000089225 | hyper |
| chr12.114845701.114846000 | ENSG00000089225 | hyper |
| chr12.114846301.114846600 | ENSG00000255399 | hyper |
| chr12.114846601.114846900 | ENSG00000255399 | hyper |
| chr12.114847501.114847800 | ENSG00000255399 | hyper |
| chr12.114878101.114878400 | ENSG00000255399 | hyper |
| chr12.114878401.114878700 | ENSG00000255399 | hyper |
| chr12.114878701.114879000 | ENSG00000255399 | hyper |
| chr12.115107301.115107600 | ENSG00000135111 | hyper |
| chr12.115109401.115109700 | ENSG00000135111 | hyper |
| chr12.115173601.115173900 | ENSG00000257817 | hyper |
| chr12.128752201.128752500 | ENSG00000181234 | hyper |
| chr12.133484701.133485000 | ENSG00000072609 | hyper |
| chr12.133485001.133485300 | ENSG00000072609 | hyper |
| chr12.133485301.133485600 | ENSG00000072609 | hyper |
| chr13.58203601.58203900 | ENSG00000118946 | hyper |
| chr13.112716601.112716900 | ENSG00000182968 | hyper |
| chr13.78493201.78493500 | ENSG00000136160 | hyper |
| chr14.38724601.38724900 | ENSG00000176435 | hyper |
| chr14.38724901.38725200 | ENSG00000176435 | hyper |
| chr14.42077401.42077700 | ENSG00000165379 | hyper |
| chr13.23500201.23500500 | ENSG00000262198 | hyper |
| chr13.25320301.25320600 | ENSG00000231417 | hyper |
| chr13.25320601.25320900 | ENSG00000231417 | hyper |
| chr13.28492201.28492500 | ENSG00000247381 | hyper |
| chr13.28552801.28553100 | ENSG00000183463 | hyper |
| chr13.28674001.28674300 | ENSG00000122025 | hyper |
| chr13.58203901.58204200 | ENSG00000118946 | hyper |
| chr13.58206001.58206300 | ENSG00000118946 | hyper |
| chr13.78492901.78493200 | ENSG00000136160 | hyper |
| chr13.79170601.79170900 | ENSG00000234377 | hyper |
| chr13.95354701.95355000 | ENSG00000238230 | hyper |
| chr13.100608601.100608900 | ENSG00000139800 | hyper |
| chr13.100620301.100620600 | ENSG00000139800 | hyper |
| chr13.100641301.100641600 | ENSG00000043355 | hyper |
| chr13.100641601.100641900 | ENSG00000043355 | hyper |
| chr13.100641901.100642200 | ENSG00000043355 | hyper |
| chr13.108520201.108520500 | ENSG00000204442 | hyper |
| chr13.108520501.108520800 | ENSG00000204442 | hyper |
| chr13.108520801.108521100 | ENSG00000204442 | hyper |
| chr13.109147501.109147800 | ENSG00000232087 | hyper |
| chr13.109148401.109148700 | ENSG00000232087 | hyper |
| chr13.109148701.109149000 | ENSG00000232087 | hyper |
| chr13.112708501.112708800 | ENSG00000200072 | hyper |
| chr13.112712401.112712700 | ENSG00000200072 | hyper |
| chr14.29234701.29235000 | ENSG00000176165 | hyper |
| chr14.29235101.29235300 | ENSG00000176165 | hyper |
| chr14.29254501.29254800 | ENSG00000186960 | hyper |
| chr14.36979801.36980100 | ENSG00000257520 | hyper |
| chr14.36982201.36982500 | ENSG00000257520 | hyper |
| chr14.36982501.36982800 | ENSG00000257520 | hyper |
| chr14.36983401.36983700 | ENSG00000257520 | hyper |
| chr14.36983701.36984000 | ENSG00000257520 | hyper |
| chr14.36991801.36992100 | ENSG00000253563 | hyper |
| chr14.37116301.37116600 | ENSG00000258661 | hyper |
| chr14.37123501.37123800 | ENSG00000258661 | hyper |
| chr14.37128601.37128900 | ENSG00000198807 | hyper |
| chr14.38724301.38724600 | ENSG00000176435 | hyper |
| chr14.42074401.42074700 | ENSG00000258636 | hyper |
| chr14.52781701.52782000 | ENSG00000125384 | hyper |
| chr15.45996601.45996900 | ENSG00000259200 | hyper |
| chr15.75251401.75251700 | ENSG00000198794 | hyper |
| chr15.79383001.79383300 | ENSG00000058335 | hyper |
| chr14.52534801.52535100 | ENSG00000087303 | hyper |
| chr14.52535101.52535400 | ENSG00000087303 | hyper |
| chr14.52535401.52535700 | ENSG00000087303 | hyper |
| chr14.52536001.52536300 | ENSG00000087303 | hyper |
| chr14.52536301.52536600 | ENSG00000087303 | hyper |
| chr14.52734901.52735200 | ENSG00000168229 | hyper |
| chr14.52735501.52735800 | ENSG00000168229 | hyper |
| chr14.57261901.57262200 | ENSG00000270163 | hyper |
| chr14.57274801.57275100 | ENSG00000165588 | hyper |
| chr14.57275101.57275400 | ENSG00000165588 | hyper |

TABLE 5-continued

A list of ctDNA derived DMRs

| windowPos (Genomic position of each DMR) | ensemblId Gene ID (a DMR related to a gene) | DMR methylation level |
|---|---|---|
| chr14.57275401.57275700 | ENSG00000165588 | hyper |
| chr14.57276301.57276600 | ENSG00000165588 | hyper |
| chr14.57278701.57279000 | ENSG00000248550 | hyper |
| chr14.57279001.57279300 | ENSG00000248550 | hyper |
| chr14.60386401.60386700 | ENSG00000261120 | hyper |
| chr14.60975301.60975600 | ENSG00000179008 | hyper |
| chr14.60976201.60976500 | ENSG00000179008 | hyper |
| chr14.60976501.60976800 | ENSG00000179008 | hyper |
| chr14.61104601.61104900 | ENSG00000258952 | hyper |
| chr14.61109101.61109400 | ENSG00000258952 | hyper |
| chr14.61109701.61110000 | ENSG00000126778 | hyper |
| chr14.61110001.61110300 | ENSG00000126778 | hyper |
| chr14.61110601.61110900 | ENSG00000126778 | hyper |
| chr14.95234701.95235000 | ENSG00000133937 | hyper |
| chr14.95237701.95238000 | ENSG00000133937 | hyper |
| chr14.95238001.95238300 | ENSG00000133937 | hyper |
| chr14.99713101.99713400 | ENSG00000127152 | hyper |
| chr15.53075701.53076000 | ENSG00000169856 | hyper |
| chr15.53076601.53076900 | ENSG00000169856 | hyper |
| chr15.53080801.53081100 | ENSG00000169856 | hyper |
| chr15.76632001.76632300 | ENSG00000159556 | hyper |
| chr15.76633201.76633500 | ENSG00000159556 | hyper |
| chr15.79382701.79383000 | ENSG00000058335 | hyper |
| chr15.81410701.81411000 | ENSG00000156206 | hyper |
| chr15.88800601.88800900 | ENSG00000260305 | hyper |
| chr15.89903401.89903700 | ENSG00000255571 | hyper |
| chr15.89949301.89949600 | ENSG00000255571 | hyper |
| chr15.89949601.89949900 | ENSG00000255571 | hyper |
| chr15.89949901.89950200 | ENSG00000255571 | hyper |
| chr15.89952001.89952300 | ENSG00000255571 | hyper |
| chr16.51189001.51189300 | ENSG00000103449 | hyper |
| chr16.54324001.54324300 | ENSG00000177508 | hyper |
| chr17.46796401.46796700 | ENSG00000159182 | hyper |
| chr17.46832101.46832400 | ENSG00000170703 | hyper |
| chr17.48042901.48043200 | ENSG00000199492 | hyper |
| chr15.95388301.95388600 | ENSG00000260521 | hyper |
| chr15.95388601.95388900 | ENSG00000260521 | hyper |
| chr16.51184801.51185100 | ENSG00000103449 | hyper |
| chr16.89268601.89268900 | ENSG00000259803 | hyper |
| chr17.5974201.5974500 | ENSG00000179314 | hyper |
| chr15.96911401.96911700 | ENSG00000259275 | hyper |
| chr15.96959401.96959700 | ENSG00000259542 | hyper |
| chr16.3220501.3220800 | ENSG00000262521 | hyper |
| chr16.12994501.12994800 | ENSG00000237515 | hyper |
| chr16.12994801.12995100 | ENSG00000237515 | hyper |
| chr16.29086201.29086500 | ENSG00000260908 | hyper |
| chr16.49314601.49314900 | ENSG00000102924 | hyper |
| chr16.49314901.49315200 | ENSG00000102924 | hyper |
| chr16.51190201.51190500 | ENSG00000103449 | hyper |
| chr16.54318001.54318300 | ENSG00000177508 | hyper |
| chr16.54322201.54322500 | ENSG00000177508 | hyper |
| chr16.54970501.54970800 | ENSG00000259711 | hyper |
| chr16.54971401.54971700 | ENSG00000259711 | hyper |
| chr16.54971701.54972000 | ENSG00000259711 | hyper |
| chr16.54972301.54972600 | ENSG00000259711 | hyper |
| chr16.55362901.55363200 | ENSG00000259283 | hyper |
| chr16.55363201.55363500 | ENSG00000259283 | hyper |
| chr16.55364701.55365000 | ENSG00000259283 | hyper |
| chr16.55365001.55365300 | ENSG00000259283 | hyper |
| chr16.55365301.55365600 | ENSG00000259283 | hyper |
| chr16.56672101.56672400 | ENSG00000205362 | hyper |
| chr16.86529901.86530200 | ENSG00000268388 | hyper |
| chr17.7976101.7976400 | ENSG00000179477 | hyper |
| chr17.8868601.8868900 | ENSG00000141506 | hyper |
| chr17.8907601.8907900 | ENSG00000065320 | hyper |
| chr17.26554801.26555100 | ENSG00000237575 | hyper |
| chr17.27942301.27942600 | ENSG00000264031 | hyper |
| chr17.35285401.35285700 | ENSG00000255509 | hyper |
| chr17.36103201.36103500 | ENSG00000108753 | hyper |
| chr17.36103501.36103800 | ENSG00000108753 | hyper |
| chr17.36103801.36104100 | ENSG00000108753 | hyper |
| chr17.36104101.36104400 | ENSG00000108753 | hyper |
| chr17.37321501.37321800 | ENSG00000141748 | hyper |
| chr17.43974601.43974900 | ENSG00000186868 | hyper |

TABLE 5-continued

A list of ctDNA derived DMRs

| windowPos (Genomic position of each DMR) | ensemblId Gene ID (a DMR related to a gene) | DMR methylation level |
|---|---|---|
| chr17.46673701.46674000 | ENSG00000120093 | hyper |
| chr17.46796101.46796400 | ENSG00000159182 | hyper |
| chr17.46811701.46812000 | ENSG00000242407 | hyper |
| chr17.46824901.46825200 | ENSG00000242407 | hyper |
| chr17.47301901.47302200 | ENSG00000173868 | hyper |
| chr17.48042301.48042600 | ENSG00000199492 | hyper |
| chr17.48042601.48042900 | ENSG00000199492 | hyper |
| chr18.19746901.19747200 | ENSG00000266010 | hyper |
| chr19.2488501.2488800 | ENSG00000099860 | hyper |
| chr17.70113301.70113600 | ENSG00000234899 | hyper |
| chr18.907201.907500 | ENSG00000265671 | hyper |
| chr18.22929301.22929600 | ENSG00000198795 | hyper |
| chr18.44335801.44336100 | ENSG00000101638 | hyper |
| chr18.49868401.49868700 | ENSG00000187323 | hyper |
| chr19.20606101.20606400 | ENSG00000231205 | hyper |
| chr19.20606401.20606700 | ENSG00000231205 | hyper |
| chr19.37287901.37288200 | ENSG00000267254 | hyper |
| chr19.37288201.37288500 | ENSG00000267254 | hyper |
| chr19.38042401.38042700 | ENSG00000267470 | hyper |
| chr17.59534701.59535000 | ENSG00000121075 | hyper |
| chr17.62075101.62075400 | ENSG00000264954 | hyper |
| chr17.70112401.70112700 | ENSG00000234899 | hyper |
| chr17.70112701.70113000 | ENSG00000234899 | hyper |
| chr17.75370201.75370500 | ENSG00000184640 | hyper |
| chr18.905101.905400 | ENSG00000265671 | hyper |
| chr18.906601.906900 | ENSG00000265671 | hyper |
| chr18.906901.907200 | ENSG00000265671 | hyper |
| chr18.10032601.10032900 | ENSG00000263630 | hyper |
| chr18.12307501.12307800 | ENSG00000176014 | hyper |
| chr18.19745701.19746000 | ENSG00000266010 | hyper |
| chr18.19747501.19747800 | ENSG00000266010 | hyper |
| chr18.22929001.22929300 | ENSG00000198795 | hyper |
| chr18.31803001.31803300 | ENSG00000101746 | hyper |
| chr18.44790001.44790300 | ENSG00000215474 | hyper |
| chr18.55105801.55106100 | ENSG00000119547 | hyper |
| chr18.63418501.63418800 | ENSG00000081138 | hyper |
| chr18.63418801.63419100 | ENSG00000081138 | hyper |
| chr18.67068601.67068900 | ENSG00000206052 | hyper |
| chr18.67068901.67069200 | ENSG00000206052 | hyper |
| chr18.74961601.74961900 | ENSG00000166573 | hyper |
| chr18.76734601.76734900 | ENSG00000263146 | hyper |
| chr19.9608701.9609000 | ENSG00000198028 | hyper |
| chr19.12306001.12306300 | ENSG00000234773 | hyper |
| chr19.16479901.16480200 | ENSG00000127527 | hyper |
| chr19.20844001.20844300 | ENSG00000269110 | hyper |
| chr19.21182701.21183000 | ENSG00000268326 | hyper |
| chr19.22715101.22715400 | ENSG00000197360 | hyper |
| chr19.38182801.38183100 | ENSG00000120784 | hyper |
| chr19.38183101.38183400 | ENSG00000120784 | hyper |
| chr20.55500001.55500300 | ENSG00000251772 | hyper |
| chr19.46907401.46907700 | ENSG00000169515 | hyper |
| chr19.46993201.46993500 | ENSG00000230510 | hyper |
| chr19.48918001.48918300 | ENSG00000105464 | hyper |
| chr19.48918301.48918600 | ENSG00000105464 | hyper |
| chr19.58238401.58238700 | ENSG00000269026 | hyper |
| chr21.38082901.38083200 | ENSG00000159263 | hyper |
| chr21.46360201.46360500 | ENSG00000160256 | hyper |
| chr19.44952301.44952600 | ENSG00000267188 | hyper |
| chr19.44952601.44952900 | ENSG00000267188 | hyper |
| chr19.46929901.46930200 | ENSG00000169515 | hyper |
| chr19.52839301.52839600 | ENSG00000269535 | hyper |
| chr19.52839601.52839900 | ENSG00000269535 | hyper |
| chr19.52873201.52873500 | ENSG00000221923 | hyper |
| chr19.53073301.53073600 | ENSG00000167562 | hyper |
| chr19.54401701.54402000 | ENSG00000126583 | hyper |
| chr19.56879701.56880000 | ENSG00000131848 | hyper |
| chr19.56904901.56905200 | ENSG00000018869 | hyper |
| chr19.56989201.56989500 | ENSG00000198046 | hyper |
| chr19.56989501.56989800 | ENSG00000166770 | hyper |
| chr19.58095001.58095300 | ENSG00000171649 | hyper |
| chr19.58220401.58220700 | ENSG00000204519 | hyper |
| chr19.58238701.58239000 | ENSG00000269026 | hyper |
| chr19.58400101.58400400 | ENSG00000204514 | hyper |
| chr19.58520701.58521000 | ENSG00000176593 | hyper |
| chr19.58873201.58873500 | ENSG00000268230 | hyper |
| chr19.58951201.58951500 | ENSG00000131849 | hyper |
| chr19.58951501.58951800 | ENSG00000131849 | hyper |
| chr20.291001.291300 | ENSG00000225377 | hyper |
| chr20.865801.866100 | ENSG00000101280 | hyper |
| chr20.5296201.5296500 | ENSG00000101292 | hyper |
| chr20.5296501.5296800 | ENSG00000101292 | hyper |
| chr20.5296801.5297100 | ENSG00000101292 | hyper |
| chr20.5297101.5297400 | ENSG00000101292 | hyper |
| chr20.9489301.9489600 | ENSG00000225988 | hyper |
| chr20.9495301.9495600 | ENSG00000225988 | hyper |
| chr20.10198501.10198800 | ENSG00000227906 | hyper |
| chr20.21501901.21502200 | ENSG00000125820 | hyper |
| chr20.21681901.21682200 | ENSG00000125813 | hyper |
| chr20.21687301.21687600 | ENSG00000125813 | hyper |
| chr20.21694201.21694500 | ENSG00000125813 | hyper |
| chr20.21694501.21694800 | ENSG00000125813 | hyper |
| chr20.21694801.21695100 | ENSG00000125813 | hyper |
| chr20.22548901.22549200 | ENSG00000259974 | hyper |
| chr20.22549201.22549500 | ENSG00000259974 | hyper |
| chr20.22558201.22558500 | ENSG00000259974 | hyper |
| chr20.22563601.22563900 | ENSG00000125798 | hyper |
| chr20.37356301.37356600 | ENSG00000101438 | hyper |
| chr20.37357501.37357800 | ENSG00000101438 | hyper |
| chr20.45087601.45087900 | ENSG00000215452 | hyper |
| chr20.45087901.45088200 | ENSG00000215452 | hyper |
| chr20.55500901.55501200 | ENSG00000251772 | hyper |
| chr21.22369801.22370100 | ENSG00000154654 | hyper |
| chr21.34398301.34398600 | ENSG00000227757 | hyper |
| chr21.34398601.34398900 | ENSG00000227757 | hyper |
| chr21.34443301.34443600 | ENSG00000227757 | hyper |
| chr21.34444201.34444500 | ENSG00000184221 | hyper |
| chr21.38066701.38067000 | ENSG00000224269 | hyper |
| chr21.38069401.38069700 | ENSG00000224269 | hyper |
| chr21.38069701.38070000 | ENSG00000224269 | hyper |
| chr21.38077201.38077500 | ENSG00000159263 | hyper |
| chr21.38077501.38077800 | ENSG00000159263 | hyper |
| chr22.48963001.48963300 | ENSG00000219438 | hyper |
| chr22.50629801.50630100 | ENSG00000170638 | hyper |
| chr22.51042001.51042300 | ENSG00000008735 | hyper |
| chr1.147736201.147736500 | ENSG00000199879 | hypo |
| chr1.27319201.27319500 | ENSG00000253368 | hypo |
| chr1.50489401.50489700 | ENSG00000186094 | hypo |
| chr1.11097601.11097900 | ENSG00000009724 | hypo |
| chr2.26593501.26593800 | ENSG00000138018 | hypo |
| chr2.39004801.39005100 | ENSG00000152147 | hypo |
| chr1.155826901.155827200 | ENSG00000116580 | hypo |
| chr2.44314201.44314500 | ENSG00000219391 | hypo |
| chr2.96810301.96810600 | ENSG00000158050 | hypo |
| chr2.96970501.96970800 | ENSG00000144028 | hypo |
| chr2.239685301.239685600 | ENSG00000226992 | hypo |
| chr4.181317301.181317600 | ENSG00000251025 | hypo |
| chr4.159644701.159645000 | ENSG00000171497 | hypo |
| chr5.391201.391500 | ENSG00000063438 | hypo |
| chr5.5886901.5887200 | ENSG00000261037 | hypo |
| chr5.34306501.34306800 | ENSG00000215158 | hypo |
| chr5.125937001.125937300 | ENSG00000164902 | hypo |
| chr6.35181601.35181900 | ENSG00000146197 | hypo |
| chr6.114180901.114181200 | ENSG00000155130 | hypo |
| chr5.170745301.170745600 | ENSG00000164438 | hypo |
| chr6.37070101.37070400 | ENSG00000216412 | hypo |
| chr7.6387901.6388200 | ENSG00000178397 | hypo |
| chr7.5553601.5553900 | ENSG00000155034 | hypo |
| chr7.57484501.57484800 | ENSG00000270957 | hypo |
| chr7.130275301.130275600 | ENSG00000239021 | hypo |
| chr8.17770201.17770500 | ENSG00000104760 | hypo |
| chr9.1009201.1009500 | ENSG00000228783 | hypo |
| chr9.132388201.132388500 | ENSG00000148335 | hypo |
| chr9.136890301.136890600 | ENSG00000235106 | hypo |
| chr10.71905201.71905500 | ENSG00000156521 | hypo |
| chr10.1584301.1584600 | ENSG00000185736 | hypo |
| chr11.1404601.1404900 | ENSG00000174672 | hypo |
| chr12.52317301.52317600 | ENSG00000139567 | hypo |
| chr12.122459101.122459400 | ENSG00000110987 | hypo |

TABLE 5-continued

A list of ctDNA derived DMRs

| windowPos (Genomic position of each DMR) | ensemblId Gene ID (a DMR related to a gene) | DMR methylation level |
|---|---|---|
| chr12.122687701.122688000 | ENSG00000158113 | hypo |
| chr12.130527001.130527300 | ENSG00000261650 | hypo |
| chr12.133050001.133050300 | ENSG00000269676 | hypo |
| chr14.50540401.50540700 | ENSG00000273065 | hypo |
| chr14.103995001.103995300 | ENSG00000260285 | hypo |
| chr17.17739301.17739600 | ENSG00000072310 | hypo |
| chr16.67562401.67562700 | ENSG00000039523 | hypo |
| chr16.84545101.84545400 | ENSG00000140950 | hypo |
| chr16.89939401.89939700 | ENSG00000141002 | hypo |
| chr17.46184401.46184700 | ENSG00000002919 | hypo |
| chr16.3209101.3209400 | ENSG00000261889 | hypo |
| chr19.17457001.17457300 | ENSG00000130299 | hypo |
| chr19.30363901.30364200 | ENSG00000267433 | hypo |
| chr17.75468301.75468600 | ENSG00000184640 | hypo |
| chr17.81082801.81083100 | ENSG00000262898 | hypo |
| chr19.8408101.8408400 | ENSG00000186994 | hypo |
| chr19.14332201.14332500 | ENSG00000240803 | hypo |
| chr20.60717001.60717300 | ENSG00000101182 | hypo |
| chr21.9438301.9438600 | ENSG00000238411 | hypo |
| chr19.45004801.45005100 | ENSG00000167384 | hypo |
| chr19.50880001.50880300 | ENSG00000131408 | hypo |
| chr20.45439801.45440100 | ENSG00000266136 | hypo |

Genomic Mutation Profile

The present disclosure provides methods, systems, and kits for producing a mutation profile of a subject that has a disease/condition or is suspected of having such disease/condition, wherein the methylation profile may be used to determine whether the subject has the disease/condition or is at risk of having the disease/condition. The samples disclosed herein are subjected to library preparation and next generation deep sequencing (e.g., CAPP-Seq). A plurality of sequencing reads is generated and analyzed. In some embodiments, deep sequencing may be configured to maximize identifying genomic mutations associated with the disease/condition. For example, not meant to be limiting, for head and neck squamous cell carcinoma (HNSCC), a panel of canonical HNSCC driver genes may be included in the selector for CAPP-seq. Further, for lung cancer, a panel of lung cancer drive genes may be included in the selector for CAPP-seq. Moreover, for pancreatic cancer, a panel of pancreatic cancer drive genes may be included in the selector for CAPP-seq. In some embodiments, including genes without known driver effects in a particular cancer type in the selector for CAPP-seq may increase the sensitivity of ctDNA detection.

In some embodiments, the relative measure of ctDNA abundance is calculate from the mean mutant allele fractions (MAFs). In some embodiments, the mean MAF of mutations identified a subject and comprised in his/her mutation profile ranges from at least about 0.01% to at least about 10%. The ctDNA fraction of a sample disclosed herein is about at least 0.01%, 0.02%, 0.03%, 0.04%, 0.05%, 0.06%, 0.07%, 0.08%, 0.09%, 0.1%, 0.15%, 0.2%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, or any percentage in between.

In some embodiments, the generated mutation profile of a subject does not include mutation variants derived from cell-free nucleic acid molecules derived from PBLs. In some embodiments, the mutation profile comprises genetic polymorphisms, such as missense variant, a nonsense variant, a deletion variant, an insertion variant, a duplication variant, an inversion variant, a frameshift variant, or a repeat expansion variant. In some embodiments, the mutation profile may comprise mutation variant derived from a fraction of cell-free nucleic acid molecules of a specific size range.

Fragment Length Profile

In some embodiment, the length of ctDNA fragments is shorter than cell-free nucleic acid molecules derived from a healthy subject. In some embodiments, the length of ctDNA comprising at least one mutation is shorter than the length of cell free nucleic acid molecule containing a corresponding reference allele. In some embodiments, a length of a ctDNA fragment containing at least one DMR is shorter than a cell-free nucleic acid molecule fragment containing the corresponding genomic region.

In some embodiments, the sequencing does not utilize bisulfite sequence because it causes degradation of ctDNA fragments and prevents the preservation of the length distribution of ctDNAs. In some embodiments, the fragment length of ctDNA is at least from 60 to 500 bp, 80 to 300 bp, 90 to 250 bp, 80 to 170 bp, or 100 to 150 bp. In some embodiments, the present disclosure provides an enrichment of the cell free nucleic acid samples based on selecting cell free molecules of a certain size. In some embodiments, the multimodal analysis comprises utilizing the mutation profile described herein and the fragment length profile by selectively including a plurality of nucleic acid molecules in the mutation profile based on their fragment length. In some embodiments, the multimodal analysis comprises utilizing the methylation profile described herein and the fragment length profile by selectively including a plurality of nucleic acid molecules in the methylation profile based on their fragment length. In some embodiments, the multimodal analysis comprises utilizing the mutation profile, methylation profile, and the fragment length profile together by selectively including a plurality of nucleic acid molecules in the mutation profile based on their fragment length and by selectively including a plurality of nucleic acid molecules in the methylation profile based on their fragment length respectively.

Methods and Systems for Detecting Cancer, Determining Tissue of Origin for Tumor, and Providing Prognosis The present disclosure provides methods and systems for determining whether a subject has or is at risk of having a disease, wherein the methods and systems comprises subjecting a plurality of nucleic acid molecules derived from a cell-free nucleic acid sample obtained from said subject to sequencing to generate at least one profile of (i) a methylation profile, (ii) a mutation profile, and (iii) a fragment length profile; and processing said at least one profile to determine whether said subject has or is at risk of said disease at a sensitivity of at least 80% or at a specificity of at least about 90%, wherein said cell-free nucleic acid sample comprises less than 30 ng/ml of said plurality of nucleic acid molecules. In some embodiments, the sensitivity is at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or any percentage in between the numbers. In some embodiments, the specificity is at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any percentage in between the numbers.

In some embodiments, the methods and systems comprises subjecting a plurality of nucleic acid molecules derived from a cell-free nucleic acid sample obtained from said subject to sequencing to generate at least two profiles of (i) a methylation profile, (ii) a mutation profile, and (iii) a fragment length profile. The methods provide a sensitivity of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or any percentage in between the numbers. In some embodiments, the sensitivity when using two profiles is increased by at least about 0.5%, 1%, 2%, 3%, 4%, 5%, 6%, 7%, 8%, 9%, 10%, or percentage in between any of the numbers compared to the sensitivity when using one profile. In some embodiments, the sensitivity when using three profiles is increased by at least about 0.5%, 1%, 2%, 3%, 4%, 5%, 6%, 7%, 8%, 9%, 10%, or percentage in between any of the numbers compared to the sensitivity when using two profile.

Further, the methods provide a specificity of at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any percentage in between the numbers. In some embodiments, the specificity when using two profiles is increased by at least about 0.5%, 1%, 2%, 3%, 4%, 5%, 6%, 7%, 8%, 9%, 10%, or percentage in between any of the numbers compared to the specificity when using one profile. In some embodiments, the specificity when using three profiles is increased by at least about 0.5%, 1%, 2%, 3%, 4%, 5%, 6%, 7%, 8%, 9%, 10%, or percentage in between any of the numbers compared to the specificity when using two profile.

The present disclosure provides methods and systems for processing a cell-free nucleic acid sample of a subject to determine whether said subject has or is at risk of having a disease, the methods and systems comprise providing said cell-free nucleic acid sample comprising a plurality of nucleic acid molecules; subjecting said plurality of nucleic acid molecules or derivatives thereof to sequencing to generate a plurality of sequencing reads; computer processing said plurality of sequencing reads to identify, for said plurality of nucleic acid molecules, (i) a methylation profile, (ii) a mutation profile, and (iii) a fragment length profile; and using at least said methylation profile, said mutation profile and said fragment length profile to determine whether said subject has or is at risk of having said disease. In some embodiments, the methods provide a sensitivity of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or any percentage in between the numbers. The methods provide a specificity of at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any percentage in between the numbers.

The present disclosure provides methods and systems for determining a tissue origin of a tumor, comprising identifying a plurality of Differentially Methylated Regions (DMRs), wherein the plurality of DMRs is specific for a particular cancer (e.g., breast cancer, colon cancer, prostate cancer, HSNCC) and derived from a fraction of cell-free nucleic acid molecules. In some embodiments, the fraction of the cell-free nucleic acid molecules is derived from ctDNA. In some embodiments, the methods provides a sensitivity of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or any percentage in between the numbers. The methods provide a specificity of at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any percentage in between the numbers.

The present disclosure describes methods and systems for providing a prognosis to a subject after receiving a treatment for a disease/condition. For example, the treatment comprises a surgical removal of a tumor, a chemotherapy designed for a specific type of cancer, a radio therapy, or an immune therapy (e.g., TCR, CAR, etc.). In some embodiments, the methods or systems comprise subjecting a plurality of nucleic acid molecules derived from a cell-free nucleic acid sample obtained from said subject to sequencing to generate at least one profile of (i) a methylation profile, (ii) a mutation profile, and (iii) a fragment length profile; and monitoring or detecting minimal residual disease (MRD) based at least based on the at least one profile.

The present disclosure provides methods and systems for determining whether a subject has a disease/condition by assaying a cell-free nucleic acid molecule from at least a portion of a sample from said subject; detecting a methylation level of at least a portion of said cell-free nucleic acid molecule comprised in a differentially methylated region (DMR) listed in Table 5; and comparing, using at least one computer processor, said methylation level detected in (b) to a methylation level of corresponding portion(s) of said cell-free nucleic acid molecules comprised in said DMR listed in Table 5. In some embodiments, the methylation level of at least about six or more, ten or more, fifteen or more, twenty or more, thirty or more, forty or more, fifty or more, sixty or more, seventy or more, eighty or more, ninety or more, or one hundred or more, two hundred or more, three hundred or more, four hundred or more, five hundred or more, six hundred or more, or seven hundred or more DMRs listed in Table 5 is measured and compared to the methylation level of the corresponding DMRs in a healthy subject as discussed herein.

Once a subject is accurately diagnosed and receives a treatment to treat the cancer, such as surgical removal, chemotherapy, radio therapy, etc., it is important to monitor the effectiveness of the treatment and predict the patient's survival rate. Further, it is important to detect minimal residual disease of cancer cells. The present disclosure provides methods and systems for determining whether a subject has a higher survival rate after receiving a treatment for a disease, the methods and systems comprise assaying a cell-free nucleic acid molecule from at least a portion of a sample from said subject; detecting a methylation level of at least a portion of said cell-free nucleic acid molecule comprised in a differentially methylated region (DMR) listed in Table 6; and comparing, using at least one computer processor, said methylation level detected in (b) to a methylation level of corresponding portion(s) of said cell-free nucleic acid molecules comprised in said DMR listed in Table 6. In some embodiments, the DMRs listed in Table 6 represent regions associated with genes ZSCAN31, LINC01391, GATA2-AS1, STK3, and OSR1.

TABLE 6

| ctDNA derived DMR | | |
| --- | --- | --- |
| windowPos-DMR genomic region | ensemblId-DMR associated gene ID | DMR |
| chr2.19555801.19556100 | ENSG00000143867 | hyper |
| chr3.128210701.128211000 | ENSG00000179348 | hyper |
| chr3.138657301.138657600 | ENSG00000244578 | hyper |
| chr6.28303801.28304100 | ENSG00000235109 | hyper |
| chr8.99951901.99952200 | ENSG00000104375 | hyper |

In some embodiments, the method further comprises the step of adding a second amount of control DNA to the sample for confirming the immunoprecipitation reaction.

As used herein, the "control" may comprise both positive and negative control, or at least a positive control.

In some embodiments, the method further comprises the step of adding a second amount of control DNA to the sample for confirming the capture of cell-free methylated DNA.

According to further aspect, there is provided use of the methods described herein for measuring a DNA methylation profile within the sample.

In some embodiments, identifying the presence of DNA from cancer cells further includes identifying the cancer cell tissue of origin.

In some instances, tumor tissue sampling may be challenging or carry significant risks, in which case diagnosing and/or subtyping the cancer without the need for tumor tissue sampling may be desired. For example, lung tumor tissue sampling may require invasive procedures such as mediastinoscopy, thoracotomy, or percutaneous needle biopsy; these procedures may result in a need for hospitalization, chest tube, mechanical ventilation, antibiotics, or other medical interventions. Some individuals may not undergo the invasive procedures needed for tumor tissue sampling either because of medical comorbidities or due to preference. In some instances, the actual procedure for tumor tissue procurement may depend on the suspected cancer subtype. In other instances, cancer subtype may evolve over time within the same individual; serial assessment with invasive tumor tissue sampling procedures is often impractical and not well tolerated by patients. Thus, non-invasive cancer subtyping via blood test may have many advantageous applications in the practice of clinical oncology.

Accordingly, in some embodiments, identifying the cancer cell tissue of origin further includes identifying a cancer subtype. Preferably, the cancer subtype differentiates the cancer based on stage (e.g., early stage lung cancer treated with surgery vs late stage lung cancer treated with chemotherapy), histology (e.g., small cell carcinoma vs adenocarcinoma vs squamous cell carcinoma in lung cancer), gene expression pattern or transcription factor activity (e.g., ER status in breast cancer), copy number aberrations (e.g., HER2 status in breast cancer), specific rearrangements (e.g., FLT3 in AML), specific gene point mutational status (e.g., IDH gene point mutations), and DNA methylation patterns (e.g., MGMT gene promoter methylation in brain cancer).

In some embodiments, comparison in step (f) is carried out genome-wide.

In other embodiments, the comparison in step (f) is restricted from genome-wide to specific regulatory regions, such as, but not limited to, FANTOM5 enhancers, CpG Islands, CpG shores, CpG Shelves, or any combination of the foregoing.

In some embodiments, the methods herein are for use in the detection of the cancer.

In some embodiments, certain steps are carried out by a computer processor.

In an aspect, there is provided a method of detecting the presence of DNA from cancer cells and identifying a cancer subtype, the method comprising: receiving sequencing data of cell-free methylated DNA from a subject sample; comparing the sequences of the captured cell-free methylated DNA to control cell-free methylated DNAs sequences from healthy and cancerous individuals; identifying the presence of DNA from cancer cells if there is a statistically significant similarity between one or more sequences of the captured cell-free methylated DNA and cell-free methylated DNAs sequences from cancerous individuals; and if DNA from cancer cells is identified, further identifying the cancer cell tissue of origin and cancer subtype based on the comparison step.

In an aspect, there is provided a method of detecting the presence of DNA from cancer cells and determining the location of the cancer from which the cancer cells arose from two or more possible organs, the method comprising: providing a sample of cell-free DNA from a subject; capturing cell-free methylated DNA from said sample, using a binder selective for methylated polynucleotides; sequencing the captured cell-free methylated DNA; comparing the sequence patterns of the captured cell-free methylated DNA to DNAs sequence patterns of two or more population(s) of control individuals, each of said two or more populations having localized cancer in a different organ; determining as to which organ the cancer cells arose on the basis of a statistically significant similarity between the pattern of methylation of the cell-free DNA and one of said two or more populations.

In some embodiments, the methods herein are for use in monitoring therapy of the cancer.

Data Analysis Systems and Methods

The methods and systems disclosed herein may comprises algorithms or uses thereof. The one or more algorithms may be used to classify one or more samples from one or more subjects. The one or more algorithms may be applied to data from one or more samples. The data may comprise biomarker expression data. The methods disclosed herein may comprise assigning a classification to one or more samples from one or more subjects. Assigning the classification to the sample may comprise applying an algorithm to the methylation profile, mutation profile, and fragment length profile. In some cases, the at least one profile is inputted to a data analysis system comprising a trained algorithm for classifying the sample as obtained from a subject has a disease or minor injuries.

A data analysis system may be a trained algorithm. The algorithm may comprise a linear classifier. In some instances, the linear classifier comprises one or more of linear discriminant analysis, Fisher's linear discriminant, Naïve Bayes classifier, Logistic regression, Perceptron, Support vector machine, or a combination thereof. The linear classifier may be a support vector machine (SVM) algorithm. The algorithm may comprise a two-way classifier. The two-way classifier may comprise one or more decision tree, random forest, Bayesian network, support vector machine, neural network, or logistic regression algorithms.

The algorithm may comprise one or more linear discriminant analysis (LDA), Basic perceptron, Elastic Net, logistic regression, (Kernel) Support Vector Machines (SVM), Diagonal Linear Discriminant Analysis (DLDA), Golub Classifier, Parzen-based, (kernel) Fisher Discriminant Classifier, k-nearest neighbor, Iterative RELIEF, Classification Tree, Maximum Likelihood Classifier, Random Forest, Nearest Centroid, Prediction Analysis of Microarrays (PAM), k-medians clustering, Fuzzy C-Means Clustering, Gaussian mixture models, graded response (GR), Gradient Boosting Method (GBM), Elastic-net logistic regression, logistic regression, or a combination thereof. The algorithm may comprise a Diagonal Linear Discriminant Analysis (DLDA) algorithm. The algorithm may comprise a Nearest Centroid algorithm. The algorithm may comprise a Random Forest algorithm. In some embodiments, for discrimination of preeclampsia and non-preeclampsia, the performance of logistic regression, random forest, and gradient boosting method (GBM) is superior to that of linear discriminant analysis (LDA), neural network, and support vector machine (SVM).

Kits

The present disclosure provides kits for identifying or monitoring a disease or disorder (e.g., cancer) of a subject. A kit may comprise probes for identifying a quantitative measure (e.g., indicative of a presence, absence, or relative amount) of sequences at each of a panel of cancer-associated genomic loci in a sample of the subject. A quantitative measure (e.g., indicative of a presence, absence, or relative amount) of sequences at each of a panel of cancer-associated genomic loci in the sample may be indicative of the disease or disorder (e.g., cancer) of the subject. The probes may be selective for the sequences at the panel of cancer-associated genomic loci (e.g., DMR listed in Tables 3, 5 and 6) in the sample. A kit may comprise instructions for using the probes to process the sample to generate datasets indicative of a quantitative measure (e.g., indicative of a presence, absence, or relative amount) of sequences at each of the panel of cancer-associated genomic loci in a sample of the subject.

The probes in the kit may be selective for the sequences at the panel of cancer-associated genomic loci in the sample. The probes in the kit may be configured to selectively enrich nucleic acid (e.g., RNA or DNA) molecules corresponding to the panel of cancer-associated genomic loci. The probes in the kit may be nucleic acid primers. The probes in the kit may have sequence complementarity with nucleic acid sequences from one or more of the panel of cancer-associated genomic loci or genomic regions. The panel of cancer-associated genomic loci or microbiome-associated genomic loci or genomic regions may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more distinct panel of cancer-associated genomic loci or genomic regions.

The instructions in the kit may comprise instructions to assay the sample using the probes that are selective for the sequences at the panel of cancer-associated genomic loci in the cell-free biological sample. These probes may be nucleic acid molecules (e.g., RNA or DNA) having sequence complementarity with nucleic acid sequences (e.g., RNA or DNA) from one or more of the plurality of panel of cancer-associated genomic loci. These nucleic acid molecules may be primers or enrichment sequences. The instructions to assay the cell-free biological sample may comprise introductions to perform array hybridization, polymerase chain reaction (PCR), or nucleic acid sequencing (e.g., DNA sequencing or RNA sequencing) to process the sample to generate datasets indicative of a quantitative measure (e.g., indicative of a presence, absence, or relative amount) of sequences at each of the panel of cancer-associated genomic loci in the sample. A quantitative measure (e.g., indicative of a presence, absence, or relative amount) of sequences at each of a panel of cancer-associated genomic loci in the sample may be indicative of a disease or disorder (e.g., cancer).

The instructions in the kit may comprise instructions to measure and interpret assay readouts, which may be quantified at one or more of the panel of cancer-associated genomic loci to generate the datasets indicative of a quantitative measure (e.g., indicative of a presence, absence, or relative amount) of sequences at each of the panel of cancer-associated genomic loci in the sample. For example, quantification of array hybridization or polymerase chain reaction (PCR) corresponding to the panel of cancer-associated genomic loci may generate the datasets indicative of a quantitative measure (e.g., indicative of a presence, absence, or relative amount) of sequences at each of the panel of cancer-associated genomic loci in the sample. Assay readouts may comprise quantitative PCR (qPCR) values, digital PCR (dPCR) values, digital droplet PCR (ddPCR) values, fluorescence values, etc., or normalized values thereof.

Computer System

Figure 8:
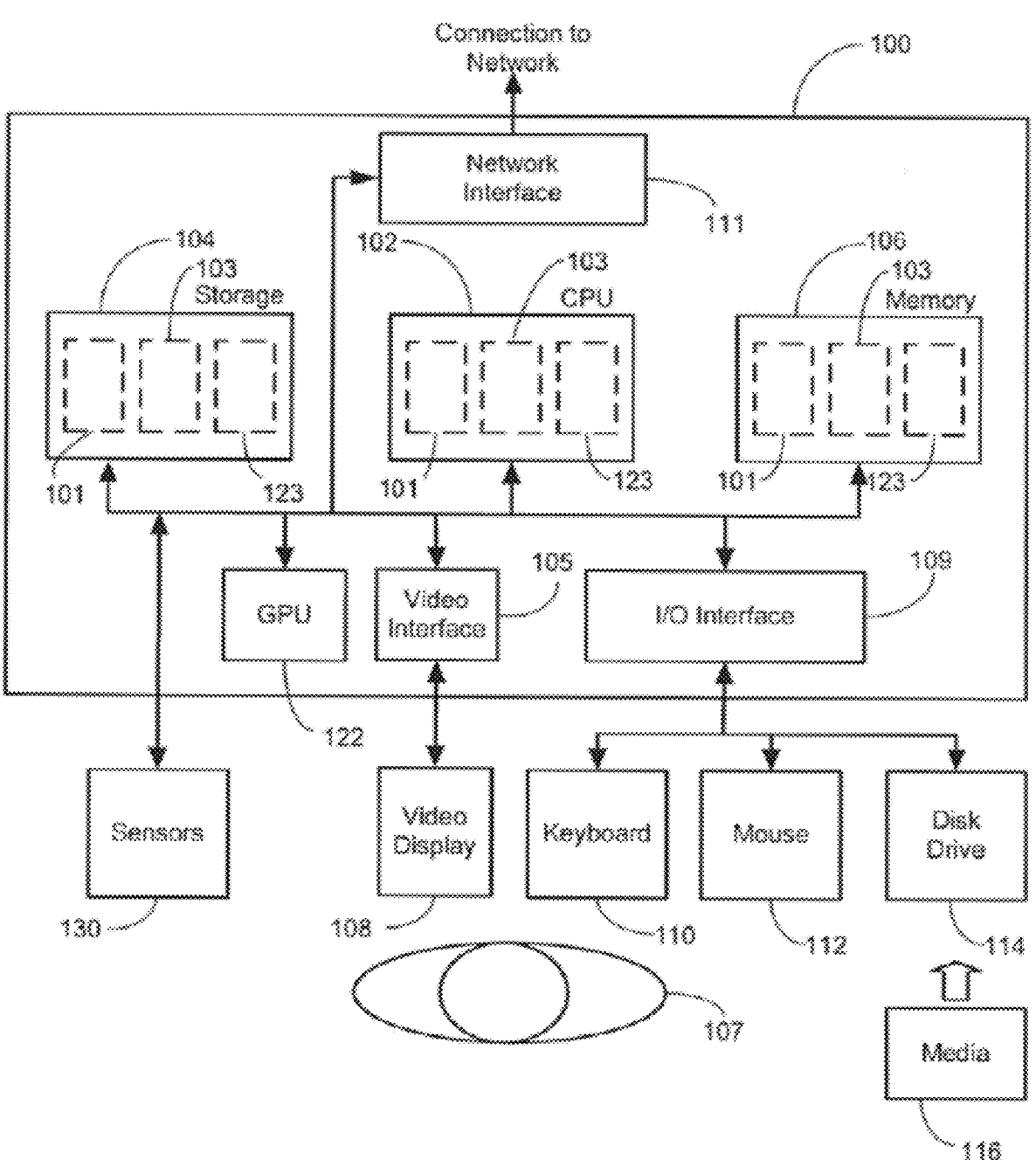
FIG. 8 shows a computer system that is programmed or otherwise configured to implement methods provided herein.

In some embodiments, certain steps are carried out by a computer processor. The present system and method may be practiced in various embodiments. A suitably configured computer device, and associated communications networks, devices, software and firmware may provide a platform for enabling one or more embodiments as described above. By way of example, FIG. 8 shows a generic computer device 100 that may include a central processing unit ("CPU") 102 connected to a storage unit 104 and to a random access memory 106. The CPU 102 may process an operating system 101, application program 103, and data 123. The operating system 101, application program 103, and data 123 may be stored in storage unit 104 and loaded into memory 106, as may be required. Computer device 100 may further include a graphics processing unit (GPU) 122 which is operatively connected to CPU 102 and to memory 106 to offload intensive image processing calculations from CPU 102 and run these calculations in parallel with CPU 102.

An operator 107 may interact with the computer device 100 using a video display 108 connected by a video interface 105, and various input/output devices such as a keyboard 115, mouse 112, and disk drive or solid state drive 114 connected by an I/O interface 109. The mouse 112 may be configured to control movement of a cursor in the video display 108, and to operate various graphical user interface (GUI) controls appearing in the video display 108 with a mouse button. The disk drive or solid state drive 114 may be configured to accept computer readable media 116. The computer device 100 may form part of a network via a network interface 111, allowing the computer device 100 to communicate with other suitably configured data processing systems (not shown). One or more different types of sensors 135 may be used to receive input from various sources.

The present system and method may be practiced on virtually any manner of computer device including a desktop computer, laptop computer, tablet computer or wireless handheld. The present system and method may also be implemented as a computer-readable/useable medium that includes computer program code to enable one or more computer devices to implement each of the various process steps in a method in accordance with the present invention. In case of more than computer devices performing the entire operation, the computer devices are networked to distribute the various steps of the operation. It is understood that the terms computer-readable medium or computer useable medium comprises one or more of any type of physical embodiment of the program code. In particular, the computer-readable/useable medium may comprise program code embodied on one or more portable storage articles of manufacture (e.g., an optical disc, a magnetic disk, a tape, etc.), on one or more data storage portioned of a computing device, such as memory associated with a computer and/or a storage system.

In an aspect, there is provided a computer-implemented method of detecting the presence of DNA from cancer cells and identifying a cancer subtype, the method comprising: receiving, at least one processor, sequencing data of cell-free methylated DNA from a subject sample; comparing, at the at least one processor, the sequences of the captured cell-free methylated DNA to control cell-free methylated DNAs sequences from healthy and cancerous individuals; identifying, at the at least one processor, the presence of DNA from cancer cells if there is a statistically significant similarity between one or more sequences of the captured cell-free methylated DNA and cell-free methylated DNAs sequences from cancerous individuals and if DNA from cancer cells is identified, further identifying the cancer cell tissue of origin and cancer subtype based on the comparison step.

In an aspect, there is provided a computer program product for use in conjunction with a general-purpose computer having a processor and a memory connected to the processor, the computer program product comprising a computer readable storage medium having a computer mechanism encoded thereon, wherein the computer program mechanism may be loaded into the memory of the computer and cause the computer to carry out the method described herein.

In an aspect, there is provided a computer readable medium having stored thereon a data structure for storing the computer program product described herein.

In an aspect, there is provided a device for detecting the presence of DNA from cancer cells and identifying a cancer subtype, the device comprising: at least one processor; and electronic memory in communication with the at one processor, the electronic memory storing processor-executable code that, when executed at the at least one processor, causes the at least one processor to: receive sequencing data of cell-free methylated DNA from a subject sample; compare the sequences of the captured cell-free methylated DNA to control cell-free methylated DNAs sequences from healthy and cancerous individuals; identify the presence of DNA from cancer cells if there is a statistically significant similarity between one or more sequences of the captured cell-free methylated DNA and cell-free methylated DNAs sequences from cancerous individuals and if DNA from cancer cells from is identified, further identify the cancer cell tissue of origin and cancer subtype based on the comparison step.

As used herein, "processor" may be any type of processor, such as, for example, any type of general-purpose microprocessor or microcontroller (e.g., an Intel™ x86, PowerPC™, ARM™ processor, or the like), a digital signal processing (DSP) processor, an integrated circuit, a field programmable gate array (FPGA), or any combination thereof.

As used herein "memory" may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), or the like. Portions of memory 102 may be organized using a conventional filesystem, controlled and administered by an operating system governing overall operation of a device.

As used herein, "computer readable storage medium" (also referred to as a machine-readable medium, a processor-readable medium, or a computer usable medium having a computer-readable program code embodied therein) is a medium capable of storing data in a format readable by a computer or machine. The machine-readable medium may be any suitable tangible, non-transitory medium, including magnetic, optical, or electrical storage medium including a diskette, compact disk read only memory (CD-ROM), memory device (volatile or non-volatile), or similar storage mechanism. The computer readable storage medium may contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations may also be stored on the computer readable storage medium. The instructions stored on the computer readable storage medium may be executed by a processor or other suitable processing device, and may interface with circuitry to perform the described tasks.

As used herein, "data structure" a particular way of organizing data in a computer so that it may be used efficiently. Data structures may implement one or more particular abstract data types (ADT), which specify the operations that may be performed on a data structure and the computational complexity of those operations. In comparison, a data structure is a concrete implementation of the specification provided by an ADT.

The advantages of the present invention are further illustrated by the following examples. The examples and their particular details set forth herein are presented for illustration only and should not be construed as a limitation on the claims of the present invention.

EXAMPLES

Example 1

Materials & Methods

HNSCC and Healthy Donor Peripheral Blood Leukocyte (PBL) and Plasma Acquisition

Patients diagnosed with HNSCC between 2014-2016 were identified from a prospective Anthology of Clinical Outcomes (Wong K. et al. 2010). All studies were approved by the Research Ethics Board at University Health Network. HNSCC patient samples were obtained from the Princess Margaret Cancer Centre's HNC Translational Research program based on the following criteria: 1) presentation of localized disease at diagnosis, 2) collection of blood at diagnosis and at least one timepoint post-treatment, 3) minimum follow-up time of 2 years after diagnosis. All patients received curative-intent treatment consisting of surgery with or without adjuvant radiotherapy. Healthy donors matched by age, gender, and current smoking status were identified from a prospective lung cancer screening program. 5-10 mL of blood was collected in Ethylene-Diamine-Tetraacetic Acid (EDTA) tubes. For HNSCC patients, blood was collected at diagnosis (baseline, BL) as well as three months after primary surgery (3M). Where applicable, additional blood was collected prior to adjuvant radiotherapy (PreRT), mid adjuvant radiotherapy (MidRT), and/or 12 months after primary surgery (12M). Plasma was isolated from blood within 1 hour of collection and stored at −80° C. until further processing. From the same blood collection for HNSCC patients at diagnosis or healthy donors, peripheral blood leukocytes were also isolated.

Cell Culture

The HPV-negative HNSCC cell line, FaDu, was kindly provided by Dr. Bradly Wouters (Princess Margaret Cancer Center) and cultured in DMEM (Gibco) supplemented with 10% fetal bovine serum and 1% penicillin/streptomycin. FaDu cell cultures were incubated in a humidified atmosphere containing 5% CO2 at 37° C. The identity of FaDu cells was confirmed by STR profiling. Cells were subjected to mycoplasma testing (e-MycoTMVALID Mycoplasma PCR Detection Kit, Intron Bio) prior to use.

Figure 9A:
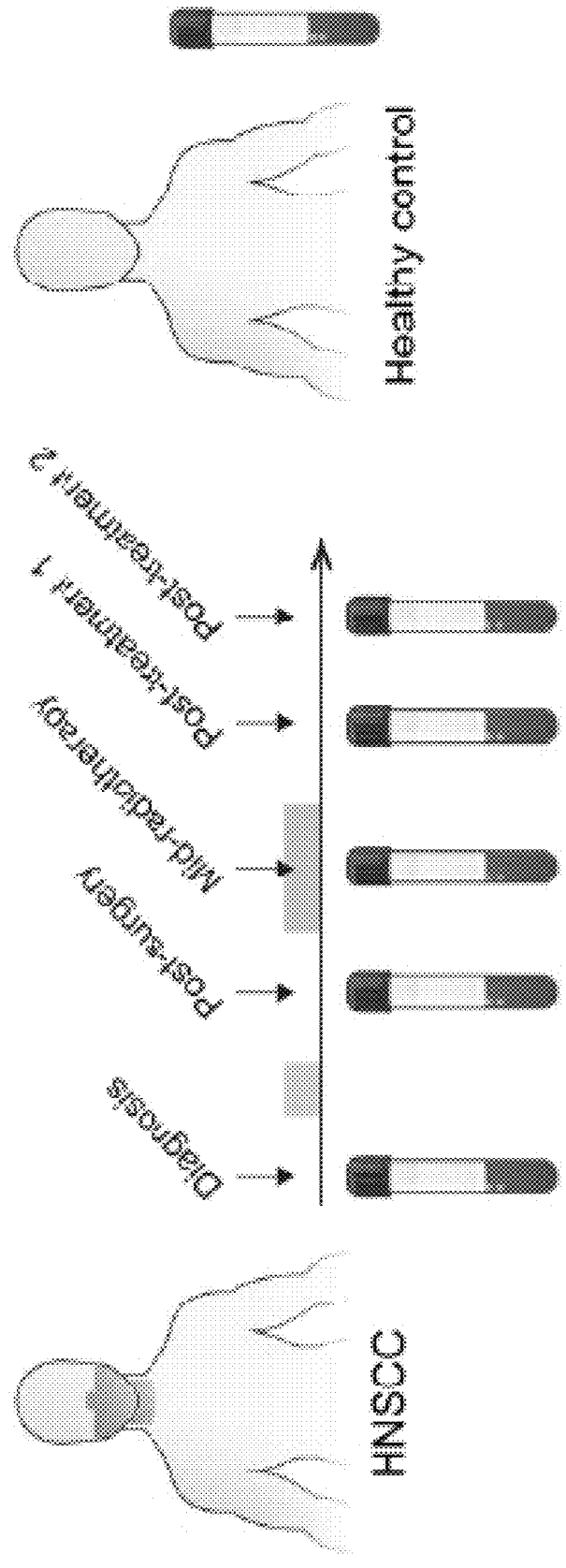
FIG. 9A-9B illustrate sample characteristics of isolated cell-free DNA from HNSCC and healthy donors.
Figure 9B:
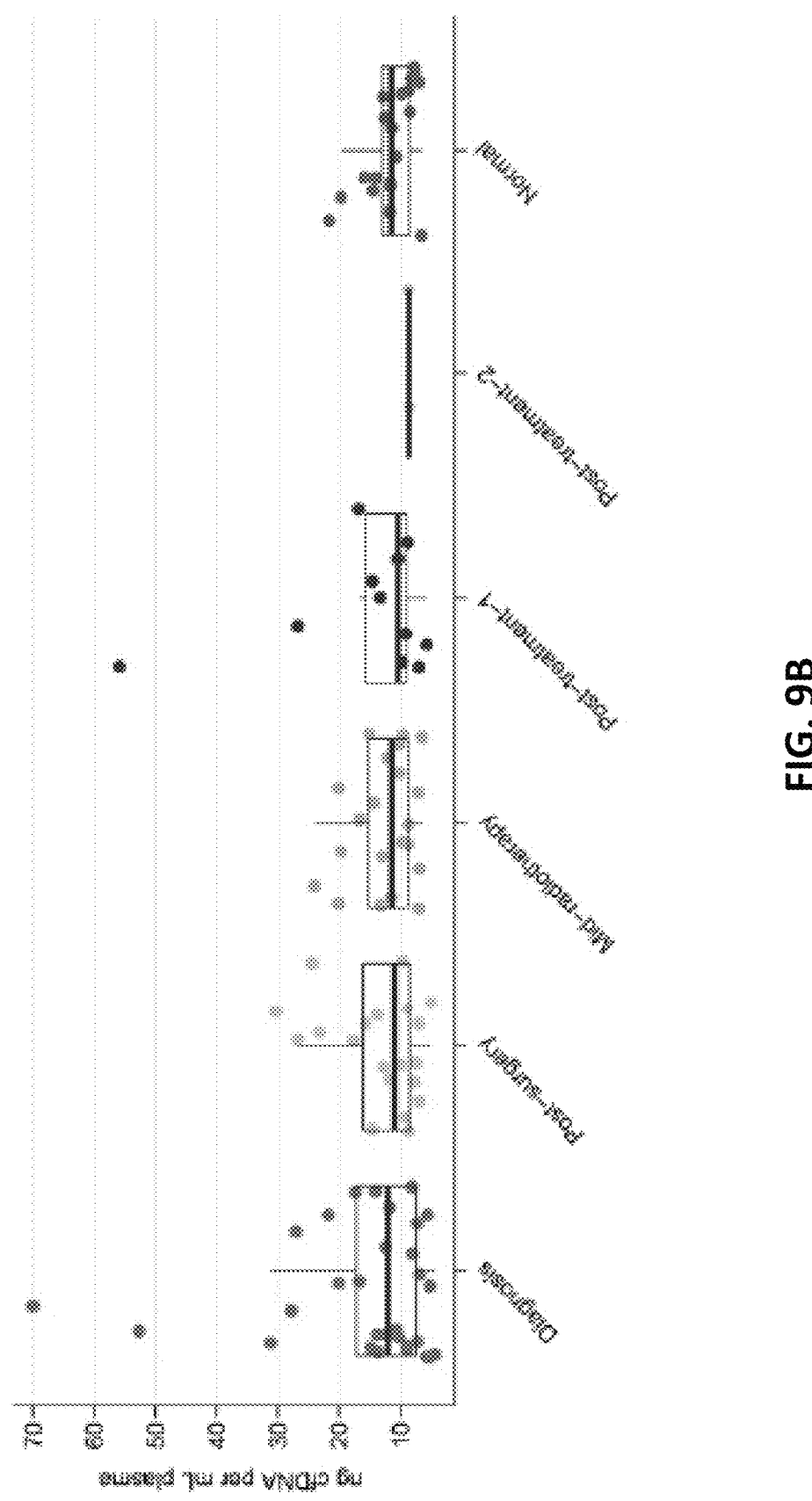

Isolation of Cell-Free DNA (cfDNA) and PBL Genomic DNA (gDNA)

cfDNA was isolated from total plasma using the QIAamp Circulating Nucleic Acid Kit (Qiagen) following manufacturer's instructions. Genomic DNA was isolated from PBLs, sheared to 150-200 base-pairs using the Covaris M220 Focused-ultrasonicator, and size-selected by AMPure XP magnetic beads (Beckman Coulter) to remove fragments above 300 base-pairs. Isolated cfDNA and sheared PBL genomic DNA were quantified by Qubit prior to library generation (FIGS. 9A and 9B).

Sequencing Library Preparation 5-10 or 10-20 ng of DNA was used as input for cfMeDIP-seq or CAPP-seq respectively. Input DNA was prepared for library generation using the KAPA HyperPrep Kit (KAPA Biosystems) with some modifications. Library adapters were utilized which incorporate a random 2-bp sequence followed by a constant 1-bp T sequence 5' adjacent to both strands of input DNA upon ligation. To minimize adapter dimerization during ligation, library adapters were added at a 100:1 adapter: DNA molar ratio (~0.07 µM per 10 ng of cfDNA) and incubated at 4° C. for 17 hours overnight. After post-ligation cleanup, input DNA was eluted in 40 uL of elution buffer (EB, 10 mM Tris-HCl, pH 8.0-8.5) prior to library generation.

Generation of CAPP-Seg Libraries

Figure 11:
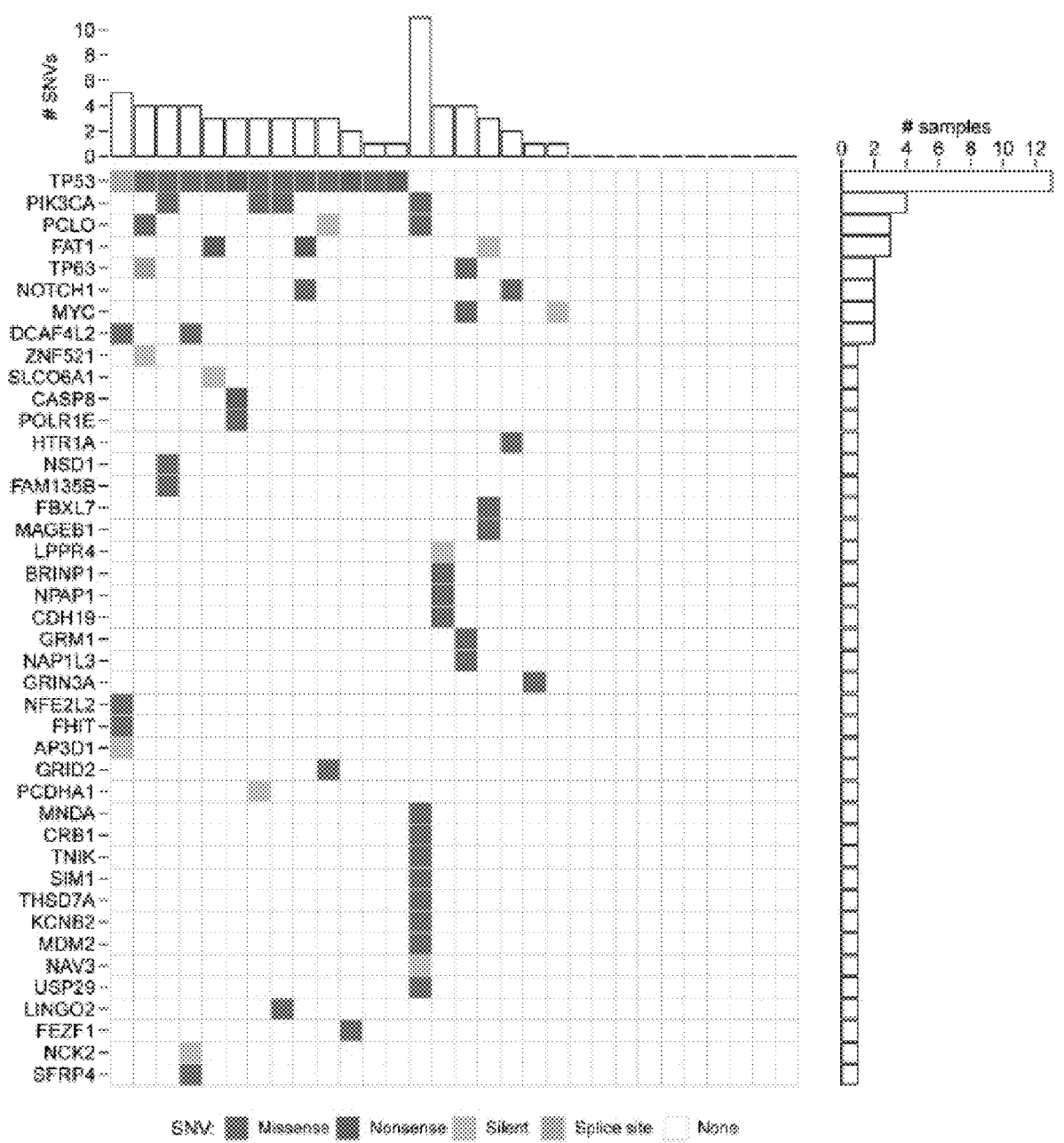
FIG. 11 shows oncoprint of all PBL-filtered SNVs identified in 20/32 HNSCC patients (Related to FIG. 2E).

Generation of CAPP-seq libraries were performed as described from Newman et al. 2014 with some modification. Libraries were PCR amplified at 10 cycles and up to 12 indexed amplified libraries were pooled together at 500-1000 ng. After the addition of COT DNA and blocking oligos, pooled libraries underwent SpeedVac treatment to evaporate all liquids and were resuspended in 13 uL resuspension mix (8.5 uL 2× Hybridization buffer, 3.4 uL Hybridization Component A, 1.1 uL nuclease-free water). 4 uL of hybridization probes (i.e., HNSCC selector) was added to the resuspension mix for a total of 17 uL prior to hybridization. After hybridization and PCR amplification/cleanup, libraries were eluted in 30 uL of IDTE pH 8.0 (1×TE solution). Multiplexed libraries were sequenced at 2×75/100/125 paired runs on the Illumina NextSeq/NovaSeq/HiSeq4000 respectively. Design of the HNSCC selector incorporated frequently recurrent genomic alterations in HNSCC from the COSMIC database as well as the E6 and E7 region of the HPV-16 genome (FIG. 11).

Alignment and Quality Control of CAPP-seq Libraries

The first two base-pairs on each 5' end of unaligned paired reads, corresponding to the incorporated random molecular barcodes, were extracted and collated to generate a 4-bp molecular identifier (UMI). The third T base-pair spacer was also removed prior to alignment. Paired reads were aligned to the human genome (genome assembly GRCh37/hg19) by BWA-mem, sorted and indexed by SAMtools (v 1.3.1) and recalibrated for base quality score using the Genome Analysis ToolKit (GATK) BaseRecalibrator (v 3.8) according to best practices (reference). Duplicated sequences from BAM files were collapsed based on their UMIs and labeled as Singletons, Single-Strand Consensus Sequences (SSCS) or Duplex Consensus Sequences (DCS) by ConsensusCruncher[44]. Quality control of each library was assessed by various metrics obtained form FastQC (Babraham Bioinformatics), as well as various scripts to obtain capture efficiency (CollectHsMetrics, Picard 2.10.9), depth of coverage (DepthOfCoverage, GATK 3.8), and base-pair position error rate (ides-bgreport.pl, Newman et al. 2016).

Detection of Somatic Nucleotide Variants (SNVs) and Quantification of ctDNA

Figure 12B:
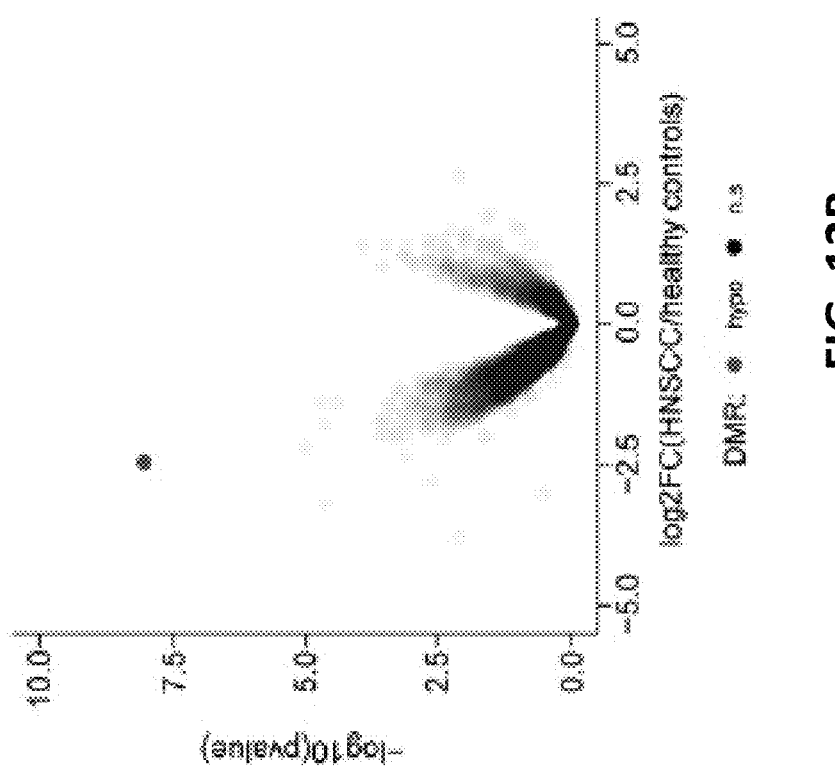
FIGS. 12A-12B illustrate related figures for identification of informative regions (related to FIG. 3B and FIG. 3C).
Figure 12A:
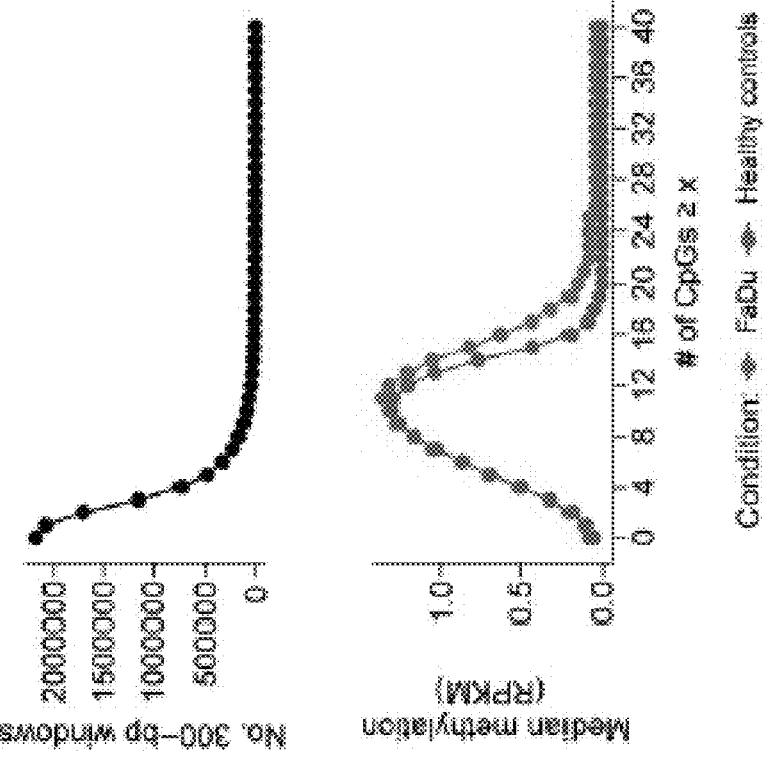

Removal of potential sequencing errors was performed by integrated Digital Error Suppression (iDES) as described by Newman et al. 2016. Background polishing was performed by utilization of our 20 healthy donor cfDNA samples as the training cohort (FIG. 12A-12B). To prevent the influence of outliers on downstream analysis, candidate SNVs within the lower $15^{th}$ or upper $85^{th}$ percentile of sequencing depth (<=1500×, >=5000×) across HNSCC cfDNA or PBL gDNA samples as well as genes with an average sequencing depth <=500× were excluded from analysis. To account for clonal hematopoiesis, non-germline mutations were defined as having a mutant allele fractions below 10% in plasma. Candidate SNVs in HNSCC cfDNA samples were identified based on the criteria of >=3 supporting reads with duplex support and complete absence in matched PBL gDNA samples. The mutant allele fraction (MAF) of identified SNVs was calculated by the number of reads corresponding to the alternative allele, divided by the sum of reads corresponding to the alternative and reference allele. For each HNSCC cfDNA sample with identifiable SNVs, the mean MAF across SNVs was calculated and used as a measure of ctDNA abundance. In cfDNA samples with only one identifiable SNV, the calculated MAF was used. Many of the detectable cancer-derived mutations may not be homozygous and may not be clonal within the tumor, and for these reasons the mean MAF may be an underestimate of the true ctDNA abundance within cell-free DNA.

Generation of cfMeDIP-Seq Libraries

The cfMeDIP-seq protocol was performed as described by Shen et al. 2019 with modifications to the library preparation step as described in "Sequencing Library Preparation". Multiplexed libraries were sequenced at 2×75/100/125 paired runs on the Illumina NextSeq/NovaSeq/HiSeq4000 respectively. For generalizability, cfMeDIP-seq libraries are described as any MeDIP-seq preparation method utilizing 5-10 ng of input DNA regardless of source (i.e., cfDNA, gDNA).

Alignment and Quality Control of cfMeDIP-Seq Libraries

Unaligned paired reads were processed, aligned, sorted and indexed as previously described in Alignment and Quality Control of CAPP-seq Libraries. Duplicated sequences from BAM files were collapsed by SAMtools. Quality control of each library was assessed by various metrics obtained form FastQC (Babraham Bioinformatics), as well as various metrics obtained from the R package MEDIPS (reference) including CpG coverage (MEDIPS.seqCoverage) and enrichment (MEDIPS.CpGenrich).

Selection of Informative Regions in cfMeDIP-Seq Profiles

Fragments generated from paired reads of cfMeDIP-seq libraries were counted within non-overlapping 300 base-pair windows by MEDIPS (MEDIPS.createSet), scaled by Reads Per Kilobase per Million (RPKM), and exported as WIG format (MEDIPS.exportWIG). WIG files from each sample were imported by R and collated as a matrix. Analysis was limited to cfDNA and PBL samples from our 20 healthy donor samples to enable applications within a non-disease context. Informative regions were based on the criteria of CpG density and correlation of RPKM values between cfDNA and matched PBLs. Employing a sliding window based on CpG density (>=n CpGs), a minimum threshold of >=8 CpGs was selected.

Calculation of Absolute Methylation from cfMeDIP-Seq Libraries

Fragments from paired reads of cfMeDIP-seq libraries were counted as previously described in Selection of Informative Regions in cfMeDIP-seq Profiles and scaled to absolute methylation levels by the MeDEStrand R package. To calculate absolute methylation from counts, a logistic regression model was used to estimate bias of DNA pull-down based on CpG density (i.e., CpG density bias) (Me-DEStrand.calibrationCurve). Based on the estimated CpG density bias, methylation within each window was corrected for fragments from the positive and negative DNA strand. Windows with corrected fragments were log transformed and scaled to values between 0 and 1 to describe absolute methylation (MeDEStrand.binMethyl). Absolute methylation levels from each cfMeDIP-seq sample was exported as a WIG-like file (i.e., WIG file format without a track-line). Design of in-Silico PBL Depletion and Evaluation of Performance To enrich for windows within the disease setting, methylation from PBLs was removed by a process termed "in-silico PBL depletion". Analysis was limited to PBL samples from our cohort of 20 healthy donor samples to enable applications within a non-cancer specific context. Our strategy for the in-silico PBL depletion was performed as followed:

1. For each informative window as described in Selection of Informative Regions in cfMeDIP-seq Profiles, calculate the median absolute methylation value across healthy donor PBL samples.
2. Define PBL-depleted windows based on the criteria of a median absolute methylation value <0.1.
3. Restrict analysis of cfDNA samples within PBL-depleted windows.

Performance of the in-silico PBL depletion strategy was evaluated by comparing absolute methylation distributions in PBL samples before and after depletion from the healthy donor cohort used as the training set, to the HNSCC cohort used as the validation set.

Differential Methylation Analysis

To enable robust detection of HNSCC-associated differentially methylated regions (DMRs), analysis was limited to HNSCC patients with detectable SNVs in plasma by CAPP-seq (n=20/32). Differential methylation analysis was limited to informative regions after in-silico PBL depletion. A collated matrix of binned fragment counts from HNSCC and healthy donor cfDNA samples, generated as previously described in Selection of Informative Regions in cfMeDIP-seq Profiles, were utilized for identification of DMRs by the DESeq2 R package. Pre-filtering was performed by removal of regions with <10 counts across all cfDNA samples. A single factor defined as condition (HNSCC vs. healthy donor) was used for contrast during differential methylation analysis. Briefly, differential methylation analysis was performed by scaling samples based on size factors and dispersion estimates, followed by fitting of a negative binomial general linear model. For each window, a P-value was calculated between the HNSCC and healthy donor conditions by Wald Test. P-values within regions above the default Cook's distance cut-off were omitted from adjusted P-value calculation (Benjamini-Hochberg). Significant hypermethylated or hypomethylated regions (hyper-/hypo-DMRs) in HNSCC cfDNA samples are defined as windows with an adjusted P-value <0.1.

Enrichment of CpG Features within HNSCC cfDNA Hyper-methylated Regions

CpG features such as islands, shores, shelves, and open sea (interCGI) are defined as per the AnnotationHub R package (reference) (hg19_cpgs annotation). ID coordinates of each hypermethylated window (i.e., "chr.start.end") within PBL-depleted regions were labeled with an overlapping CpG feature using an inhouse R package that utilizes the "annotatr" and "GenomicRanges" R packages (FIG. 13).

To determine the probability of enrichment for an observed overlap of features versus a null distribution, 1000 random samplings was performed. For each sampling, an equal number of bins were chosen based on the number hypermethylated windows, while maintaining an identical distribution of CpGs. The observed number of overlaps for each CpG feature across samplings were used to generate their respective null distributions, which were subsequently transformed onto a z-score scale. The observed overlap of hypermethylated regions for each CpG feature were also z-scored transformed, deriving summary statistics from the null distribution. The estimated P-value of the observed overlap from hypermethylated windows was calculated as the number of random samplings with overlap equal or greater/lesser than the observed overlap of the null distribution.

Enrichment of HNSCC cfDNA Hypermethylated Regions with Cancer-Specific Hypermethylated Cytosines from the Tumor Cancer Genome Atlas (TCGA)

File information from publicly available hm450k profiles of all primary tumors from breast (BRCA), colorectal (COAD), head and neck (HNSC), prostate (PRAD), pancreatic (PAAD), lung adeno (LUAD), and lung squamous (LUSC) were downloaded from the TCGA. Due to the majority of our HNSCC cohort presenting with tumors of the oral cavity, files from the HNSC group were limited to patients with primary site at the "floor of mouth" (n=55). An equal number of hm450k files were randomly selected from each of the remaining cancer types, as well as from a separate database of healthy PBLs (GEO series GSE67393). A manifest of downloaded files is provided in FIG. 14.

To generate "tumor-specific" hyper-methylated cytosines, differential methylation analysis by limma was performed for each cancer type, with individual comparisons to each other cancer type as well as PBLs (i.e., contrast). For a given contrast, a linear model is fitted for each probed cytosine incorporating the residual variance and sample beta value, the P-value of observed difference between contrasts is then calculated by the empirical Bayes smoothing. Hypermethylated cytosines with elevated methylation in a given cancer type versus an individual comparison was defined by a log foldchange >=0.25 and an adjusted P-value (Benjamini-Hochberg)<0.01. Hypermethylated cytosines unique to an individual cancer type were designated as "tumor-specific". For the cases of LUSC, LUAD, and PAAD, either no or very little tumor-specific hypermethylated cytosines were identified (0, 15, 18) and therefore were omitted from subsequent analysis. For comparison with cfMeDIP-seq libraries, base-pair positions from tumor-specific hypermethylated cytosines were overlapped with informative windows after in-silico PBL depletion as described in Design of In-silico PBL Depletion and Evaluation of Performance.

The enrichment of overlap for HNSCC cfDNA hypermethylated regions with tumor-specific regions from TCGA was evaluated by 10,000 random samplings using the same methods described in Enrichment of CpG Features with HNSCC cfDNA Hypermethylated Regions.

Sensitivity and Specificity of ctDNA Detection by cfMeDIP-Seq

For cfMeDIP-seq libraries from our cohort of 32 HNSCC and 20 healthy donor cfDNA samples, ctDNA detection was defined based on the observation of a mean RPKM value across HNSCC cfDNA hypermethylated regions within an individual HNSCC cfDNA sample greater than the max mean RPKM value across healthy donor cfDNA samples. The sensitivity and specificity of ctDNA detection based on this definition was evaluated by Receiver Operating Characteristic (ROC) curve analysis. To minimize any confounding results due to the potential lack of ctDNA release in a subset of patients, ROC curve analysis was also performed in only 20 of the 32 HNSCC cfDNA samples with detectable ctDNA by CAPP-seq. Cross validation to assess the accuracy of ctDNA detection by DMR analysis was performed. Briefly, CAPP-Seq positive patients and healthy donors were randomly assigned to training (60%, n=24) and validation sets (40%, n=16) while maintaining similar ctDNA abundance (as determined by CAPP-Seq) between both sets. Hyper-DMRs were identified by differential methylation analysis between HNSCC and healthy donor samples within the training set. The sensitivity of ctDNA detection within these hyper-DMRs were assessed as previously described (FIG. 2C) within the validation set to obtain an AUROC value. A total of 50 random samplings were performed.

Fragment Length Analysis of ctDNA Detected by CAPP-Seq and cfMeDIP-Seq

For each HNSCC cfDNA CAPP-seq library, the median fragment length from all supporting paired reads of a specified SNV (i.e., singletons, SCSs, DCSs) as well as for paired reads containing the reference allele was measured. In cases where the median fragment length was reported for patients with >1 SNV, the median value across the median fragment length from each SNV was calculated. For each HNSCC cfDNA cfMeDIP-seq library, the median fragment length from all fragments mapping to the previously determined HNSCC cfDNA hypermethylated regions was calculated. Due to the relative absence of methylation within our cohort of 20 healthy donors, the fragment length of each healthy donor cfMeDIP-seq library was collated prior to any calculations. In both types of libraries, fragment length analysis was limited to cfDNA within the $1^{st}$ peak (i.e., <220 base-pairs).

Enrichment of fragments (100-150 bp or 100-220 bp) within hyper-DMRs was calculated as followed. A null distribution of expected counts was generated from random 300-bp bins within our previously designed PBL-depleted windows at identical number and CpG density distribution, from a total of 30 samplings. Observed counts for each sample were determined based on read counts across hyper-DMRs. For each sample, enrichment was calculated based on the mean observed count divided by the mean expected count.

Supervised Hierarchal Clustering

Prior to clustering, a pseudocount of 0.1 was added to all RPKM values of cfMeDIP-seq libraries to enable log 2 transformation. Values were scaled by Euclidean transformation and clustered by Ward's method. An arbitrary number of three distinct clusters were selected (k=3), designated as methylation clusters 1-3, and used in subsequent analysis.

Metrics of ctDNA Detection and Quantification on HNSCC Patient Clinical Outcomes The potential clinical utility of ctDNA detection was evaluated by three metrics: 1) detection of SNVs by CAPP-seq, 2) detection of increased mean RPKM in hypermethylated regions by cfMeDIP-seq. For comparative analysis, patients were stratified based on the following criteria: 1) presence or absence of SNVs, 2) methylation cluster 1 vs. methylation cluster 2+3. Patient characteristics are described in Table 1.

TABLE 1

Patient Characteristics

| sample ID | pathology | smoking status | smoking | age | gender | dx site | subsite | t stage | n stage | m stage | clinical stage | hpv status | chemo-therapy | treatment | vital status | cause of death | relapse |
|---|---|---|---|---|---|---|---|---|---|---|---|---|---|---|---|---|---|
| 1 | HNSCC | Current | 37 | 76 | Male | Lip & Oral Cavity | Tongue | T1 | N0 | M0 | I | NA | No | Sx only | Alive | NA | No |
| 2 | HNSCC | Ex-smoker | 20 | 81 | Male | Paranasal Sinus | Maxillary | T3 | N0 | M0 | III | Negative | No | post-op | Dead | Cancer | Yes |
| 3 | HNSCC | Current | 15 | 54 | Female | Lip & Oral Cavity | Tongue | T2 | N2b | M0 | IVA | NA | Yes | post-op | Alive | NA | No |
| 4 | HNSCC | Ex-smoker | 20 | 63 | Male | Lip & Oral Cavity | Retromolar Trigone | T4a | N2b | M0 | IVA | NA | No | post-op | Alive | NA | No |
| 5 | HNSCC | Current | 30 | 47 | Male | Lip & Oral Cavity | Tongue | T4a | N2b | M0 | IVA | Negative | No | post-op | Dead | Cancer | Yes |
| 6 | HNSCC | Current | 2 | 22 | Male | Lip & Oral Cavity | Tongue | T2 | N1 | M0 | III | NA | Yes | post-op C | Dead | Cancer | Yes |
| 7 | HNSCC | Ex-smoker | 40 | 69 | Male | Lip & Oral Cavity | Floor of Mouth | T4a | N2c | M0 | IVA | NA | No | post-op | Alive | NA | No |
| 8 | HNSCC | Ex-smoker | 10 | 80 | Male | Lip & Oral Cavity | Lower Alveolus & | T4a | N2b | M0 | IVA | NA | No | post-op | Dead | Cancer | Yes |
| 9 | HNSCC | Current | 50 | 62 | Male | Hypopharynx | Post-cricoid | T4a | N2c | M0 | IVA | Negative | No | post-op | Dead | Cancer | Yes |
| 10 | HNSCC | Current | 50 | 63 | Female | Lip & Oral Cavity | Floor of Mouth | T3 | N2c | M0 | IVA | NA | Yes | post-op C | Dead | Index Cancer | Yes |
| 11 | HNSCC | Non-smoker | NA | 68 | Male | Lip & Oral Cavity | Lower Alveolus & Floor of Mouth | [T4a] | N2b | M0 | IVA | NA | Yes | post-op C | Dead | Cancer | Yes |
| 12 | HNSCC | Ex-smoker | 15 | 78 | Male | Lip & Oral Cavity | Floor of Mouth | T1 | N1 | M0 | III | NA | No | Sx only | Alive | NA | No |
| 13 | HNSCC | Non-smoker | NA | 53 | Male | Lip & Oral Cavity | Tongue | T2 | N2b | M0 | IVA | Negative | Yes | post-op C | Alive | NA | No |
| 14 | HNSCC | Ex-smoker | 5 | 59 | Female | Lip & Oral Cavity | Floor of Mouth | T1 | N0 | M0 | I | NA | No | Sx only | Alive | NA | No |
| 15 | HNSCC | Ex-smoker | 25 | 79 | Male | Larynx | Supraglottis | T4a | N1 | M0 | IVA | Negative | No | post-op | Alive | NA | No |
| 16 | HNSCC | Current | 55 | 74 | Male | Lip & Oral Cavity | Floor of Mouth | T2 | N0 | M0 | II | NA | No | Sx only | Dead | Unknown | No |
| 17 | HNSCC | Current | 40 | 64 | Male | Lip & Oral Cavity | Lower Alveolus & Floor of Mouth | T4a | N1 | M0 | IVA | NA | Yes | post-op C | Alive | NA | No |
| 18 | HNSCC | Current | 35 | 65 | Female | Lip & Oral Cavity | Floor of Mouth | T4a | N0 | M0 | IVA | NA | No | post-op | Alive | NA | No |
| 19 | HNSCC | Current | 30 | 52 | Female | Lip & Oral Cavity | Tongue | T2 | N2c | M0 | IVA | Negative | Yes | post-op C | Alive | NA | No |
| 20 | HNSCC | Current | 30 | 46 | Male | Larynx | Glottis | T4a | N2c | M0 | IVA | Negative | Yes | post-op C | Alive | NA | Yes |
| 21 | HNSCC | Non-smoker | NA | 46 | Male | Larynx | Supraglottis | T4a | N2b | M0 | IVA | Negative | No | post-op | Alive | NA | No |
| 22 | HNSCC | Current | 75 | 74 | Male | Hypopharynx | Pyriform | T4a | N2c | M0 | IVA | NA | No | post-op | Dead | Cancer | Yes |
| 23 | HNSCC | Current | 35 | 56 | Male | Lip & Oral Cavity | Tongue | T1 | N2c | M0 | IVA | NA | Yes | post-op C | Alive | NA | No |
| 24 | HNSCC | Non-smoker | NA | 33 | Male | Lip & Oral Cavity | Tongue | T1 | N0 | M0 | I | NA | No | Sx only | Alive | NA | No |
| 25 | HNSCC | Non-smoker | NA | 60 | Female | Lip & Oral Cavity | Tongue | T1 | N1 | M0 | III | NA | Yes | post-op C | Alive | NA | No |
| 26 | HNSCC | Current | 40 | 65 | Male | Hypopharynx | Pyriform | T3 | N0 | M0 | III | NA | No | post-op | Dead | Unknown | No |
| 27 | HNSCC | Current | 15 | 49 | Male | Lip & Oral Cavity | Floor of Mouth | T4a | N0 | M0 | IVA | NA | No | post-op | Alive | NA | No |
| 28 | HNSCC | Current | 30 | 54 | Male | Lip & Oral Cavity | Floor of Mouth | T4a | N2c | M0 | IVA | NA | Yes | post-op C | Alive | NA | No |

TABLE 1-continued

Patient Characteristics

| sample ID | pathology | smoking status | smoking | age | gender | dx site | subsite | t stage | n stage | m stage | clinical stage | hpv status | chemo-therapy | treatment | vital status | cause of death | relapse |
|---|---|---|---|---|---|---|---|---|---|---|---|---|---|---|---|---|---|
| 29 | HNSCC | Non-smoker | NA | 54 | Male | Lip & Oral Cavity | Tongue | T1 | N0 | M0 | I | Negative | No | post-op | Alive | NA | No |
| 30 | HNSCC | Current | 30 | 56 | Male | Lip & Oral Cavity | Floor of Mouth | T2 | N0 | M0 | II | NA | No | post-op | Alive | NA | No |
| 1 | Healthy dono | Ex-smoker | 35 | 69 | Male | NA | NA | NA | NA | NA | NA | NA | NA | NA | NA | NA | NA |
| 2 | Healthy dono | Current | 84 | 74 | Male | NA | NA | NA | NA | NA | NA | NA | NA | NA | NA | NA | NA |
| 3 | Healthy dono | Ex-smoker | 40 | 77 | Male | NA | NA | NA | NA | NA | NA | NA | NA | NA | NA | NA | NA |
| 4 | Healthy dono | Ex-smoker | NA | 82 | Male | NA | NA | NA | NA | NA | NA | NA | NA | NA | NA | NA | NA |
| 5 | Healthy dono | Ex-smoker | 14 | 61 | Male | NA | NA | NA | NA | NA | NA | NA | NA | NA | NA | NA | NA |
| 6 | Healthy dono | Current | 55 | 71 | Male | NA | NA | NA | NA | NA | NA | NA | NA | NA | NA | NA | NA |
| 7 | Healthy dono | Current | 50 | 65 | Male | NA | NA | NA | NA | NA | NA | NA | NA | NA | NA | NA | NA |
| 8 | Healthy dono | Ex-smoker | 30 | 69 | Male | NA | NA | NA | NA | NA | NA | NA | NA | NA | NA | NA | NA |
| 9 | Healthy dono | Ex- | 41 | 57 | Female | NA | NA | NA | NA | NA | NA | NA | NA | NA | NA | NA | NA |
| 10 | Healthy dono | Current | 10 | 81 | Male | NA | NA | NA | NA | NA | NA | NA | NA | NA | NA | NA | NA |
| 11 | Healthy dono | Current | 39 | 64 | Female | NA | NA | NA | NA | NA | NA | NA | NA | NA | NA | NA | NA |
| 12 | Healthy dono | Ex-smoker | 30 | 65 | Female | NA | NA | NA | NA | NA | NA | NA | NA | NA | NA | NA | NA |
| 13 | Healthy dono | Current | 17.5 | 64 | Male | NA | NA | NA | NA | NA | NA | NA | NA | NA | NA | NA | NA |
| 14 | Healthy dono | Ex-smoker | 50 | 77 | Male | NA | NA | NA | NA | NA | NA | NA | NA | NA | NA | NA | NA |
| 15 | Healthy dono | Ex-smoker | 10 | 59 | Female | NA | NA | NA | NA | NA | NA | NA | NA | NA | NA | NA | NA |
| 16 | Healthy dono | Non-smoker | NA | 64 | Male | NA | NA | NA | NA | NA | NA | NA | NA | NA | NA | NA | NA |
| 17 | Healthy dono | Ex-smoker | 20 | 66 | Male | NA | NA | NA | NA | NA | NA | NA | NA | NA | NA | NA | NA |
| 18 | Healthy dono | Ex-smoker | 24.75 | 60 | Female | NA | NA | NA | NA | NA | NA | NA | NA | NA | NA | NA | NA |
| 19 | Healthy dono | Ex-smoker | 15 | 56 | Male | NA | NA | NA | NA | NA | NA | NA | NA | NA | NA | NA | NA |
| 20 | Healthy dono | Non-smoker | NA | 83 | Male | NA | NA | NA | NA | NA | NA | NA | NA | NA | NA | NA | NA |

Cross-Validation of ctDNA-Derived Methylation by cfMe-DIP-Seq Analysis

To evaluate the robustness of cfMeDIP-seq for identifying ctDNA-derived methylation, Receiver Operating Characteristics (ROC) curve analysis was performed. To minimize confounding results due to low/absent ctDNA, analysis was limited to HNSCC patients with detectable ctDNA by CAPP-seq. Patient and healthy control cfMeDIP-seq profiles were split into a training set (HNSCC: n=12/20; healthy control: n=12/20) and testing set (HNSCC: n=8/20; healthy control: n=8/20). Training and testing sets were balanced for ctDNA abundance as determined by CAPP-Seq analysis. A total of 50 splits were performed with ROC curve analysis performed on each iteration.

Identification of Prognostic Regions in HNSCC by TCGA Analysis

All available HNSCC cases from TCGA with matched legacy hm450k and RNA expression data were selected (n=520). Survival data was obtained from Jianfang et al. With regards to the hm450k data, methylation was summarized to 300-bp regions as described previously by calculating the mean beta-value between probe IDs within a particular region. To identify regions hypermethylated in HNSCC primary tumors compared to adjacent normal tissue, independent Wilcoxon tests were performed for each region. Regions with an adjusted p-value <0.05 (Holms method) as well as a log-fold change >=1 in primary tumors compared to adjacent normal tissue, were selected for subsequent analysis. To identify hypermethylated regions associated with prognosis, multivariate Cox Regression was performed, considering age, gender, and clinical stage, selecting regions with p-values <0.05. Survival analysis was limited to a maximum follow-up time of 5 years post-diagnosis, reflecting what was observed within the HNSCC cfDNA cohort. To further identify prognostic regions associated with changes in gene expression, Spearman's correlation was calculated for hm450k primary tumor profiles for each region, to matched RNA expression profiles for transcripts within a 2-Kb window. Regions with absolute Rho values >0.3 and a false discovery rate <0.05 were selected, resulting in the final identification of 5 prognostic regions associated with ZNF323/ZSCAN31, LINC01395, GATA2-AS1, OSR1, and STK3/MST2 expression. For TCGA patient profiles, the Composite Methylation Score (CMS) was obtained by calculating the sum of beta-values across all 5 prognostic regions. For cfMeDIP-seq profiles, RPKM values across all 943 hyper-DMRs were scaled to a total sum of 1 and the CMS was obtained by calculating the sum of these scaled RPKM values across all 5 prognostic regions.

Longitudinal Monitoring of Post-Treatment Plasma Samples by cfMeDIP-Seq cfMeDIP-seq libraries were successfully generated for 30/32 patients (FIGS. 17A-17D). For the remaining two patients, insufficient material was isolated from plasma and/or did not pass quality metrics. ctDNA quantification of post-treatment cfMeDIP-seq libraries was performed as previously described, calculating the mean RPKM values across identified hypermethylated regions by differential methylation analysis. For ease on interpretation, both pre-treatment and post-treatment cfMeDIP-seq libraries were converted to percent DNA values based on linear regression against mean MAF calculated by matched CAPP-Seq profiles. To achieve high confidence detection of residual disease, a minimum ctDNA fraction of 0.2% was required in post-treatment samples, corresponding to the maximum of mean RPKM values observed across all healthy controls.

Results & Discussion

Multimodal Profiling of Cell-Free DNA in Localized HNSCC

To examine the ability of multimodal profiling to characterize ctDNA in the setting of localized cancer, we recruited 32 HNSCC patients into a prospective observational study in which peripheral blood samples were collected at serial timepoints (FIG. 9A; Table 1). All patients were treated with surgery, with a subset receiving adjuvant radiotherapy (n=14) or chemoradiotherapy (n=11). With a median follow up of 43.2 months, 9/32 patients (28%) developed recurrence (actuarial 2-year recurrence-free survival: 88%).

As the majority of patients exhibited a heavy smoking history, which is well-described to alter the genomic/epigenomic landscape of somatic tissue and contribute to premalignant lesions, we also analyzed blood samples from 20 risk-matched healthy donors previously enrolled in a lung cancer screening program[34-37]. Cell-free DNA from plasma as well as genomic DNA (gDNA) from PBLs were co-isolated from blood and subjected to quantification and analysis (FIG. 9A). In contrast to other studies that have demonstrated significantly elevated levels of total plasma cell-free DNA in metastatic disease compared to healthy controls[38-41], no significant difference was observed between our HNSCC cohort and healthy donors (FIG. 9B).

Figure 1:
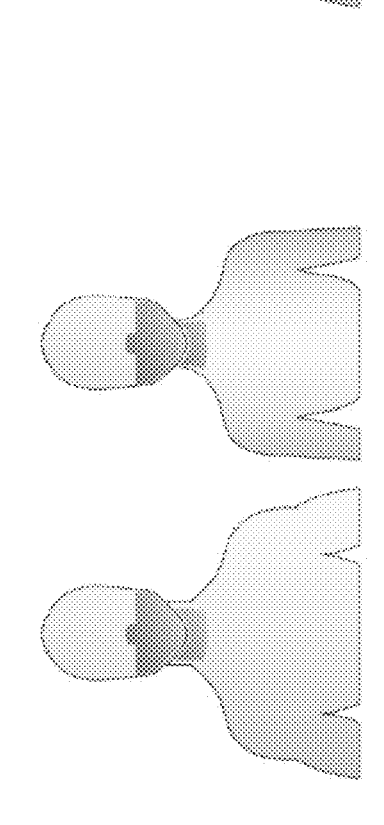
FIG. 1 illustrates multimodal profiling of cell-free DNA and PBL gDNA from patients and healthy controls.
Figure 1:
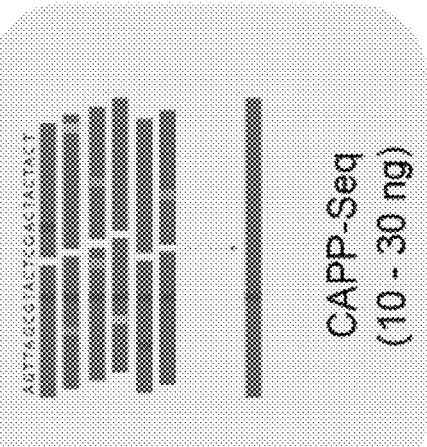
Figure 1:
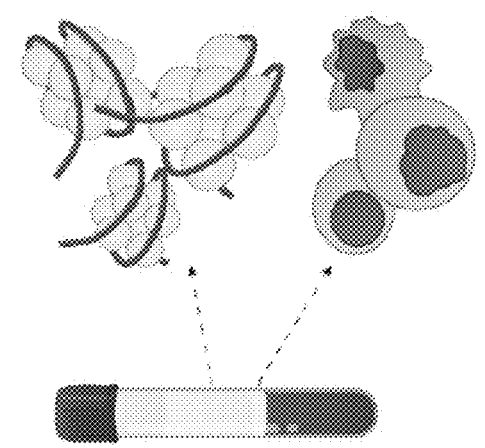
Figure 1:
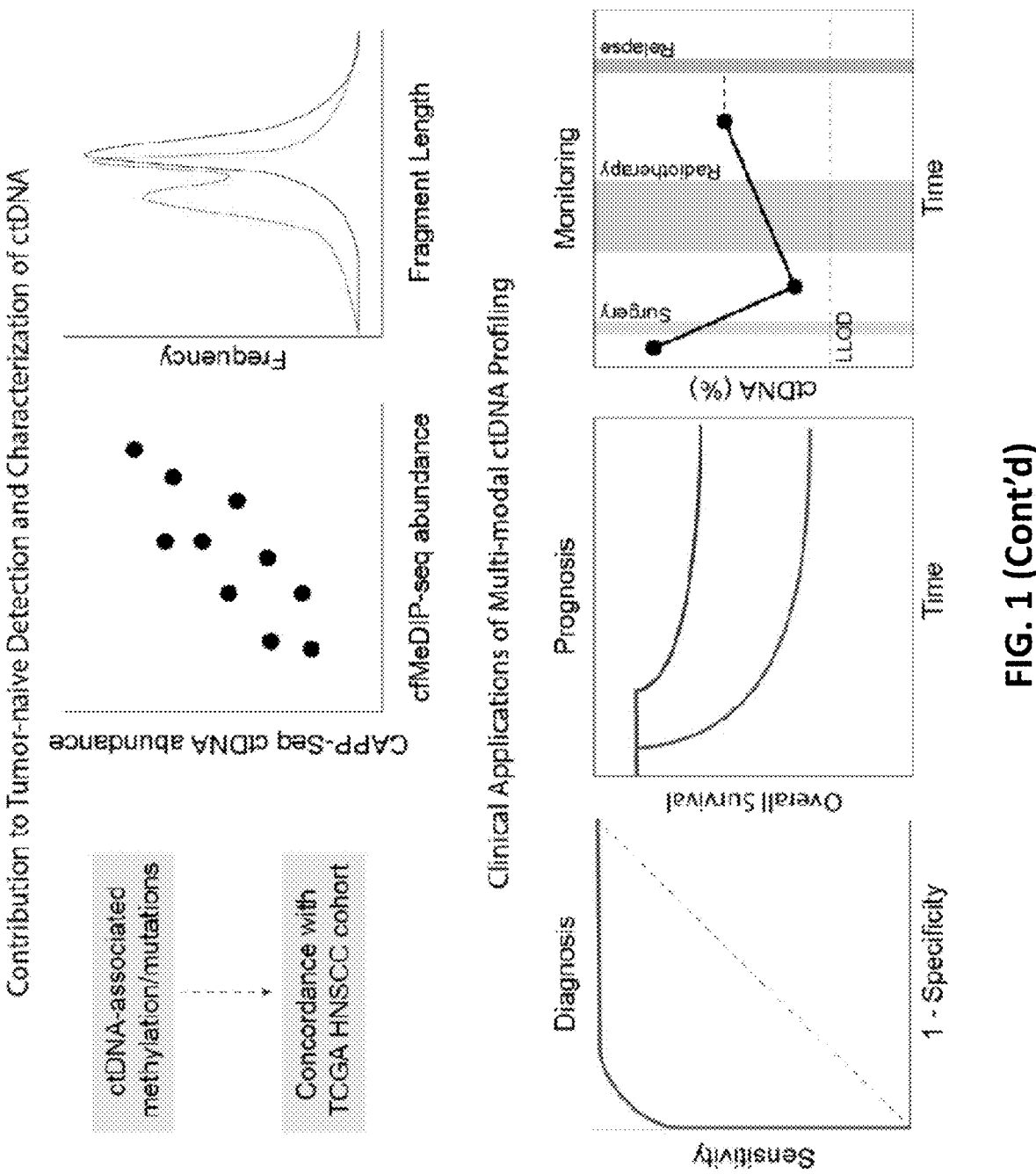

Multimodal profiling of cell-free DNA and PBL gDNA from patients and healthy controls were conducted (FIG. 1). By subjecting the same samples to both mutation and methylome profiling, we were able to evaluate their contributions to tumor-naïve detection and characterization of ctDNA. Mutations and methylation were independently profiled using CAncer Personalized Profiling by deep Sequencing (CAPP-Seq) and cell-free Methylated DNA ImmunoPrecipitation and high-throughput sequencing (cfMeDIP-seq), respectively. In addition, paired-end sequencing was utilized for both methodologies in order to obtain the lengths of sequenced cell-free DNA fragments.

Tumor-Naïve Detection of Mutation-Based ctDNA from Pre-Treatment Plasma

We first evaluated approaches to improve our confidence of mutation-based ctDNA detection without confirmation within matched tumor samples. Recent studies have illustrated that genes frequently targeted for ctDNA detection, such as TP53, can harbor mutations derived from clonally expanded PBLs. Additionally, as ctDNA contains both genetic and epigenetic features of the tumor, we reasoned that orthogonal analysis of both features in patient cell-free DNA may provide increased confidence of ctDNA detection. Therefore, to achieve tumor-naïve detection of low-abundance ctDNA with high confidence, mutations and methylation were independently profiled by CAPP-Seq and cfMeDIP-seq, respectively, for both cfDNA and matched PBLs.

Figure 2A:
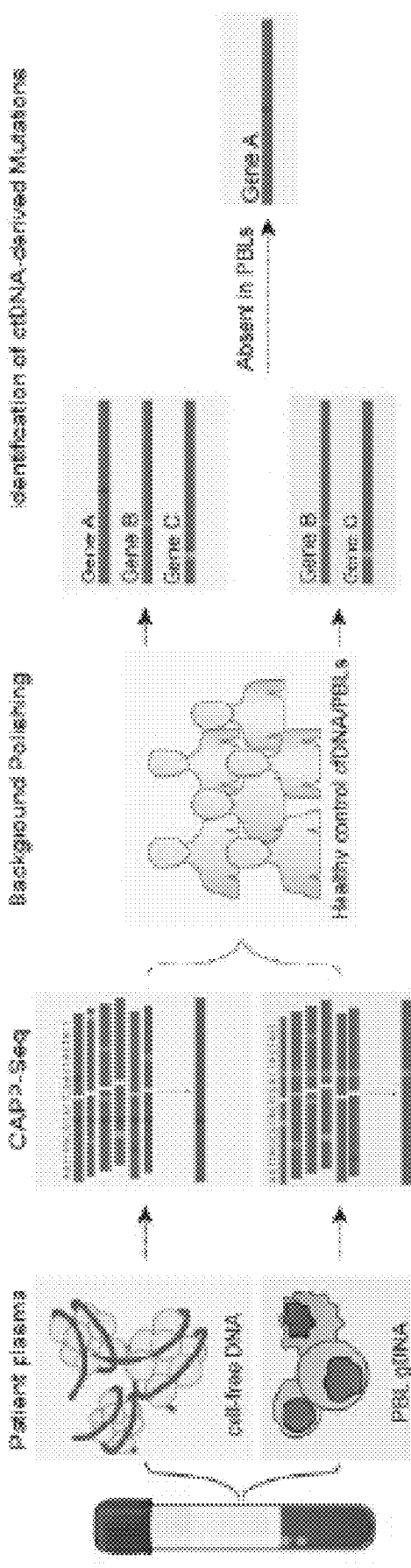
FIG. 2A illustrates utilization of PBL-filtering for detection of ctDNA by CAPP-Seq.
Figure 10:
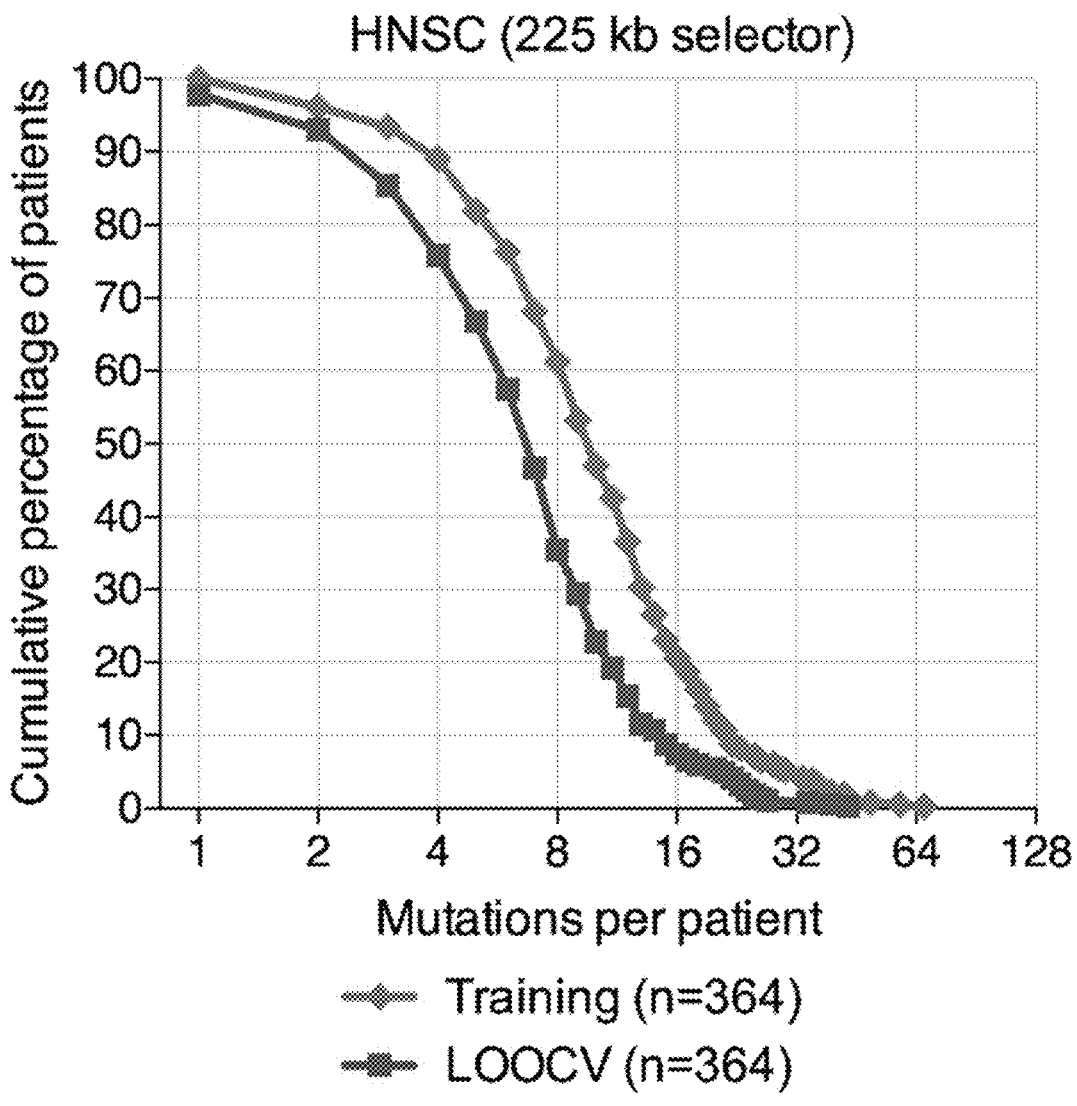
FIG. 10 shows analysis of the number of SNVs per HNSCC patient covered by the CAPP-Seq selector assessed either among all 364 patients in the HNSC TCGA cohort (blue diamonds) or using leave-one-out cross-validation (LOOCV; red squares).

To evaluate the sensitivity of ctDNA detection in HPV-negative HNSCC without prior knowledge from the tumor, we first measured the abundance of mutations in baseline plasma samples (FIG. 2A). CAPP-Seq was conducted with a sequencing panel designed to maximize the number of HNSCC-associated mutations (Table 3 and FIG. 10). We also employed established error suppression methodologies to remove background base substitution errors.

TABLE 6

| ctDNA derived DMR | | |
| --- | --- | --- |
| windowPos - DMR genomic region | ensemblId - DMR associated gene ID | DMR |
| chr2.19555801.19556100 | ENSG00000143867 | hyper |
| chr3.128210701.128211000 | ENSG00000179348 | hyper |
| chr3.138657301.138657600 | ENSG00000244578 | hyper |
| chr6.28303801.28304100 | ENSG00000235109 | hyper |
| chr8.99951901.99952200 | ENSG00000104375 | hyper |

Plasma and PBL samples from HNSCC patients at diagnosis and healthy donors by CAPP-Seq, utilizing 10-30 ng of input DNA were profiled. To achieve sensitive detection of ctDNA at low abundance, we applied a CAPP-Seq selector optimized to maximize the number of detected mutations in HNSCC (Table 2 and FIG. 10). We further improved our analytical sensitivity through integrated Digital Error Suppression (iDES), incorporating custom molecular barcodes and removing background base substitution errors as identified within healthy donor plasma samples (Methods).

TABLE 2

| Reported yields of cell-free DNA normalized to total plasma volume | | |
| --- | --- | --- |
| sampleID | dsDNApermLPlasma | timepoint |
| 1 | 10.69473684 | Normal |
| 2 | 19.6137931 | Normal |
| 3 | 11.2 | Normal |
| 4 | 9.76 | Normal |
| 5 | 11.57 | Normal |
| 6 | 7.72 | Normal |
| 7 | 15.83283582 | Normal |
| 1 | 5.09 | Diagnosis |
| 1 | 9.6 | Post-surgery |
| 2 | 12.34 | Diagnosis |
| 2 | 16.65 | Mid-radiotherapy |
| 3 | 5.55 | Diagnosis |
| 3 | 6.443076923 | Mid-radiotherapy |
| 3 | 5.659701493 | Post-treatment-1 |
| 3 | 8.516129032 | Post-treatment-2 |
| 4 | 13.65 | Diagnosis |
| 4 | 13.18 | Mid-radiotherapy |
| 5 | 11.76 | Diagnosis |
| 5 | 8.66 | Mid-radiotherapy |
| 6 | 6.75 | Diagnosis |
| 6 | 9.6 | Mid-radiotherapy |
| 6 | 13.23 | Post-treatment-1 |
| 6 | 8.68 | Post-treatment-2 |
| 7 | 10.28571429 | Diagnosis |
| 7 | 15.08571429 | Mid-radiotherapy |
| 7 | 4.96875 | Post-surgery |
| 7 | 6.941538462 | Post-treatment-1 |
| 8 | 16.68 | Diagnosis |
| 8 | 12.93 | Mid-radiotherapy |
| 8 | 23.21 | Post-surgery |
| 9 | 20.01509434 | Diagnosis |
| 9 | 20.05970149 | Mid-radiotherapy |
| 10 | 12.18 | Diagnosis |
| 10 | 14.32 | Mid-radiotherapy |
| 10 | 8.93 | Post-surgery |
| 11 | 27.04 | Diagnosis |
| 11 | 20.06 | Mid-radiotherapy |

TABLE 2-continued

| Reported yields of cell-free DNA normalized to total plasma volume | | |
| --- | --- | --- |
| sampleID | dsDNApermLPlasma | timepoint |
| 11 | 26.68 | Post-surgery |
| 11 | 9.07 | Post-treatment-1 |
| 12 | 7.2 | Diagnosis |
| 12 | 6.93 | Post-surgery |
| 13 | 8.87 | Diagnosis |
| 13 | 7.69 | Post-surgery |
| 14 | 5.73 | Diagnosis |
| 14 | 9.28 | Post-surgery |
| 15 | 17.31940299 | Diagnosis |
| 15 | 19.63636364 | Mid-radiotherapy |
| 16 | 21.75 | Diagnosis |
| 16 | 30.28 | Post-surgery |
| 17 | 14.02 | Diagnosis |
| 17 | 15.65 | Post-surgery |
| 18 | 8.076 | Diagnosis |
| 18 | 8.671 | Mid-radiotherapy |
| 18 | 7.504 | Post-surgery |
| 18 | 10.386 | Post-treatment-1 |
| 19 | 5.16 | Diagnosis |
| 19 | 11.41333333 | Mid-radiotherapy |
| 19 | 17.6 | Post-surgery |
| 20 | 52.58181818 | Diagnosis |
| 20 | 9.523809524 | Mid-radiotherapy |
| 20 | 24.38709677 | Post-surgery |
| 20 | 55.8 | Post-treatment-1 |
| 21 | 8.903225806 | Diagnosis |
| 21 | 10.28571429 | Mid-radiotherapy |
| 21 | 14.55 | Post-surgery |
| 21 | 9.68 | Post-treatment-1 |
| 22 | 69.96 | Diagnosis |
| 22 | 10.25 | Mid-radiotherapy |
| 22 | 26.71 | Post-treatment-1 |
| 23 | 8.023880597 | Diagnosis |
| 23 | 6.889655172 | Mid-radiotherapy |
| 23 | 13.73333333 | Post-surgery |
| 24 | 4.34 | Diagnosis |
| 24 | 11.78 | Post-surgery |
| 25 | 13.76 | Diagnosis |
| 25 | 10 | Post-surgery |
| 26 | 31.16 | Diagnosis |
| 26 | 24 | Mid-radiotherapy |
| 26 | 16.8 | Post-treatment-1 |
| 27 | 7.219047619 | Diagnosis |
| 27 | 6.978461538 | Mid-radiotherapy |
| 27 | 6.95625 | Post-surgery |
| 28 | 27.78 | Diagnosis |
| 28 | 7.1 | Mid-radiotherapy |
| 28 | 8.62 | Post-surgery |
| 29 | 14.86451613 | Diagnosis |
| 29 | 12.16 | Mid-radiotherapy |
| 29 | 8.828571429 | Post-treatment-1 |
| 30 | 10.575 | Diagnosis |
| 30 | 12.75 | Post-surgery |
| 30 | 14.55 | Post-treatment-1 |
| 4 | 14.42033898 | Normal |
| 4 | 8.66 | Normal |
| 4 | 6.92 | Normal |
| 4 | 12.51764706 | Normal |
| 4 | 11.70526316 | Normal |
| 4 | 13.99148936 | Normal |
| 4 | 7.670588235 | Normal |
| 4 | 11.328 | Normal |
| 4 | 8.465454545 | Normal |
| 4 | 8.27 | Normal |
| 4 | 6.498461538 | Normal |

TABLE 2-continued

Reported yields of cell-free DNA normalized to total plasma volume

| sampleID | dsDNApermLPlasma | timepoint |
|----------|------------------|-----------|
| 4 | 12.72 | Normal |
| 4 | 21.63 | Normal |

Figures 2B, 2C:
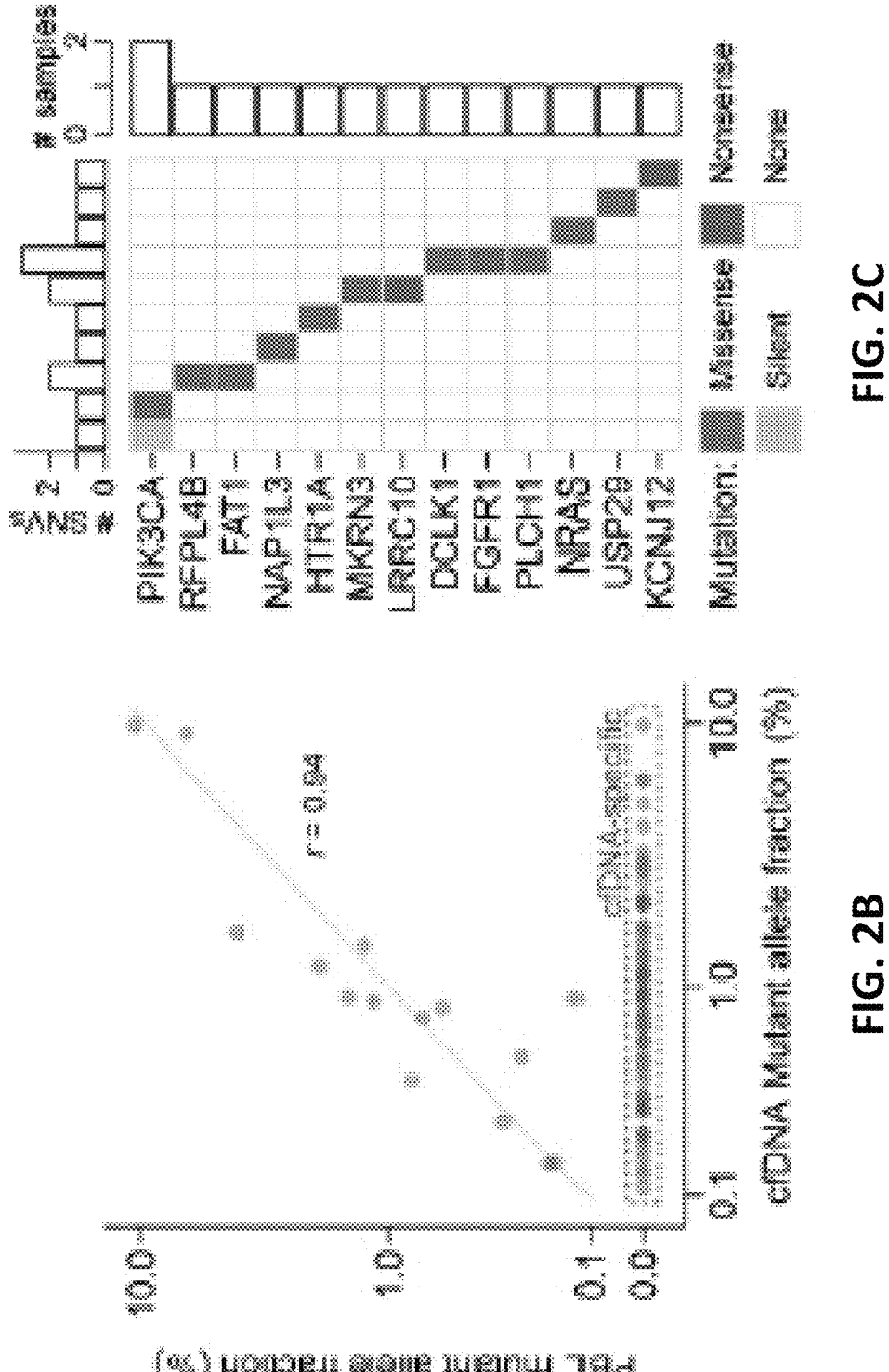
FIG. 2B shows mutant allele fraction of candidate SNVs identified in matched patient plasma and/or PBLs. Pearson's correlation was performed on SNVs strictly found in both matched patient plasma and PBLs. Candidate SNVs found only in patient plasma are denoted within the dashed red box.
FIG. 2C shows oncoprint of candidate SNVs identified in both matched patient plasma and PBLs. The top histogram denotes the number of SNVs per patient whereas the right histogram denotes the number of patients with a specified gene mutated.
Figure 2D:
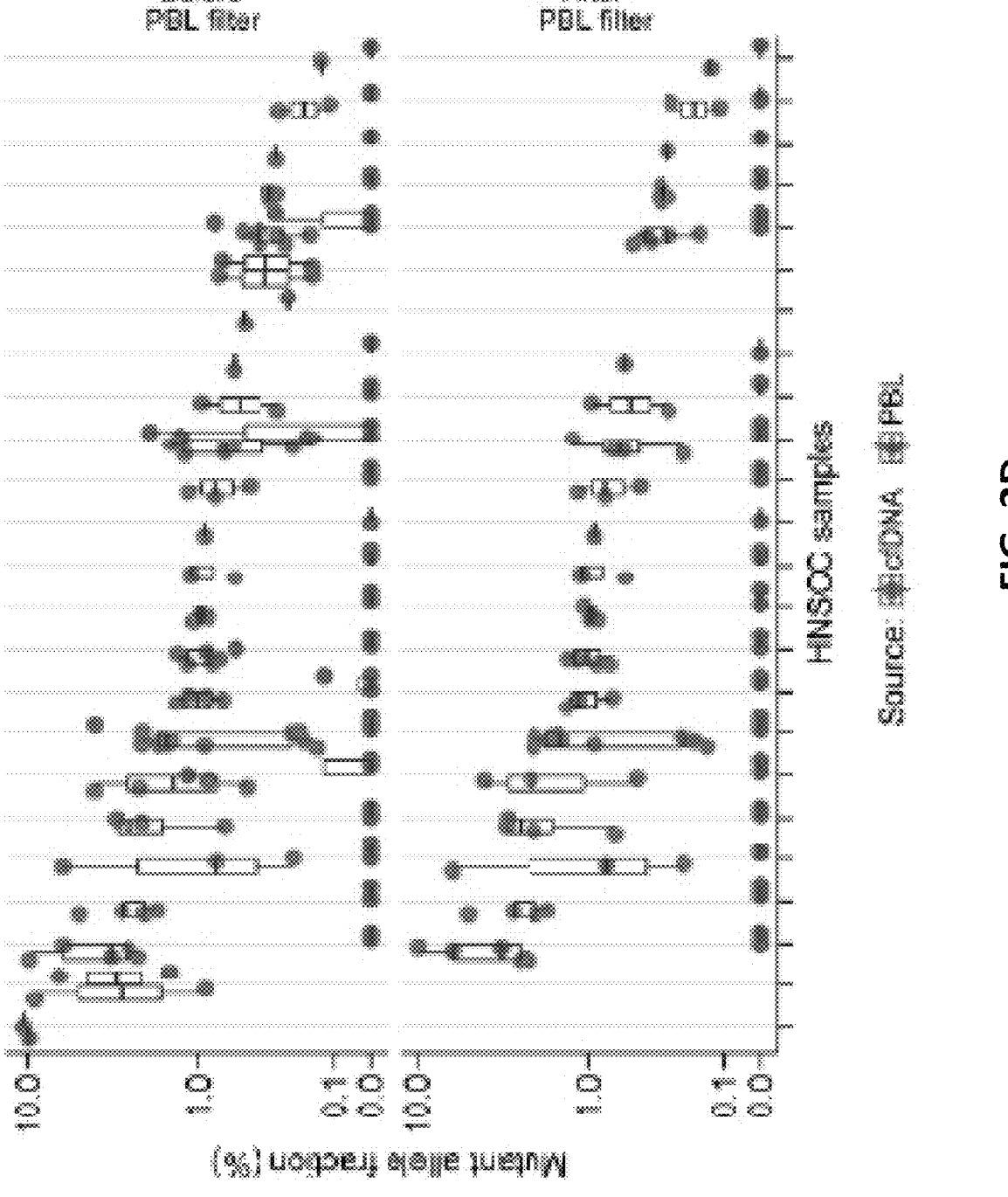
FIG. 2D shows mean MAF of candidate SNVs across HNSCC patient cfDNA (red circle) and PBL (blue circle) before and after removal of PBL-associated SNVs. Patients with SNVs absent after PBL filtering are indictive of false positive detection of ctDNA.

After selecting for candidate somatic single nucleotide variants (SNVs) based on plasma profiling and removal of likely germline mutations, we characterized potential false-positives due to clonal hematopoiesis (CH) by comparison with matched PBL profiles. Of the 24 patients with identifiable candidate SNVs, 10 demonstrated identical SNVs within their matched PBL profile with highly correlated mutant allele fractions (MAFs) (R=0.94, p=1.392e$^{-07}$, FIG. 2B). With the exception of PIK3CA, genes harboring these SNVs were unique to each patient (FIG. 2C). As genes that are commonly affected by CH, such as DNMT3A, TET2, and ASXL1, were not included within the CAPP-Seq selector, our findings of patient-unique SNVs within matched cfDNA and PBL samples further emphasizes the benefit of this approach over gene level filtering. Plasma samples from 4 patients were strictly positive for SNVs derived from CH (FIG. 2D), suggesting that matched PBL profiling may greatly minimize false-positive detection of ctDNA at low abundance.

Figure 2E:
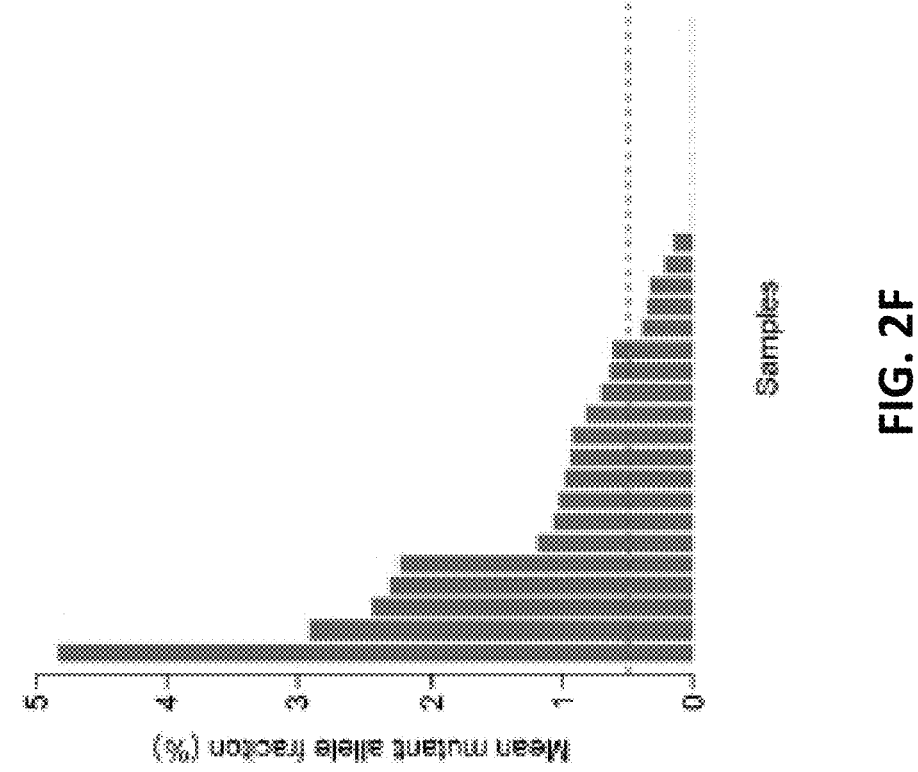
FIG. 2E shows oncoprint of selected PBL-filtered SNVs identified in 20/32 HNSCC patients. The top and right histograms denote that as previously described in FIG. 2C.

After removing candidate SNVs potentially reflective of CH, ctDNA was detected within plasma of 20 patients (median [range]: 3 [1-10] SNVs per patient). To evaluate the plausibility of these SNVs, we compared our results to whole-exome sequencing data from 279 HNSCC tumors published by The Cancer Genome Atlas (TCGA)[45], observing similarities in frequently mutated genes including TP53 (65% vs. 72%), PIK3CA (20% vs. 21%), FAT1 (15% vs. 23%), and NOTCH1 (10% vs. 19%) (FIG. 2E). Interestingly, two patients presented with single SNVs not found within these genes (GRIN3A and MYC, FIG. 11), demonstrating the added utility of profiling genes with unknown/non-driver effects to increase detection sensitivity OF ctDNA.

Figure 2F:
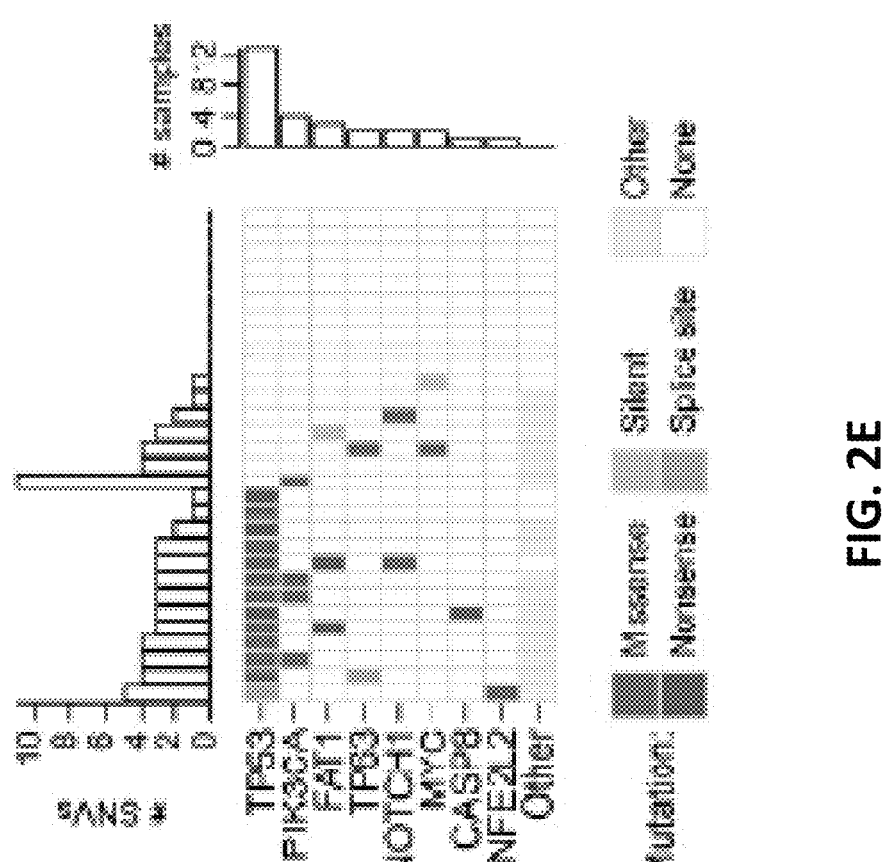
FIG. 2F shows mean mutant allele percentage of PBL-filtered SNVs across all HNSCC patients. For each SNV per patient, the mutant allele percentage was calculated by the fraction of reads containing the SNV of interest, compared to reads that contained the native sequence overlapping the SNV base-pair position.

Calculating ctDNA abundance based on the mean MAF of SNVs, ctDNA levels ranged from 0.14% to 4.83% (FIG. 2F). This lower limit of detection is similar to that previously described by others utilizing tumor-naïve CAPP-Seq analysis, estimated at ~0.14%. Including patients with undetectable ctDNA, the median ctDNA abundance across our HNSCC cohort was 0.49%-similar to what has been observed in localized NSCLC by CAPP-Seq.

Tumor-Naive Detection of Methylation-Based ctDNA from Baseline Plasma

Figure 3A:
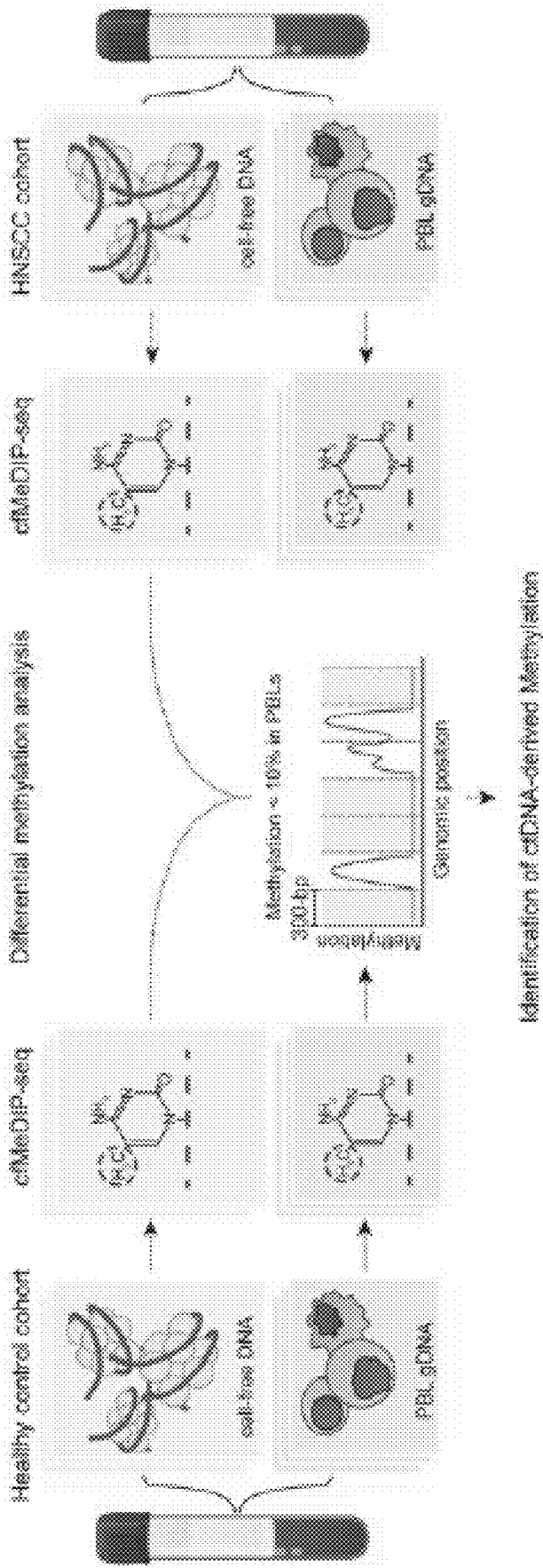
FIG. 3A illustrates identification of informative regions for detection of ctDNA by cfMeDIP-seq.

Next, we sought to define ctDNA-associated methylation patterns in the HNSCC and healthy control samples. As the CAPP-Seq results illustrated the impact of false positive mutations arising from PBLs, we reasoned that a reduction of false positive ctDNA-associated methylation may be achieved by removal of PBL-derived DNA methylation signals. Therefore, we used matched PBL MeDIP-seq profiles from the HNSCC and healthy control samples to suppress their contribution to the cell-free DNA methylation signal (FIG. 3A). We evaluated whether matched PBL analysis may also enable methylation-based ctDNA detection (FIG. 3A). Pre-treatment HNSCC and healthy donor plasma as well as PBLs were profiled by cfMeDIP-seq, utilizing 5-10 ng of input DNA. As previously described, methylation abundance was defined within nonoverlapping 300 bp windows across chromosomes 1-22 (n=9,603,454 windows) with read counts normalized to reads per kilobase per million (RPKM) (Methods).

As the anti-5mC antibody utilized for methylation pull-down preferentially binds to DNA fragments at increasing CpG densities, including CpG islands, we first characterized this interaction to identify regions likely to be highly represented within cfMeDIP-seq data. We also applied MeDIP-seq to the HNSCC cell-line FaDu to assess the preferential binding of cancer-derived methylated DNA fragments. Comparing DNA fragment pulldown abundance (median RPKM) across windows with varying numbers of CpGs, we observed increasing enrichment up to ≥8 CpGs for both PBLs and FaDu (FIGS. 12A and 12B). FaDu demonstrated greater enrichment compared to PBLs at ≥8 CpGs per 300 bp window. This result is consistent with the established phenomenon of CpG island hypermethylation in cancer cells including FaDu. Based on these observations, we determined that windows with ≥8 CpGs (n=702,488) may be most informative for ctDNA detection and were therefore utilized for all subsequent analysis.

Figure 3B:
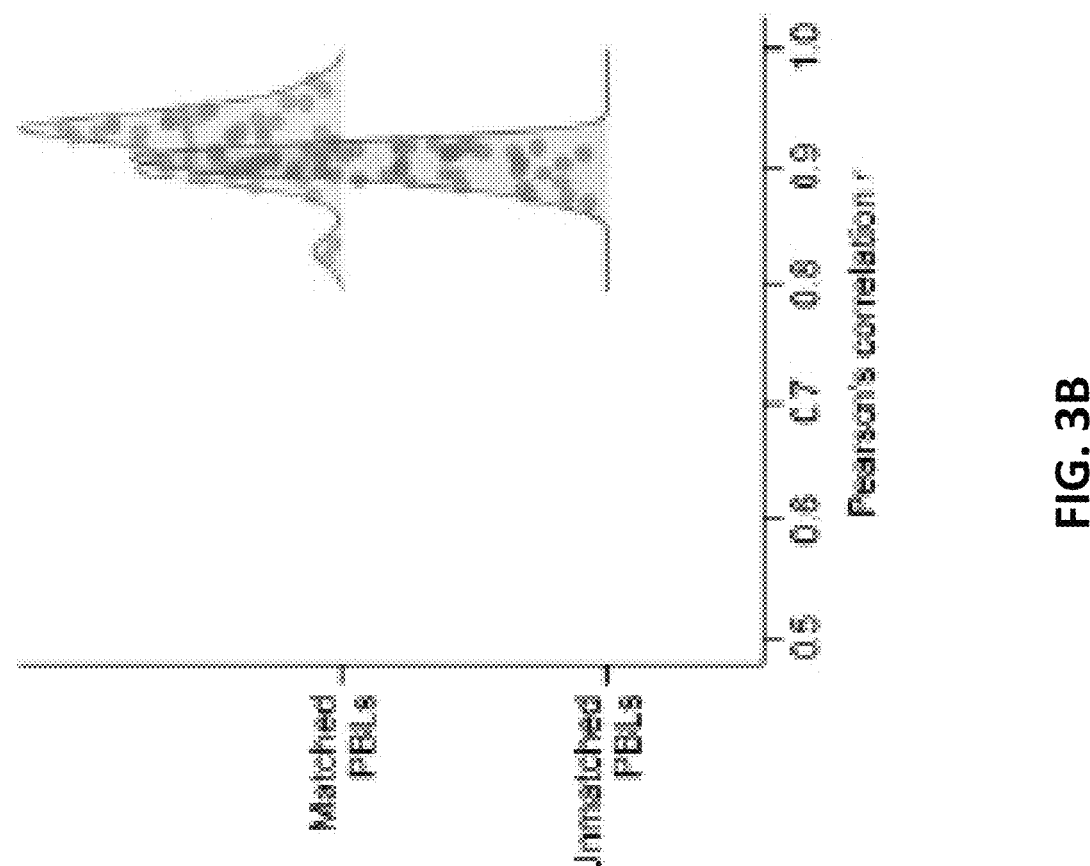
FIG. 3B shows Pearson's correlation of 300-bp non-overlapping windows with >=8 CpGs from patient and healthy donor cfDNA cfMeDIP-seq profiles (n=52) against FaDu genomic DNA (gDNA) [1×1×52 comparisons], unmatched PBL gDNA [1×51×52 comparisons], and matched PBL gDNA [1×1×52 comparisons] MeDIP-seq profiles.

For patients with localized cancer, the vast majority of plasma cell-free DNA originates from PBLs. Therefore, we sought to exploit PBL MeDIP-seq profiles to bioinformatically suppress this contribution to the cell-free DNA signal. We compared RPKM values for each window within cfMeDIP-seq profiles generated from HNSCC and healthy donor cfDNA, to MeDIP-seq profiles generated from FaDu (1-by-1 comparison), unpaired PBLs (1-by-51 comparison), or paired PBLs (1-by-1 comparison). In accordance with PBLs being the main contributor of plasma cell-free DNA, genome-wide methylation profiles were highly correlated between plasma cell-free DNA and either paired or unpaired PBLs (modal R=0.92 and R=0.91, respectively). The strengths of these correlations likely reflect the known outsize contribution of PBLs to plasma cfDNA. In contrast, correlations were weaker between plasma cell-free DNA and FaDu (modal R=0.78) (FIG. 3B).

To select a threshold of decreased methylation across PBLs while considering preferential pulldown, we scaled and normalized PBL cfMeDIP-seq profiles to absolute methylation levels (0-1) based on logistic regression modelling via the MeDEStrand R package (Methods). We selected 99,997 windows that demonstrated median absolute methylation values <0.1 across healthy donor PBLs. When these windows were applied to left-out HNSCC PBLs we observed similar distributions of absolute methylation to that of the utilized healthy donor PBLs (FIG. 3B), demonstrating generalizability of this approach. Likewise, none of these windows individually showed significantly higher methylation across HNSCC PBLs compared to healthy donor PBLs (FIG. 3C and FIG. 12B), limiting any source of HNSCC-specific PBL methylation that may confound ctDNA detection. In other words, these results confirm that the main source of cfDNA methylation in both control and locoregionally confined HPV-negative HNSCC plasma are derived from PBLs and that bioinformatic removal of PBL-derived methylation may limit signals that confound ctDNA quantification.

Tumor-Naïve Detection of Pre-Treatment Methylation-Based ctDNA

Figure 3C:
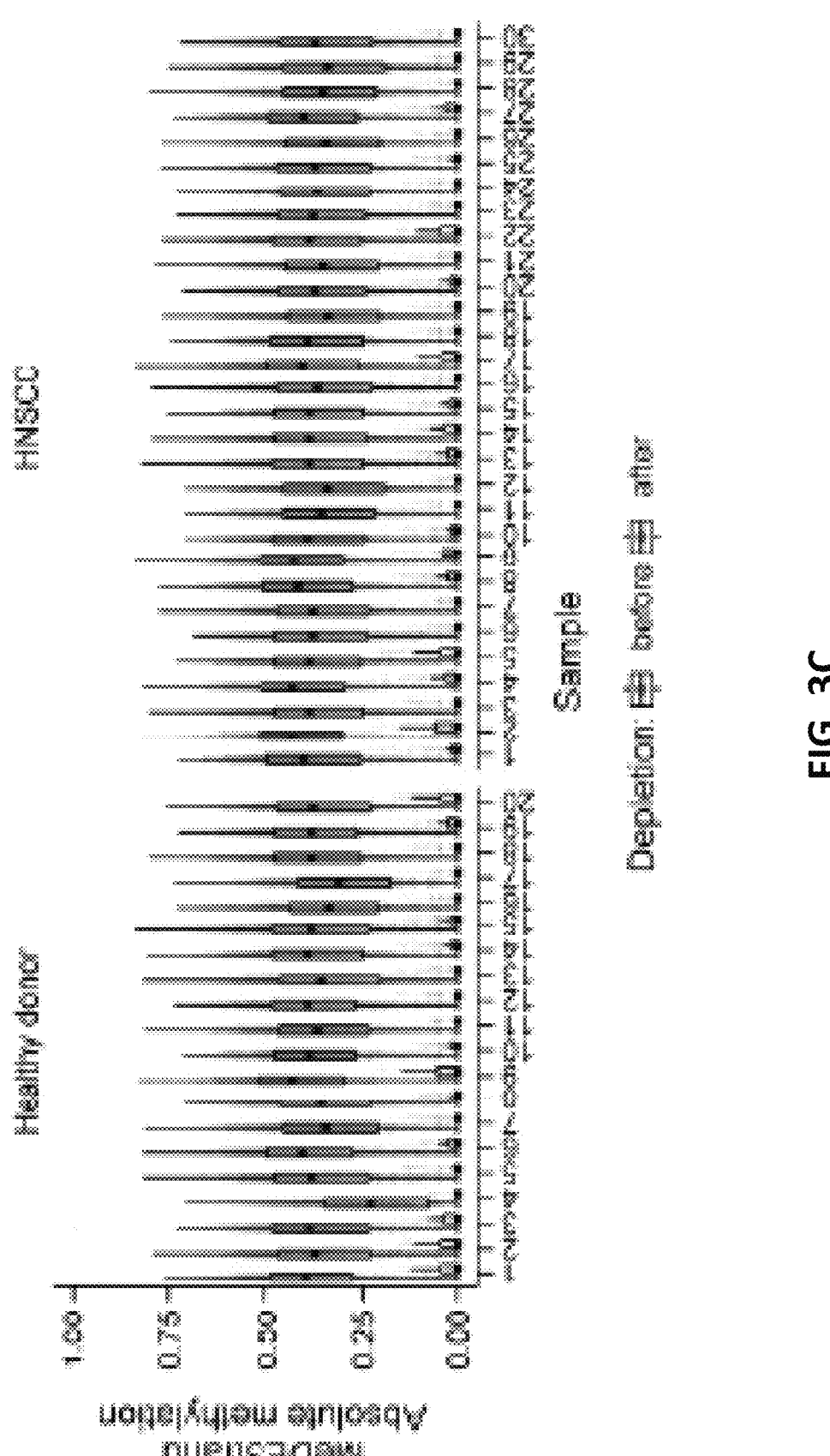
FIG. 3C shows performance of in-silico PBL-depletion in healthy donor (right) and HNSCC (left) PBL MeDIP-seq profiles. Absolute methylation scores were calculated from MeDIP-seq counts via MeDEStrand (Methods). 300-bp non-overlapping windows before PBL-depletion (blue) correspond with all windows from chromosome 1-22 with >=8 CpGs (n=702,488). 300-bp non-overlapping windows after PBL-depletion (red) include an additional filter where the median absolute methylation across healthy donor PBLs is <0.1 (n=99,997).
Figure 3D:
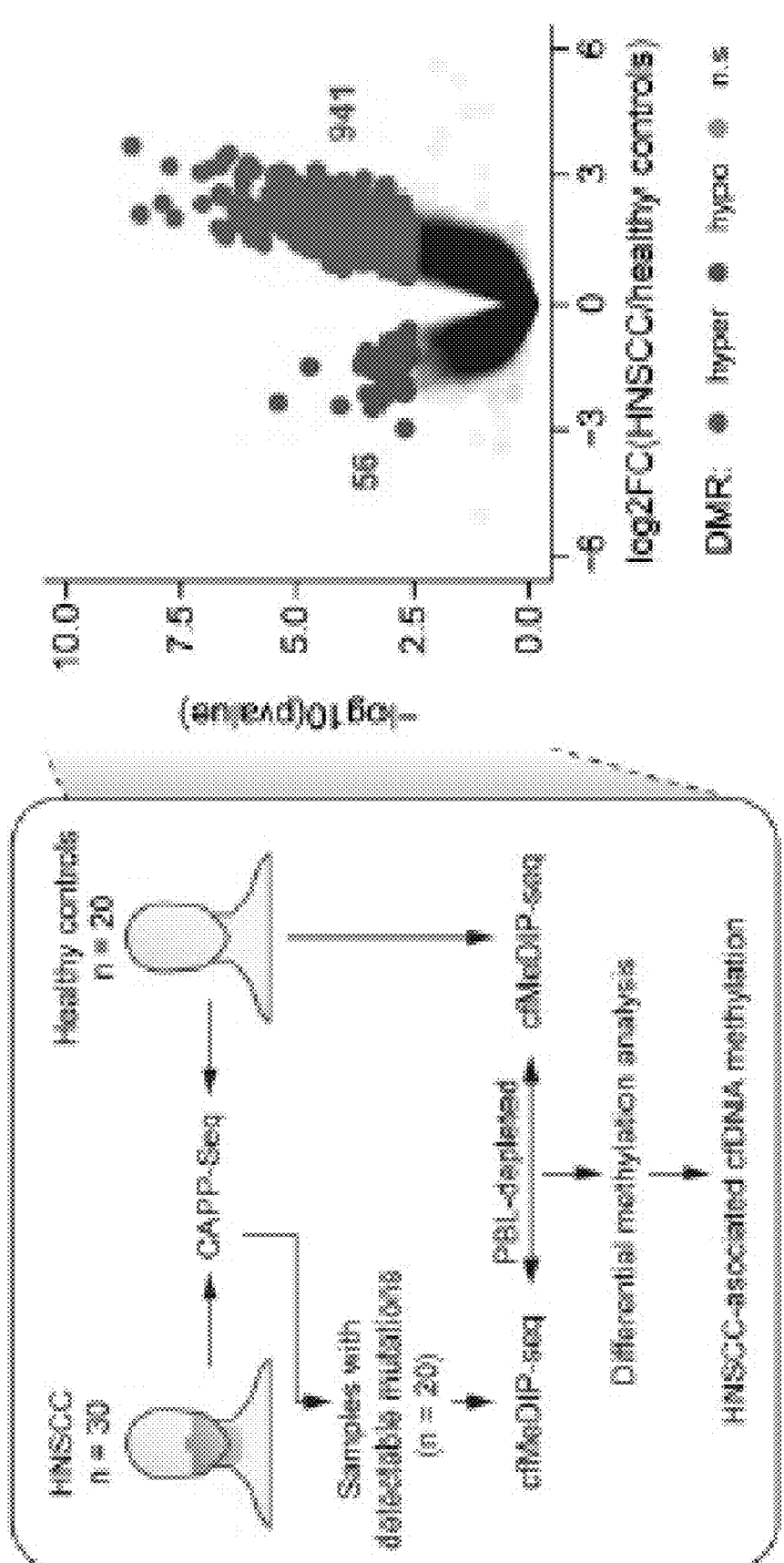
FIG. 3D illustrates workflow of ctDNA detection by differential methylation analysis of HNSCC and healthy donor cfMeDIP-seq profiles. cfMeDIP-seq profiles from HNSCC patients with detectable SNVs by CAPP-Seq (i.e., CAPP-Seq positive, n=20) were compared to healthy donors (n=20) within PBL-depleted windows to identify HNSCC-associated cfDNA methylation. Hyper- and hypo-methylated regions are denoted as regions with higher or lower methylation in the HNSCC cohort compared to healthy donors at an FDR <10%.
Figures 3E, 3F:
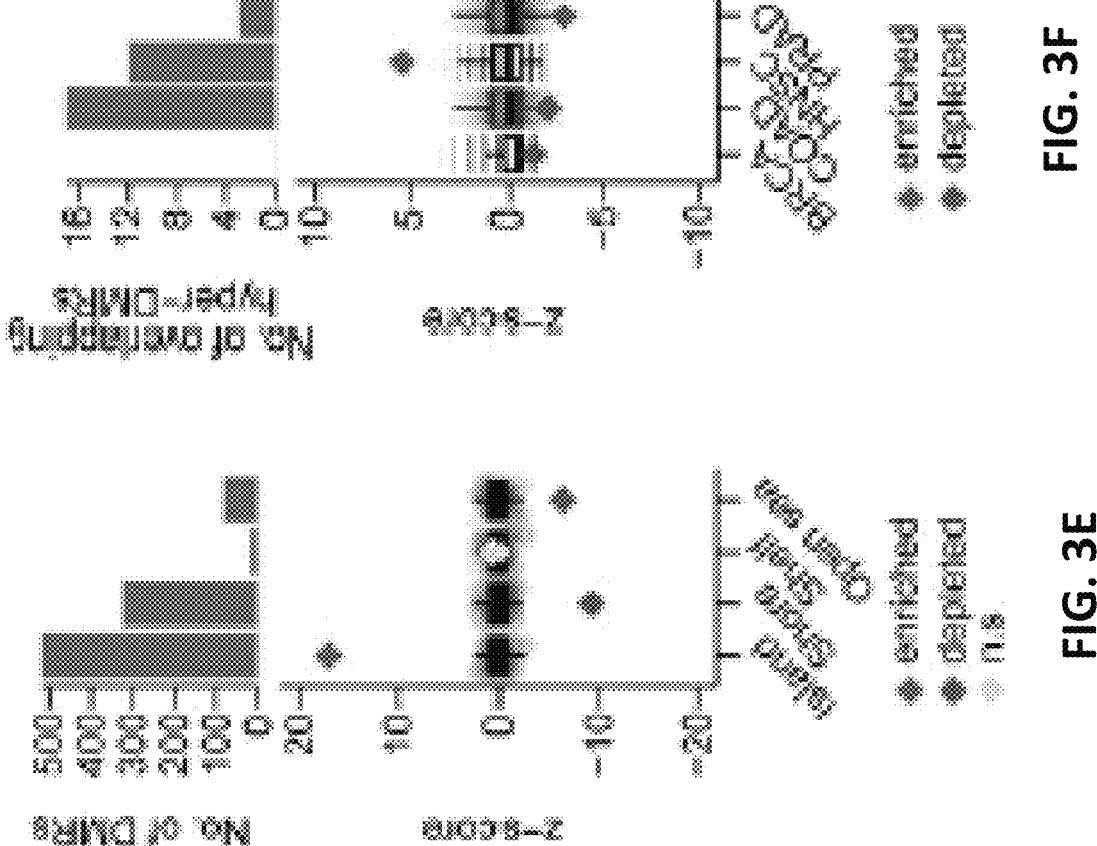
FIG. 3E shows permutation analysis of hyper-methylated regions annotated by CpG site (n=10,000 total permutations). Significant enrichment/depletion is denoted as observed z-scores with a p-value less than 0.05.
FIG. 3F shows permutation analysis of hyper-methylated regions within tumor-specific methylated cytosines from TCGA (n=1000 permutations total). Significant enrichment/depletion is denoted as observed z-scores with a p-value less than 0.05.
Figure 13B:
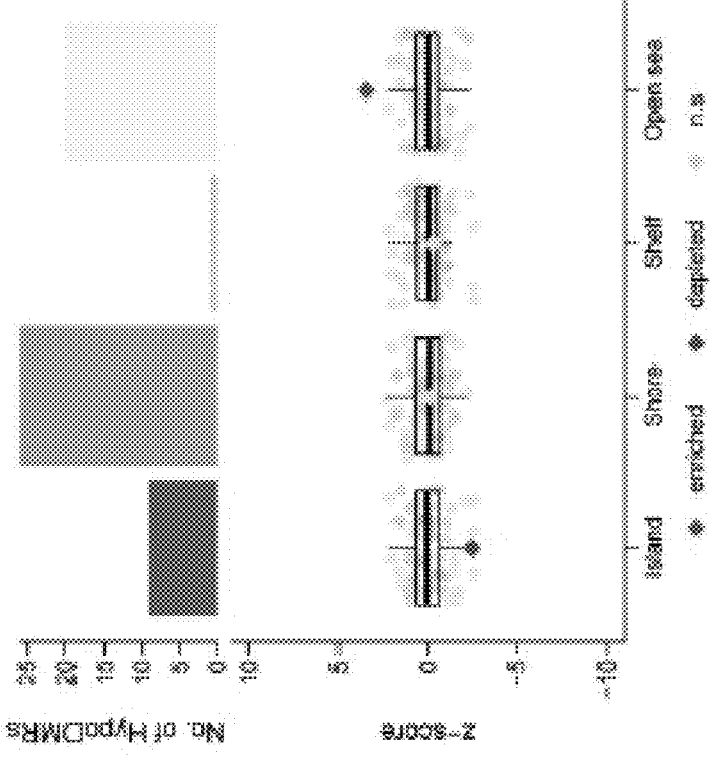
FIGS. 13A-13B illustrate related figures to results of differential methylation analysis between HNSCC and healthy donor cfDNA samples within PBL-depleted windows (related to FIG. 2D).
Figure 13A:
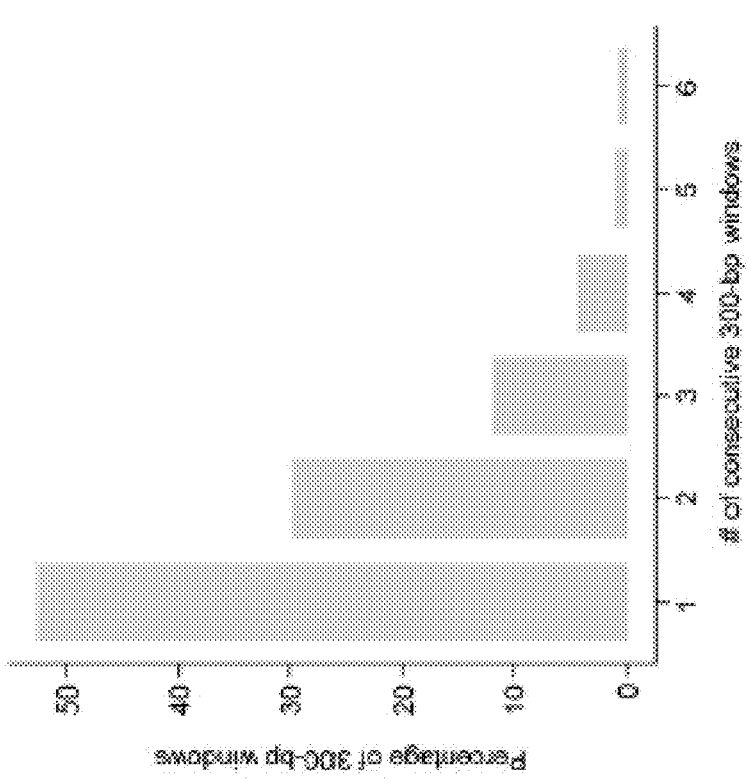

To identify common ctDNA-derived hypermethylated regions within our HNSCC cohort, we performed differential methylation analysis comparing HNSCC patients with detectable ctDNA by CAPP-Seq (n=20) to healthy donors. Utilizing the 99,994 300-bp windows depleted for methylation in PBLs, we identified ctDNA-derived differentially methylated regions (DMRs) by comparing the 20 HNSCC patients with CAPP-Seq-detectable ctDNA to the 20 healthy controls. In total we identified 997 differentially methylated regions (DMRs) (hypermethylated: 941, hypomethylated: 56) across HNSCC samples (FIG. 3C). Approximately half of hypermethylated regions (hyper-DMRs) were found to be immediately adjacent to one another, with blocks of hyper-methylation extending up to 1800 base-pairs in length (FIG. 13A). These data suggest the presence of CpG islands within the identified hyper-DMRs. Conversely, no adjacent hypomethylated regions (hypo-DMRs) were observed. Of the 300-bp hyper-DMRs, 47.5% resided in contiguous blocks of hypermethylation signals extending up to 1800 bp in length (FIG. 13A), indicative of CpG islands that typically span 300-3000-bp in length. Indeed, CpG islands were significantly enriched for hyper-DMRs (FIG. 3E). In contrast, CpG islands were significantly depleted for hypo-DMRs (FIG. 13B).

To determine whether these hyper-DMRs were indeed enriched for CpG islands, we next assessed the enrichment of hyper-DMRs for CpG islands, shores, shelves, and open seas by permutation analysis (Methods). As expected, a significant enrichment of CpG islands as well as a significant depletion of shores and open sea was observed within the hyper-DMRs (FIG. 3E). In contrast, the hypo-DMRs were significantly enriched for open sea and depleted for CpG islands (FIG. 13B), in accordance with hypomethylation of CpG-sparse regions frequently observed across cancers.

Figure 14:
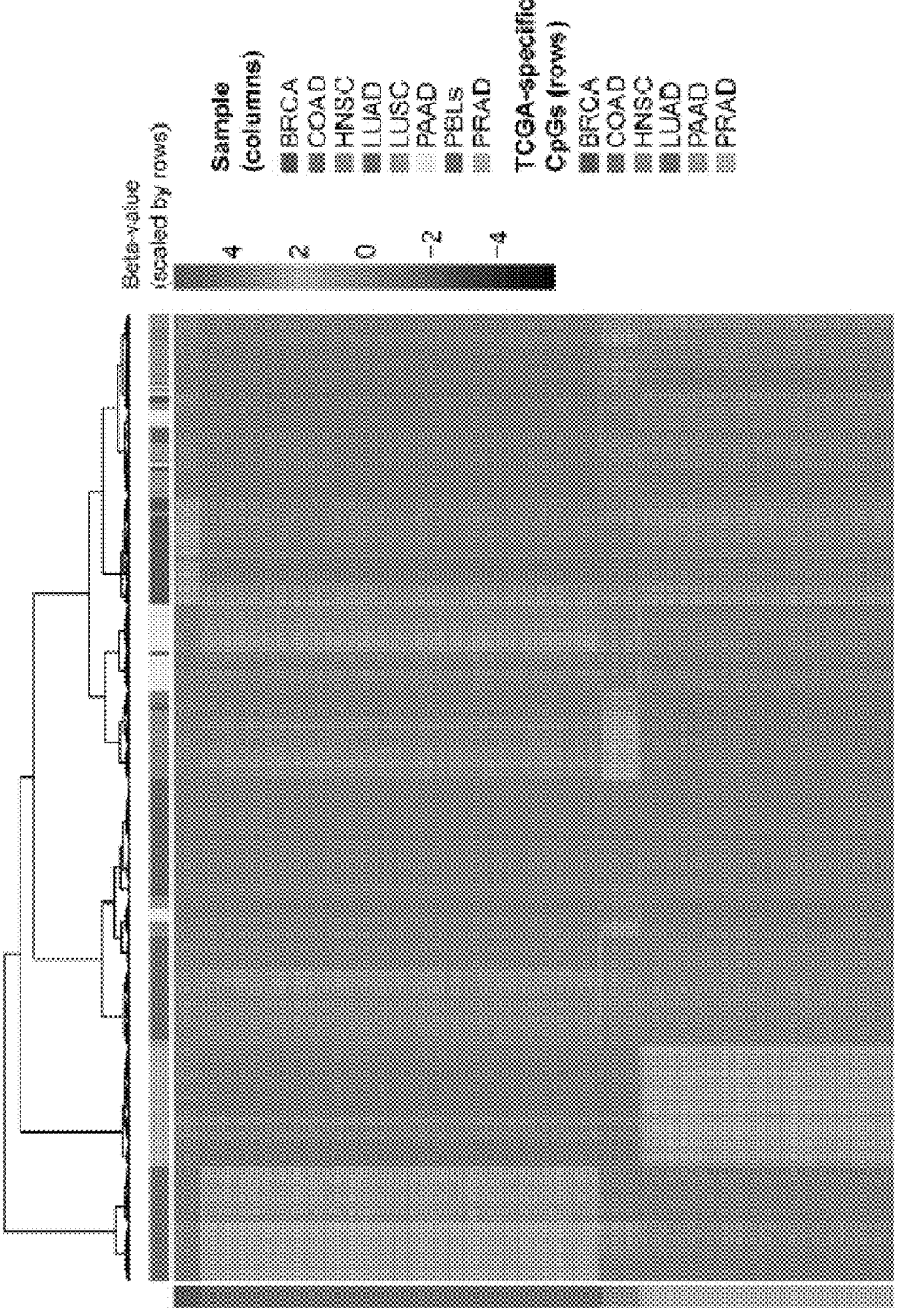
FIG. 14 shows supervised hierarchical clustering of TCGA primary tumors based on identified of cancer-specific differentially methylated cytosines. Cancer_type (column) refers to the classification of each primary tumor or PBL sample, whereas cancer_DMCs (row) refers to cancer-specific differentially methylated cytosines identified for each cancer type (PBLs excluded).

Finally, as methylation of certain regions may distinguish tissue-of-origin as previously described using cfMeDIP-seq, we also investigated whether the hyper-DMRs contained regions specific to HNSCC or other cancers. To identify tumor-specific methylated regions, we utilized HumanMethylation450K (hm450k) data generated from primary tumors provided by TCGA (Methods). Comparing primary tumors from breast invasive carcinoma (BRCA), colon adenocarcinoma (COAD), lung squamous cell carcinoma (LUSC), prostate adenocarcinoma (PRAD), HNSCC, pancreatic adenocarcinoma (PAAD), and PBLs, we identified sufficient hypermethylated CpGs (≥50) specific for BRCA, COAD, PRAD, and HNSCC (Methods) (FIG. 14). As expected, we observed significant enrichment of the plasma-derived DMRs overlapping with HNSC-specific hypermethylated CpGs, as well as a significant depletion of overlap across BRCA-, COAD-, and PRAD-specific hyper-methylated CpGs (FIG. 3F), suggesting that the hyper-DMRs contain regions specific to HNSCC origin when compared to various other cancer types.

Mutation-Based and Methylation-Based ctDNA Detection are Highly Concordant

A growing number of studies have described ctDNA to be associated with decreased fragment length compared to healthy sources of plasma cell-free DNA, providing an additional metric for robust tumor-naïve detection. As targeted sequencing has been previously shown to detect ctDNA at reduced fragment length, we first utilized our CAPP-Seq profiles to determine whether we may observe similar trends within HNSCC patients. For each identified SNV per patient (FIG. 2E), we measured the median length of fragments containing the SNV allele as well as the overlapping reference allele. For cases where multiple SNVs were identified within a patient sample, the median value across all SNVs and their reference alleles was used. In accordance with previous findings, we observed a consistent decrease in ctDNA fragment size compared to healthy cell-free DNA across patients (median [range] Δ=−17.5

Figure 4B:
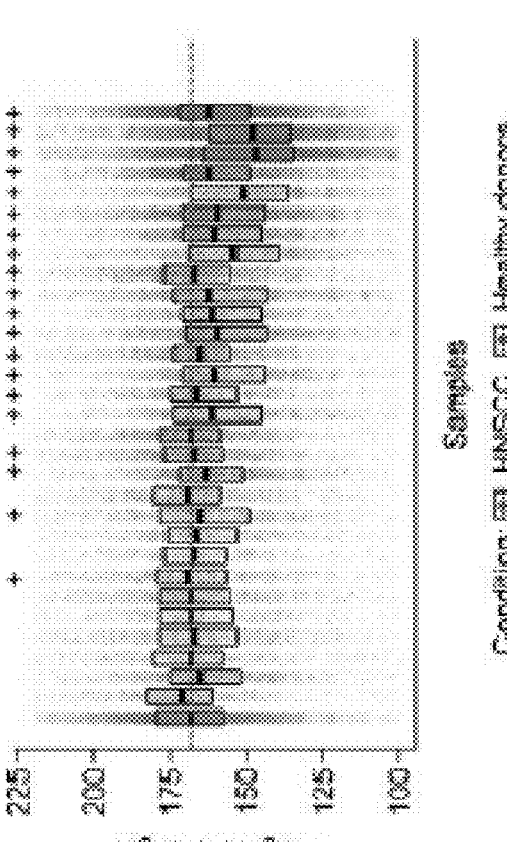
FIGS. 4A-4J illustrate concordance of ctDNA detection and abundance between CAPP-Seq and cfMeDIP-seq profiles.
Figure 4A:
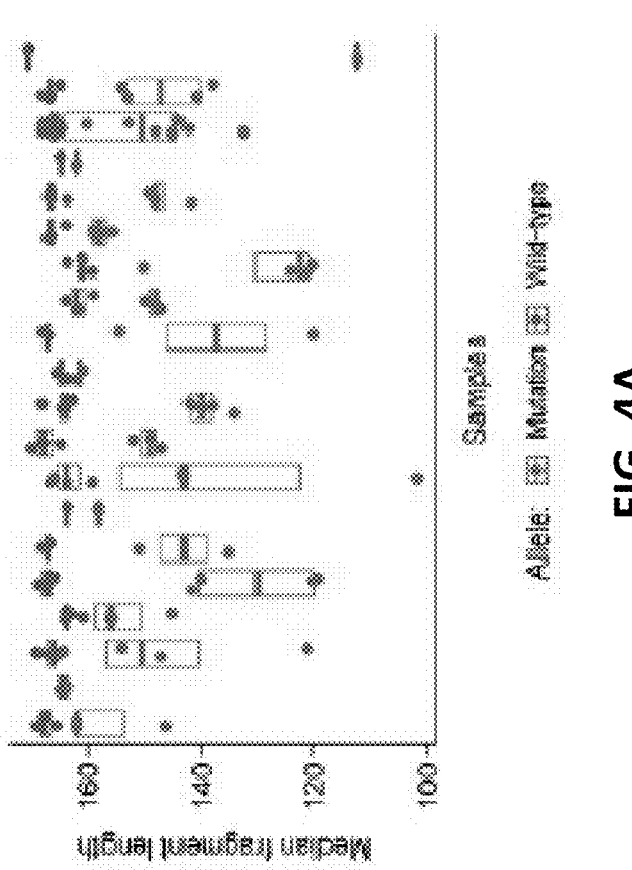
Figure 15B:
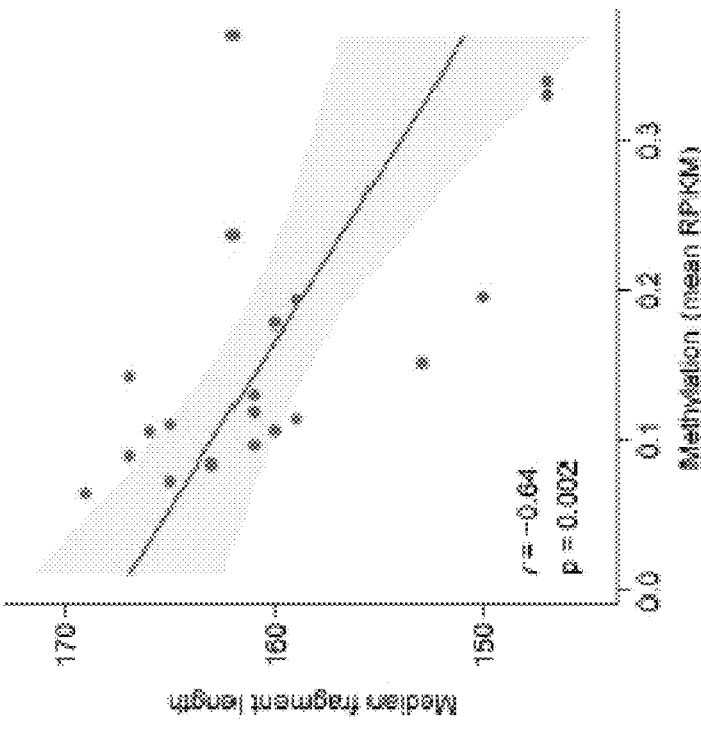
FIGS. 15A-15B shows related figures to FIGS. 4A-4J.
Figure 15A:
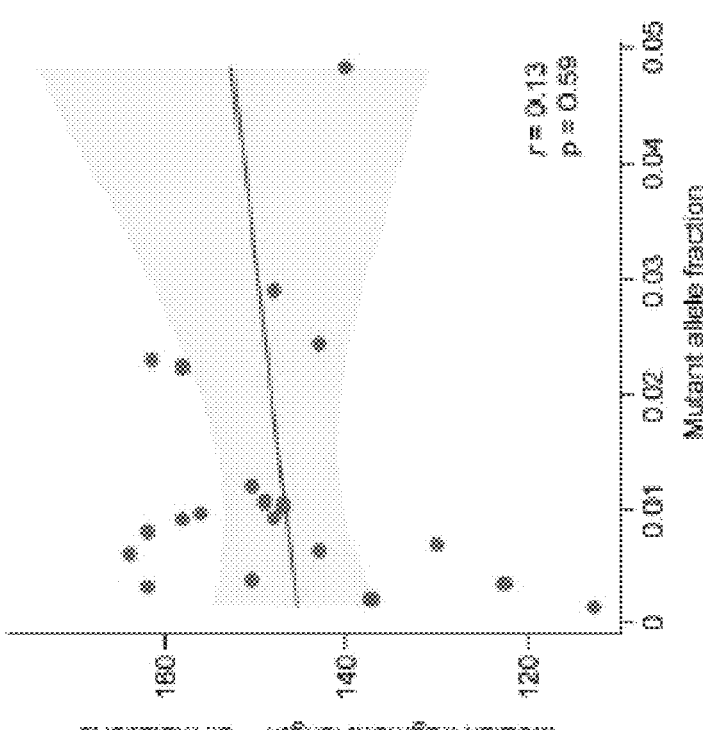

[1-58] bp) (FIG. 4A). There was no significant association between the mean MAF of these mutations and fragment length (FIG. 15A).

Figure 4D:
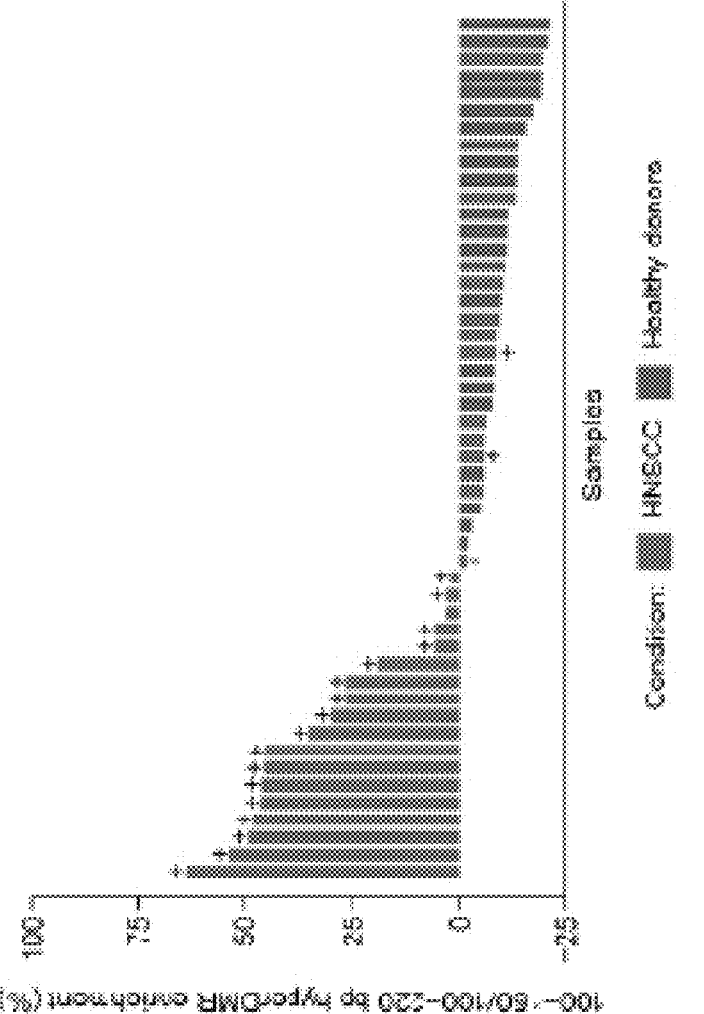
Figure 4C:
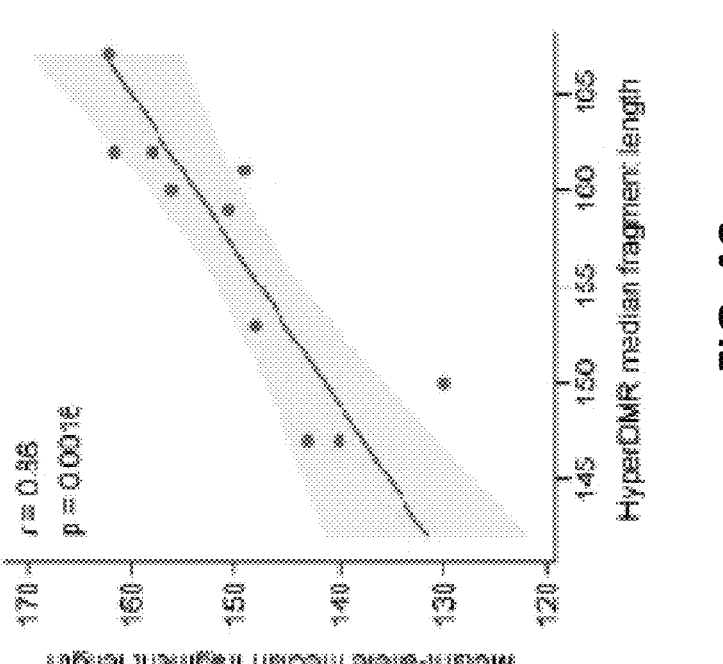

Unlike bisulfite-based DNA methylation approaches, cfMeDIP-seq does not cause DNA degradation and, therefore, preserves the original fragment size distribution. This provides a novel opportunity to map DNA methylation and fragment lengths concomitantly. The distribution of fragment lengths within the previously identified plasma derived hyper-DMRs for each patient was assessed. Due to the nature of these regions having low methylation across our healthy donors, DNA fragments across donors were combined for comparison. Similar to the mutation-based analysis, we observed a reduction in fragment length from 19/20 CAPP-Seq positive patients compared to grouped healthy controls (median [range] Δ=−7 [1-21] bp) (FIG. 4B). This represented a smaller reduction in fragment lengths compared with the mutation-based analysis, possibly due to partial contribution by healthy tissues of cell-free DNA fragments within the hyper-DMRs. Supporting this notion, the samples with the shortest hyper-DMR fragments displayed higher methylated ctDNA abundance (Pearson r=−0.64, p=0.002) (FIG. 15B). When the ratio of small (100-150 bp) versus large (151-220 bp) fragments were used for our hyper-DMRs, an approach previously described to enrich for ctDNA, we observed a similar trend of ctDNA enrichment across the majority of CAPP-Seq positive HNSCC samples (median [range]=28 [−8 to 63] %) (FIG. 4C).

Figures 4E, 4F:
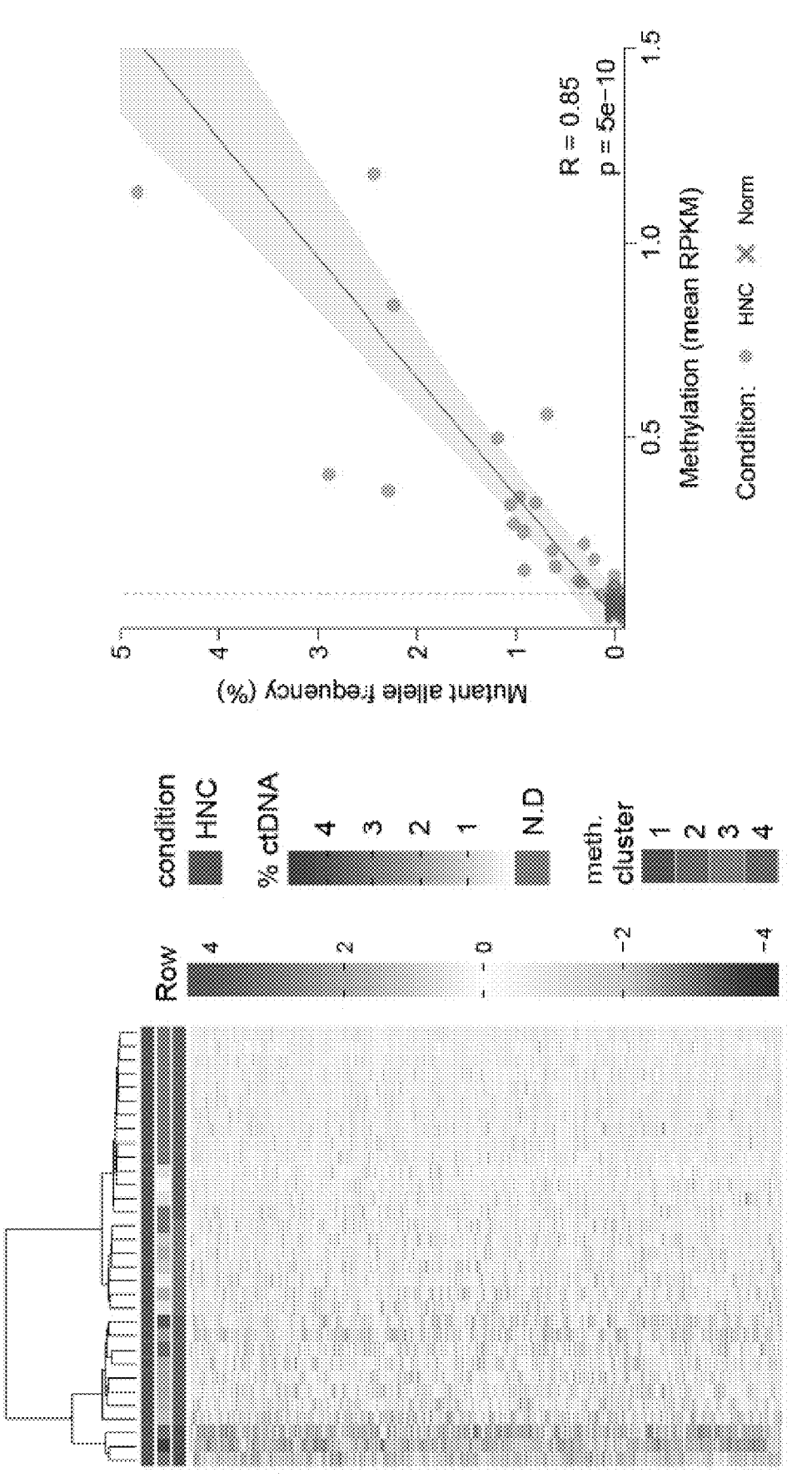
Figure 16A:
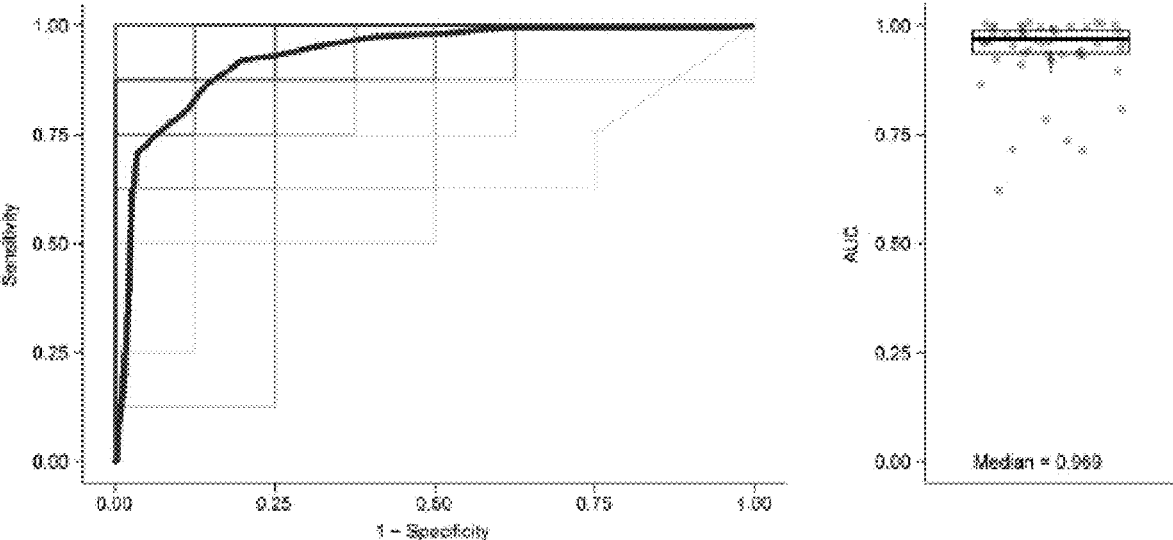
FIGS. 16A-16D illustrates related figures to CAPP-Seq and cfMeDIP-seq concordance analysis (related to FIG. 4E).
Figure 16B:
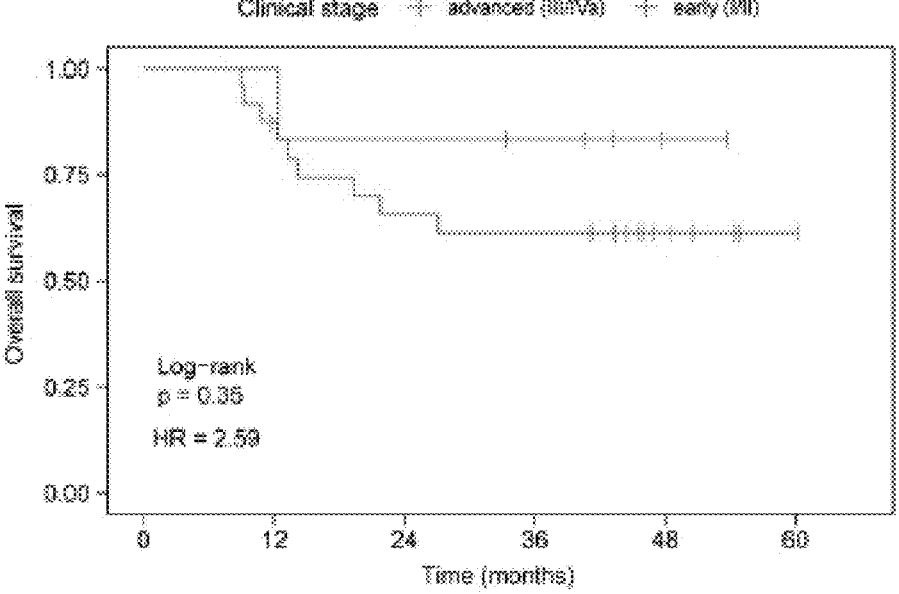
Figure 16D:
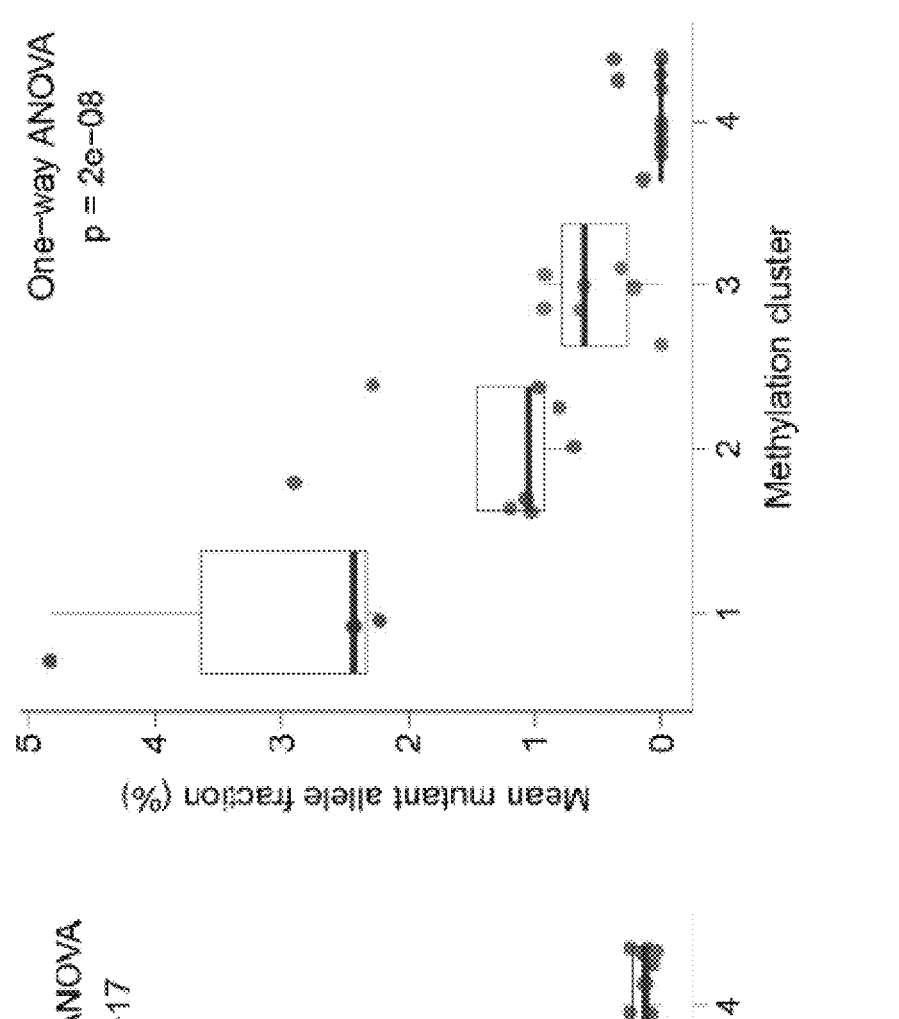
Figure 16C:
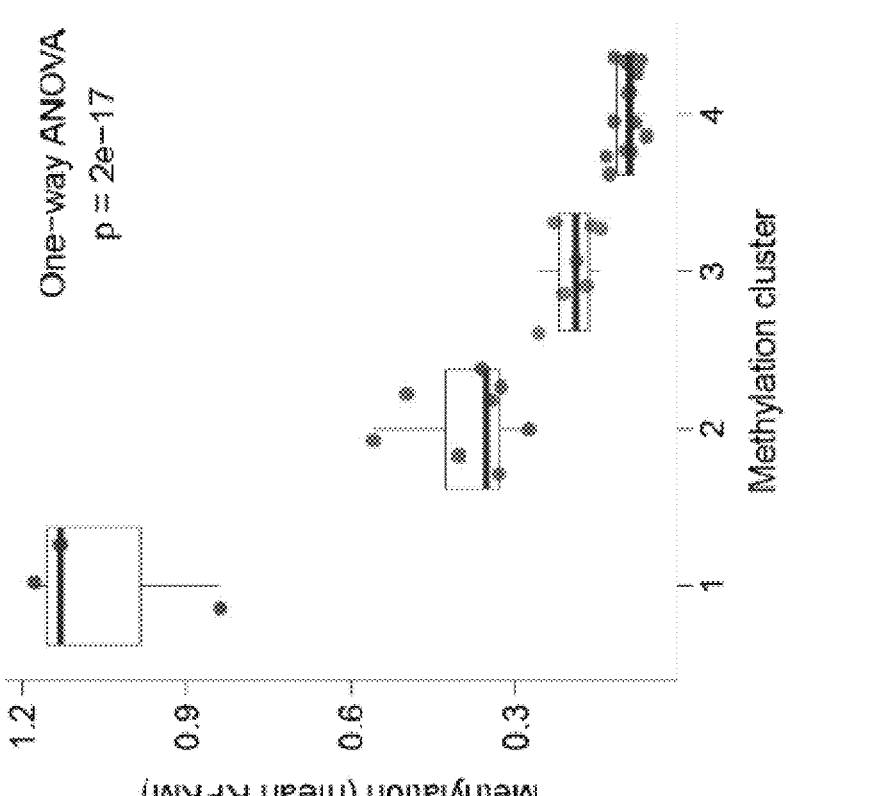

To assess how the plasma cell-free DNA hyper-DMRs identified in our HNSCC cohort may vary across individuals within these small fragments (100-150 bp), we first performed hierarchical clustering. Four dominant clusters emerged utilizing the ConsensusClusterPlus R package, each with distinct levels of methylation across the hyper-DMRs (FIG. 4E and FIG. 16C). Likewise, the three clusters were defined by distinct ctDNA abundance as determined by CAPP-Seq (FIG. 16D), suggesting a potential relationship between mean hyper-DMR methylation and mutation-based ctDNA abundance.

We next investigated whether fragment lengths were concordant between ctDNA molecules Identified by both CAPP-Seq and cfMeDIP-seq, potentially providing an additional layer of validation towards our multimodal approach. To minimize the possibility of background DNA fragments confounding the calculated fragment length of ctDNA within cfMeDIP-seq profiles, we limited analysis to patients above the median methylation levels across hyper-DMRs (n=10 HNSCC patients). Strikingly, ctDNA fragment length was highly concordant between paired CAPP-Seq and cfMeDIP-seq profiles for each patient (Pearson r=0.86, p=0.0016) (FIG. 4C) despite entirely different genomic regions being represented with these two profiling approaches (CAPP-Seq: 43 distinct mutations, cfMeDIP-seq: 941 hyper-DMRs).

Figure 4H:
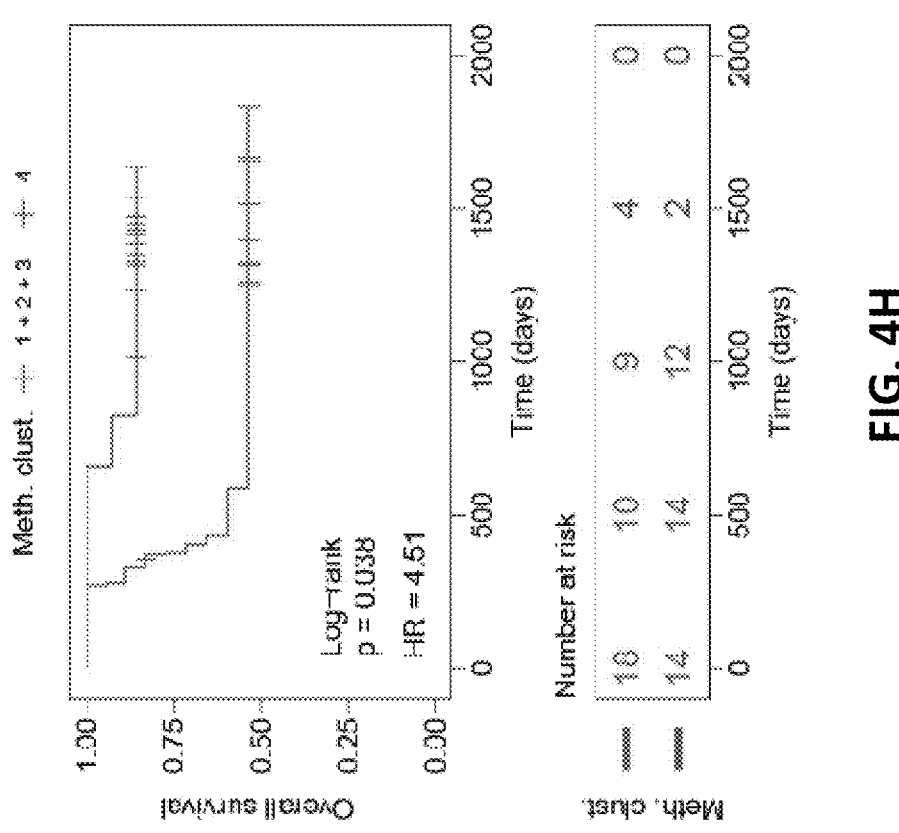
Figure 4G:
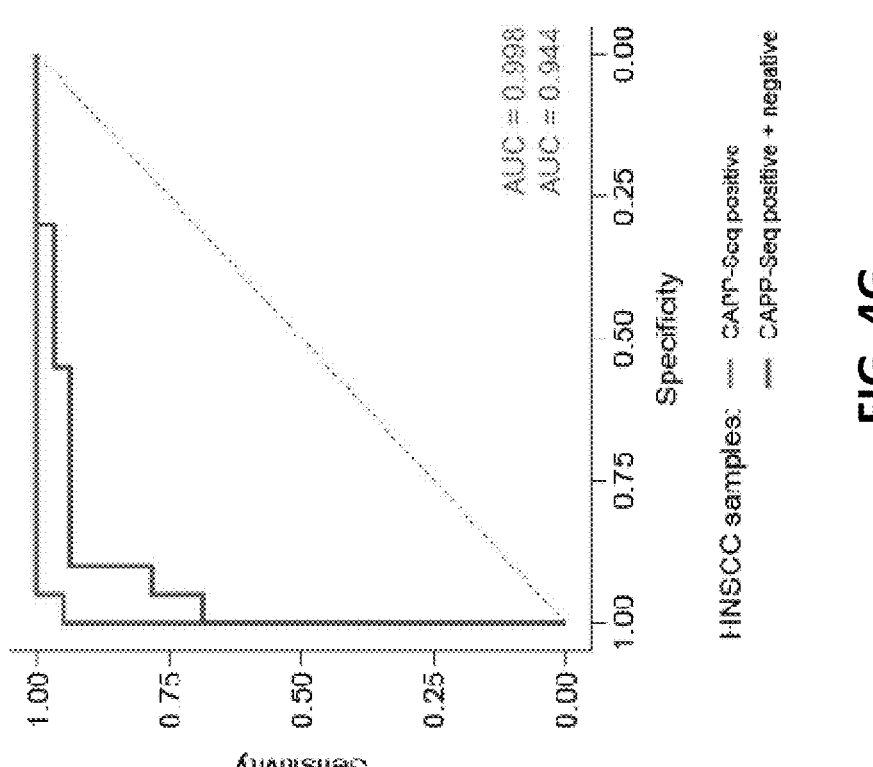
Figure 4J:
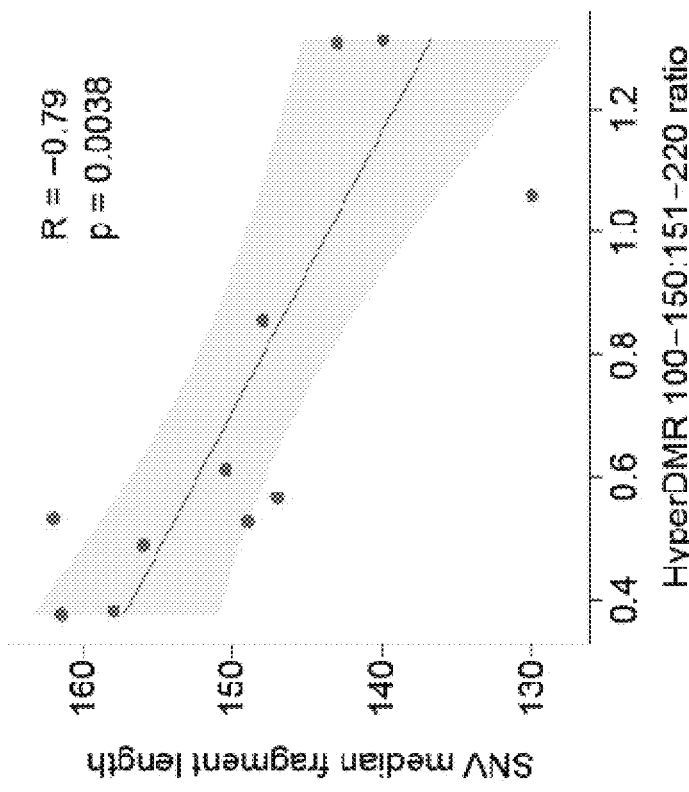

To further characterize the relationship between hyper-DMR methylation levels and mutation-based ctDNA abundance, we compared the mean RPKM values across the 941 hyper-DMRs to the mean MAF values determined by CAPP-Seq for each patient. Similar to the trends we observed between methylation clusters, we observed a significant positive correlation (Pearson correlation, R=0.85, p=5e-10) (FIG. 4F). To evaluate the sensitivity of ctDNA detection within these hyper-DMRs by cfMeDIP-seq, we compared mean RPKM values between our HNSCC cohort and healthy donors. For CAPP-Seq positive patients (n=20), ctDNA detection was highly concordant (AUC=0.998) with a marginal decrease in performance upon incorporation of CAPP-Seq negative patients (n=12) (AUC=0.944) (FIG. 4G). Cross validation (n=50 samplings) across CAPP-Seq positive patients and healthy donors resulted in a median AUC value of 0.984 (FIG. 16A), demonstrating the robustness of the approach disclosed herein.

Based on these observations, we evaluated whether we may enrich ctDNA within cfMeDIP-seq profiles by limiting analysis to cell-free DNA fragments of reduced length. We assessed the proportion of cell-free DNA fragments within hyper-DMRs consisting of small (100 to 150 bp) fragments, as similar methods have been described to enrich for ctDNA using non-methylation-based approaches. Indeed, this resulted in ctDNA enrichment across the majority of CAPP-Seq positive HNSCC samples (median [range]=28 [−8 to 63] %) but not for any of the healthy controls (FIG. 4D). Thus, in silico size selection of cell-free DNA fragments enriches for ctDNA within cfMeDIP-seq libraries and may contribute to tumor-naive multimodal ctDNA analysis.

In patients with localized non-metastatic cancer, detection of ctDNA by CAPP-Seq at diagnosis has previously been described to be associated with poor prognosis. Likewise, ctDNA levels as assessed by methylation of SHOX2 and SEPT9 are associated with poor prognosis in HNSCC. Therefore, we asked whether detection or quantification of ctDNA by CAPP-Seq and cfMeDIP-seq at diagnosis would be associated with clinical outcomes within our HNSCC cohort. Indeed, detection of ctDNA by CAPP-Seq (i.e., CAPP-Seq positive vs. CAPP-Seq negative) (hazard ratio [HR]=7.6, log-rank p=0.026) as well as increased methylation within our previously identified hyper-DMRs (i.e., methylation cluster 1+2+3 vs. methylation cluster 4) (HR=4.51, p=0.038; FIG. 4G), was correlated with shorter survival times. Consistent with this finding, mean RPKM across the hyper-DMRs correlated with cancer stage.

Figure 4I:
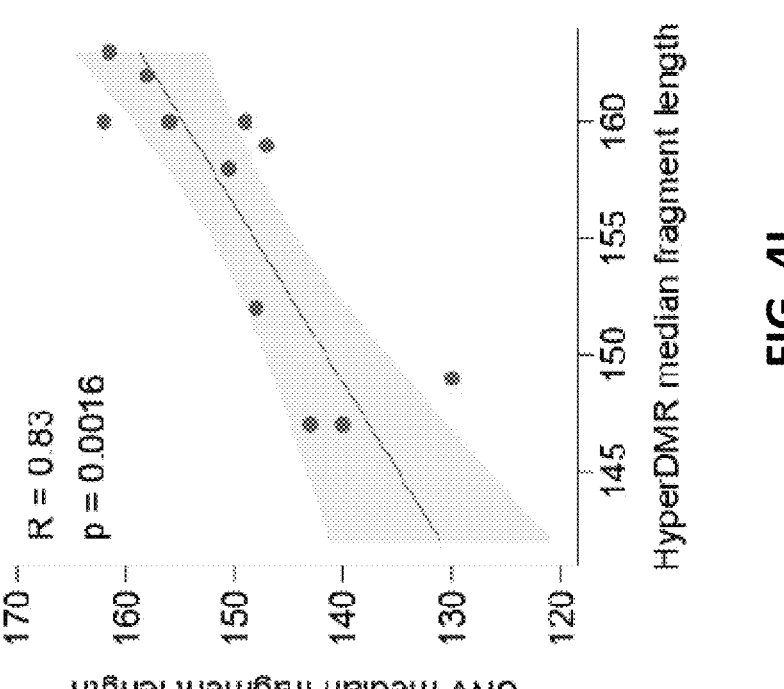

We next compared the median fragment length of ctDNA identified by either mutation- or methylation-based profiling. To minimize the possibility of background DNA fragments confounding the calculated fragment length of ctDNA within cfMeDIP-seq profiles, we selected patients with high ctDNA abundance as defined by hierarchical clustering (i.e., methylation clusters 1 and 2, FIG. 4D, FIGS. 16A-16B). With this approach, ctDNA fragment length was highly concordant between paired CAPP-Seq and cfMeDIP-seq profiles for each patient (R=0.83, p=0.0016) (FIG. 4H) despite entirely different genomic regions being represented with these two profiling approaches. In addition, similar to our analysis with fragments of all lengths, we observed the same relationship between small fragment ratio and ctDNA fragment length by CAPP-Seq (R=−0.79, p=0.0038) (FIG. 4I).

These results suggest that the similar decrease in fragment length observed from ctDNA detected by CAPP-Seq and cfMeDIP-seq may be a result of inherent properties of the tumor, rather than by genomic region, and that utilization of shorter fragment lengths may contribute to more specific identification of ctDNA.

Application of Multimodal ctDNA Detection for Prognostication

Figure 5B:
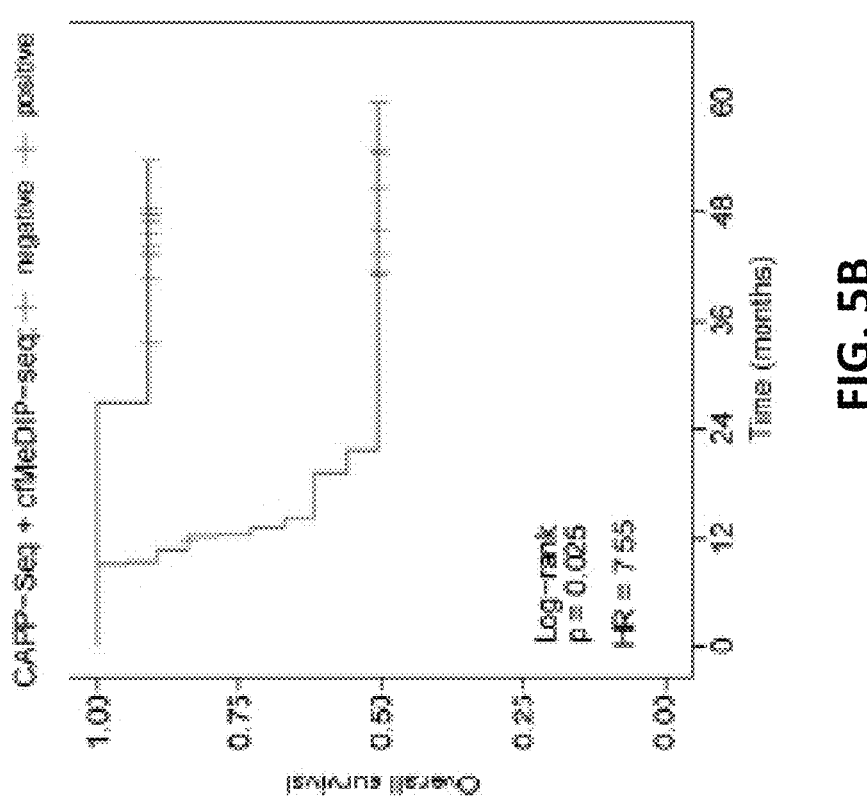
FIGS. 5A-5H illustrates prognostic utility of specific methylated regions within ctDNA detected by cfMeDIP-seq.
Figure 5A:
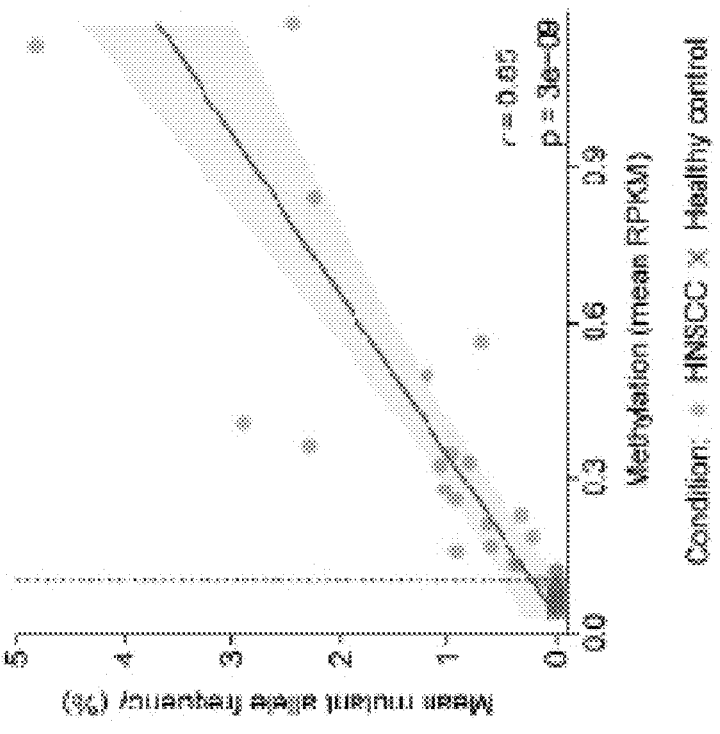
Figure 5C:
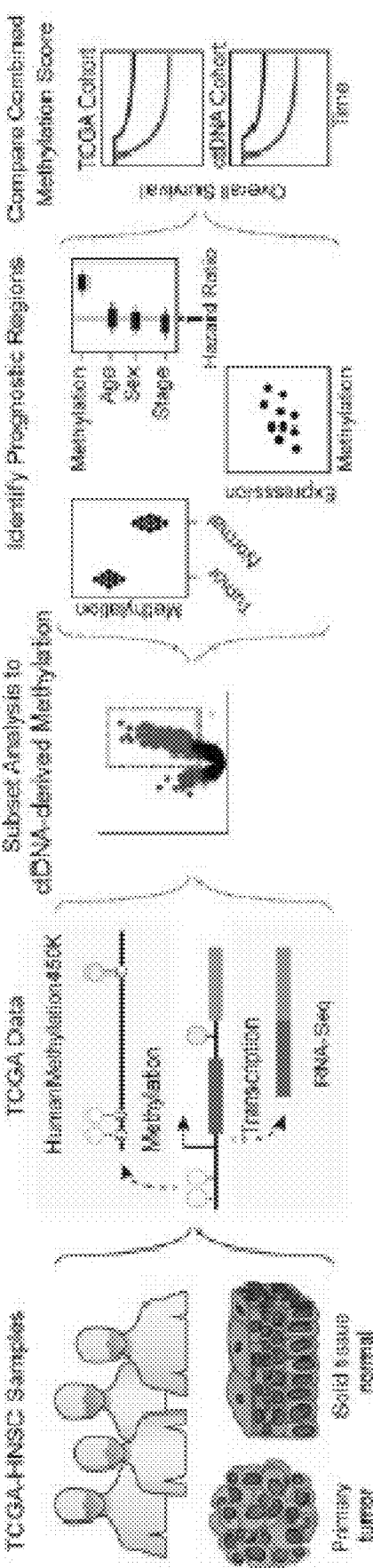
Figures 5D, 5E, 5F:
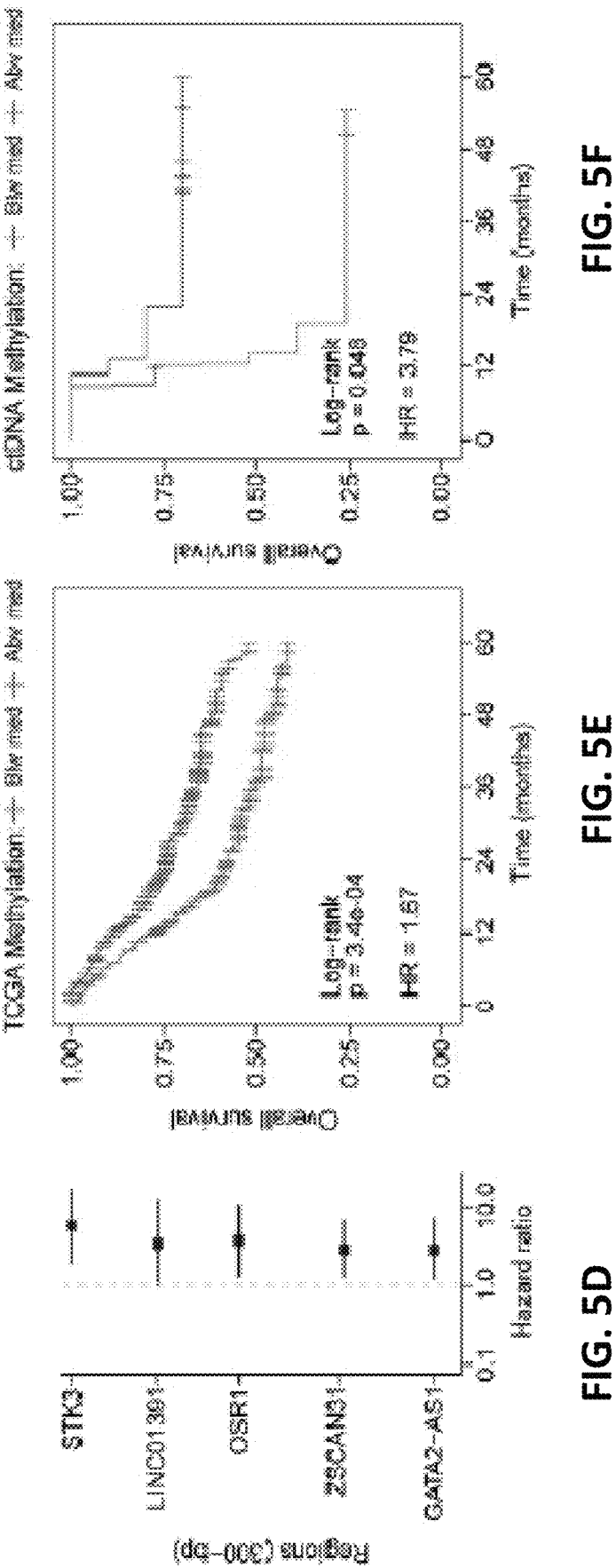
Figure 5H:
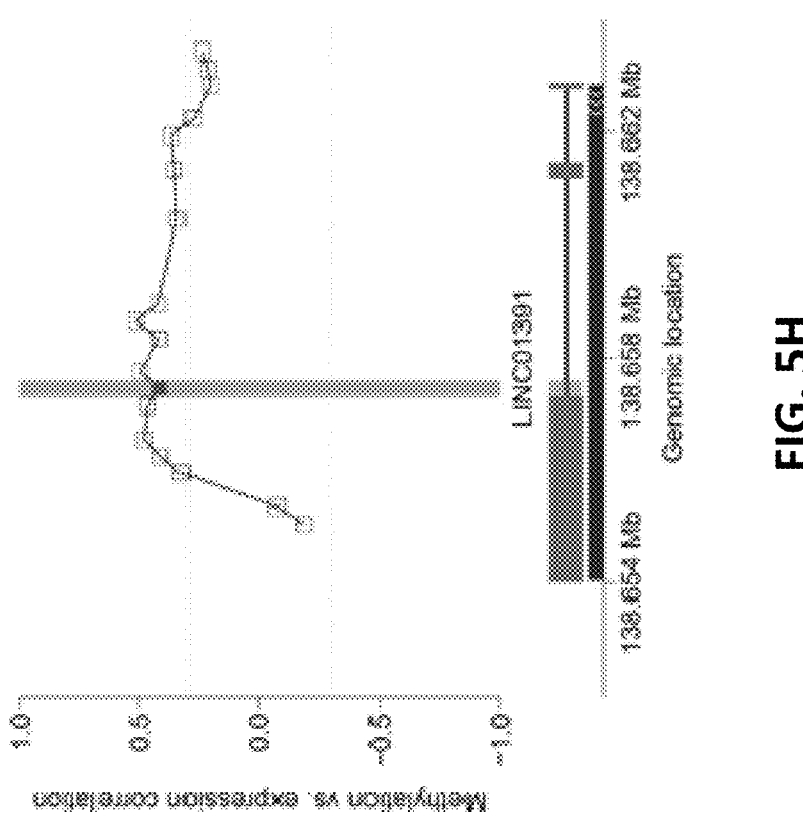
Figure 5G:
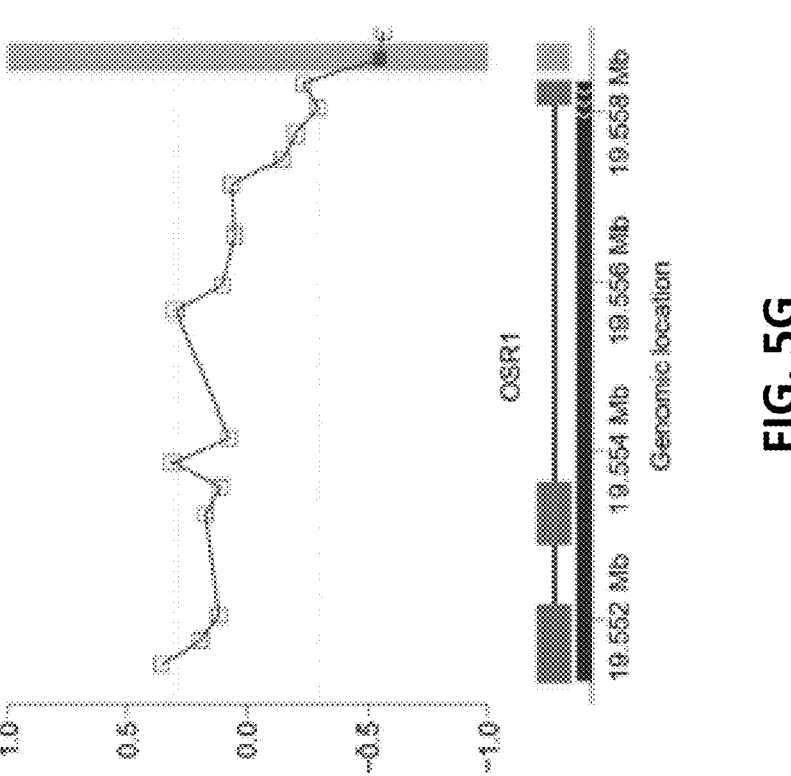

To evaluate the potential clinical applications of tumor-naive multimodal ctDNA analysis, we compared ctDNA with clinical outcomes in the HNSCC cohort. Fragment-length informed cfMeDIP-seq profiles were strongly associated with MAFs in matched CAPP-Seq profiles (Pearson r=0.85, p=3×10-9), suggesting that methylation intensity within the 941 hyper-DMRs is indeed reflective of ctDNA abundance (FIG. 5C). Importantly, cross-validation analysis confirmed the robustness of these hyper-DMRs for detecting ctDNA (FIG. 16C). Patients with ctDNA detected in baseline plasma by both mutation- and methylation-based methods (n=19) were significantly more likely to have advanced disease (i.e., stage III-IVA) (n=18/19) when compared to patients with no detectable ctDNA (n=8/13) (Fisher's exact test p=0.028) and displayed dramatically worse overall survival (hazard ratio [HR]=7.55, 95% confidence interval [CI]=[0.95 to 59.94], log-rank p=0.025) (FIG. 5G). In comparison, stage alone was unable to predict patients with worse overall survival (HR=2.59, 95% CI=[0.32 to 20.46], log-rank p=0.35) (FIG. 16D), further demonstrating the potential clinical utility of multimodal ctDNA profiling.

Figure 17F:
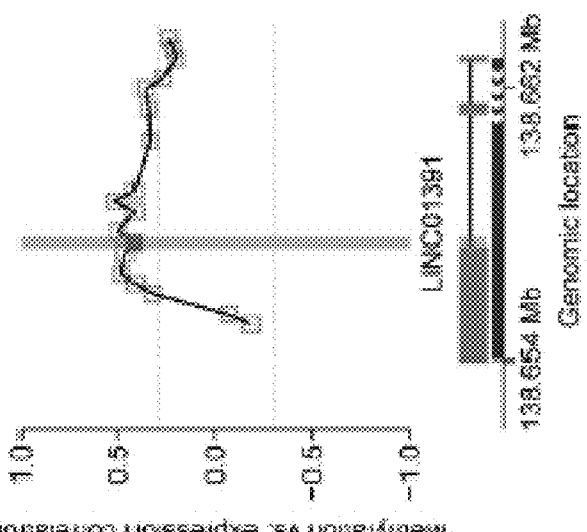
FIGS. 17A-17D illustrate identification of regions of potential clinical utility (related to FIGS. 6A-6C).
FIGS. 17G-17H shows Welch's two-sided t-test evaluating the relationship of methylation associated with ctDNA abundance (i.e., mean methylation across all 941 HNSCC hyper-DMRs) (FIG. 17G) or mutant allele fraction of mutations identified by CAPP-Seq (FIG. 17H) between ctDNA-positive patients by both assays (n=19) above and below the median combined methylation score (CMS). Black bar: median mean methylation. Box: interquartile range (IQR) of mean methylation values. Whisker: most extreme value within quartile±1.5 IQR of mean methylation values.
Figure 17E:
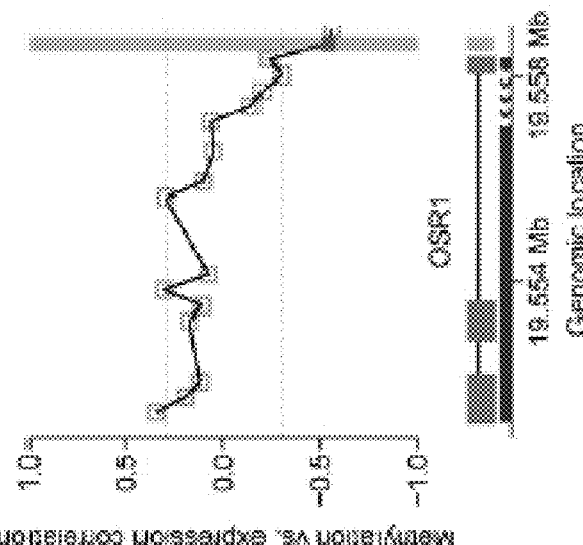
Figure 17D:
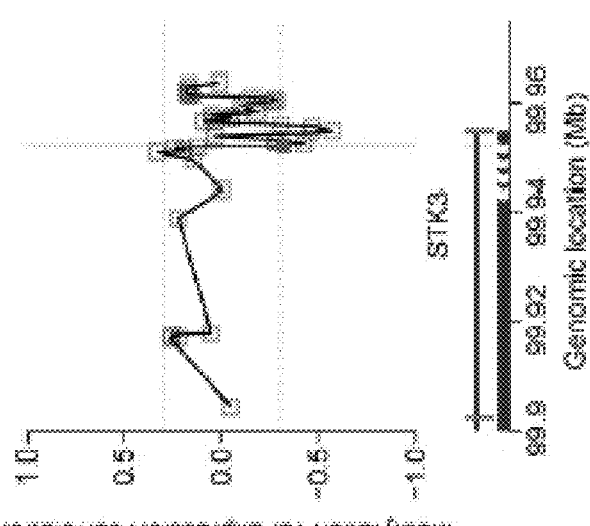
Figures 17G, 17H:
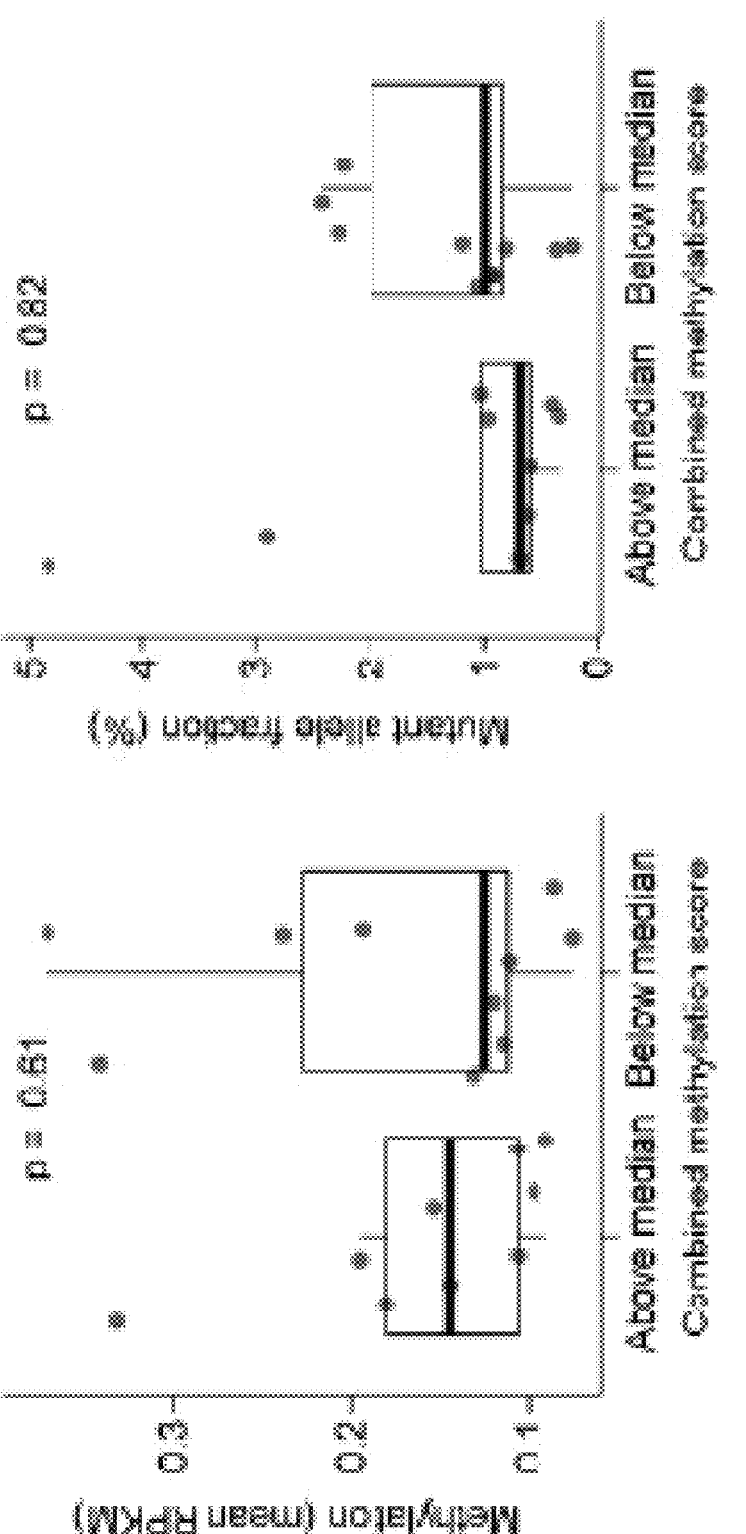

Due to the known effects of DNA methylation on gene expression and resultant functional activity of cancer drivers, we reasoned that ctDNA methylation patterns at particular loci might have prognostic significance independent of ctDNA abundance. To evaluate whether our previously identified hyper-DMRs contain specific regions associated with prognosis independent of ctDNA abundance, we interrogated DNA methylation, RNA expression, and clinical outcome data provided by the TCGA for all available HNSCC patients (n=520) (FIG. 5C). First, we calculated mean B-values across all CpGs contained within distinct 300-bp windows from TCGA hm450k methylation array data. Limiting analysis to probed hm450k regions overlapping with our plasma-derived hyper-DMRs (n=764/941), we identified 483 hypermethylated regions in primary tumors (n=520) compared to adjacent normal tissue (n=50) (Wilcoxon test, FDR <0.05, log 2FC >1). We observed that several of these hypermethylated regions overlapped or were located near CpGs within genes that are profiled by commercially available methylation-based ctDNA diagnostic tests, including SEPT9 and SHOX2 which have been previously assessed in HNSCC, as well as TWIST1 and ONE-CUT2 (FIG. 17A). These results provide further evidence supporting the potential clinical relevance of our plasma derived hyper-DMRs.

To further probe the potential clinical utility of these hypermethylated regions held in common by our HNSCC cohort and TCGA HNSC hm450k profiles, we performed univariate Cox proportional-hazards regression across all TCGA HNSCC patients with available hm450k profiles and disease-specific survival (DSS) outcomes (n=493/520). We identified 33 regions that were significantly associated with DSS (p<0.05). To further select prognostic regions likely to have a functional role in tumorigenesis, we compared the methylation levels of each region (n=33) to the expression of surrounding gene transcripts within 2 kb. Next, we used the TCGA HNSCC cohort to identify a subset of the 483 DMRs that were associated with (1) prognosis in multivariable Cox regression and (2) expression of neighboring gene transcripts. Five regions were identified to satisfy both criteria, with increased methylation of each region resulting in higher expression of ZNF323/ZSCAN31, LINC01391, and GATA2-AS1 (FIG. 5G, FIGS. 17A-17C), as well as lower expression of STK3/MST2 and OSR1, respectively (FIG. 5H) (FIG. 5D). The regions associated with decreased and increased expression as a result of methylation were found to reside within the promoter or $1^{st}$ exon/intron and gene body, respectively. We constructed a composite methylation score (CMS) from these 5 regions (Table 6) and stratified the TCGA HNSCC cohort according to this score (FIG. 5E). A higher CMS was significantly associated with inferior survival outcomes (HR=1.67, 95% CI=[1.25, 2.21], log-rank p=3.4×10$^{-4}$).

Finally, we evaluated whether the CMS may also provide similar prognostic information when applied to ctDNA. To enrich for ctDNA, analysis of cfMeDIP-seq libraries were limited to fragments between 100-150 bp in length as described above (FIG. 4E). To account for the relative contribution of ctDNA methylation levels provided by the 5 putative prognostic markers, we normalized the cfMeDIP-seq RPKM values from these regions to the entire 941 hyper-DMRs. This produced a similar trend with higher CMS being marginally associated with worse survival (log-rank p=0.1; HR=3.06) (FIG. 5F) suggesting that increased methylation of these putative prognostic regions identified from TCGA may also be informative within cfMeDIP-seq profiles. Moreover, these results highlight how plasma cell-free DNA methylome profiling may be leveraged in combination with existing multi-omic cancer databases for biomarker discovery.

Disease Surveillance after Definitive Treatment by cfMe-DIP-Seg

As cfMeDIP-seq achieved sensitive and quantitative ctDNA detection in HNSCC patients, we reasoned that as with CAPP-seq, cfMeDIP-seq may also be capable of monitoring therapy-related changes in ctDNA abundance. To quantify percent ctDNA within posttreatment cfMeDIP-seq profiles, we applied a linear transformation of mean RPKM across the previously identified plasma-derived hyper-DMRs (n=941), limiting fragment size between 100 to 150 bp to further enrich ctDNA. We calculated the detection threshold of 0.2% ctDNA based on the maximum of mean RPKM values observed across all healthy controls. For CAPP-Seq positive HNSCC patients with one or more available post-treatment samples (n=20), cfMeDIP-seq was performed utilizing 10 ng of input cfDNA.

Figure 6A:
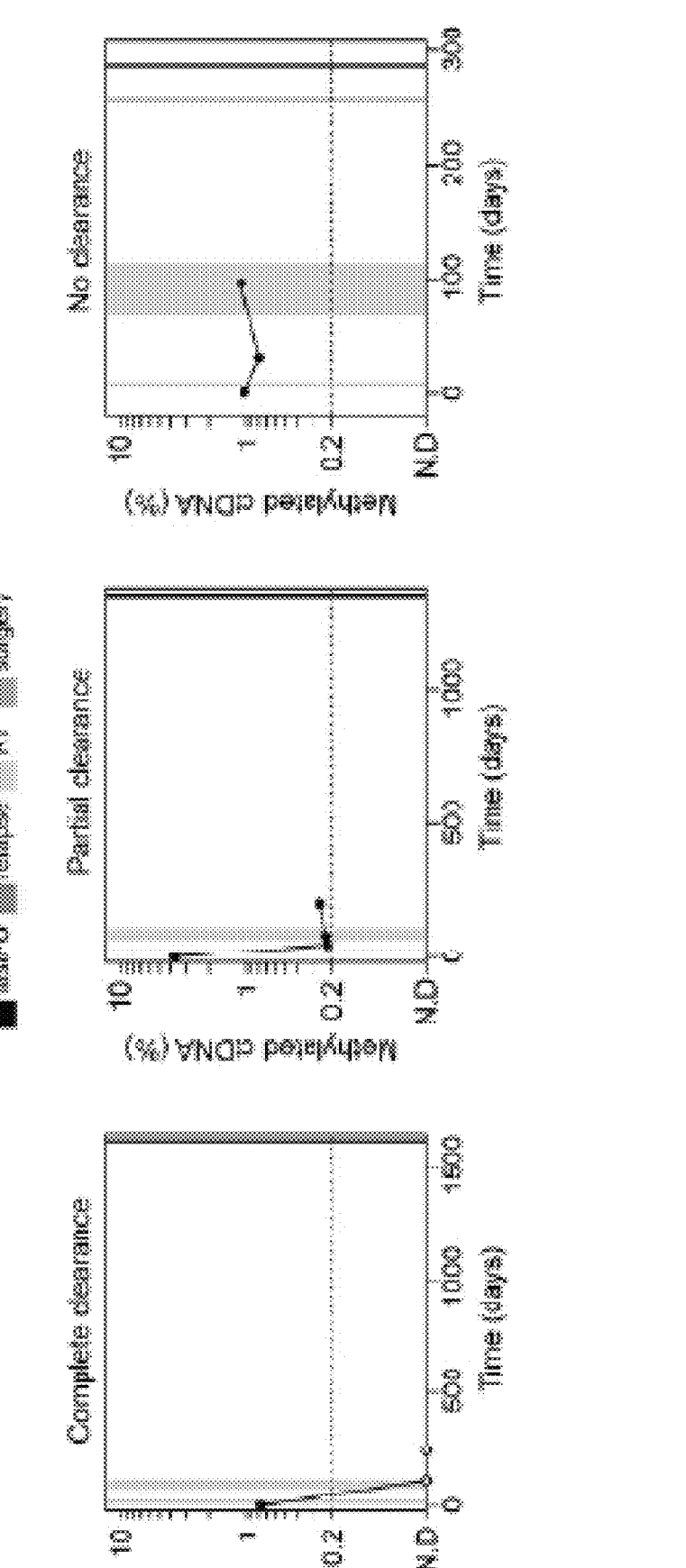
FIGS. 6A-6C illustrate clinical utility of ctDNA detection by cfMeDIP-seq for longitudinal monitoring.
Figure 6C:
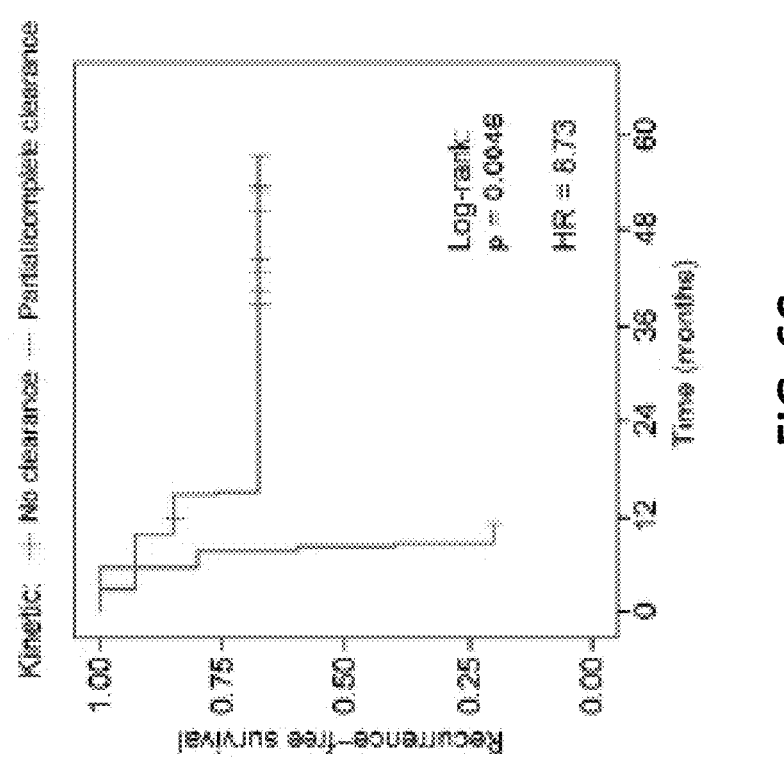
Figure 6B:
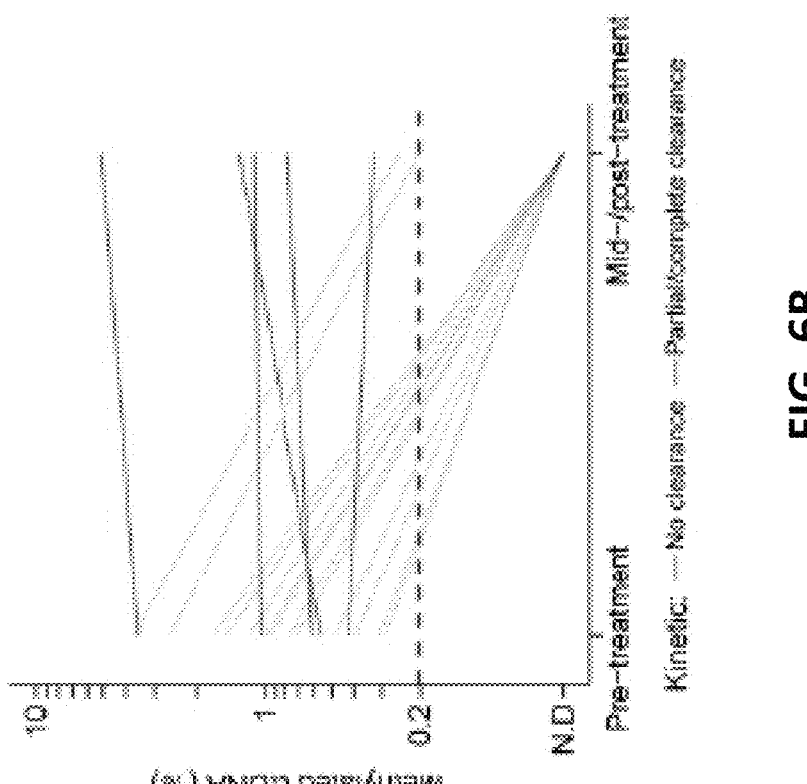
Figure 7A:
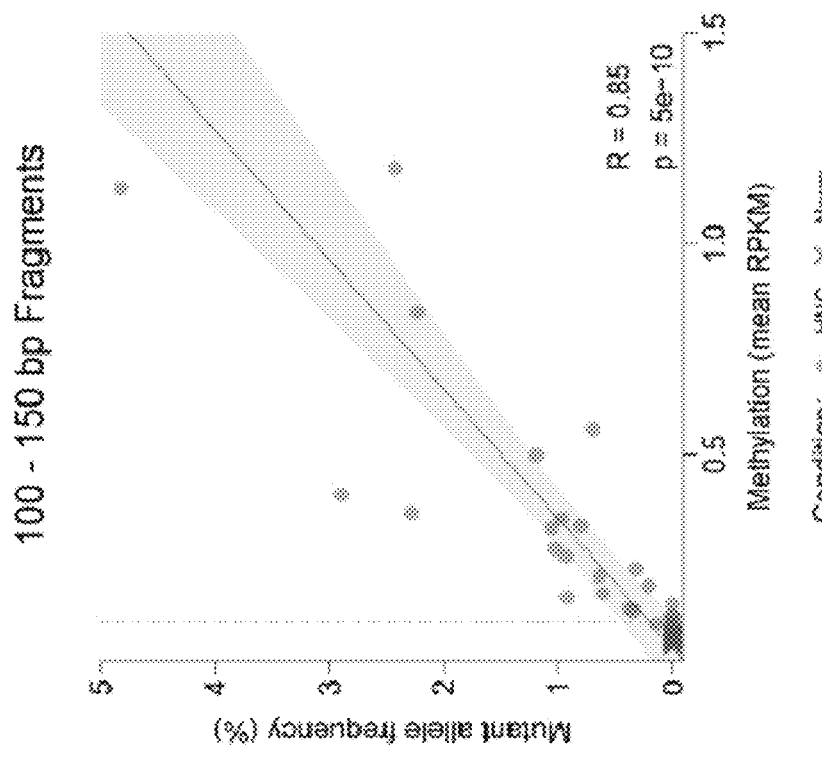
FIGS. 7A-7C illustrate comparison of cfMeDIP-seq analysis performed on all or ctDNA-enriched fragments. ctDNA-enriched fragments are defined as fragments ranging from 100-150 bp in length.
Figure 7A:
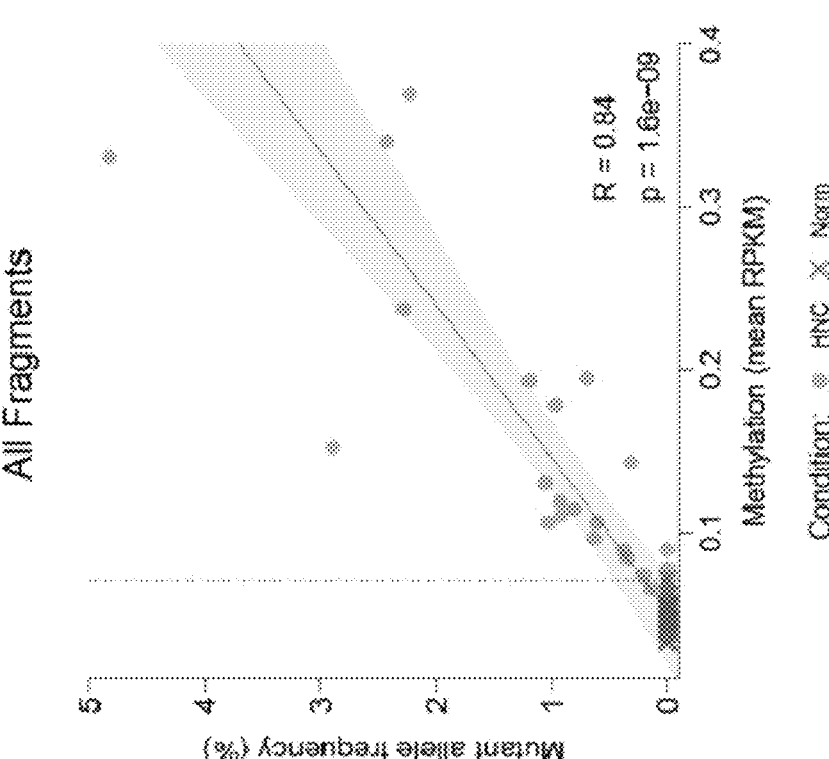
Figure 7B:
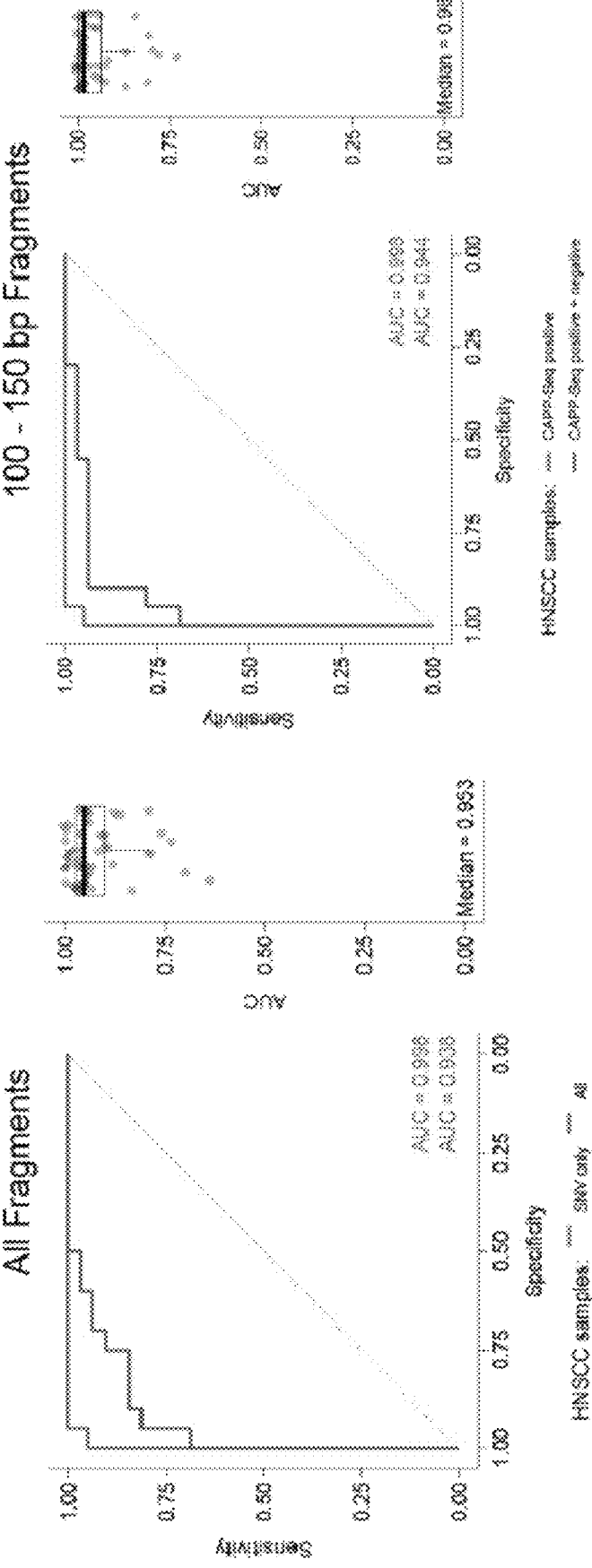
Figure 7C:
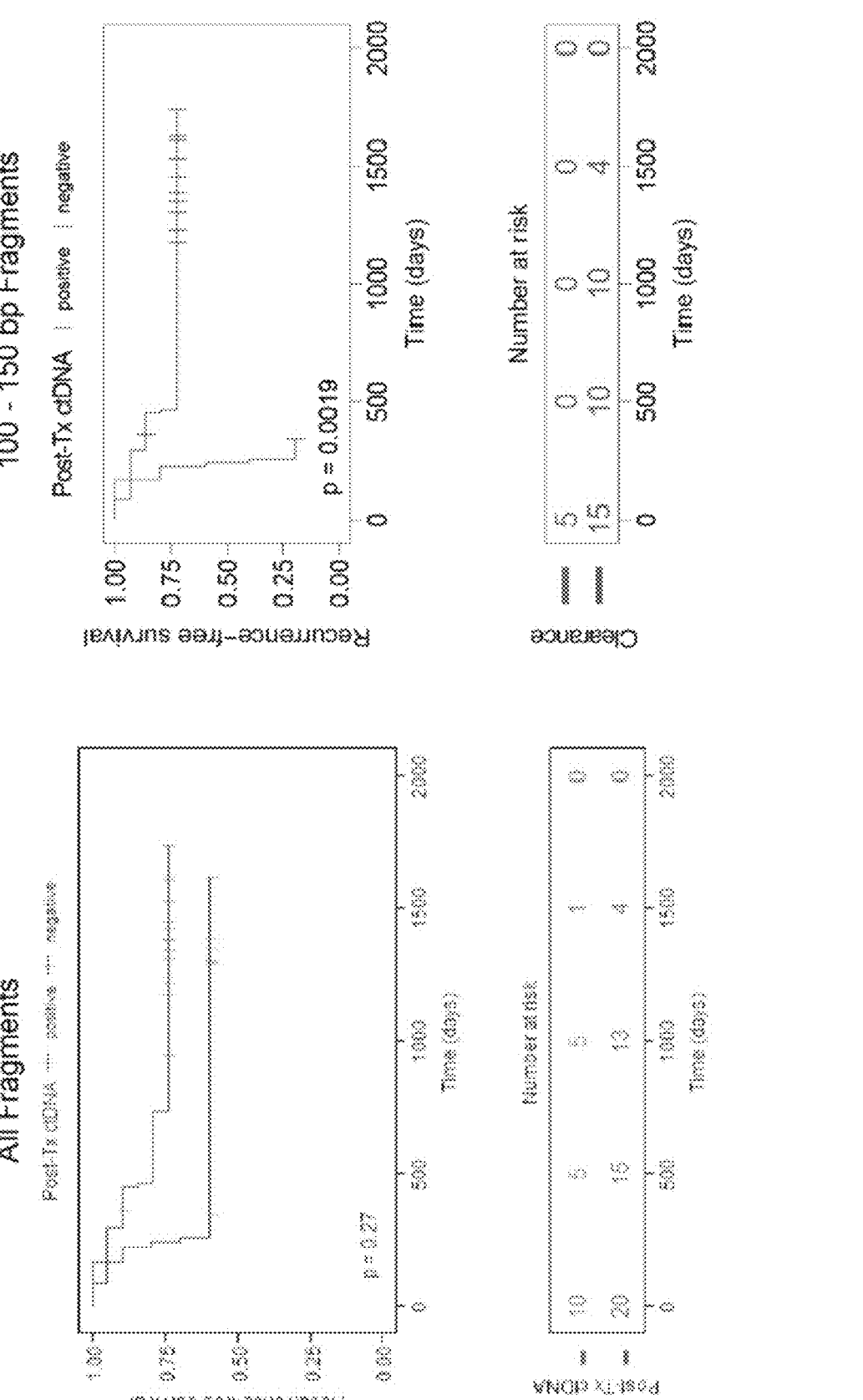
Figure 18:
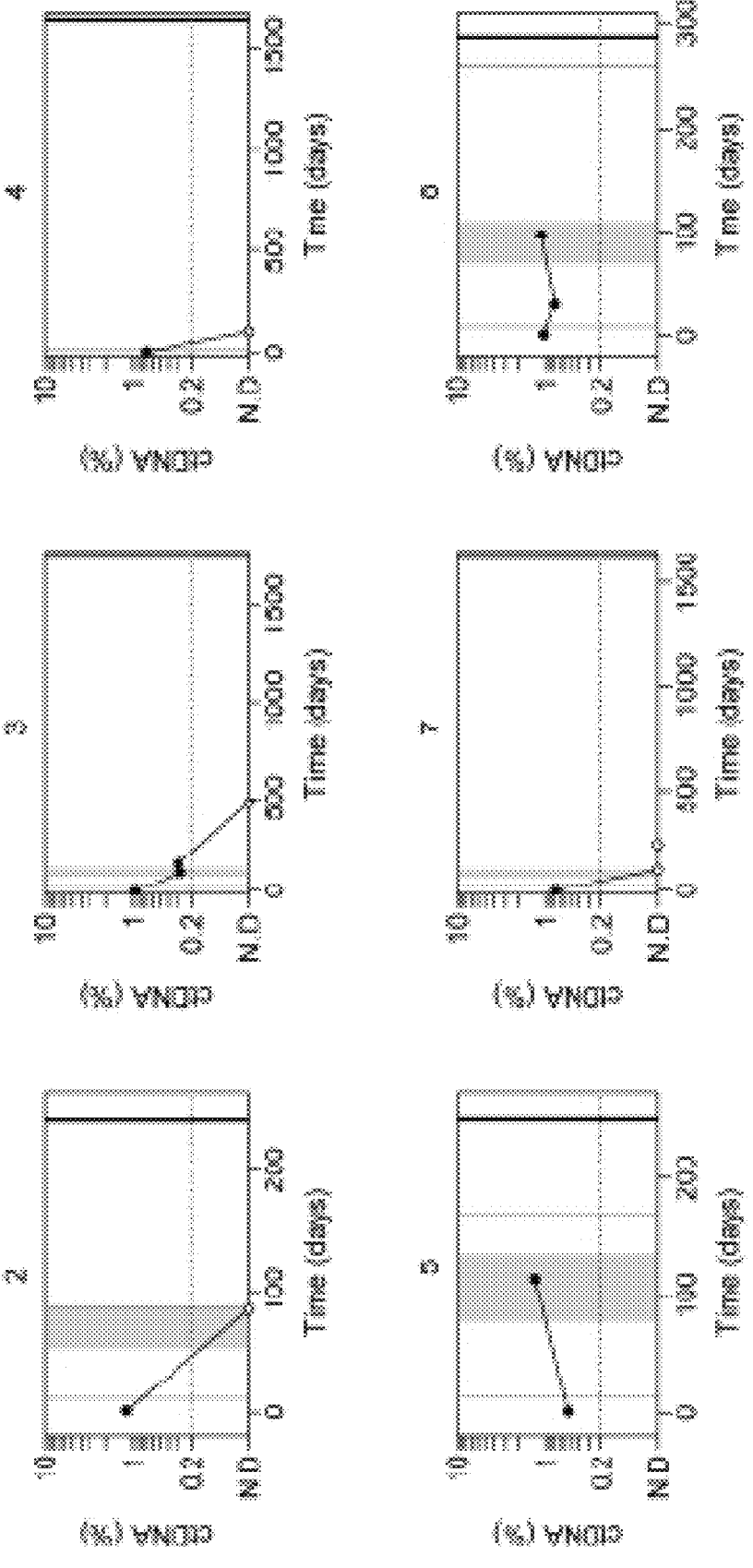
FIG. 18 is an extension of FIG. 6A, displaying changes in ctDNA abundance by cfMeDIP-seq throughout treatment for all HNSCC patients (n=32).
Figure 18:
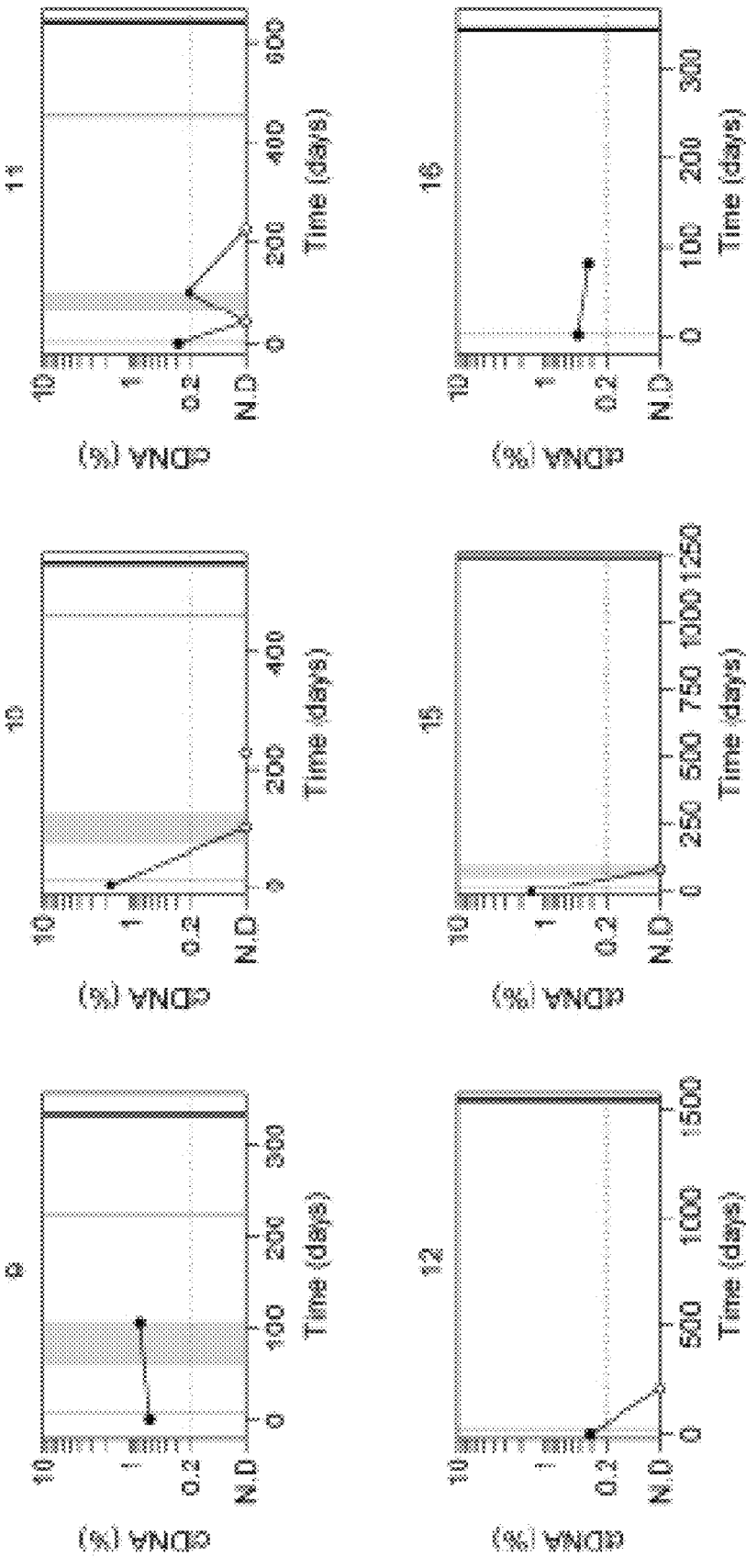
Figure 18:
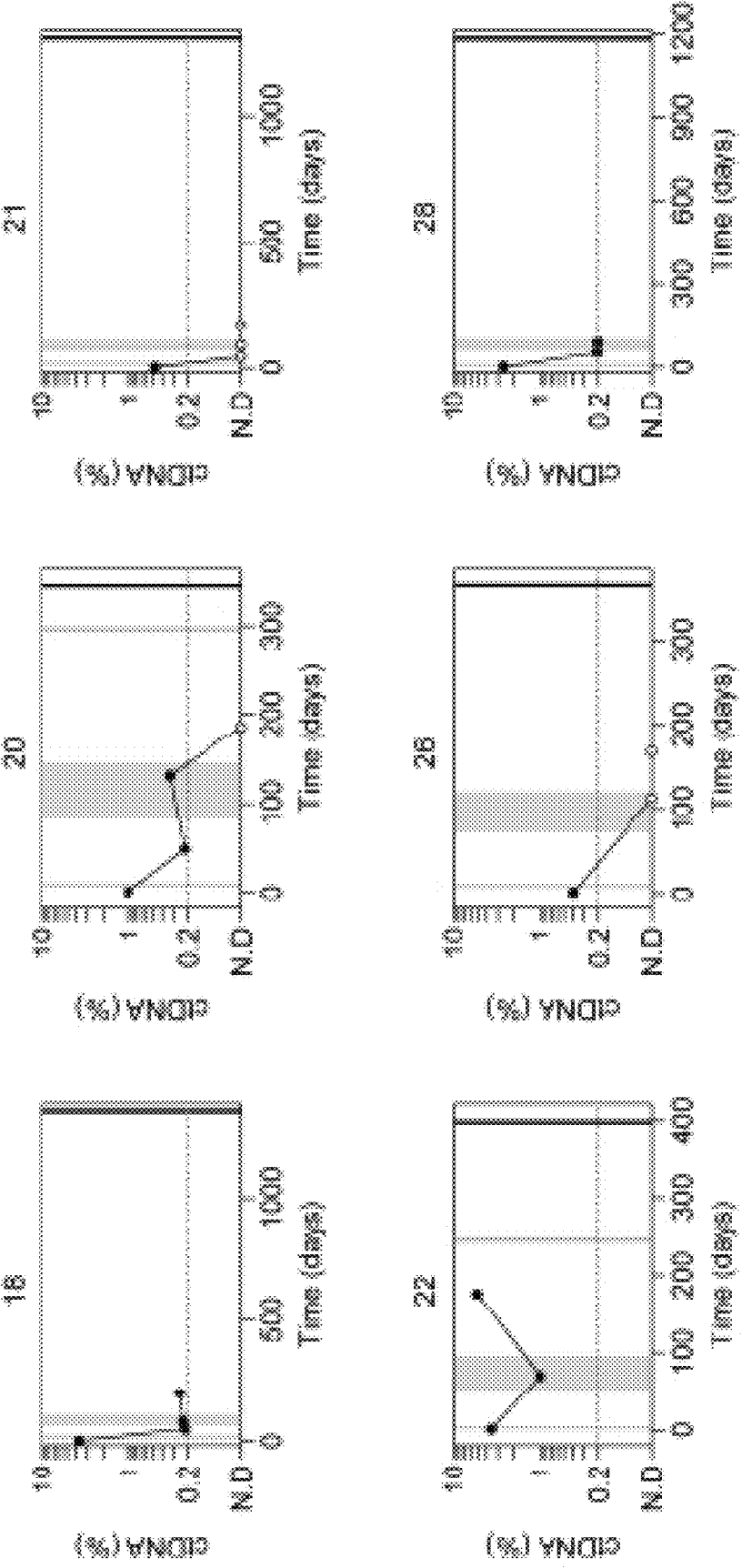

Measuring changes in ctDNA abundance throughout treatment, we observed a variety of kinetics indicative of complete clearance (CC), partial clearance (PC; greater than 90% reduction), or no clearance (NC) (FIG. 6A, FIG. 18). Among 18 eligible patients, 5 (28%) demonstrated No Clearance (FIG. 6B). No Clearance patients were more likely to experience disease recurrence compared with those with Complete or Partial Clearance (HR=8.73, 95% CI= [1.5, 50.92], log-rank p=0.0046) (FIG. 6C). Interestingly, all patients with ctDNA abundance greater at last sample collection compared to at diagnosis, demonstrated disease recurrence. In addition, the only patient who did not have documented disease recurrence within this group was lost to follow-up but died within a year after treatment from unknown cause. For the 13 patients with undetectable post-treatment ctDNA by cfMeDIP-seq, 9 remained disease-free with a median of 44.4 months of follow up (min=12.2, max=58.7). Among the other 4 patients, one had persistent disease within regional lymph nodes, and the others experienced relapse 3.5 to 7.7 months (median 7.4 months) after last collection. Of note, these relapses among the patients with undetectable post-treatment ctDNA were considerably more delayed compared to the 4 relapses among the patients with detectable post-treatment ctDNA (median [range]: 3.0 [1.7 to 5.2] months) after last collection. Taken together, these results demonstrate that plasma cell-free DNA methylome profiling by cfMeDIP-seq may be used to assess response to definitive treatment and identify patients at high risk of rapid recurrence.

Discussion

Broad implementation of ctDNA in clinical settings may be accelerated by methods that can be applied across patients and in the absence of tumor material. In the work described, we evaluated the capabilities of multimodal genome-wide cell-free DNA profiling techniques for tumor-naïve detection of ctDNA within an exploratory cohort of low-ctDNA HNSCC patients. We show that incorporation of matched PBLs improves ctDNA detection using both mutations (i.e., CAPP-Seq) as well as DNA methylation (i.e., cfMeDIP-seq). Furthermore, by utilizing CAPP-Seq to stratify patients with detectable and non-detectable ctDNA, we achieved robust identification of ctDNA-derived methylation patterns. We showed for the first time that biophysical properties of plasma cell-free DNA reflective of tumor origin (i.e., reduced fragment length) are conserved across molecular aberrations and detection platforms. Tumor-naïve ctDNA detection and quantification find multiple clinical uses, and the prognostic association of ctDNA abundance and methylation patterns are investigated.

Tumor-naive ctDNA detection currently encounters several limitations due to low ctDNA abundance. Recent studies have profiled paired PBLs and/or healthy control plasma to identify mutations derived from clonal hematopoiesis, a main contributor to false positive detection of ctDNA; however, the incorporation of orthogonal metrics may further improve accuracy and clinical applicability. Here, we evaluated the capabilities of multimodal genome-wide cell-free DNA profiling techniques for tumor-naive ctDNA detection within a cohort of HNSCC patients with low ctDNA abundance. We demonstrated a high degree of concordance between ctDNA metrics (abundance and fragment lengths) detected by mutation-based and methylation-based profiling methods. Moreover, we showed that tumor-naive multimodal ctDNA profiling may provide value by identifying putative prognostic biomarkers independent of ctDNA abundance, as well as by monitoring ctDNA abundance in serial samples.

Tumor-naïve detection of ctDNA has numerous practical advantages in both research and clinical settings. Recent studies have utilized matched tumor profiling for validation of identified ctDNA-derived regions at low abundance in early stage disease to improve sensitivity. However, one limitation of these approaches is the number of informative regions lost due to sampling heterogeneity of the tumor, which may be further exacerbated when applied to post-treatment ctDNA derived from previously unsampled subclones. Additionally, the clinical benefit of these tumor-informed detection methods is limited to cancers readily accessible by biopsy, circumventing one of the main strengths of non-invasive liquid biopsies. By utilizing a tumor-naïve multimodal profiling strategy, we achieved similar results in early stage cancers without the disadvantages of tumor-informed methods.

This is the first work to utilize mutation and methylation profiling for comprehensive detection of ctDNA from a cohort of localized cancer patients. Extending this multimodal profiling approach to other cancer types and disease settings will be important to the continued development of liquid biopsies. Additionally, while numerous ctDNA studies in HNSCC have been described utilizing detection methods based on mutation, methylation, or HPV profiling, here we described the first application of genome-wide mutation/methylation profiling methods identifying previously known targets (i.e., TP53 mutations or SEPT9/SHOX2 methylation) in addition to less-/non-investigated targets.

Tumor-naive detection of ctDNA has numerous practical advantages in both research and clinical settings. Although tumor mutational profiling may identify patient-specific markers for ctDNA detection at low abundance, such personalized approaches rely on high purity tumor samples from cancer types with sufficient mutational load. Mutational profiling for personalized assay design may be costly and time consuming, and it rarely accounts for genomic heterogeneity within primary tumors or across metastatic clones. Additionally, ctDNA detection methods that depend on access to tumor tissue diminish a key advantage of non-invasive liquid biopsies. By integrating independent cell-free DNA properties, we achieved sensitive ctDNA detection in early stage cancers without the disadvantages of tumor-informed methods.

In our analysis, we selected patients with detectable ctDNA by CAPP-Seq in order to identify ctDNA-derived methylation patterns using cfMeDIP-seq. This approach provided additional validation of the tumor-derived nature of plasma cell-free DNA in our cohort. The ctDNA methylation patterns were able to quantify ctDNA abundance in a similar manner to ctDNA mutations. In addition, methylation patterns revealed the tumor-of-origin and identified putative prognostic and dynamic biomarkers. The combination of CAPP-Seq and cfMeDIP-seq enabled an in-depth molecular characterization of low-abundance ctDNA. Mutation-based ctDNA quantification contributed to the discovery of HNSCC-specific hyper-DMRs in plasma, some of which were confirmed to be prognostic even after adjusting for ctDNA abundance. Thus, simultaneous profiling of mutations and methylation may complement one another by revealing quantitative, tissue-specific, and prognostic ctDNA biomarkers. Moreover, methylome profiling may prove particularly useful in cancer types with few recurrent or clonal mutations.

Similar to previous studies, we also observed a decreased in ctDNA fragment length compared to healthy donor cell-free DNA using both mutation- and methylation-based approaches. Unlike healthy cell-free DNA, which is consistently at ~166-167 bp on average, the length of ctDNA between patients may be highly variable. Factors that influence ctDNA fragment length may include position-dependant fragmentation[49], metastatic vs. non-metastatic disease[73], as well as dysregulated kinetics of various intra/extracellular DNases responsible for healthy cell-free DNA fragmentation[74]. Interestingly, we observed high concordance between fragment lengths of ctDNA identified by CAPP-Seq and cfMeDIP-seq for eligible patients despite both techniques probing different regions and tumor-derived aberrations. These compelling data provide further evidence regarding the relevance and reproducibility of plasma cell-free DNA fragmentation in cancer patients.

We observed that detectable ctDNA by CAPP-Seq or elevated ctDNA abundance by cfMeDIP-seq, was associated with poor prognosis within our HNSCC cohort. These results are in accordance with previous HNSCC ctDNA studies, where detection of ctDNA by methylation[56], as well as increased abundance by copy number aberrations[75] or HPV detection[76], identified high-risk patients. There was an imperfect association with tumor stage, suggesting that other unmeasured features of tumor biology may contribute to ctDNA abundance.

To our knowledge, no study has previously identified prognostic regions in HNSCC cell-free DNA independent of ctDNA detection/abundance, perhaps in part due to limitation of commonly used ctDNA detection methods. We demonstrated that cell-free DNA methylome profiles may serve as a discovery tool, which in conjunction with TCGA data, identified novel prognostic methylation biomarkers in HNSCC. A composite methylation score comprised of 5 DMRs demonstrated consistent prognostic associations across methylation detection platforms (hm450k and cfMeDIP-seq) and biospecimen types (tumor tissue and plasma cell-free DNA). Although future larger cohorts are needed to validate our findings, this study indicates that genome-wide identification of methylated regions by cfMeDIP-seq may enable discovery of novel prognostic biomarkers.

The performance of cfMeDIP-seq was evaluated in connection with disease prognosis. By applying a stringent threshold greater than ~0.2% ctDNA post-treatment as detectable disease, we were able to predict disease recurrence for 4 out of 9 patients. For the remaining 5 patients that relapsed (n=4) or had persistent disease (n=1), who failed to have detectable ctDNA post-treatment, we observed typically longer times to recurrence suggesting that the fraction of ctDNA at those timepoints may have been below cfMeDIP-seq's lower limit of detection. In subsequent studies utilizing cfMeDIP-seq for tumor-naïve disease surveillance, more frequent plasma collection post-treatment may help address these limitations.

As we have demonstrated the potential clinical utility of multimodal profiling within localized disease and HNSCC, these methods contribute to future biomarker discovery and ultimately clinal utility for patients with a variety of cancer types. This study makes multiple notable contributions. It is the first to combine analyses of cell-free DNA mutations, methylation, and fragment lengths. Moreover, we methodically profiled plasma samples and paired PBLs from both HNSCC patients and risk-matched healthy controls. These analyses have revealed key insights regarding the optimal handling of multimodal profiling for ctDNA detection and characterization. For instance, our unique approaches to removing the contributing methylation signals from leukocytes and using fragment length characteristics to enrich for tumor-derived methylation will prove useful for future studies.

In conclusion, we demonstrate that tumor-naïve CAPP-Seq profiling of ctDNA enables high-confidence identification of ctDNA-derived methylation by cfMeDIP-seq. Utilizing the strength of epigenetic profiling by cfMeDIP-seq, we further show that these ctDNA-derived methylated regions demonstrate potential as markers of tumor-of-origin, prognosis, and treatment response. The incorporation of several approaches that we have described for improved sensitivity of ctDNA detection by cfMeDIP-seq in HNSCC, such as PBL-depleted windows and restriction of analysis to short fragments, may also be applied to various other localized cancers for clinical benefit. The disclosed framework are widely applicable to other clinical settings where tumor tissue availability may be limited.

Example 2

DNA methylation profiles are cell-type specific and are disrupted in cancer. Using a robust and sensitive method designed for methylome analysis of minute amounts of circulating cell-free DNA (cfDNA), we identified thousands of Differentially Methylated Regions (DMRs) that distinguish multiple tumor types from each other and from healthy individuals. Methylome analysis of cfDNA is highly sensitive and suitable for detecting circulating tumor DNA (ctDNA) in early stage patients. A machine-learning derived classifier using cfDNA methylomes was able to correctly classify 196 plasma samples from patients with 5 cancer types and healthy donors based on cross-validation. In an independent validation, using the same DMRs identified in the plasma cfDNA, the classifier was able to correctly classify AML, lung cancer, and healthy donors, as well as both early and late stage lung cancer. Therefore, methylome analysis of cfDNA can be used for non-invasive early stage detection of ctDNA and robustly classify cancer types.

Methods and Materials

Donor Recruitment and Sample Acquisition CRC, Breast cancer, and GBM samples were obtained from the University Health Network BioBank; AML samples were obtained from the University Health Network Leukemia BioBank; Lastly, healthy controls were recruited through the Family Medicine Centre at Mount Sinai Hospital (MSH) in Toronto, Canada. All samples collected with patient consent, were obtained with institutional approval from the Research Ethics Board, from University Health Network and Mount Sinai Hospital in Toronto, Canada.

Specimen Processing—cfDNA

EDTA and ACD plasma samples were obtained from the BioBanks and from the Family Medicine Centre at Mount Sinai Hospital (MSH) in Toronto, Canada. All samples were either stored at −80° C. or in vapour phase liquid nitrogen until use. Cell-free DNA was extracted from 0.5-3.5 ml of plasma using the QIAamp Circulating Nucleic Acid Kit (Qiagen). The extracted DNA was quantified through Qubit prior to use.

Specimen Processing—PDX cfDNA

Human colorectal tumor tissue obtained with patient consent from the University Health Network Biobank as approved by the Research Ethics Board at University Health Network, was digested to single cells using collagenase A. Single cells were subcutaneously injected into 4-6 week old NOD/SCID male mouse. Mice were euthanized by CO2 inhalation prior to blood collection by cardiac puncture and stored in EDTA tubes. From the collected blood samples, the plasma was isolated and stored at −80 C. Cell-free DNA was extracted from 0.3-0.7 ml of plasma using the QIAamp Circulating Nucleic Acid Kit (Qiagen). All animal work was carried out in compliance with the ethical regulations approved by the Animal Care Committee at University Health Network.

cfMeDIP-seq

A schematic representation of the cfMeDIP-seq protocol is shown in WO2017/190215. Prior to cfMeDIP, the DNA samples were subjected to library preparation using the Kapa Hyper Prep Kit (Kapa Biosystems). The manufacturer protocol was followed with some modifications. Briefly, the DNA of interest was added to 0.2 mL PCR tube and subjected to end-repair and A-Tailing. Adapter ligation was followed using NEBNext adapter (from the NEBNext Multiplex Oligos for Illumina kit, New England Biolabs) at a final concentration of 0.181 μM, incubated at 20° C. for 20 mins and purified with AMPure XP beads. The eluted library was digested using the USER enzyme (New England Biolabs Canada) followed by purification with Qiagen MinElute PCR Purification Kit prior to MeDIP.

The prepared libraries were combined with the pooled methylated/unmethylated A PCR product to a final DNA amount of 100 ng and subjected to MeDIP using the protocol from Taiwo et al. 2012[7] with some modifications. Briefly, for MeDIP, the Diagenode MagMeDIP kit (Cat #C02010021) was used following the manufacturer's protocol with some modifications. After the addition of 0.3 ng of the control methylated and 0.3 ng of the control unmethylated A. thaliana DNA, the filler DNA (to complete the total amount of DNA [cfDNA+Filler+Controls] to 100 ng) and the buffers to the PCR tubes containing the adapter ligated DNA, the samples were heated to 95° C. for 10 mins, then immediately placed into an ice water bath for 10 mins.

Each sample was partitioned into two 0.2 mL PCR tubes: one for the 10% input control and the other one for the sample to be subjected to immunoprecipitation. The included 5-mC monoclonal antibody 33D3 (Cat #C15200081) from the MagMeDIP kit was diluted 1:15 prior to generating the diluted antibody mix and added to the sample. Washed magnetic beads (following manufacturer instructions) were also added prior to incubation at 4° C. for 17 hours. The samples were purified using the Diagenode iPure Kit and eluted in 50 μl of Buffer C. The success of the reaction (QC1) was validated through qPCR to detect the presence of the spiked-in A. thaliana DNA, ensuring a % recovery of unmethylated spiked-in DNA <1% and the % specificity of the reaction >99% (as calculated by 1-[recovery of spiked-in unmethylated control DNA over recovery of spiked-in methylated control DNA]), prior to proceeding to the next step. The optimal number of cycles to amplify each library was determined through the use of qPCR, after which the samples were amplified using the KAPA HiFi Hotstart Mastermix and the NEBNext multiplex oligos added to a final concentration of 0.3 μM. The PCR settings used to amplify the libraries were as follows: activation at 95° C. for 3 min, followed by predetermined cycles of 98° C. for 20 sec, 65° C. for 15 sec and 72° C. for 30 sec and a final extension of 72° C. for 1 min. The amplified libraries were purified using MinElute PCR purification column and then gel size selected with 3% Nusieve GTG agarose gel to remove any adapter dimers. Prior to submission for sequencing, the fold enrichment of a methylated human DNA region (testis-specific H2B, TSH2B) and an unmethylated human DNA region (GAPDH promoter) was determined for the MeDIP-seq and cfMeDIP-seq libraries generated from the HCT116 cell line DNA sheared to mimic cell free DNA (Cell line obtained from ATCC, mycoplasma free). The final libraries were submitted for BioAnalyzer analysis prior to sequencing at the UHN Princess Margaret Genomic Centre on an Illumina HiSeq 2000.

Ultra-Deep Targeted Sequencing for Point Mutation Detection

We used the QIAgen Circulating Nucleic Acid kit to isolate cell-free DNA from ~20 mL of plasma (4-5×10 mL EDTA blood tubes) from patients with matched tumor tissue molecular profiling data generated prior to enrolment in early phase clinical trials at the Princess Margaret Cancer Centre. DNA was extracted from cell lines (dilution of CRC and MM cell lines) using the PureGene Gentra kit, fragmented to ~180 bp using a Covaris sonicator, and larger size fragments excluded using Ampure beads to mimic the fragment size of cell-free DNA. DNA sequencing libraries were constructed from 83 ng of fragmented DNA using the KAPA Hyper Prep Kit (Kapa Biosystems, Wilmington, MA) utilizing NEXTflex-96 DNA Barcode adapters (Bio Scientific, Austin, TX) adapters. To isolate DNA fragments containing known mutations, we designed biotinylated DNA capture probes (xGen Lockdown Custom Probes Mini Pool, Integrated DNA Technologies, Coralville, IA) targeting mutation hotspots from 48 genes tested by the clinical laboratory using the Illumina TruSeq Amplicon Cancer Panel. The barcoded libraries were pooled and then applied the custom hybrid capture library following manufacturer's instructions (IDT xGEN Lockdown protocol version 2.1). These fragments were sequenced to >10,000× read coverage using an Illumina HiSeq 2000 instrument. Resulting reads were aligned using bwa-mem and mutations detected using samtools and muTect version 1.1.4.

Modelling Relationships Between Number of Tumor-Specific Features and Probability of Detection by Sequencing Depth We created 145,000 simulated genomes, with the proportion of cancer-specific methylated DMRs set to 0.001%, 0.01%, 0.1%, 1%, and 10% and consisting of 1, 10, 100, 1000 and 10000 independent DMRs respectively. We sampled 14,500 diploid genomes (representing 100 ng of DNA) from these original mixtures and further sampled 10, 100, 1000, and 10000 reads per locus to represent sequencing coverage at those depths. This process was repeated 100 times for each combination of coverage, abundance, and number of features. We estimated the frequency of successful detection of at least 1 DMR for each combination of parameters and plotted probability curves (FIG. 19A) to visually evaluate the influence of the number of features on the probability of successful detection conditional on sequencing depths.

Derivation of Tissue-Distinctive Features, Development of a Multi-Tissue Classifier and Validation in 450k Data cfDNA MeDIP profiles were quantified using the MEDIPS R package[8], converted to RPKMs, and afterwards transformed into log 2 counts-per-million. Subsequently, a linear model was fit using limma-trend[9] on a matrix of features that mapped to FANTOM5 enhancers, CpG Islands, CpG shores and CpG Shelves, with the percentage of spike-in methylated DNA recovered included as a covariate to control for pulldown efficiency variation. Pairwise contrasts were evaluated for each pair of tissue types and the top 150 and the bottom 150 DMRs were selected for elastic net classifier training and validation of cancer-type specificity. Performance metrics were derived by majority class votes on out-of-fold calls from the model with the highest Kappa value in cross-validation, a heuristic previously employed in Chakravarthy et al [10].

Machine Learning Analyses for Evaluation of Classification Accuracy

Model Training and Evaluation on the Discovery Cohort

In order to evaluate the performance of cfMeDIP data in tumor classification without high computational cost, we reduced the initial set of possible candidate features to windows encompassing CpG Islands, shores, shelves and FANTOM5 enhancers (hereby labelled "regulatory features"), yielding a matrix of 196 samples and 505,027 features. We then used the caret R package to partition the discovery cohort data into 50 independent training and test sets in an 80%-20% manner (FIG. 20A). The splits were performed while class proportions across the discovery cohort were maintained. Then, we selected the top 300 DMRs by moderated t-statistic (150 hypermethylated, 150 hypomethylated) on the training data partition using limma-trend for each class versus other classes. A binomial GLMnet was then trained using these DMRs (up to 300 DMRs×7 other classes=2100 features) with the use of 3 iterations of 10-Fold Cross-Validation (CV) to optimize values of the mixing parameter (alpha, values=0, 0.2, 0.5, 0.8 and 1) and the penalty (lambda, values=0-0.05 in increments of 0.01) using Cohen's Kappa as the performance metric. For each training set, this yielded a collection of 6 one-class vs-other-classes binomial classifiers.

We then estimated classification performance on the held-out test set using the AUROC (area under the receiver operating characteristic curve). These estimates represent unbiased measures of classification, as the held-out test set samples were not used for either DMR pre-selection or GLMnet training and tuning. The 50 independent training and test sets also permitted for minimization of optimistic estimates due to training-set bias.

Model Evaluation on the Validation Cohort

For each validation cohort cfMeDIP sample, we estimated class probabilities for the AML, LUC and normal one-vs-all binomial classifiers trained on the 50 different training sets within the discovery cohort. The probabilities from the 50 models were averaged to produce a single score that was then used for AUROC estimation. We also evaluated if disease stage affected performance by estimating AUROC when either early (Stages I and II) or late stage LUC samples (Stages III and IV) were left out for the one-vs-all classifier.

Results and Discussion

Figure 19B:
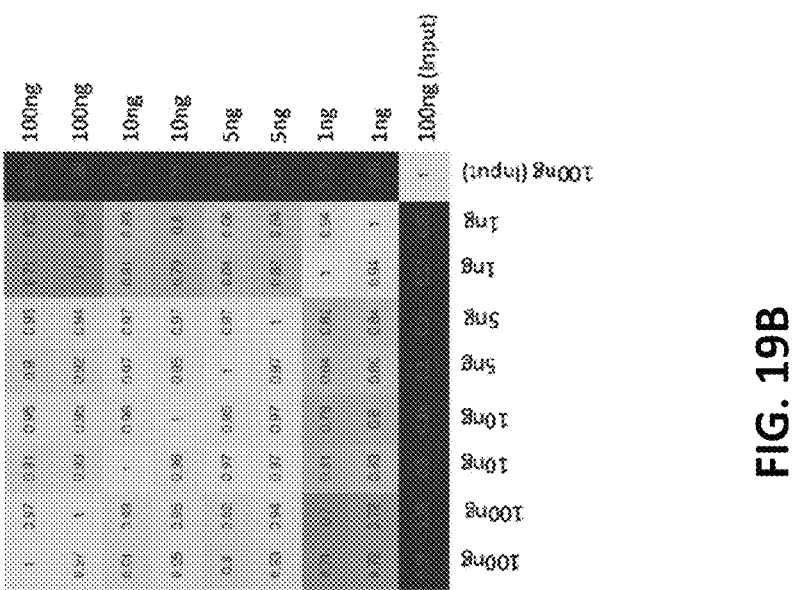
FIGS. 19A-19G show methylome analysis of cfDNA is a highly sensitive approach to enrich and detect ctDNA in low amounts of input DNA.
Figure 19A:
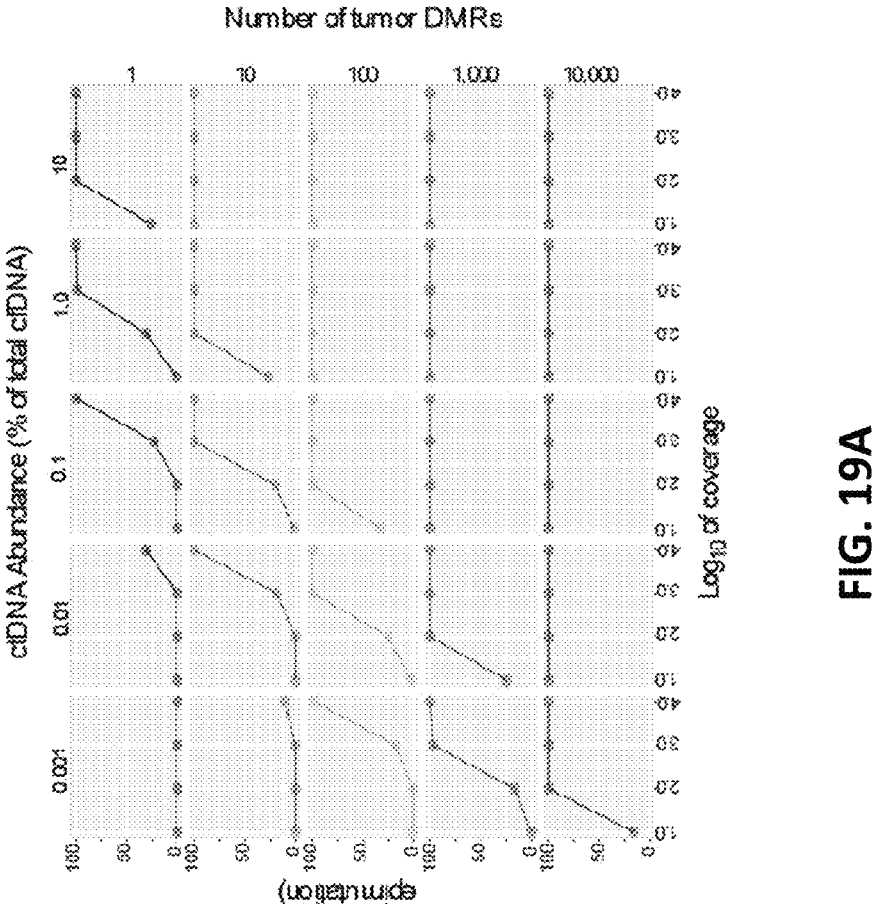

We bioinformatically simulated mixtures with different proportions of ctDNA, from 0.001% to 10% (FIG. 19A, column facets). We also simulated scenarios where the ctDNA had 1, 10, 100, 1000, or 10000 DMRs (Differentially Methylated Regions) as compared to normal cfDNA (FIG. 19A, row facets). Reads were then sampled at varying sequencing depths at each locus (10×, 100×, 1000×, and 10000×) (FIG. 19A, x-axis). We found an increasing probability of detecting of at least 1 cancer-specific event (FIG. 19A) as the number of DMRs increased, even at low abundance of cancer ctDNA and shallow coverage. Moreover, pan-cancer data from The Cancer Genome Atlas (TCGA) shows large numbers of DMRs between tumor and normal tissues across virtually all tumor types[11]. Therefore, these findings highlighted that an assay that successfully recovered cancer-specific DNA methylation alterations from ctDNA could serve as a very sensitive tool to detect, classify, and monitor malignant disease with low sequencing-associated costs.

However, genome-wide mapping of DNA methylation in plasma cfDNA is challenging due to the very low quantities and fragmentation of DNA in circulation[12]. As a result, previous efforts at methylation profiling of cfDNA has mainly been restricted to locus specific PCR-based assays[2, 3], such as an FDA approved SEPT9 methylation assay for colorectal cancer screening[13]. While recent efforts have been made to perform whole-genome bisulfite-sequencing of fragmented cfDNA[14-16], the low genome-wide abundance of CpGs is likely to reduce the amount of useful methylation-related information available from sequencing. Therefore, the main issues with WGBS on plasma DNA are the high cost, low efficiency, and DNA losses associated with the bisulfite conversion. On the other hand, a method that selectively enriches for CpG-rich features prone to methylation is likely to maximize the amount of useful information available per read, decrease the cost, and decrease the DNA losses.

A Genome-Wide Method Suitable for cfDNA Methylation Mapping

We developed a new method termed cfMeDIP-seq (cell-free Methylated DNA Immunoprecipitation and high-throughput sequencing) to perform genome-wide DNA methylation mapping using cell-free DNA. The cfMeDIP-seq method described here was developed through the modification of an existing low input MeDIP-seq protocol [7] that in our experience is very robust down to 100 ng of input DNA. However, the majority of plasma samples yield much less than 100 ng of DNA. To overcome this challenge, we added exogenous λ DNA (filler DNA) to the adapter-ligated cfDNA library in order to artificially inflate the amount of starting DNA to 100 ng. This minimizes the amount of non-specific binding by the antibody and also minimizes the amount of DNA lost due to binding to plasticware. The filler DNA consisted of amplicons similar in size to an adapter-ligated cfDNA library and was composed of unmethylated and in vitro methylated DNA at different CpG densities. The addition of this filler DNA also serves a practical use, as different patients will yield different amounts of cfDNA, allowing for the normalization of input DNA amount to 100 ng. This ensures that the downstream protocol remains exactly the same for all samples regardless of the amount of available cfDNA.

We first validated the cfMeDIP-seq protocol using DNA from human colorectal cancer cell line HCT116, sheared to a fragment size similar to that observed in cfDNA. HCT116 was chosen because of the availability of public DNA methylation data. We simultaneously performed the gold standard MeDIP-seq protocol[7] using 100 ng of sheared cell line DNA and the cfMeDIP-seq protocol using 10 ng, 5 ng, and 1 ng of the same sheared cell line DNA. This was performed in two biological replicates. For all the conditions, we obtained more than 99% specificity of the reaction (1-[recovery of spiked-in unmethylated control DNA over recovery of spiked-in methylated control DNA]), and a very high enrichment of a known methylated region over an unmethylated region (TSH2B0 and GAPDH, respectively) (FIG. 23F).

Figure 19C:
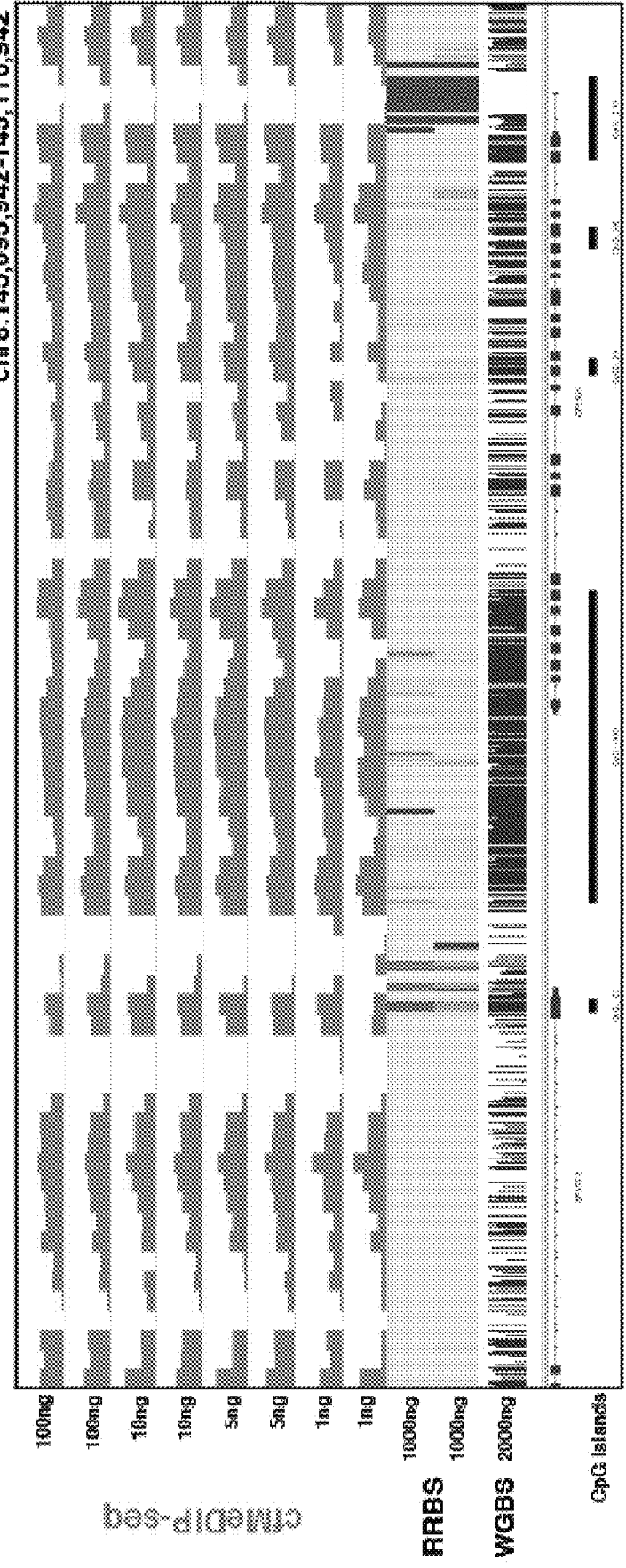

The libraries were sequenced to saturation (FIGS. 23A-23E) at around 30 to 70 million reads per library (Supplementary Table 4). The raw reads were aligned to both the human genome and the λ genome, and found virtually no alignment was found to the λ genome (Supplementary Table 4). Therefore, the addition of the exogenous λ DNA as filler DNA did not interfere with the generation of sequencing data. Finally, we calculate the CpG Enrichment Score as a quality control measure for the immunoprecipitation step[8]. All the libraries showed similar enrichment for CpGs while the input control, as expected, showed no enrichment (FIG. 23G), validating our immunoprecipitations even at extremely low inputs (1 ng). Genome-wide correlation estimates comparing different input DNA levels show that both MeDIP-seq (100 ng) and cfMeDIP-seq (10, 5, and 1 ng) methods were very robust, with Pearson correlation of at least 0.94 between any two biological replicates (FIG. 1B). The analysis also demonstrates that cfMeDIP-seq at 5 and 10 ng of input DNA can robustly recapitulate the methylation profile obtained by traditional MeDIP-seq at 100 ng (Pairwise Pearson correlation of at least 0.9) (FIG. 19B). The performance of cfMeDIP-seq at 1 ng of input DNA is reduced compared to MeDIP-seq at 100 ng but still shows a strong Pearson correlation at >0.7 (FIG. 19B). We also observed that the cfMeDIP-seq protocol recapitulates the DNA methylation profile of HCT116 using gold standard RRBS (Reduced Representation Bisulfite Sequencing) and WGBS (Whole-Genome Bisulfite Sequencing) (FIG. 19C). Altogether, our data suggests that cfMeDIP-seq is a robust protocol for genome-wide methylation mapping of fragmented and low input DNA material, such as circulating cfDNA.

cfMeDIP-Seq Displays High-Sensitivity for Detection of Tumor-Derived ctDNA

Figure 19D:
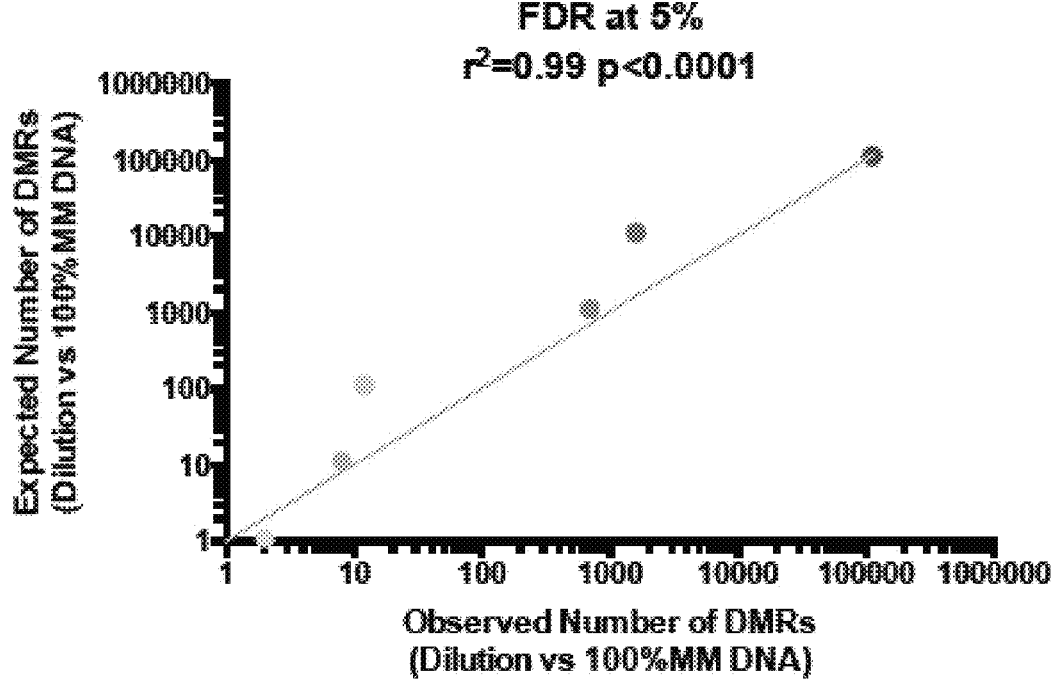
Figure 19E:
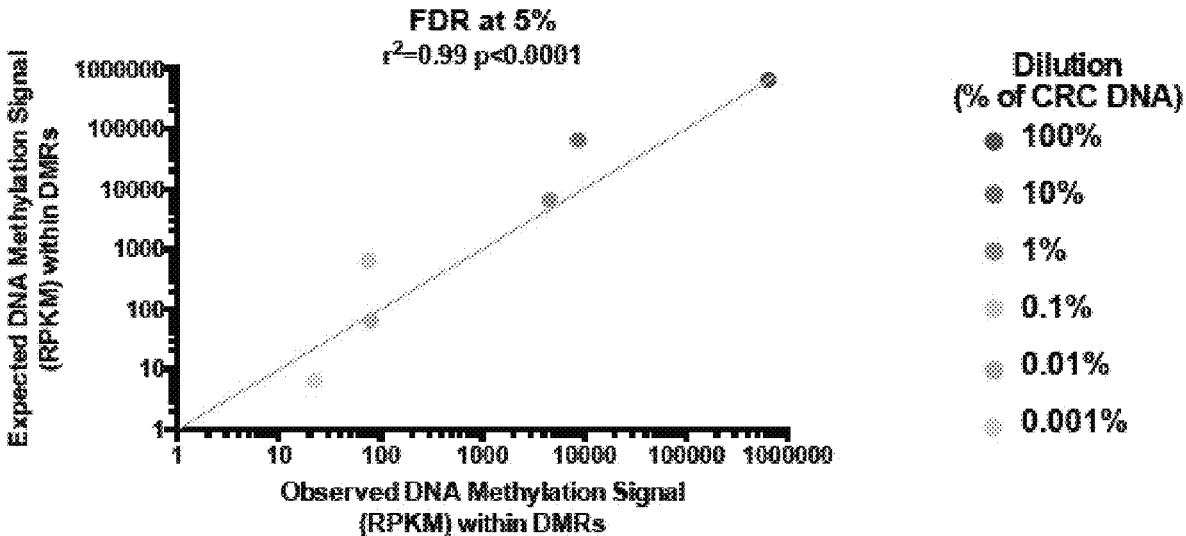
Figure 19F:
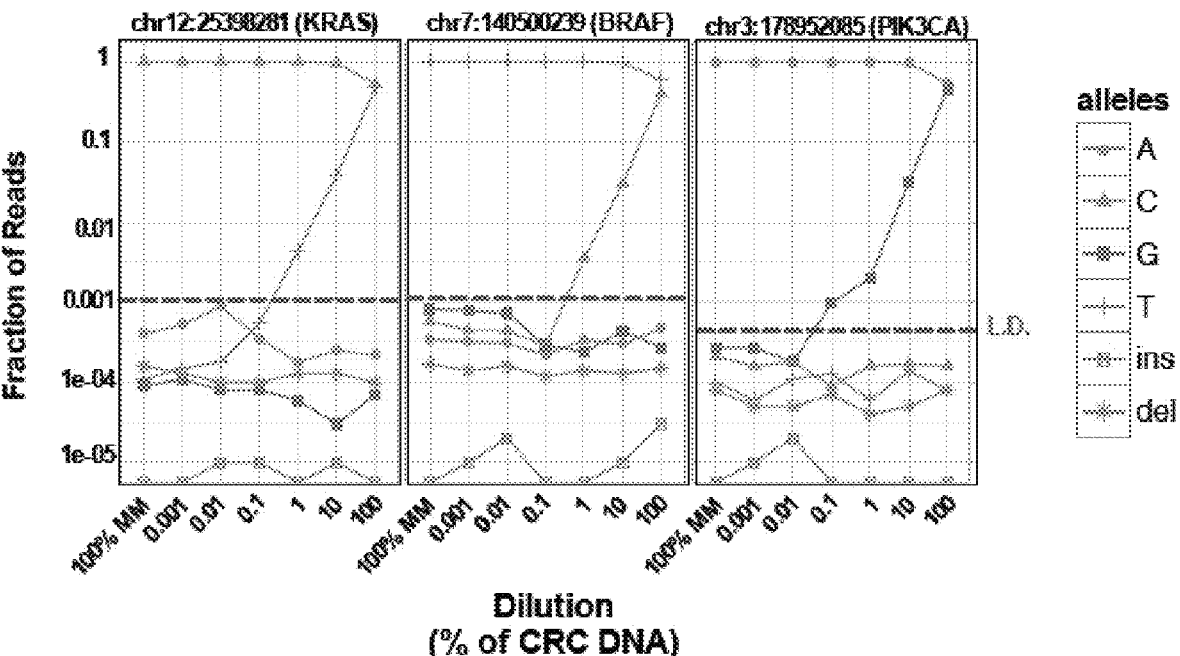

To evaluate the sensitivity of the cfMeDIP-seq protocol, we performed a serial dilution of Colorectal Cancer (CRC) HCT116 cell line DNA into a Multiple Myeloma (MM) MM1.S cell line DNA, both sheared to mimic cfDNA sizes. We diluted the CRC DNA from 100%, 10%, 1%, 0.1%, 0.01%, 0.001%, to 0% and performed cfMeDIP-seq on each of these dilutions. We also performed ultra-deep (10,000× median coverage) targeted sequencing for detection of three point mutations in the same samples. The observed number of DMRs identified at each CRC dilution point versus the pure MM DNA using a 5% False Discovery rate (FDR) threshold was almost perfectly linear ($r^2=0.99$, p<0.0001) with the expected number of DMRs based on the dilution factor (FIG. 19D) down to a 0.001% dilution. Moreover, the DNA methylation signal within these DMRs also shows almost perfect linearity ($r^2=0.99$, p<0.0001) between the observed versus expected signal (FIG. 19E; Supplementary Table 8). In comparison, beyond the 1% dilution, ultra-deep targeted sequencing could not reliably distinguish between the CRC-specific variants and the spurious variants due to PCR or sequencing-errors (FIG. 19F; Supplementary Table 7). Thus, cfMeDIP-seq displays excellent sensitivity for the detection of cancer-derived DNA, exceeding the performance of variant detection by ultra-deep targeted sequencing using a standard protocol.

Figure 19G:
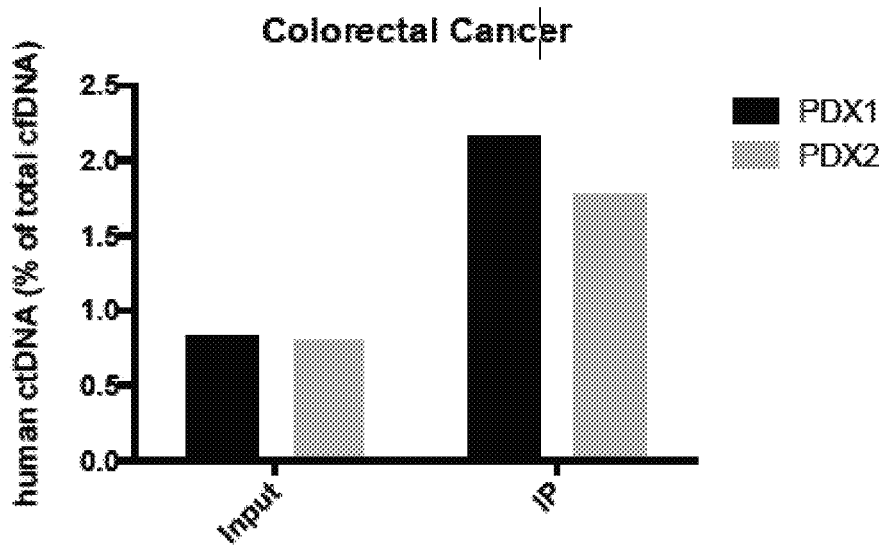

Cancer DNA is frequently hypermethylated at CpG-rich regions[17]. Since cfMeDIP-seq specifically targets methylated CpG-rich sequences, we hypothesized that ctDNA would be preferentially enriched during the immunoprecipitation procedure. To test this, we generated patient-derived xenografts (PDXs) from two colorectal cancer patients and collected the mouse plasma. Tumor-derived human cfDNA was present at less than 1% frequency within the total cfDNA pool in the input samples and at 2-fold greater abundance following immunoprecipitation (FIG. 19G; Supplementary Table 9). These results suggest that through biased sequencing of ctDNA, the cfMeDIP procedure could further increase ctDNA detection sensitivity.

Circulating Plasma cfDNA Methylation Profile can Distinguish Between Multiple Cancer Types and Healthy Donors DNA methylation patterns are tissue-specific, and have been used to stratify cancer patients into clinically relevant disease subgroups in glioblastoma[18], ependymomas[6], colorectal[19], and breast[20, 21], among many other cancer types. We asked if cfDNA associated profiles could be used to identify tissues-of-origin for multiple tumor types. To this end, we profiled 196 samples from 5 different tumor types and normal controls from early and late stage tumors. We used linear modeling to identify the top 300 DMRs mapping to CpG shores, shelves, islands and FANTOM5 enhancers for each pairwise comparison, leading to a total of 2,100 unique DMRs (FIG. 20A). Density clustering based on t-Distributed Stochastic Neighbor Embedding (tSNE)[22] of the 196 plasma samples based on the methylation status of these features revealed distinct clustering of samples based on tissue-of-origin and tumor types (FIG. 20B, FIG. 20C). Using an elastic net multi-cancer classifier fit with these features (FIG. 20A), we observed highly accurate discrimination between different tumor types (FIG. 20D).

Discrimination of Disease Subtypes

We evaluated the ability of cfDNA MeDIP profiles to discriminate between disease subtypes in five distinct cases-gene expression pattern (ER status in breast cancer), copy number aberration (HER2 status in breast cancer), rearrangement (FLT3 ITD status in AML), point mutation (IDH mutation in GBM), and finally histology in lung cancer. In each case, linear models were used to select and rank features as described earlier. In each case, hierarchical clustering was used to evaluate the grouping of samples. Density clustering based on t-Distributed Stochastic Neighbor Embedding (tSNE)[22] based on the methylation status of selected features revealed distinct clustering of samples based on each of these five distinct examples of cancer subtype classification.

Detection of Cancers and Classification of Cancer Types Using Machine Learning

In order to rigorously evaluate the ability of cfMeDIP profiles to detect cancers and further classify cancer types, we then conducted a set of machine learning analyses on our discovery cohort. To allow for accelerated computational analysis, we initially reduced our cfMeDIP discovery cohort to features mapping to CpG islands, shores, shelves and FANTOM5 enhancers (n=505,027 windows). We then implemented a strategy on our discovery cohort samples to derive unbiased estimates of performance, while accounting for training-set biases.

Herein, we split the discovery cohort into balanced training and test sets (80% training set, 20% test set). Using only the samples in the training set, we selected the top 300 DMRs for each class (sample type) versus other classes, based on limma-trend test statistics, and trained a series of one-versus-other-classes GLMnets using these features on the training set data. The training procedure consisted of 3 rounds of 10-Fold Cross-Validation (CV) across a grid of values for alpha and lambda with optimisation for Cohen's Kappa. The use of multiple rounds of 10-Fold CV was motivated by a desire to leverage additional randomisation for more generalisable model tuning.

Performance was then evaluated using AUROC (area under the receiver operating characteristic curve) derived from test set samples (held-out during the DMR selection and the subsequent GLMnet training/tuning steps). This process was repeated with 50 different splits of the discovery cohort into training and test sets to mitigate the influence of training-set biases. This culminated in a collection of 50 models for each one-vs other-classes comparison (480 models in total). Hereby, we refer to this collection of models as E50.

Subsequently, we evaluated performance across batches by generating a validation cohort of additional 152 plasma samples: AML (n=35), lung cancer (n=55) and healthy control (n=62) samples. For each class, we averaged the class probabilities output by the models in E50, and estimated AUROC for the one class vs. all others classes (FIG. 21A). The classifiers showed high AUROC values for the classification of AML vs others (0.993), LUC vs others (0.943) and normal vs others (1.000). This further confirmed the ability of cfMeDIP-seq coupled with a machine learning approach to accurately detect and classify tumor type. Finally, we observed that the classifiers were as accurate in early stage samples (0.950) as in late stage samples (0.934) (FIG. 21B), suggested that this approach is applicable for cancer early detection and for detection of cancer at both early stages and late stages.

Additional Advantages of cfDNA Methylome Profiling with cfMeDIP-Seq

The ability of cfDNA methylation patterns to accurately represent tissue-of-origin also overcomes limitations of mutation-based assays, wherein specificity for tissues-of-origin may be low due to the recurrent nature of many potential driver mutations across cancers in different tissues [23]. Mutation based assays may also be rendered insensitive by the clonal structure of tumors, where subclonal drivers may be harder to detect by virtue of lower abundance in ctDNA[24]. Mutation based ctDNA approaches are also vulnerable to potential confounding by driver mutations in benign tissues, which have been observed[25], and documented to display evidence of positive selection[26].

Taken together, our findings—based on the largest collection of cancer cfDNA methylomes derived to date—establish cfMeDIP-seq as an efficient and cost-effective tool with the potential to influence management of cancer and early detection. The accuracy and versatility of cfMeDIP-seq may be useful to inform therapeutic decisions in settings where resistance is correlated to epigenetic alterations, such as sensitivity to androgen receptor inhibition in prostate cancer[27]. The potential opportunities for early diagnosis and screening may be particularly evident in lung cancer, a disease in which screening has already shown clinical utility but for which existing screening tests (i.e., low dose CT scanning) has significant limitations such as ionizing radiation exposure and high false positive rate.

In conclusion, our findings underscore the utility of cfDNA methylation profiles as a basis for non-invasive, cost-effective, sensitive, highly accurate early tumor detection, multi-cancer classification, and cancer subtype classification.

TABLE 1

Number of reads and mapping efficiency of sequenced MeDIP-seq (100 ng Rep 1 and Rep 2) and cfMeDIP-seq (10 ng, 5 ng and 1 ng, Rep 1 and Rep 2) libraries prepared using various tarring inputs of HCT116 cell line DNA sheared to mimic cfDNA, to human (Hg19) genome and λ genome. Two biological replicates were used for starting input DNA. For starting inputs less than 100 ng, the samples were topped up with exogenous λ DNA to artificially increase the starting amount to 100 ng prior to MeDIP.

| Sample | # of raw reads | # of aligned reads to human genome (Hg19) | Mapping efficiency to human genome (Hg19) | # of aligned reads to λ genome | Mapping efficiency to λ genome |
|---|---|---|---|---|---|
| Input | 74,504,053 | 71,343,168 | 95.76 | 12 | 0.00 |
| 100 ng Replicate 1 | 55,396,238 | 50,472,273 | 91.11 | 0 | 0.00 |
| 100 ng Replicate 2 | 66,569,209 | 60,770,277 | 91.29 | 1 | 0.00 |
| 10 ng Replicate 1 | 70,054,607 | 64,020,441 | 91.39 | 0 | 0.00 |
| 10 ng Replicate 2 | 58,297,539 | 53,308,777 | 91.44 | 0 | 0.00 |
| 5 ng Replicate 1 | 65,845,430 | 60,540,743 | 91.94 | 1 | 0.00 |
| 5 ng Replicate 2 | 64,750,879 | 59,358,412 | 91.67 | 0 | 0.00 |
| 1 ng Replicate 1 | 35,102,361 | 32,258,451 | 91.90 | 0 | 0.00 |
| 1 ng Replicate 2 | 33,881,118 | 31,194,711 | 92.07 | 0 | 0.00 |

TABLE 2A

Mean coverage of ultra-deep targetd variant sequencing using dilution
series of CRC cell line HCT116 DNA into MM cell line MM1.S DNA

| Dilution (% of CRC DNA) | Uncollapsed reads mean target coverage | SSCS (single strand consensus sequences) mean target coverage | DCS (duplex consensus sequences) mean target coverage |
|---|---|---|---|
| 100 | 155,964 | 4284 | 655 |
| 10 | 154,657 | 4877 | 654 |
| 1 | 154,419 | 4890 | 654 |
| 0.1 | 183,271 | 5674 | 887 |
| 0.01 | 238,291 | 8068 | 1602 |
| 0.001 | 199,766 | 7337 | 1299 |
| 0.0001 | 187,695 | 6891 | 1181 |
| 0 | 216,434 | 7721 | 1412 |

TABLE 2B

Resultant observed DMRs and DNA methylation
signal from the dilution series of CRC cell
line HCT116 DNA into MM cell line MM1.S DNA

| Dilution (% of CRC DNA) | Observed number of DMRs | Observed DNA methylation signal (sum of RPKMs within DMRs) |
|---|---|---|
| 100 | 111,472 | 645,683.90 |
| 10 | 1,597 | 8,775.61 |
| 1 | 692 | 4,521.60 |
| 0.1 | 12 | 75.71 |
| 0.01 | 8 | 79.73 |
| 0.001 | 2 | 22.42 |

TABLE 3

Number of reads and mapping efficiency of cfMeDIP-
seq libraries of PDX and Input Control samples
after aligning to human (Hg19) genome

| Sample | # of Raw reads | # of Aligned reads to human genome (Hg19) | Mapping efficiency to human genome |
|---|---|---|---|
| Input Control 1 | 45,857,633 | 389,073 | 0.83 |
| Input Control 2 | 35,658,454 | 283,799 | 0.80 |
| PDX 1 | 49,997,949 | 1,080,277 | 2.16 |
| PDX 2 | 34,802,767 | 614,988 | 1.77 |

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

The invention claimed is:

1. A method for determining whether a subject has or is at risk of having a disease, comprising:
 (a) providing a cell-free nucleic acid sample derived from a subject, wherein said cell-free nucleic acid sample comprises a plurality of nucleic acid molecules;
 (b) subjecting said plurality of nucleic acid molecules, or derivatives thereof, to sequencing to generate a plurality of sequencing reads;
 (c) computer processing said plurality of sequencing reads to identify, for said plurality of nucleic acid molecules, at least one profile, wherein said at least one profile comprises a methylation profile, wherein said methylation profile comprises a plurality of differentially methylated regions (DMRs) comprising a CpG density of at least 8 CpG dinucleotides per 300 base-pairs; and
 (d) using said at least one profile to determine whether said subject has or is at risk of having said disease.

2. The method of claim 1, wherein said at least one profile further comprises a mutation profile or a fragment length profile.

3. The method of claim 1, wherein said disease comprises a cancer, and wherein said cancer is selected from the group consisting of adrenal cancer, anal cancer, bile duct cancer, bladder cancer, bone cancer, brain/CNS tumors, breast cancer, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (gist), gestational trophoblastic disease, Hodgkin disease, Kaposi sarcoma, kidney cancer, laryngeal and hypopharyngeal cancer, leukemia (acute lymphocytic, acute myeloid, chronic lymphocytic, chronic myeloid, chronic myelomonocytic), liver cancer, lung cancer (non-small cell, small cell, lung carcinoid tumor), lymphoma, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, penile cancer, pituitary tumors, prostate cancer, retinoblastoma, rhabdomyosarcoma, salivary gland cancer, sarcoma-adult soft tissue cancer, skin cancer (basal and squamous cell, melanoma, Merkel cell), small intestine cancer, stomach cancer, testicular cancer, thymus cancer, thyroid cancer, uterine sarcoma, vaginal cancer, vulvar cancer, Waldenstrom macroglobulinemia, Wilms tumor, squamous cell carcinoma, and head and neck squamous cell carcinoma.

4. The method of claim 3, wherein said cancer is head and neck squamous cell carcinoma.

5. The method of claim 1, wherein said plurality of nucleic acid molecules comprises circulating tumor DNA (ctDNA).

6. The method of claim 1, wherein said plurality of nucleic acid molecules comprises circulating tumor RNA.

7. The method of claim 1, wherein said plurality of DMRs is ctDNA derived.

8. The method of claim 1, wherein a plurality of DMRs derived from peripheral blood leukocytes is absent from said methylation profile.

9. The method of claim 1, wherein said plurality of DMRs comprises at least about 56 genomic regions with hypomethylation levels compared to corresponding genomic regions from a normal healthy subject.

10. The method of claim 1, wherein said plurality of DMRs comprises at least about 941 genomic regions with hyper-methylation levels compared to corresponding genomic regions from a normal healthy subject.

11. The method of claim 1, wherein a DMR of said plurality of DMRs comprises a size of at least about 100 base pairs.

12. The method of claim 1, wherein a DMR of said plurality of DMRs comprises a size of at least about 200 base pairs.

13. The method of claim 9, wherein said normal healthy subject comprises a same set of risk factors as said subject.

14. The method of claim 2, wherein said mutation profile comprises a missense variant, a nonsense variant, a deletion variant, an insertion variant, a duplication variant, an inversion variant, a frameshift variant, or a repeat expansion variant.

15. The method of claim 2, wherein any variant that is derived from clonal hematopoiesis is absent from said mutation profile.

16. The method of claim 15, wherein said mutation profile does not comprise a variant of gene DNMT3A, TET2, or ASXL1.

17. The method of claim 2, wherein said mutation profile does not comprise a canonical cancer driver gene.

18. The method of claim 2, wherein said mutation profile comprises a non-canonical cancer driver gene, where said non-canonical cancer driver gene is GRIN3A or MYC.

19. The method of claim 2, wherein said fragment length profile comprises selecting cell free nucleic acid molecules based at least on a range of fragment lengths of from about 80 base pairs to 170 base pairs.

20. The method of claim 5, wherein said circulating tumor DNA is enriched.

21. The method of claim 1, further comprising mixing said cell-free nucleic acid sample with filler DNA molecules.

22. The method of claim 1, wherein said sequencing does not comprise bisulfite sequencing.

23. The method of claim 2, wherein any variant that is present in a genomic DNA sample obtained from one or more peripheral blood leukocytes obtained from said subject is absent from said mutation profile.

\* \* \* \* \*